US009447474B2

(12) United States Patent
Darvasi et al.

(10) Patent No.: US 9,447,474 B2
(45) Date of Patent: Sep. 20, 2016

(54) SYSTEM AND METHOD FOR ANALYZING DNA MIXTURES

(75) Inventors: Ariel Darvasi, Mevasseret Zion (IL); Lev Voskoboinik, Jerusalem (IL)

(73) Assignee: YISSUM RESEARCH DEVELOPMENT COMPANY OF THE HEBREW UNIVERSITY OF JERUSALEM, LTD., Jerusalem (IL)

( * ) Notice: Subject to any disclaimer, the term of this patent is extended or adjusted under 35 U.S.C. 154(b) by 0 days.

(21) Appl. No.: 13/512,959

(22) PCT Filed: Dec. 2, 2010

(86) PCT No.: PCT/IL2010/001019
§ 371 (c)(1),
(2), (4) Date: May 31, 2012

(87) PCT Pub. No.: WO2011/067765
PCT Pub. Date: Jun. 9, 2011

(65) Prior Publication Data
US 2012/0245052 A1 Sep. 27, 2012

Related U.S. Application Data

(60) Provisional application No. 61/266,292, filed on Dec. 3, 2009, provisional application No. 61/286,271, filed on Dec. 14, 2009.

(51) Int. Cl.
*C12Q 1/68* (2006.01)
*C07H 21/02* (2006.01)
*C07H 21/04* (2006.01)
*G06F 19/18* (2011.01)

(52) U.S. Cl.
CPC .......... *C12Q 1/6888* (2013.01); *C12Q 1/6827* (2013.01); *G06F 19/18* (2013.01); *C12Q 2600/156* (2013.01)

(58) Field of Classification Search
None
See application file for complete search history.

(56) References Cited

U.S. PATENT DOCUMENTS 6,582,908 B2 * 6/2003 Fodor ............... B01J 19/0046
435/288.3

FOREIGN PATENT DOCUMENTS

| WO | 2005/007816 A2 | 1/2005 |
| WO | WO2005007816 | * 1/2005 |
| WO | 2010/011776 A1 | 1/2010 |

OTHER PUBLICATIONS

Jacobs et al. Nat Genet. Nov. 2009;41(11):1253-7.*
Egeland et al. Int J Legal Med. Oct. 2003;117(5):271-5.*
Illumina Technical Note: DNA Analysis: Designing Custom GoldenGate® Genotyping Assays. Pub. No. 370-2007-020 current as of Jul. 30, 2010.*
Gill et al. Int J Legal Med (2001) 114:204-210.*
Homer et al. PLoS Genet 4(8): e1000167. pp. 1-9.*
Illumina. Data Sheet: SNP Genotyping. HumanCVD Genotyping BeadChip. Oct. 2008. available via url: <.illumina.com/documents/products/datasheets/datasheet_humancvd.pdf>.*
Webb et al Human Molecular Genetics. 2006. 15(21): 3263-3271.*
Cross et al BMC Medical Genomics. Published online Apr. 20, 2009. 2:17, pp. 1-18.*
Kryukov et al. AJHG. Apr. 2007. 80: 727-739.*
Gorlov et al. AMJHG. Jan. 2008. 82: 100-112.*
Westen, et al., "Tri-allelic SNP markers enable analysis of mixed and degraded DNA samples", Forensic Science International: Genetics, vol. 3, pp. 233-241, (2009).
Egeland, et al., "Estimating the number of contributors to a DNA profile", Int J Legal Med, vol. 117, pp. 271-275, (2003).
Voskoboinik, et al., "Forensic identification of an individual in complex DNA mixtures", Forensic Science International: Genetics, [Online] Oct. 2, 2010, XP002622794.
Gill, "An assessment of the utility of single nucleotide polymorphisms (SNPs) for forensic purposes", Int J Legal Med, vol. 114, pp. 204-210, (2001).
Ragoussis, "Genotyping Technologies for Genetic Research", Annu. Rev. Genomics Hum. Genet., vol. 10, pp. 117-133, (2009).
Jacobs, et al., "A new statistic and its power to infer membership in a genome-wide association study using genotype frequencies", Nature Genetics, vol. 41, No. 11, pp. 1253-1259, (2009).
Homer, et al., "Resolving Individuals Contributing Trace Amounts of DNA to Highly Complex Mixtures Using High-Density SNP Genotyping Microarrays", PLoS Genet, vol. 4, Issue 8, e1000167 9 pages; (2008).
Hu, et al., "Evaluation of DNA mixtures involving two pairs of relatives", Int J Legal Med, vol. 119, pp. 251-259, (2005).
Buckleton, et al., "Forensic DNA evidence interpretation", 531 pages, CRC Press, Boca Raton, 2005.
The International HapMap Consortium, "The International HapMap Project", Nature, vol. 426, pp. 789-796, (2003).
Kidd, et al., "Developing a SNP panel for forensic identification of individuals", Forensic Science International, vol. 164, pp. 20-32, (2006).
Budowle, et al., "Forensically relevant SNP classes", BioTechniques 25th Anniversary, vol. 44, No. 5, pp. 603-610, (2008).

(Continued)

*Primary Examiner* — Carla Myers
(74) *Attorney, Agent, or Firm* — Browdy and Neimark, PLLC

(57) ABSTRACT

Provided is a method for determining the presence or absence of an individual's DNA in a sample containing DNA from two or more contributors. A panel of a plurality of single nucleotide polymorphisms (SNPs) is used. For each SNP in the panel, it is determined whether the minor allele of the SNP is present in the sample, and whether the minor allele is present in the individual's DNA. If the number of minor alleles that are present in the individual's DNA that are also present in the DNA sample is above a predetermined threshold, the individual's DNA is concluded to be present in the sample. Also provided is an array of DNA molecules for use in the method, as well as a method for estimating the number of individuals contributing to a DNA containing sample.

8 Claims, 95 Drawing Sheets

(56) References Cited

OTHER PUBLICATIONS

Foreman, et al., "Statistical analyses to support forensic interpretation for a new ten-locus STR profiling system", Int J Legal Med, vol. 114, pp. 147-155, (2001).
Fan, et al., "Highly Parallel SNP Genotyping", Cold Spring Herb. Symp. Quant. Biol., vol. 68, pp. 69-78, (2003).
Ladd, et al., "Interpretation of Complex Forensic DNA Mixtures", Croat Med J, vol. 42, pp. 244-246, (2001).
Gill, et al., "Interpretation of complex DNA profiles using empirical models and a method to measure their robustness", Forensic Science International: Genetics, vol. 2, pp. 91-103, (2008).
Lovrich, et al., "National Forensic DNA Study Report", National Institute of Justice, 473 pages, (2003).
Butler, "Short tandem repeat typing technologies used in human identity testing", BioTechniques, vol. 43, Supplement to vol. 43, No. 4, pp. ii-v, (2007).
Pakstis, et al., "Candidate SNPs for a universal individual identification panel", Hum Genet, vol. 121, pp. 305-317, (2007).
International Search Report for International application No. PCT/IL2010/001019; mailed Mar. 10, 2011; three pages.

* cited by examiner

Fig. 9

| rs# | chrom | pos | strand | YRI MAF | JPT+CHI CEU MAF | | rs# | chrom | pos | strand | YRI MAF | JPT+CH | CEU MAF |
|---|---|---|---|---|---|---|---|---|---|---|---|---|---|
| 1 rs12138618 | chr1 | 740098 | + | 0.93 | 0.943 | 0.946 | 3040 rs6437105 | chr2 | 158103059 | + | 0.075 | 0.079 | 0.09 |
| 2 rs903901 | chr1 | 2300053 | + | 0.933 | 0.92 | 0.91 | 3041 rs7581896 | chr2 | 158777675 | + | 0.933 | 0.922 | 0.95 |
| 3 rs2643901 | chr1 | 2304179 | + | 0.058 | 0.062 | 0.063 | 3042 rs13415523 | chr2 | 159295502 | + | 0.915 | 0.944 | 0.932 |
| 4 rs10799171 | chr1 | 4015436 | + | 0.083 | 0.061 | 0.098 | 3043 rs17494000 | chr2 | 159750239 | + | 0.933 | 0.95 | 0.932 |
| 5 rs12562995 | chr1 | 4259026 | + | 0.942 | 0.91 | 0.932 | 3044 rs2303336 | chr2 | 159827662 | + | 0.092 | 0.056 | 0.062 |
| 6 rs12564602 | chr1 | 4259243 | + | 0.942 | 0.911 | 0.932 | 3045 rs174266 | chr2 | 159840641 | + | 0.908 | 0.944 | 0.938 |
| 7 rs16839093 | chr1 | 4443102 | + | 0.915 | 0.927 | 0.923 | 3046 rs622593 | chr2 | 163351604 | + | 0.927 | 0.939 | 0.946 |
| 8 rs2235441 | chr1 | 4751069 | + | 0.95 | 0.939 | 0.946 | 3047 rs7561377 | chr2 | 163919959 | + | 0.917 | 0.906 | 0.946 |
| 9 rs2235443 | chr1 | 4751163 | + | 0.949 | 0.948 | 0.95 | 3048 rs7602086 | chr2 | 163920061 | + | 0.917 | 0.906 | 0.946 |
| 10 rs12403173 | chr1 | 4909453 | + | 0.908 | 0.95 | 0.902 | 3049 rs16848321 | chr2 | 163920410 | + | 0.917 | 0.906 | 0.923 |
| 11 rs7516707 | chr1 | 6993958 | + | 0.915 | 0.92 | 0.929 | 3050 rs16848323 | chr2 | 163920608 | + | 0.917 | 0.906 | 0.923 |
| 12 rs6697897 | chr1 | 7540142 | + | 0.925 | 0.91 | 0.95 | 3051 rs6722154 | chr2 | 163922956 | + | 0.905 | 0.941 | 0.946 |
| 13 rs1317725 | chr1 | 7569469 | + | 0.949 | 0.95 | 0.938 | 3052 rs16850317 | chr2 | 165852660 | + | 0.908 | 0.928 | 0.928 |
| 14 rs11585947 | chr1 | 7640942 | + | 0.95 | 0.933 | 0.923 | 3053 rs6726130 | chr2 | 166015072 | + | 0.908 | 0.91 | 0.919 |
| 15 rs6658296 | chr1 | 7657967 | + | 0.915 | 0.917 | 0.902 | 3054 rs16853103 | chr2 | 167721949 | + | 0.917 | 0.933 | 0.932 |
| 16 rs12134193 | chr1 | 8099213 | + | 0.925 | 0.91 | 0.937 | 3055 rs10497320 | chr2 | 167749152 | + | 0.942 | 0.933 | 0.911 |
| 17 rs9442600 | chr1 | 9353170 | + | 0.931 | 0.944 | 0.92 | 3056 rs16853181 | chr2 | 167752825 | + | 0.942 | 0.933 | 0.932 |
| 18 rs17037397 | chr1 | 11784750 | + | 0.95 | 0.906 | 0.932 | 3057 rs989008 | chr2 | 167762866 | + | 0.938 | 0.922 | 0.911 |
| 19 rs3737965 | chr1 | 11789038 | + | 0.95 | 0.906 | 0.938 | 3058 rs989007 | chr2 | 167763062 | + | 0.942 | 0.927 | 0.911 |
| 20 rs2076004 | chr1 | 11809400 | + | 0.949 | 0.906 | 0.918 | 3059 rs2390548 | chr2 | 167763985 | + | 0.942 | 0.927 | 0.931 |
| 21 rs2272803 | chr1 | 11821376 | + | 0.95 | 0.906 | 0.932 | 3060 rs16855271 | chr2 | 168884616 | + | 0.924 | 0.911 | 0.95 |
| 22 rs5063 | chr1 | 11830235 | + | 0.95 | 0.916 | 0.932 | 3061 rs6728233 | chr2 | 168994035 | + | 0.91 | 0.916 | 0.941 |
| 23 rs12562952 | chr1 | 11849643 | + | 0.908 | 0.933 | 0.905 | 3062 rs16855658 | chr2 | 169219350 | + | 0.932 | 0.938 | 0.92 |
| 24 rs12403086 | chr1 | 11912784 | + | 0.933 | 0.937 | 0.927 | 3063 rs11895864 | chr2 | 170044895 | + | 0.924 | 0.916 | 0.911 |
| 25 rs2297729 | chr1 | 12092875 | + | 0.924 | 0.904 | 0.911 | 3064 rs11901329 | chr2 | 170044905 | + | 0.94 | 0.916 | 0.905 |
| 26 rs12135103 | chr1 | 12838434 | + | 0.908 | 0.916 | 0.905 | 3065 rs3474350 | chr2 | 171207550 | + | 0.925 | 0.928 | 0.95 |
| 27 rs1203438 | chr1 | 13738714 | + | 0.917 | 0.911 | 0.91 | 3066 rs17580984 | chr2 | 172246776 | + | 0.925 | 0.911 | 0.946 |
| 28 rs11588651 | chr1 | 13820492 | + | 0.908 | 0.917 | 0.937 | 3067 rs17615013 | chr2 | 172254297 | + | 0.925 | 0.925 | 0.946 |
| 29 rs12403548 | chr1 | 14328873 | + | 0.94 | 0.943 | 0.929 | 3068 rs3770443 | chr2 | 172419384 | + | 0.95 | 0.91 | 0.946 |
| 30 rs2789742 | chr1 | 14543351 | + | 0.942 | 0.921 | 0.936 | 3069 rs12473516 | chr2 | 172549115 | + | 0.948 | 0.904 | 0.945 |
| 31 rs4111265 | chr1 | 14561194 | + | 0.908 | 0.916 | 0.911 | 3070 rs4972760 | chr2 | 172849120 | + | 0.075 | 0.051 | 0.099 |
| 32 rs4661709 | chr1 | 16351768 | + | 0.069 | 0.067 | 0.05 | 3071 rs1774290 | chr2 | 173836132 | + | 0.95 | 0.906 | 0.905 |
| 33 rs3763583 | chr1 | 17438001 | + | 0.95 | 0.922 | 0.911 | 3072 rs10497398 | chr2 | 173838050 | + | 0.95 | 0.906 | 0.905 |
| 34 rs7522439 | chr1 | 17449981 | + | 0.917 | 0.917 | 0.911 | 3073 rs1469522 | chr2 | 175067336 | + | 0.075 | 0.09 | 0.081 |

Fig. 9 Cont. 1

| # | SNP | chr | pos | strand | v1 | v2 | v3 | # | SNP | chr | pos | strand | v1 | v2 | v3 |
|---|---|---|---|---|---|---|---|---|---|---|---|---|---|---|---|
| 35 | rs2256787 | chr1 | 17765403 | + | 0.092 | 0.067 | 0.068 | 3074 | rs12995802 | chr2 | 175608179 | + | 0.908 | 0.922 | 0.932 |
| 36 | rs2246282 | chr1 | 17772306 | + | 0.92 | 0.933 | 0.941 | 3075 | rs12621883 | chr2 | 176554838 | + | 0.917 | 0.92 | 0.914 |
| 37 | rs10749613 | chr1 | 18241297 | + | 0.096 | 0.094 | 0.089 | 3076 | rs12464144 | chr2 | 176558565 | + | 0.917 | 0.911 | 0.914 |
| 38 | rs9662299 | chr1 | 18352678 | + | 0.95 | 0.928 | 0.902 | 3077 | rs12467858 | chr2 | 176572369 | + | 0.917 | 0.911 | 0.911 |
| 39 | rs12076563 | chr1 | 18623569 | + | 0.941 | 0.937 | 0.924 | 3078 | rs17223864 | chr2 | 176597313 | + | 0.949 | 0.916 | 0.911 |
| 40 | rs9439738 | chr1 | 18951762 | + | 0.948 | 0.944 | 0.938 | 3079 | rs17223990 | chr2 | 176601174 | + | 0.942 | 0.911 | 0.911 |
| 41 | rs4920532 | chr1 | 18970564 | + | 0.092 | 0.067 | 0.063 | 3080 | rs2593775 | chr2 | 176617951 | + | 0.95 | 0.933 | 0.919 |
| 42 | rs6603910 | chr1 | 18985645 | + | 0.068 | 0.072 | 0.064 | 3081 | rs934798 | chr2 | 178340725 | + | 0.942 | 0.916 | 0.923 |
| 43 | rs4603153 | chr1 | 19121703 | + | 0.058 | 0.1 | 0.085 | 3082 | rs1370655 | chr2 | 178341039 | + | 0.942 | 0.917 | 0.929 |
| 44 | rs4271183 | chr1 | 20035877 | + | 0.917 | 0.92 | 0.92 | 3083 | rs10171486 | chr2 | 178494566 | + | 0.931 | 0.927 | 0.911 |
| 45 | rs12137940 | chr1 | 20037970 | + | 0.933 | 0.925 | 0.914 | 3084 | rs10497483 | chr2 | 178513647 | + | 0.925 | 0.927 | 0.911 |
| 46 | rs12117495 | chr1 | 20056032 | + | 0.915 | 0.922 | 0.928 | 3085 | rs7586133 | chr2 | 180635388 | + | 0.907 | 0.916 | 0.927 |
| 47 | rs10916672 | chr1 | 20120681 | + | 0.922 | 0.903 | 0.917 | 3086 | rs17794144 | chr2 | 180697211 | + | 0.907 | 0.921 | 0.918 |
| 48 | rs12080954 | chr1 | 20265160 | + | 0.922 | 0.936 | 0.929 | 3087 | rs10211135 | chr2 | 181813601 | + | 0.925 | 0.916 | 0.929 |
| 49 | rs645548 | chr1 | 20739286 | + | 0.95 | 0.909 | 0.937 | 3088 | rs17455865 | chr2 | 181826804 | + | 0.95 | 0.911 | 0.941 |
| 50 | rs10916837 | chr1 | 20827770 | + | 0.907 | 0.935 | 0.919 | 3089 | rs12105509 | chr2 | 183908947 | + | 0.917 | 0.944 | 0.946 |
| 51 | rs12409944 | chr1 | 20896334 | + | 0.95 | 0.921 | 0.946 | 3090 | rs10497636 | chr2 | 184318055 | + | 0.947 | 0.948 | 0.902 |
| 52 | rs7550977 | chr1 | 21815544 | + | 0.917 | 0.949 | 0.95 | 3091 | rs17403192 | chr2 | 185953898 | + | 0.933 | 0.921 | 0.905 |
| 53 | rs829387 | chr1 | 21895738 | + | 0.068 | 0.067 | 0.072 | 3092 | rs11676655 | chr2 | 186003297 | + | 0.932 | 0.938 | 0.902 |
| 54 | rs2031749 | chr1 | 22869966 | + | 0.941 | 0.928 | 0.922 | 3093 | rs13014616 | chr2 | 186005602 | + | 0.933 | 0.939 | 0.902 |
| 55 | rs12085531 | chr1 | 22873179 | + | 0.942 | 0.928 | 0.928 | 3094 | rs6731674 | chr2 | 186008555 | + | 0.931 | 0.937 | 0.901 |
| 56 | rs389865 | chr1 | 25239227 | + | 0.098 | 0.058 | 0.094 | 3095 | rs11675192 | chr2 | 186053393 | + | 0.917 | 0.938 | 0.917 |
| 57 | rs3008428 | chr1 | 26249194 | + | 0.1 | 0.056 | 0.091 | 3096 | rs11681517 | chr2 | 186057590 | + | 0.925 | 0.938 | 0.901 |
| 58 | rs6703872 | chr1 | 26671231 | + | 0.906 | 0.932 | 0.932 | 3097 | rs6708098 | chr2 | 186060852 | + | 0.927 | 0.938 | 0.902 |
| 59 | rs1002487 | chr1 | 26738558 | + | 0.933 | 0.933 | 0.931 | 3098 | rs13007661 | chr2 | 186085731 | + | 0.925 | 0.938 | 0.902 |
| 60 | rs6704457 | chr1 | 28937626 | + | 0.096 | 0.091 | 0.059 | 3099 | rs13030807 | chr2 | 186143312 | + | 0.92 | 0.939 | 0.902 |
| 61 | rs7547259 | chr1 | 29042465 | + | 0.949 | 0.911 | 0.929 | 3100 | rs7556993 | chr2 | 186172763 | + | 0.925 | 0.938 | 0.902 |
| 62 | rs6697404 | chr1 | 29043045 | + | 0.94 | 0.92 | 0.927 | 3101 | rs9789468 | chr2 | 186286973 | + | 0.933 | 0.944 | 0.918 |
| 63 | rs6697423 | chr1 | 29043082 | + | 0.939 | 0.923 | 0.946 | 3102 | rs13031528 | chr2 | 186444456 | + | 0.933 | 0.938 | 0.905 |
| 64 | rs2298895 | chr1 | 29051511 | + | 0.925 | 0.916 | 0.929 | 3103 | rs12616304 | chr2 | 186464459 | + | 0.933 | 0.933 | 0.911 |
| 65 | rs16837730 | chr1 | 29052601 | + | 0.933 | 0.911 | 0.929 | 3104 | rs12620075 | chr2 | 186495414 | + | 0.933 | 0.933 | 0.92 |
| 66 | rs9426359 | chr1 | 29654117 | + | 0.917 | 0.928 | 0.911 | 3105 | rs6750727 | chr2 | 190701961 | + | 0.949 | 0.939 | 0.909 |
| 67 | rs9426466 | chr1 | 29677399 | + | 0.945 | 0.924 | 0.907 | 3106 | rs6749371 | chr2 | 191610429 | + | 0.933 | 0.906 | 0.902 |
| 68 | rs12117057 | chr1 | 31074773 | + | 0.92 | 0.95 | 0.915 | 3107 | rs6715106 | chr2 | 191621279 | + | 0.929 | 0.91 | 0.932 |
| 69 | rs511409 | chr1 | 33985974 | + | 0.942 | 0.95 | 0.927 | 3108 | rs4502362 | chr2 | 192048047 | + | 0.917 | 0.921 | 0.937 |

Fig. 9 Cont. 2

| | | | | | | | | | |
|---|---|---|---|---|---|---|---|---|---|
| 70 | rs538027 | chr1 | 33985576 | + | 0.93 | 0.949 | 0.935 | 3109 | rs11897727 chr2 | 192872685 | + | 0.943 | 0.918 | 0.934 |
| 71 | rs490984 | chr1 | 33988898 | + | 0.95 | 0.95 | 0.92 | 3110 | rs10169437 chr2 | 193071967 | + | 0.925 | 0.944 | 0.911 |
| 72 | rs12723958 | chr1 | 34202538 | + | 0.909 | 0.909 | 0.941 | 3111 | rs1478127 chr2 | 194249012 | + | 0.089 | 0.066 | 0.086 |
| 73 | rs2294190 | chr1 | 34659241 | + | 0.933 | 0.927 | 0.941 | 3112 | rs10497745 chr2 | 194387445 | + | 0.95 | 0.949 | 0.925 |
| 74 | rs1741972 | chr1 | 35062460 | + | 0.067 | 0.1 | 0.077 | 3113 | rs12693727 chr2 | 194904314 | + | 0.051 | 0.056 | 0.055 |
| 75 | rs750829 | chr1 | 36824007 | + | 0.915 | 0.949 | 0.927 | 3114 | rs7563951 chr2 | 194907040 | + | 0.05 | 0.051 | 0.062 |
| 76 | rs6426013 | chr1 | 37464036 | + | 0.075 | 0.051 | 0.099 | 3115 | rs1901377 chr2 | 194913841 | + | 0.05 | 0.05 | 0.062 |
| 77 | rs3856137 | chr1 | 37804559 | + | 0.933 | 0.937 | 0.937 | 3116 | rs4850531 chr2 | 194914159 | + | 0.083 | 0.05 | 0.062 |
| 78 | rs12745452 | chr1 | 38265491 | + | 0.948 | 0.935 | 0.914 | 3117 | rs7573436 chr2 | 194920218 | + | 0.05 | 0.051 | 0.062 |
| 79 | rs12058961 | chr1 | 38289897 | + | 0.91 | 0.933 | 0.948 | 3118 | rs7573264 chr2 | 194920269 | + | 0.05 | 0.05 | 0.063 |
| 80 | rs2068122 | chr1 | 38315755 | + | 0.927 | 0.927 | 0.907 | 3119 | rs1451704 chr2 | 194921911 | + | 0.05 | 0.051 | 0.063 |
| 81 | rs7413818 | chr1 | 38569327 | + | 0.948 | 0.922 | 0.92 | 3120 | rs16839067 chr2 | 195824034 | + | 0.908 | 0.939 | 0.946 |
| 82 | rs6679637 | chr1 | 38579217 | + | 0.95 | 0.922 | 0.914 | 3121 | rs17794252 chr2 | 196173269 | + | 0.942 | 0.928 | 0.918 |
| 83 | rs13375066 | chr1 | 38582383 | + | 0.95 | 0.928 | 0.92 | 3122 | rs17382934 chr2 | 201352911 | + | 0.95 | 0.949 | 0.91 |
| 84 | rs1930578 | chr1 | 38939693 | + | 0.911 | 0.922 | 0.914 | 3123 | rs13003798 chr2 | 205064013 | + | 0.933 | 0.917 | 0.932 |
| 85 | rs17484974 | chr1 | 38959381 | + | 0.908 | 0.949 | 0.919 | 3124 | rs7593793 chr2 | 205598643 | + | 0.925 | 0.944 | 0.92 |
| 86 | rs12084082 | chr1 | 39070616 | + | 0.929 | 0.903 | 0.926 | 3125 | rs6754606 chr2 | 205632522 | + | 0.925 | 0.944 | 0.923 |
| 87 | rs3795348 | chr1 | 40734036 | + | 0.925 | 0.949 | 0.941 | 3126 | rs13397179 chr2 | 205740361 | + | 0.938 | 0.912 | 0.923 |
| 88 | rs3795344 | chr1 | 40753817 | + | 0.925 | 0.95 | 0.941 | 3127 | rs16837138 chr2 | 205849227 | + | 0.95 | 0.922 | 0.941 |
| 89 | rs6693885 | chr1 | 45283937 | + | 0.058 | 0.072 | 0.054 | 3128 | rs13021171 chr2 | 206084603 | + | 0.931 | 0.939 | 0.92 |
| 90 | rs1995403 | chr1 | 45290167 | + | 0.058 | 0.067 | 0.055 | 3129 | rs12612185 chr2 | 211820267 | + | 0.92 | 0.916 | 0.929 |
| 91 | rs1969084 | chr1 | 45308014 | + | 0.067 | 0.067 | 0.055 | 3130 | rs13019783 chr2 | 212246660 | + | 0.933 | 0.944 | 0.923 |
| 92 | rs346704 | chr1 | 45324270 | + | 0.921 | 0.931 | 0.945 | 3131 | rs2272024 chr2 | 212252325 | + | 0.933 | 0.944 | 0.923 |
| 93 | rs346703 | chr1 | 45326612 | + | 0.933 | 0.933 | 0.941 | 3132 | rs13388956 chr2 | 212988683 | + | 0.95 | 0.95 | 0.92 |
| 94 | rs346689 | chr1 | 45373876 | + | 0.933 | 0.933 | 0.946 | 3133 | rs12467575 chr2 | 216919462 | + | 0.942 | 0.917 | 0.937 |
| 95 | rs346718 | chr1 | 45383016 | + | 0.933 | 0.933 | 0.931 | 3134 | rs3276 chr2 | 217245243 | + | 0.933 | 0.927 | 0.941 |
| 96 | rs346720 | chr1 | 45390258 | + | 0.933 | 0.933 | 0.946 | 3135 | rs11679550 chr2 | 220360542 | + | 0.908 | 0.922 | 0.95 |
| 97 | rs346725 | chr1 | 45400250 | + | 0.933 | 0.933 | 0.941 | 3136 | rs10211177 chr2 | 220805575 | + | 0.935 | 0.913 | 0.938 |
| 98 | rs346711 | chr1 | 45402012 | + | 0.933 | 0.933 | 0.946 | 3137 | rs13387982 chr2 | 220900757 | + | 0.93 | 0.946 | 0.906 |
| 99 | rs1612575 | chr1 | 45409479 | + | 0.932 | 0.938 | 0.941 | 3138 | rs7590789 chr2 | 221476730 | + | 0.917 | 0.917 | 0.927 |
| 100 | rs17105333 | chr1 | 49207979 | + | 0.911 | 0.924 | 0.938 | 3139 | rs2946560 chr2 | 222157724 | + | 0.06 | 0.099 | 0.085 |
| 101 | rs17105335 | chr1 | 49208694 | + | 0.907 | 0.904 | 0.928 | 3140 | rs2946558 chr2 | 222159044 | + | 0.059 | 0.1 | 0.086 |
| 102 | rs17105418 | chr1 | 49258623 | + | 0.904 | 0.906 | 0.939 | 3141 | rs2710490 chr2 | 222164379 | + | 0.058 | 0.089 | 0.086 |
| 103 | rs171334 | chr1 | 49517287 | + | 0.942 | 0.915 | 0.941 | 3142 | rs16863738 chr2 | 230045043 | + | 0.95 | 0.922 | 0.901 |
| 104 | rs375899 | chr1 | 49954912 | + | 0.942 | 0.916 | 0.941 | 3143 | rs3768877 chr2 | 225355278 | + | 0.95 | 0.944 | 0.938 |

Fig. 9 Cont. 3

| | | | | | | | | | |
|---|---|---|---|---|---|---|---|---|---|
| 105 | rs11808682 | chr1 | 49566659 | + | 0.935 | 0.919 | 0.941 | 3144 rs3768879 chr2 | 225359663 + | 0.95 | 0.95 | 0.91 |
| 106 | rs11803165 | chr1 | 49727288 | + | 0.942 | 0.917 | 0.94 | 3145 rs1897227 chr2 | 226138301 + | 0.917 | 0.933 | 0.92 |
| 107 | rs1180330c | chr1 | 50163727 | + | 0.942 | 0.915 | 0.941 | 3146 rs1748247c chr2 | 226161645 + | 0.925 | 0.911 | 0.927 |
| 108 | rs6588391 | chr1 | 50897748 | + | 0.05 | 0.084 | 0.063 | 3147 rs16823282 chr2 | 227748664 + | 0.941 | 0.906 | 0.941 |
| 109 | rs6692340 | chr1 | 51052720 | + | 0.058 | 0.085 | 0.073 | 3148 rs1682328c chr2 | 227749591 + | 0.933 | 0.906 | 0.941 |
| 110 | rs4926884 | chr1 | 51472314 | + | 0.917 | 0.948 | 0.914 | 3149 rs10933172 chr2 | 227829391 + | 0.942 | 0.927 | 0.905 |
| 111 | rs17106481 | chr1 | 51521299 | + | 0.925 | 0.95 | 0.914 | 3150 rs11692634 chr2 | 227924237 + | 0.93 | 0.939 | 0.946 |
| 112 | rs12734773 | chr1 | 51527314 | + | 0.908 | 0.925 | 0.905 | 3151 rs1116885c chr2 | 228004388 + | 0.932 | 0.938 | 0.941 |
| 113 | rs1999900 | chr1 | 53610875 | + | 0.907 | 0.95 | 0.929 | 3152 rs10498222 chr2 | 228291147 + | 0.908 | 0.939 | 0.901 |
| 114 | rs17110221 | chr1 | 54518055 | + | 0.922 | 0.917 | 0.919 | 3153 rs7595272 chr2 | 228323996 + | 0.092 | 0.067 | 0.072 |
| 115 | rs17101268 | chr1 | 54557697 | + | 0.933 | 0.916 | 0.928 | 3154 rs6746278 chr2 | 228329802 + | 0.078 | 0.062 | 0.054 |
| 116 | rs12043386 | chr1 | 55725992 | + | 0.95 | 0.928 | 0.932 | 3155 rs16825801 chr2 | 228463310 + | 0.922 | 0.904 | 0.927 |
| 117 | rs1741633c | chr1 | 55742336 | + | 0.95 | 0.928 | 0.932 | 3156 rs16824157 chr2 | 228466824 + | 0.915 | 0.911 | 0.929 |
| 118 | rs1120661c | chr1 | 55763224 | + | 0.942 | 0.928 | 0.929 | 3157 rs16824173 chr2 | 228468580 + | 0.917 | 0.911 | 0.927 |
| 119 | rs7529841 | chr1 | 55768057 | + | 0.932 | 0.912 | 0.932 | 3158 rs16824203 chr2 | 228487463 + | 0.95 | 0.906 | 0.927 |
| 120 | rs1740113 | chr1 | 55777765 | + | 0.907 | 0.949 | 0.91 | 3159 rs16825564 chr2 | 229584711 + | 0.95 | 0.917 | 0.941 |
| 121 | rs12731002 | chr1 | 56547434 | + | 0.938 | 0.933 | 0.944 | 3160 rs7563172 chr2 | 229591741 + | 0.95 | 0.917 | 0.946 |
| 122 | rs10493215 | chr1 | 57352198 | + | 0.942 | 0.911 | 0.923 | 3161 rs10490035 chr2 | 229593322 + | 0.95 | 0.917 | 0.946 |
| 123 | rs1120071c | chr1 | 58495186 | + | 0.917 | 0.911 | 0.932 | 3162 rs7580152 chr2 | 229600992 + | 0.917 | 0.91 | 0.936 |
| 124 | rs583128 | chr1 | 58505609 | + | 0.058 | 0.084 | 0.068 | 3163 rs7580295 chr2 | 229601301 + | 0.917 | 0.911 | 0.932 |
| 125 | rs552352 | chr1 | 58505638 | + | 0.05 | 0.085 | 0.068 | 3164 rs3111779 chr2 | 231501259 + | 0.925 | 0.904 | 0.914 |
| 126 | rs545696 | chr1 | 585179911 | + | 0.075 | 0.089 | 0.068 | 3165 rs1190468 chr2 | 233062148 + | 0.942 | 0.921 | 0.938 |
| 127 | rs6668411 | chr1 | 58518904 | + | 0.075 | 0.089 | 0.073 | 3166 rs1190464 chr2 | 233065722 + | 0.933 | 0.943 | 0.945 |
| 128 | rs635459 | chr1 | 58520335 | + | 0.059 | 0.084 | 0.068 | 3167 rs13432541 chr2 | 233817248 + | 0.941 | 0.91 | 0.941 |
| 129 | rs650221 | chr1 | 60308952 | + | 0.904 | 0.941 | 0.907 | 3168 rs12472475 chr2 | 233850498 + | 0.933 | 0.917 | 0.92 |
| 130 | rs12126737 | chr1 | 61327215 | + | 0.924 | 0.915 | 0.928 | 3169 rs11679064 chr2 | 233866396 + | 0.925 | 0.938 | 0.95 |
| 131 | rs11207695 | chr1 | 61327515 | + | 0.949 | 0.91 | 0.932 | 3170 rs4663421 chr2 | 233866439 + | 0.932 | 0.91 | 0.941 |
| 132 | rs11207695 | chr1 | 61328582 | + | 0.915 | 0.911 | 0.909 | 3171 rs11563233 chr2 | 234407760 + | 0.908 | 0.916 | 0.932 |
| 133 | rs12409737 | chr1 | 61344550 | + | 0.95 | 0.91 | 0.911 | 3172 rs13024275 chr2 | 234409663 + | 0.924 | 0.917 | 0.92 |
| 134 | rs4915728 | chr1 | 61346790 | + | 0.083 | 0.057 | 0.071 | 3173 rs6727154 chr2 | 234453473 + | 0.908 | 0.938 | 0.925 |
| 135 | rs12142294 | chr1 | 61363205 | + | 0.949 | 0.91 | 0.932 | 3174 rs28948674 chr2 | 234572911 + | 0.917 | 0.921 | 0.946 |
| 136 | rs10789092 | chr1 | 61371710 | + | 0.95 | 0.911 | 0.928 | 3175 rs1786567c chr2 | 234584327 + | 0.908 | 0.921 | 0.937 |
| 137 | rs334732 | chr1 | 61372987 | + | 0.092 | 0.056 | 0.054 | 3176 rs11562948 chr2 | 234587909 + | 0.908 | 0.921 | 0.946 |
| 138 | rs4915729 | chr1 | 61375551 | + | 0.95 | 0.92 | 0.928 | 3177 rs7567269 chr2 | 234776701 + | 0.917 | 0.928 | 0.927 |
| 139 | rs4915730 | chr1 | 61375746 | + | 0.95 | 0.909 | 0.911 | 3178 rs13430135 chr2 | 235651511 + | 0.904 | 0.907 | 0.941 |

Fig. 9 Cont. 4

| | | | | | | | | | | | | |
|---|---|---|---|---|---|---|---|---|---|---|---|---|
| 140 | rs112077714 | chr1 | 61454062 | + | 0.933 | 0.95 | 0.905 | 3179 | rs7599884 | chr2 | 235812015 | + | 0.926 | 0.943 | 0.911 |
| 141 | rs7540527 | chr1 | 61478661 | + | 0.95 | 0.95 | 0.901 | 3180 | rs13420609 | chr2 | 235831667 | + | 0.92 | 0.938 | 0.909 |
| 142 | rs11808959 | chr1 | 64788987 | + | 0.933 | 0.906 | 0.905 | 3181 | rs12052405 | chr2 | 235832375 | + | 0.914 | 0.939 | 0.905 |
| 143 | rs11208469 | chr1 | 64815818 | + | 0.948 | 0.932 | 0.913 | 3182 | rs10186208 | chr2 | 235915635 | + | 0.95 | 0.928 | 0.946 |
| 144 | rs1469877 | chr1 | 64816186 | + | 0.925 | 0.917 | 0.901 | 3183 | rs13394581 | chr2 | 237472806 | + | 0.914 | 0.927 | 0.909 |
| 145 | rs2889130 | chr1 | 65407018 | + | 0.917 | 0.928 | 0.946 | 3184 | rs11682514 | chr2 | 238315502 | + | 0.92 | 0.939 | 0.945 |
| 146 | rs12133189 | chr1 | 66081021 | + | 0.917 | 0.911 | 0.902 | 3185 | rs11693524 | chr2 | 238315725 | + | 0.935 | 0.94 | 0.936 |
| 147 | rs11208759 | chr1 | 66081931 | + | 0.907 | 0.911 | 0.902 | 3186 | rs10180757 | chr2 | 238330704 | + | 0.942 | 0.933 | 0.946 |
| 148 | rs10493389 | chr1 | 66083453 | + | 0.917 | 0.911 | 0.901 | 3187 | rs6735617 | chr2 | 238349772 | + | 0.925 | 0.944 | 0.945 |
| 149 | rs10493391 | chr1 | 66087484 | + | 0.915 | 0.916 | 0.901 | 3188 | rs606531 | chr2 | 239807055 | + | 0.052 | 0.078 | 0.077 |
| 150 | rs4405117 | chr1 | 66088837 | + | 0.917 | 0.911 | 0.902 | 3189 | rs3771551 | chr2 | 241964309 | + | 0.942 | 0.91 | 0.923 |
| 151 | rs12130802 | chr1 | 66091284 | + | 0.93 | 0.92 | 0.917 | 3190 | rs3821280 | chr2 | 241983181 | + | 0.942 | 0.91 | 0.923 |
| 152 | rs11208761 | chr1 | 66093192 | + | 0.917 | 0.916 | 0.907 | 3191 | rs929408 | chr2 | 242032601 | + | 0.942 | 0.91 | 0.923 |
| 153 | rs12134350 | chr1 | 66103182 | + | 0.941 | 0.916 | 0.909 | 3192 | rs16843765 | chr2 | 242066926 | + | 0.925 | 0.917 | 0.946 |
| 154 | rs7537687 | chr1 | 66188503 | + | 0.917 | 0.949 | 0.932 | 3193 | rs2196239 | chr20 | 28655 | + | 0.093 | 0.05 | 0.095 |
| 155 | rs7553566 | chr1 | 66193619 | + | 0.942 | 0.944 | 0.932 | 3194 | rs6117860 | chr20 | 757837 | + | 0.908 | 0.903 | 0.928 |
| 156 | rs17417957 | chr1 | 66194475 | + | 0.942 | 0.95 | 0.932 | 3195 | rs6078493 | chr20 | 1225099 | + | 0.941 | 0.939 | 0.905 |
| 157 | rs2186125 | chr1 | 66201554 | + | 0.95 | 0.948 | 0.927 | 3196 | rs1610304 | chr20 | 2097912 | + | 0.085 | 0.056 | 0.081 |
| 158 | rs17418207 | chr1 | 66208848 | + | 0.942 | 0.95 | 0.932 | 3197 | rs1610309 | chr20 | 2101661 | + | 0.939 | 0.912 | 0.938 |
| 159 | rs17452121 | chr1 | 66209263 | + | 0.942 | 0.95 | 0.932 | 3198 | rs10854247 | chr20 | 2112954 | + | 0.921 | 0.906 | 0.941 |
| 160 | rs12085651 | chr1 | 66213141 | + | 0.944 | 0.946 | 0.914 | 3199 | rs10854248 | chr20 | 2113259 | + | 0.929 | 0.906 | 0.941 |
| 161 | rs9436757 | chr1 | 66301480 | + | 0.083 | 0.051 | 0.065 | 3200 | rs214808 | chr20 | 2242328 | + | 0.908 | 0.922 | 0.911 |
| 162 | rs17129313 | chr1 | 66908786 | + | 0.939 | 0.945 | 0.936 | 3201 | rs6049764 | chr20 | 2453645 | + | 0.915 | 0.939 | 0.902 |
| 163 | rs17129315 | chr1 | 66908863 | + | 0.915 | 0.935 | 0.936 | 3202 | rs17317517 | chr20 | 2463431 | + | 0.942 | 0.949 | 0.905 |
| 164 | rs17129318 | chr1 | 66908953 | + | 0.924 | 0.912 | 0.936 | 3203 | rs11697186 | chr20 | 3133123 | + | 0.929 | 0.909 | 0.928 |
| 165 | rs1579514 | chr1 | 68390825 | + | 0.907 | 0.937 | 0.941 | 3204 | rs4813706 | chr20 | 4556997 | + | 0.907 | 0.904 | 0.936 |
| 166 | rs1713076 | chr1 | 68677991 | + | 0.917 | 0.95 | 0.95 | 3205 | rs236111 | chr20 | 5881535 | + | 0.932 | 0.922 | 0.905 |
| 167 | rs1713077 | chr1 | 68673132 | + | 0.912 | 0.941 | 0.917 | 3206 | rs17804047 | chr20 | 6674127 | + | 0.942 | 0.916 | 0.941 |
| 168 | rs1713078 | chr1 | 68928375 | + | 0.911 | 0.948 | 0.928 | 3207 | rs714079 | chr20 | 6685384 | + | 0.908 | 0.906 | 0.919 |
| 169 | rs1327881 | chr1 | 70192249 | + | 0.908 | 0.911 | 0.919 | 3208 | rs17336019 | chr20 | 7980730 | + | 0.95 | 0.933 | 0.911 |
| 170 | rs12033628 | chr1 | 70194006 | + | 0.915 | 0.916 | 0.923 | 3209 | rs6118252 | chr20 | 8495496 | + | 0.942 | 0.95 | 0.927 |
| 171 | rs12030987 | chr1 | 70195184 | + | 0.908 | 0.911 | 0.911 | 3210 | rs16995928 | chr20 | 9374718 | + | 0.933 | 0.944 | 0.902 |
| 172 | rs12038059 | chr1 | 70195453 | + | 0.908 | 0.91 | 0.935 | 3211 | rs3746548 | chr20 | 9386172 | + | 0.925 | 0.944 | 0.914 |
| 173 | rs12038061 | chr1 | 70195489 | + | 0.908 | 0.911 | 0.902 | 3212 | rs725567 | chr20 | 9952874 | + | 0.1 | 0.1 | 0.063 |
| 174 | rs12045965 | chr1 | 70196250 | + | 0.908 | 0.909 | 0.911 | 3213 | rs2038991 | chr20 | 10867713 | + | 0.068 | 0.065 | 0.095 |

Fig. 9 Cont. 5

| | | | | | | | | | | |
|---|---|---|---|---|---|---|---|---|---|---|
| 175 | rs12032951 | chr1 | 70197030 | + | 0.942 | 0.911 | 0.923 | 3214 rs1327232 chr20 | 10906910 + | 0.933 | 0.944 | 0.901 |
| 176 | rs12036363 | chr1 | 70201961 | + | 0.942 | 0.911 | 0.909 | 3215 rs2104252 chr20 | 12286620 + | 0.933 | 0.926 | 0.914 |
| 177 | rs1203967C | chr1 | 70202378 | + | 0.942 | 0.91 | 0.911 | 3216 rs12480885 chr20 | 12562084 + | 0.925 | 0.911 | 0.931 |
| 178 | rs12040177 | chr1 | 70213150 | + | 0.942 | 0.91 | 0.923 | 3217 rs1048576C chr20 | 12597066 + | 0.942 | 0.911 | 0.946 |
| 179 | rs12043911 | chr1 | 70216624 | + | 0.942 | 0.911 | 0.907 | 3218 rs1156282 chr20 | 12826426 + | 0.908 | 0.922 | 0.941 |
| 180 | rs1015819 | chr1 | 70217673 | + | 0.942 | 0.911 | 0.919 | 3219 rs550630 chr20 | 12838927 + | 0.1 | 0.072 | 0.098 |
| 181 | rs12046022 | chr1 | 70218770 | + | 0.942 | 0.919 | 0.922 | 3220 rs552504 chr20 | 12839137 + | 0.1 | 0.072 | 0.098 |
| 182 | rs12028648 | chr1 | 70220634 | + | 0.942 | 0.911 | 0.907 | 3221 rs3898706 chr20 | 12849895 + | 0.092 | 0.094 | 0.072 |
| 183 | rs12030588 | chr1 | 70222572 | + | 0.949 | 0.916 | 0.926 | 3222 rs3903704 chr20 | 12917909 + | 0.942 | 0.91 | 0.919 |
| 184 | rs12048494 | chr1 | 70223037 | + | 0.941 | 0.911 | 0.911 | 3223 rs16993611 chr20 | 12927073 + | 0.925 | 0.922 | 0.901 |
| 185 | rs12023579 | chr1 | 70223052 | + | 0.941 | 0.92 | 0.918 | 3224 rs6105032 chr20 | 13004586 + | 0.942 | 0.943 | 0.917 |
| 186 | rs12030875 | chr1 | 70223451 | + | 0.933 | 0.908 | 0.919 | 3225 rs6109692 chr20 | 13019816 + | 0.942 | 0.95 | 0.914 |
| 187 | rs1203177C | chr1 | 70223937 | + | 0.942 | 0.911 | 0.911 | 3226 rs1699533C chr20 | 15053590 + | 0.949 | 0.916 | 0.938 |
| 188 | rs12024182 | chr1 | 70226774 | + | 0.942 | 0.908 | 0.911 | 3227 rs16997071 chr20 | 15997287 + | 0.948 | 0.933 | 0.945 |
| 189 | rs12024298 | chr1 | 70227165 | + | 0.941 | 0.911 | 0.911 | 3228 rs8118662 chr20 | 16262978 + | 0.93 | 0.938 | 0.905 |
| 190 | rs12033282 | chr1 | 70230569 | + | 0.942 | 0.911 | 0.902 | 3229 rs1361510 chr20 | 17209954 + | 0.083 | 0.061 | 0.089 |
| 191 | rs12027422 | chr1 | 70232242 | + | 0.942 | 0.92 | 0.919 | 3230 rs7263316 chr20 | 19632036 + | 0.95 | 0.906 | 0.932 |
| 192 | rs1202487C | chr1 | 70232717 | + | 0.942 | 0.911 | 0.911 | 3231 rs4450689 chr20 | 19682079 + | 0.902 | 0.944 | 0.918 |
| 193 | rs12035355 | chr1 | 70232826 | + | 0.942 | 0.911 | 0.922 | 3232 rs17370078 chr20 | 19688858 + | 0.925 | 0.939 | 0.914 |
| 194 | rs12040135 | chr1 | 70243270 | + | 0.908 | 0.908 | 0.917 | 3233 rs6035436 chr20 | 19705555 + | 0.924 | 0.944 | 0.926 |
| 195 | rs12040089 | chr1 | 70243521 | + | 0.908 | 0.911 | 0.913 | 3234 rs13037004 chr20 | 19872286 + | 0.933 | 0.904 | 0.911 |
| 196 | rs1203338C | chr1 | 70251812 | + | 0.908 | 0.911 | 0.911 | 3235 rs13039938 chr20 | 19876690 + | 0.925 | 0.91 | 0.91 |
| 197 | rs12036805 | chr1 | 70252048 | + | 0.947 | 0.91 | 0.907 | 3236 rs11699817 chr20 | 19878405 + | 0.918 | 0.91 | 0.911 |
| 198 | rs8179494 | chr1 | 70253700 | + | 0.915 | 0.91 | 0.919 | 3237 rs11699866 chr20 | 19878427 + | 0.925 | 0.91 | 0.927 |
| 199 | rs12035813 | chr1 | 70258204 | + | 0.908 | 0.91 | 0.911 | 3238 rs17718943 chr20 | 20753284 + | 0.917 | 0.933 | 0.932 |
| 200 | rs17131217 | chr1 | 70355538 | + | 0.927 | 0.903 | 0.901 | 3239 rs2424408 chr20 | 21872173 + | 0.908 | 0.944 | 0.907 |
| 201 | rs4649924 | chr1 | 70801011 | + | 0.1 | 0.067 | 0.054 | 3240 rs11696756 chr20 | 22930087 + | 0.905 | 0.917 | 0.937 |
| 202 | rs6662613 | chr1 | 71736865 | + | 0.925 | 0.933 | 0.917 | 3241 rs6048506 chr20 | 22944625 + | 0.907 | 0.927 | 0.909 |
| 203 | rs1486110 | chr1 | 72277933 | + | 0.921 | 0.93 | 0.929 | 3242 rs6132569 chr20 | 23075661 + | 0.942 | 0.911 | 0.918 |
| 204 | rs516569 | chr1 | 74554867 | + | 0.914 | 0.95 | 0.95 | 3243 rs6113974 chr20 | 23097749 + | 0.95 | 0.906 | 0.946 |
| 205 | rs1358375 | chr1 | 74604411 | + | 0.949 | 0.904 | 0.938 | 3244 rs6113975 chr20 | 23099564 + | 0.925 | 0.907 | 0.946 |
| 206 | rs3765667 | chr1 | 74608816 | + | 0.908 | 0.904 | 0.938 | 3245 rs6113976 chr20 | 23099730 + | 0.924 | 0.906 | 0.946 |
| 207 | rs10518473 | chr1 | 74924774 | + | 0.925 | 0.928 | 0.928 | 3246 rs6113978 chr20 | 23105247 + | 0.924 | 0.906 | 0.946 |
| 208 | rs11163464 | chr1 | 75028723 | + | 0.917 | 0.949 | 0.946 | 3247 rs6113979 chr20 | 23105275 + | 0.924 | 0.939 | 0.937 |
| 209 | rs12057582 | chr1 | 76385208 | + | 0.941 | 0.911 | 0.902 | 3248 rs6113980 chr20 | 23107340 + | 0.949 | 0.906 | 0.946 |

Fig. 9 Cont. 6

| | | | | | | | | | |
|---|---|---|---|---|---|---|---|---|---|
| 210 | rs10493588 | chr1 | 76465955 | + | 0.908 | 0.944 | 0.917 | 3249 | rs6113997 | chr20 | 23145219 | + | 0.917 | 0.906 | 0.945 |
| 211 | rs17098434 | chr1 | 76470700 | + | 0.907 | 0.944 | 0.932 | 3250 | rs6114008 | chr20 | 23174411 | + | 0.947 | 0.917 | 0.935 |
| 212 | rs17098457 | chr1 | 76474927 | + | 0.942 | 0.944 | 0.929 | 3251 | rs7261602 | chr20 | 23176455 | + | 0.949 | 0.917 | 0.946 |
| 213 | rs7541592 | chr1 | 76605599 | + | 0.917 | 0.95 | 0.946 | 3252 | rs7264999 | chr20 | 23621897 | + | 0.941 | 0.928 | 0.944 |
| 214 | rs478580 | chr1 | 76935626 | + | 0.058 | 0.073 | 0.098 | 3253 | rs7271100 | chr20 | 23624624 | + | 0.947 | 0.928 | 0.911 |
| 215 | rs479666 | chr1 | 76935799 | + | 0.058 | 0.073 | 0.1 | 3254 | rs6049057 | chr20 | 23673528 | + | 0.95 | 0.937 | 0.932 |
| 216 | rs1166702 | chr1 | 78168150 | + | 0.092 | 0.09 | 0.072 | 3255 | rs16986484 | chr20 | 24276308 | + | 0.925 | 0.904 | 0.928 |
| 217 | rs9659938 | chr1 | 78169214 | + | 0.092 | 0.09 | 0.073 | 3256 | rs6083497 | chr20 | 24278115 | + | 0.925 | 0.906 | 0.928 |
| 218 | rs750720 | chr1 | 78194373 | + | 0.904 | 0.91 | 0.928 | 3257 | rs6076223 | chr20 | 24281428 | + | 0.939 | 0.94 | 0.95 |
| 219 | rs6656888 | chr1 | 78253633 | + | 0.093 | 0.09 | 0.068 | 3258 | rs13038092 | chr20 | 25197734 | + | 0.933 | 0.939 | 0.937 |
| 220 | rs12750112 | chr1 | 79166714 | + | 0.943 | 0.926 | 0.915 | 3259 | rs11699811 | chr20 | 31007997 | + | 0.911 | 0.92 | 0.918 |
| 221 | rs17102848 | chr1 | 79384665 | + | 0.915 | 0.931 | 0.905 | 3260 | rs13042412 | chr20 | 31871245 | + | 0.917 | 0.916 | 0.937 |
| 222 | rs3887577 | chr1 | 81413918 | + | 0.942 | 0.921 | 0.919 | 3261 | rs17310467 | chr20 | 33009277 | + | 0.938 | 0.944 | 0.907 |
| 223 | rs12142340 | chr1 | 81466056 | + | 0.933 | 0.944 | 0.937 | 3262 | rs2889873 | chr20 | 33110502 | + | 0.946 | 0.943 | 0.913 |
| 224 | rs531940 | chr1 | 81830116 | + | 0.083 | 0.073 | 0.063 | 3263 | rs6060524 | chr20 | 33684569 | + | 0.941 | 0.928 | 0.909 |
| 225 | rs12090448 | chr1 | 81976150 | + | 0.942 | 0.92 | 0.928 | 3264 | rs12481545 | chr20 | 33871112 | + | 0.908 | 0.927 | 0.902 |
| 226 | rs12726534 | chr1 | 82005345 | + | 0.925 | 0.949 | 0.927 | 3265 | rs6060632 | chr20 | 33886015 | + | 0.912 | 0.931 | 0.914 |
| 227 | rs10518661 | chr1 | 82153968 | + | 0.933 | 0.907 | 0.95 | 3266 | rs7273668 | chr20 | 33906145 | + | 0.941 | 0.933 | 0.902 |
| 228 | rs17470239 | chr1 | 82164860 | + | 0.905 | 0.908 | 0.946 | 3267 | rs10485510 | chr20 | 33908578 | + | 0.942 | 0.93 | 0.902 |
| 229 | rs17431038 | chr1 | 82206814 | + | 0.95 | 0.911 | 0.937 | 3268 | rs4504072 | chr20 | 33912187 | + | 0.942 | 0.933 | 0.917 |
| 230 | rs1327029 | chr1 | 82241846 | + | 0.942 | 0.91 | 0.945 | 3269 | rs6060642 | chr20 | 33913254 | + | 0.942 | 0.933 | 0.926 |
| 231 | rs17472507 | chr1 | 82252036 | + | 0.95 | 0.939 | 0.927 | 3270 | rs7271036 | chr20 | 33930629 | + | 0.942 | 0.933 | 0.901 |
| 232 | rs17432307 | chr1 | 82253874 | + | 0.94 | 0.933 | 0.945 | 3271 | rs6060669 | chr20 | 33943971 | + | 0.949 | 0.933 | 0.908 |
| 233 | rs17108037 | chr1 | 82486885 | + | 0.925 | 0.911 | 0.905 | 3272 | rs6058354 | chr20 | 33954524 | + | 0.942 | 0.936 | 0.911 |
| 234 | rs17101506 | chr1 | 83460826 | + | 0.922 | 0.938 | 0.95 | 3273 | rs8125393 | chr20 | 33959576 | + | 0.942 | 0.932 | 0.918 |
| 235 | rs4907027 | chr1 | 83658978 | + | 0.95 | 0.949 | 0.901 | 3274 | rs6060676 | chr20 | 33961965 | + | 0.949 | 0.933 | 0.909 |
| 236 | rs12723316 | chr1 | 84086858 | + | 0.945 | 0.903 | 0.906 | 3275 | rs17431878 | chr20 | 33965521 | + | 0.941 | 0.933 | 0.901 |
| 237 | rs12090806 | chr1 | 85016996 | + | 0.908 | 0.95 | 0.902 | 3276 | rs6058364 | chr20 | 33971304 | + | 0.942 | 0.933 | 0.918 |
| 238 | rs12024356 | chr1 | 85054608 | + | 0.925 | 0.928 | 0.932 | 3277 | rs11167279 | chr20 | 33972521 | + | 0.942 | 0.933 | 0.926 |
| 239 | rs761602 | chr1 | 85623896 | + | 0.1 | 0.063 | 0.086 | 3278 | rs6060704 | chr20 | 33993684 | + | 0.942 | 0.936 | 0.911 |
| 240 | rs433577 | chr1 | 86573442 | + | 0.907 | 0.938 | 0.934 | 3279 | rs3829829 | chr20 | 34000574 | + | 0.942 | 0.933 | 0.901 |
| 241 | rs2791514 | chr1 | 86720757 | + | 0.933 | 0.933 | 0.905 | 3280 | rs11699815 | chr20 | 34006539 | + | 0.942 | 0.922 | 0.901 |
| 242 | rs4655977 | chr1 | 87858740 | + | 0.075 | 0.061 | 0.081 | 3281 | rs17432470 | chr20 | 34011177 | + | 0.942 | 0.922 | 0.911 |
| 243 | rs4656036 | chr1 | 88588238 | + | 0.05 | 0.05 | 0.09 | 3282 | rs11700299 | chr20 | 34012279 | + | 0.942 | 0.922 | 0.918 |
| 244 | rs693691 | chr1 | 88618082 | + | 0.092 | 0.061 | 0.071 | 3283 | rs11167280 | chr20 | 34023940 | + | 0.95 | 0.921 | 0.91 |

Fig. 9 Cont. 7

| | | | | | | | | | | | |
|---|---|---|---|---|---|---|---|---|---|---|---|
| 245 | rs6428513 | chr1 | 89555139 | + | 0.058 | 0.084 | 0.078 | 3284 | rs2425207 | chr20 | 34322457 | + | 0.925 | 0.927 | 0.946 |
| 246 | rs6428514 | chr1 | 89555628 | + | 0.06 | 0.096 | 0.099 | 3285 | rs16986831 | chr20 | 35685756 | + | 0.915 | 0.949 | 0.917 |
| 247 | rs10157553 | chr1 | 91230199 | + | 0.921 | 0.909 | 0.906 | 3286 | rs6096781 | chr20 | 35960629 | + | 0.925 | 0.939 | 0.937 |
| 248 | rs7366102 | chr1 | 94304850 | + | 0.082 | 0.075 | 0.062 | 3287 | rs805595 | chr20 | 36676378 | + | 0.051 | 0.056 | 0.08 |
| 249 | rs10874852 | chr1 | 94637080 | + | 0.925 | 0.92 | 0.927 | 3288 | rs6071860 | chr20 | 37971160 | + | 0.931 | 0.921 | 0.909 |
| 250 | rs12121091 | chr1 | 95122908 | + | 0.933 | 0.939 | 0.919 | 3289 | rs6129446 | chr20 | 37993827 | + | 0.949 | 0.927 | 0.911 |
| 251 | rs12144222 | chr1 | 95123808 | + | 0.942 | 0.939 | 0.943 | 3290 | rs8122168 | chr20 | 38537651 | + | 0.942 | 0.949 | 0.914 |
| 252 | rs2275612 | chr1 | 95140004 | + | 0.941 | 0.938 | 0.914 | 3291 | rs6029745 | chr20 | 39694083 | + | 0.918 | 0.92 | 0.92 |
| 253 | rs7527765 | chr1 | 95243399 | + | 0.917 | 0.933 | 0.936 | 3292 | rs6130130 | chr20 | 40500918 | + | 0.908 | 0.922 | 0.919 |
| 254 | rs13375091 | chr1 | 95807644 | + | 0.933 | 0.95 | 0.941 | 3293 | rs126180 | chr20 | 40541559 | + | 0.942 | 0.922 | 0.911 |
| 255 | rs12047025 | chr1 | 95857356 | + | 0.95 | 0.925 | 0.909 | 3294 | rs172981 | chr20 | 40543116 | + | 0.933 | 0.904 | 0.928 |
| 256 | rs11116583C | chr1 | 97522764 | + | 0.932 | 0.938 | 0.936 | 3295 | rs6030307 | chr20 | 40598420 | + | 0.1 | 0.072 | 0.098 |
| 257 | rs17117759 | chr1 | 98373206 | + | 0.908 | 0.944 | 0.911 | 3296 | rs10485697 | chr20 | 40875802 | + | 0.942 | 0.95 | 0.919 |
| 258 | rs11165958 | chr1 | 98375019 | + | 0.908 | 0.944 | 0.911 | 3297 | rs6030819 | chr20 | 41449455 | + | 0.058 | 0.051 | 0.092 |
| 259 | rs13343096 | chr1 | 98740848 | + | 0.925 | 0.928 | 0.92 | 3298 | rs800684 | chr20 | 43834811 | + | 0.093 | 0.05 | 0.099 |
| 260 | rs659030 | chr1 | 100140479 | + | 0.933 | 0.949 | 0.905 | 3299 | rs17446462 | chr20 | 43940068 | + | 0.917 | 0.917 | 0.946 |
| 261 | rs17121644 | chr1 | 100158018 | + | 0.933 | 0.95 | 0.932 | 3300 | rs4810475 | chr20 | 43942281 | + | 0.917 | 0.906 | 0.946 |
| 262 | rs510463 | chr1 | 100269679 | + | 0.909 | 0.941 | 0.928 | 3301 | rs1206805 | chr20 | 45102828 | + | 0.907 | 0.937 | 0.905 |
| 263 | rs17122019 | chr1 | 100417476 | + | 0.949 | 0.944 | 0.932 | 3302 | rs4809722 | chr20 | 46787415 | + | 0.95 | 0.904 | 0.923 |
| 264 | rs1335760 | chr1 | 100805620 | + | 0.911 | 0.92 | 0.923 | 3303 | rs6066837 | chr20 | 46790744 | + | 0.95 | 0.916 | 0.929 |
| 265 | rs2050476 | chr1 | 100820281 | + | 0.922 | 0.91 | 0.923 | 3304 | rs6095272 | chr20 | 46790924 | + | 0.949 | 0.935 | 0.936 |
| 266 | rs17409394 | chr1 | 101274896 | + | 0.925 | 0.95 | 0.911 | 3305 | rs6066838 | chr20 | 46793358 | + | 0.95 | 0.917 | 0.919 |
| 267 | rs11589468 | chr1 | 101282178 | + | 0.925 | 0.949 | 0.911 | 3306 | rs16999411C | chr20 | 46794237 | + | 0.95 | 0.917 | 0.92 |
| 268 | rs4409674 | chr1 | 101315977 | + | 0.908 | 0.949 | 0.901 | 3307 | rs6095276 | chr20 | 46796637 | + | 0.95 | 0.917 | 0.919 |
| 269 | rs12741164 | chr1 | 101324101 | + | 0.915 | 0.95 | 0.901 | 3308 | rs6095277 | chr20 | 46796664 | + | 0.95 | 0.917 | 0.919 |
| 270 | rs12031393 | chr1 | 101628581 | + | 0.933 | 0.927 | 0.946 | 3309 | rs6095278 | chr20 | 46796820 | + | 0.95 | 0.917 | 0.92 |
| 271 | rs11586094 | chr1 | 102000839 | + | 0.95 | 0.938 | 0.91 | 3310 | rs6090900 | chr20 | 46797527 | + | 0.948 | 0.915 | 0.92 |
| 272 | rs11587732 | chr1 | 102175333 | + | 0.95 | 0.926 | 0.937 | 3311 | rs6095280 | chr20 | 46798479 | + | 0.95 | 0.917 | 0.92 |
| 273 | rs17125793 | chr1 | 102177049 | + | 0.947 | 0.926 | 0.937 | 3312 | rs11086263 | chr20 | 46798692 | + | 0.95 | 0.917 | 0.927 |
| 274 | rs11585635 | chr1 | 102178555 | + | 0.95 | 0.928 | 0.911 | 3313 | rs6066843 | chr20 | 46806224 | + | 0.95 | 0.917 | 0.92 |
| 275 | rs1536565 | chr1 | 102193130 | + | 0.942 | 0.927 | 0.937 | 3314 | rs6095283 | chr20 | 46807789 | + | 0.942 | 0.916 | 0.92 |
| 276 | rs12726148 | chr1 | 102860260 | + | 0.943 | 0.908 | 0.932 | 3315 | rs6066844 | chr20 | 46808560 | + | 0.95 | 0.91 | 0.92 |
| 277 | rs12089733 | chr1 | 104603172 | + | 0.907 | 0.921 | 0.941 | 3316 | rs2426097 | chr20 | 46818874 | + | 0.95 | 0.904 | 0.91 |
| 278 | rs2173273 | chr1 | 104625153 | + | 0.925 | 0.92 | 0.918 | 3317 | rs3091540 | chr20 | 46824888 | + | 0.943 | 0.913 | 0.939 |
| 279 | rs9787106 | chr1 | 105279206 | + | 0.924 | 0.904 | 0.937 | 3318 | rs2426103 | chr20 | 46827897 | + | 0.95 | 0.911 | 0.923 |

Fig. 9 Cont. 8

| | | | | | | | | | | |
|---|---|---|---|---|---|---|---|---|---|---|
| 280 rs7554785 chr1 | 105294083 | + | 0.932 | 0.904 | 0.936 | 3319 rs12625166 chr20 | 47600610 | + | 0.95 | 0.944 | 0.95 |
| 281 rs12037787 chr1 | 106048987 | + | 0.902 | 0.932 | 0.925 | 3320 rs6063437 chr20 | 47863701 | + | 0.929 | 0.939 | 0.901 |
| 282 rs17016501 chr1 | 106239859 | + | 0.925 | 0.95 | 0.914 | 3321 rs17785895 chr20 | 47866466 | + | 0.948 | 0.933 | 0.91 |
| 283 rs6659454 chr1 | 106446021 | + | 0.902 | 0.944 | 0.925 | 3322 rs6067235 chr20 | 47868161 | + | 0.95 | 0.939 | 0.929 |
| 284 rs10494036 chr1 | 106455756 | + | 0.908 | 0.929 | 0.929 | 3323 rs719218 chr20 | 47868388 | + | 0.95 | 0.938 | 0.929 |
| 285 rs12049569 chr1 | 106485564 | + | 0.917 | 0.939 | 0.941 | 3324 rs6067237 chr20 | 47871636 | + | 0.95 | 0.932 | 0.933 |
| 286 rs12025896 chr1 | 106487694 | + | 0.917 | 0.939 | 0.936 | 3325 rs6067238 chr20 | 47871823 | + | 0.95 | 0.938 | 0.929 |
| 287 rs12023420 chr1 | 106487706 | + | 0.917 | 0.939 | 0.941 | 3326 rs17786027 chr20 | 47880003 | + | 0.908 | 0.95 | 0.905 |
| 288 rs12023510 chr1 | 106487913 | + | 0.917 | 0.939 | 0.938 | 3327 rs17786130 chr20 | 47902971 | + | 0.908 | 0.933 | 0.905 |
| 289 rs12035243 chr1 | 106487913 | + | 0.917 | 0.939 | 0.945 | 3328 rs559883 chr20 | 47909654 | + | 0.05 | 0.061 | 0.071 |
| 290 rs12026453 chr1 | 106496898 | + | 0.931 | 0.932 | 0.926 | 3329 rs645182 chr20 | 47912061 | + | 0.05 | 0.062 | 0.073 |
| 291 rs4378237 chr1 | 106497564 | + | 0.925 | 0.944 | 0.927 | 3330 rs517501 chr20 | 47915576 | + | 0.05 | 0.061 | 0.074 |
| 292 rs11184774 chr1 | 106498070 | + | 0.925 | 0.944 | 0.932 | 3331 rs662708 chr20 | 47917030 | + | 0.05 | 0.062 | 0.09 |
| 293 rs1450817 chr1 | 106499594 | + | 0.924 | 0.944 | 0.941 | 3332 rs652217 chr20 | 47921886 | + | 0.05 | 0.061 | 0.09 |
| 294 rs1450816 chr1 | 106499680 | + | 0.925 | 0.944 | 0.929 | 3333 rs666052 chr20 | 47922748 | + | 0.092 | 0.074 | 0.089 |
| 295 rs12404111 chr1 | 106499760 | + | 0.925 | 0.944 | 0.929 | 3334 rs6020156 chr20 | 48021040 | + | 0.058 | 0.062 | 0.071 |
| 296 rs17431569 chr1 | 106499962 | + | 0.925 | 0.944 | 0.92 | 3335 rs6125888 chr20 | 48133058 | + | 0.917 | 0.906 | 0.91 |
| 297 rs957318 chr1 | 106502616 | + | 0.924 | 0.95 | 0.935 | 3336 rs6125980 chr20 | 48402431 | + | 0.91 | 0.903 | 0.923 |
| 298 rs10159409 chr1 | 106507432 | + | 0.924 | 0.949 | 0.929 | 3337 rs11905232 chr20 | 48875047 | + | 0.907 | 0.93 | 0.914 |
| 299 rs8179427 chr1 | 106517479 | + | 0.908 | 0.95 | 0.922 | 3338 rs1883805 chr20 | 49247924 | + | 0.933 | 0.928 | 0.944 |
| 300 rs7531200 chr1 | 106523504 | + | 0.925 | 0.95 | 0.929 | 3339 rs228839 chr20 | 49504065 | + | 0.058 | 0.056 | 0.095 |
| 301 rs7542677 chr1 | 107663576 | + | 0.95 | 0.911 | 0.905 | 3340 rs16996300 chr20 | 49930384 | + | 0.917 | 0.939 | 0.91 |
| 302 rs12047673 chr1 | 111624696 | + | 0.917 | 0.921 | 0.901 | 3341 rs7261729 chr20 | 50149455 | + | 0.917 | 0.916 | 0.937 |
| 303 rs17722309 chr1 | 112241403 | + | 0.95 | 0.906 | 0.914 | 3342 rs4809898 chr20 | 50302723 | + | 0.942 | 0.928 | 0.902 |
| 304 rs2147597 chr1 | 113545090 | + | 0.933 | 0.91 | 0.917 | 3343 rs17806622 chr20 | 50782403 | + | 0.948 | 0.926 | 0.906 |
| 305 rs7555991 chr1 | 113556541 | + | 0.95 | 0.916 | 0.919 | 3344 rs4811393 chr20 | 50789927 | + | 0.933 | 0.928 | 0.914 |
| 306 rs17014869 chr1 | 113575504 | + | 0.933 | 0.944 | 0.937 | 3345 rs16997396 chr20 | 51041890 | + | 0.917 | 0.939 | 0.946 |
| 307 rs1767259 chr1 | 116212750 | + | 0.915 | 0.916 | 0.941 | 3346 rs6123242 chr20 | 51056288 | + | 0.917 | 0.933 | 0.946 |
| 308 rs2488452 chr1 | 116351419 | + | 0.1 | 0.075 | 0.064 | 3347 rs6126720 chr20 | 51062773 | + | 0.909 | 0.935 | 0.912 |
| 309 rs2995522 chr1 | 116360178 | + | 0.1 | 0.084 | 0.071 | 3348 rs16997425 chr20 | 51062836 | + | 0.908 | 0.933 | 0.92 |
| 310 rs4480343 chr1 | 117294535 | + | 0.917 | 0.916 | 0.909 | 3349 rs6022211 chr20 | 51063037 | + | 0.908 | 0.939 | 0.923 |
| 311 rs4659063 chr1 | 117384771 | + | 0.908 | 0.916 | 0.946 | 3350 rs6013600 chr20 | 51063832 | + | 0.917 | 0.933 | 0.923 |
| 312 rs3738413 chr1 | 117460875 | + | 0.917 | 0.904 | 0.917 | 3351 rs6013601 chr20 | 51064187 | + | 0.908 | 0.939 | 0.923 |
| 313 rs17037423 chr1 | 117923157 | + | 0.921 | 0.901 | 0.914 | 3352 rs1293422 chr20 | 51180329 | + | 0.933 | 0.939 | 0.901 |
| 314 rs2762733 chr1 | 143658125 | + | 0.915 | 0.944 | 0.909 | 3353 rs16997769 chr20 | 51277141 | + | 0.925 | 0.933 | 0.946 |

Fig. 9 Cont. 9

| | | | | | | | | | |
|---|---|---|---|---|---|---|---|---|---|
| 315 | rs4439318 | chr1 | 143658315 | + | 0.917 | 0.949 | 0.909 | 3354 | rs2762917 | chr20 | 52166451 | + | 0.931 | 0.903 | 0.901 |
| 316 | rs2798885 | chr1 | 143658336 | + | 0.915 | 0.943 | 0.909 | 3355 | rs2585444 | chr20 | 52168979 | + | 0.925 | 0.906 | 0.901 |
| 317 | rs2798883 | chr1 | 143658574 | + | 0.915 | 0.938 | 0.909 | 3356 | rs2762919 | chr20 | 52178149 | + | 0.95 | 0.933 | 0.913 |
| 318 | rs3766503 | chr1 | 145847510 | + | 0.939 | 0.921 | 0.95 | 3357 | rs11698394 | chr20 | 54593147 | + | 0.908 | 0.933 | 0.932 |
| 319 | rs2999714 | chr1 | 146227439 | + | 0.05 | 0.084 | 0.055 | 3358 | rs6069905 | chr20 | 54844347 | + | 0.05 | 0.067 | 0.05 |
| 320 | rs7515124 | chr1 | 146228507 | + | 0.933 | 0.924 | 0.945 | 3359 | rs13040929 | chr20 | 55159138 | + | 0.925 | 0.949 | 0.901 |
| 321 | rs11157681C | chr1 | 149978825 | + | 0.948 | 0.915 | 0.907 | 3360 | rs17451846 | chr20 | 56646763 | + | 0.941 | 0.944 | 0.918 |
| 322 | rs11588634 | chr1 | 150047310 | + | 0.95 | 0.906 | 0.911 | 3361 | rs6015477 | chr20 | 57357749 | + | 0.917 | 0.939 | 0.923 |
| 323 | rs11588258 | chr1 | 150047352 | + | 0.95 | 0.906 | 0.919 | 3362 | rs6070774 | chr20 | 57365418 | + | 0.917 | 0.938 | 0.946 |
| 324 | rs6587626 | chr1 | 150102061 | + | 0.076 | 0.078 | 0.072 | 3363 | rs6015499 | chr20 | 57476063 | + | 0.925 | 0.933 | 0.923 |
| 325 | rs1015803C | chr1 | 150109303 | + | 0.083 | 0.072 | 0.072 | 3364 | rs6026904 | chr20 | 57480872 | + | 0.942 | 0.939 | 0.928 |
| 326 | rs2338200 | chr1 | 150112193 | + | 0.085 | 0.072 | 0.08 | 3365 | rs6026910 | chr20 | 57486389 | + | 0.933 | 0.938 | 0.946 |
| 327 | rs4845385 | chr1 | 150113343 | + | 0.076 | 0.073 | 0.08 | 3366 | rs6071036 | chr20 | 57950070 | + | 0.93 | 0.943 | 0.949 |
| 328 | rs3014878 | chr1 | 151609802 | + | 0.93 | 0.945 | 0.909 | 3367 | rs10485469 | chr20 | 58743518 | + | 0.95 | 0.922 | 0.932 |
| 329 | rs2916217 | chr1 | 151619822 | + | 0.907 | 0.933 | 0.91 | 3368 | rs2224998 | chr20 | 58848565 | + | 0.942 | 0.933 | 0.946 |
| 330 | rs3006483 | chr1 | 151623137 | + | 0.905 | 0.933 | 0.91 | 3369 | rs1779395C | chr20 | 58855929 | + | 0.942 | 0.933 | 0.946 |
| 331 | rs11265303 | chr1 | 152456587 | + | 0.942 | 0.915 | 0.95 | 3370 | rs1555350 | chr20 | 59115193 | + | 0.092 | 0.073 | 0.099 |
| 332 | rs1126531C | chr1 | 152463750 | + | 0.941 | 0.915 | 0.95 | 3371 | rs2253331 | chr20 | 59585281 | + | 0.907 | 0.906 | 0.901 |
| 333 | rs4518899 | chr1 | 155645151 | + | 0.946 | 0.946 | 0.936 | 3372 | rs13040995 | chr20 | 59766333 | + | 0.907 | 0.939 | 0.902 |
| 334 | rs22109185 | chr1 | 155949980 | + | 0.914 | 0.949 | 0.945 | 3373 | rs6142680 | chr20 | 59770071 | + | 0.914 | 0.939 | 0.907 |
| 335 | rs1211834C | chr1 | 156270866 | + | 0.95 | 0.917 | 0.941 | 3374 | rs12481701 | chr20 | 60772300 | + | 0.932 | 0.944 | 0.901 |
| 336 | rs10430045 | chr1 | 156272925 | + | 0.95 | 0.916 | 0.941 | 3375 | rs6011853 | chr20 | 61582016 | + | 0.059 | 0.09 | 0.062 |
| 337 | rs1256189C | chr1 | 156289956 | + | 0.95 | 0.917 | 0.905 | 3376 | rs7264220 | chr20 | 62023877 | + | 0.946 | 0.935 | 0.937 |
| 338 | rs7367687 | chr1 | 156306501 | + | 0.942 | 0.917 | 0.91 | 3377 | rs3810500 | chr20 | 62037435 | + | 0.924 | 0.901 | 0.935 |
| 339 | rs857855 | chr1 | 157031189 | + | 0.95 | 0.927 | 0.901 | 3378 | rs2275293 | chr20 | 62046863 | + | 0.942 | 0.92 | 0.937 |
| 340 | rs12122337 | chr1 | 158153046 | + | 0.905 | 0.948 | 0.928 | 3379 | rs6062630 | chr20 | 62205589 | + | 0.058 | 0.05 | 0.09 |
| 341 | rs6664438 | chr1 | 158587983 | + | 0.942 | 0.938 | 0.95 | 3380 | rs1153360 | chr21 | 15014530 | + | 0.95 | 0.949 | 0.936 |
| 342 | rs6677637 | chr1 | 158591395 | + | 0.942 | 0.942 | 0.95 | 3381 | rs17275302 | chr21 | 15822777 | + | 0.941 | 0.943 | 0.918 |
| 343 | rs17370655 | chr1 | 158598705 | + | 0.917 | 0.95 | 0.938 | 3382 | rs4452233 | chr21 | 18634926 | + | 0.907 | 0.914 | 0.917 |
| 344 | rs4078017 | chr1 | 159340716 | + | 0.933 | 0.916 | 0.905 | 3383 | rs2226393 | chr21 | 19959392 | + | 0.942 | 0.944 | 0.911 |
| 345 | rs17389237 | chr1 | 159359385 | + | 0.933 | 0.917 | 0.905 | 3384 | rs2827053 | chr21 | 22104660 | + | 0.939 | 0.91 | 0.909 |
| 346 | rs1135783 | chr1 | 159360814 | + | 0.933 | 0.92 | 0.905 | 3385 | rs2827112 | chr21 | 22182219 | + | 0.949 | 0.904 | 0.937 |
| 347 | rs3813620 | chr1 | 159411629 | + | 0.933 | 0.916 | 0.91 | 3386 | rs10482924 | chr21 | 22476979 | + | 0.917 | 0.91 | 0.914 |
| 348 | rs1739257C | chr1 | 159414395 | + | 0.948 | 0.925 | 0.914 | 3387 | rs9977914 | chr21 | 23396316 | + | 0.915 | 0.938 | 0.938 |
| 349 | rs16832694 | chr1 | 159443430 | + | 0.948 | 0.904 | 0.914 | 3388 | rs11910207 | chr21 | 23590065 | + | 0.908 | 0.917 | 0.925 |

Fig. 9 Cont. 10

| | | | | | | | | | |
|---|---|---|---|---|---|---|---|---|---|
| 350 | rs11265585 | chr1 | 159550921 | + | 0.908 | 0.911 | 0.928 | 3389 rs2828033 chr21 | 23599808 + | 0.908 | 0.921 | 0.911 |
| 351 | rs12069801 | chr1 | 159558036 | + | 0.908 | 0.91 | 0.928 | 3390 rs2828038 chr21 | 23601114 + | 0.933 | 0.917 | 0.936 |
| 352 | rs12078337 | chr1 | 159936051 | + | 0.945 | 0.917 | 0.913 | 3391 rs2828046 chr21 | 23605602 + | 0.933 | 0.906 | 0.946 |
| 353 | rs10218544 | chr1 | 160247046 | + | 0.908 | 0.933 | 0.938 | 3392 rs2828056 chr21 | 23613848 + | 0.941 | 0.906 | 0.946 |
| 354 | rs12116496 | chr1 | 160908140 | + | 0.933 | 0.928 | 0.946 | 3393 rs2828059 chr21 | 23616521 + | 0.908 | 0.921 | 0.905 |
| 355 | rs4303055 | chr1 | 161144568 | + | 0.925 | 0.916 | 0.941 | 3394 rs1783252 chr21 | 23655627 + | 0.05 | 0.1 | 0.068 |
| 356 | rs12402634 | chr1 | 161305308 | + | 0.921 | 0.937 | 0.923 | 3395 rs1626981 chr21 | 23657394 + | 0.05 | 0.096 | 0.069 |
| 357 | rs16852295 | chr1 | 161538896 | + | 0.942 | 0.95 | 0.95 | 3396 rs2828494 chr21 | 24038001 + | 0.942 | 0.928 | 0.928 |
| 358 | rs2791136 | chr1 | 161737139 | + | 0.069 | 0.073 | 0.061 | 3397 rs2828504 chr21 | 24048326 + | 0.933 | 0.928 | 0.908 |
| 359 | rs6657417 | chr1 | 162764152 | + | 0.933 | 0.95 | 0.91 | 3398 rs2828512 chr21 | 24051399 + | 0.933 | 0.933 | 0.928 |
| 360 | rs6660684 | chr1 | 162770843 | + | 0.915 | 0.95 | 0.918 | 3399 rs16999090 chr21 | 24272159 + | 0.908 | 0.944 | 0.946 |
| 361 | rs16835287 | chr1 | 163070094 | + | 0.933 | 0.939 | 0.936 | 3400 rs10482958 chr21 | 25244692 + | 0.942 | 0.922 | 0.902 |
| 362 | rs12137588 | chr1 | 163085419 | + | 0.95 | 0.944 | 0.936 | 3401 rs13050339 chr21 | 25244872 + | 0.942 | 0.922 | 0.902 |
| 363 | rs12141982 | chr1 | 163092122 | + | 0.925 | 0.906 | 0.936 | 3402 rs1892677 chr21 | 25248432 + | 0.942 | 0.921 | 0.902 |
| 364 | rs16835577 | chr1 | 163095629 | + | 0.924 | 0.906 | 0.932 | 3403 rs2829588 chr21 | 25457324 + | 0.917 | 0.91 | 0.901 |
| 365 | rs10494426 | chr1 | 163101964 | + | 0.917 | 0.906 | 0.937 | 3404 rs467778 chr21 | 26528446 + | 0.908 | 0.916 | 0.923 |
| 366 | rs10800104 | chr1 | 163737250 | + | 0.933 | 0.949 | 0.932 | 3405 rs2830351 chr21 | 26969760 + | 0.95 | 0.906 | 0.911 |
| 367 | rs12084656 | chr1 | 163737938 | + | 0.917 | 0.949 | 0.927 | 3406 rs2830352 chr21 | 26969816 + | 0.95 | 0.906 | 0.911 |
| 368 | rs206236 | chr1 | 163776888 | + | 0.932 | 0.928 | 0.909 | 3407 rs2830353 chr21 | 26970630 + | 0.95 | 0.906 | 0.911 |
| 369 | rs12067790 | chr1 | 167210444 | + | 0.925 | 0.95 | 0.919 | 3408 rs2830354 chr21 | 26970884 + | 0.95 | 0.904 | 0.911 |
| 370 | rs1320975 | chr1 | 167289358 | + | 0.924 | 0.922 | 0.91 | 3409 rs2830361 chr21 | 26973119 + | 0.949 | 0.904 | 0.928 |
| 371 | rs10919045 | chr1 | 167296264 | + | 0.908 | 0.922 | 0.911 | 3410 rs2830362 chr21 | 26974372 + | 0.95 | 0.906 | 0.918 |
| 372 | rs12078922 | chr1 | 167297055 | + | 0.908 | 0.922 | 0.911 | 3411 rs2830363 chr21 | 26974585 + | 0.95 | 0.904 | 0.911 |
| 373 | rs10919053 | chr1 | 167309205 | + | 0.917 | 0.922 | 0.914 | 3412 rs2830364 chr21 | 26975423 + | 0.95 | 0.906 | 0.911 |
| 374 | rs10919203 | chr1 | 167880615 | + | 0.925 | 0.906 | 0.907 | 3413 rs8129757 chr21 | 26975940 + | 0.95 | 0.906 | 0.911 |
| 375 | rs12735952 | chr1 | 168646799 | + | 0.948 | 0.93 | 0.904 | 3414 rs2830368 chr21 | 26976255 + | 0.95 | 0.906 | 0.911 |
| 376 | rs7532920 | chr1 | 168845556 | + | 0.917 | 0.91 | 0.909 | 3415 rs7279338 chr21 | 26977890 + | 0.918 | 0.903 | 0.917 |
| 377 | rs2038111 | chr1 | 169110501 | + | 0.95 | 0.906 | 0.928 | 3416 rs2830374 chr21 | 26978042 + | 0.95 | 0.906 | 0.909 |
| 378 | rs12145527 | chr1 | 169908368 | + | 0.925 | 0.91 | 0.936 | 3417 rs2830376 chr21 | 26978402 + | 0.95 | 0.906 | 0.911 |
| 379 | rs12090953 | chr1 | 170286178 | + | 0.076 | 0.079 | 0.054 | 3418 rs2830390 chr21 | 26982482 + | 0.95 | 0.904 | 0.928 |
| 380 | rs4641331 | chr1 | 170306078 | + | 0.058 | 0.084 | 0.054 | 3419 rs4817135 chr21 | 26986868 + | 0.907 | 0.906 | 0.919 |
| 381 | rs4916242 | chr1 | 170326620 | + | 0.092 | 0.083 | 0.054 | 3420 rs2830411 chr21 | 26994110 + | 0.942 | 0.906 | 0.928 |
| 382 | rs4244191 | chr1 | 170334728 | + | 0.083 | 0.072 | 0.054 | 3421 rs2830413 chr21 | 26994635 + | 0.942 | 0.904 | 0.911 |
| 383 | rs2761186 | chr1 | 170365038 | + | 0.95 | 0.916 | 0.946 | 3422 rs8126661 chr21 | 26999793 + | 0.942 | 0.906 | 0.911 |
| 384 | rs1112468 | chr1 | 171520353 | + | 0.083 | 0.084 | 0.075 | 3423 rs2830415 chr21 | 27000030 + | 0.942 | 0.904 | 0.917 |

Fig. 9 Cont. 11

| | | | | | | | | | | |
|---|---|---|---|---|---|---|---|---|---|---|
| 385 | rs10158732 | chr1 | 173798810 | + | 0.933 | 0.904 | 0.904 | 3424 | rs2830418 | chr21 | 27001505 | + | 0.942 | 0.904 | 0.928 |
| 386 | rs10913005 | chr1 | 173801968 | + | 0.933 | 0.916 | 0.905 | 3425 | rs2830426 | chr21 | 27007113 | + | 0.95 | 0.904 | 0.911 |
| 387 | rs6693370 | chr1 | 173803567 | + | 0.917 | 0.904 | 0.905 | 3426 | rs2831237 | chr21 | 28191732 | + | 0.913 | 0.938 | 0.944 |
| 388 | rs173776176 | chr1 | 173876070 | + | 0.94 | 0.927 | 0.929 | 3427 | rs7275242 | chr21 | 28327012 | + | 0.905 | 0.922 | 0.929 |
| 389 | rs10913182 | chr1 | 174718843 | + | 0.95 | 0.95 | 0.914 | 3428 | rs10470156 | chr21 | 28414820 | + | 0.95 | 0.911 | 0.942 |
| 390 | rs10913183 | chr1 | 174719823 | + | 0.95 | 0.95 | 0.914 | 3429 | rs7278275 | chr21 | 28704502 | + | 0.92 | 0.918 | 0.928 |
| 391 | rs10913185 | chr1 | 174725602 | + | 0.95 | 0.95 | 0.914 | 3430 | rs4420778 | chr21 | 28737076 | + | 0.925 | 0.939 | 0.914 |
| 392 | rs6425387 | chr1 | 174732623 | + | 0.949 | 0.949 | 0.914 | 3431 | rs9974938 | chr21 | 28769700 | + | 0.941 | 0.948 | 0.927 |
| 393 | rs6425388 | chr1 | 174732788 | + | 0.95 | 0.949 | 0.929 | 3432 | rs2833286 | chr21 | 31421448 | + | 0.908 | 0.91 | 0.938 |
| 394 | rs6689487 | chr1 | 174733116 | + | 0.95 | 0.95 | 0.914 | 3433 | rs9967977 | chr21 | 33058897 | + | 0.908 | 0.91 | 0.905 |
| 395 | rs12084712 | chr1 | 174749724 | + | 0.95 | 0.949 | 0.914 | 3434 | rs11702471 | chr21 | 34656717 | + | 0.092 | 0.056 | 0.08 |
| 396 | rs104894735 | chr1 | 174754323 | + | 0.95 | 0.944 | 0.929 | 3435 | rs2834601 | chr21 | 35010924 | + | 0.908 | 0.938 | 0.931 |
| 397 | rs12133739 | chr1 | 174871187 | + | 0.95 | 0.949 | 0.932 | 3436 | rs9978027 | chr21 | 35257275 | + | 0.942 | 0.928 | 0.946 |
| 398 | rs12144032 | chr1 | 174871501 | + | 0.949 | 0.95 | 0.932 | 3437 | rs6517272 | chr21 | 35357238 | + | 0.075 | 0.056 | 0.071 |
| 399 | rs12118152 | chr1 | 174901548 | + | 0.942 | 0.95 | 0.911 | 3438 | rs2249858 | chr21 | 35380512 | + | 0.092 | 0.09 | 0.073 |
| 400 | rs12121635 | chr1 | 174909321 | + | 0.943 | 0.928 | 0.915 | 3439 | rs2834755 | chr21 | 35385708 | + | 0.092 | 0.073 | 0.072 |
| 401 | rs12120886 | chr1 | 174909418 | + | 0.941 | 0.947 | 0.911 | 3440 | rs7279722 | chr21 | 35387848 | + | 0.083 | 0.083 | 0.082 |
| 402 | rs12128112 | chr1 | 174926556 | + | 0.941 | 0.944 | 0.932 | 3441 | rs17192026 | chr21 | 35498595 | + | 0.905 | 0.914 | 0.934 |
| 403 | rs12060149 | chr1 | 175360815 | + | 0.925 | 0.944 | 0.901 | 3442 | rs17192041 | chr21 | 35502110 | + | 0.908 | 0.906 | 0.911 |
| 404 | rs10798497 | chr1 | 175363180 | + | 0.925 | 0.95 | 0.901 | 3443 | rs2836101 | chr21 | 38288396 | + | 0.908 | 0.938 | 0.932 |
| 405 | rs10913603 | chr1 | 176912183 | + | 0.907 | 0.917 | 0.928 | 3444 | rs11702396 | chr21 | 38670394 | + | 0.907 | 0.95 | 0.919 |
| 406 | rs1999184 | chr1 | 176940266 | + | 0.908 | 0.942 | 0.937 | 3445 | rs2211871 | chr21 | 38744520 | + | 0.083 | 0.062 | 0.059 |
| 407 | rs75519811 | chr1 | 176988428 | + | 0.908 | 0.903 | 0.928 | 3446 | rs17826655 | chr21 | 40149332 | + | 0.933 | 0.906 | 0.923 |
| 408 | rs3818587 | chr1 | 177787045 | + | 0.904 | 0.948 | 0.91 | 3447 | rs16999959 | chr21 | 40832814 | + | 0.917 | 0.931 | 0.95 |
| 409 | rs12041396 | chr1 | 177853407 | + | 0.942 | 0.928 | 0.908 | 3448 | rs12152034 | chr21 | 40990729 | + | 0.933 | 0.932 | 0.909 |
| 410 | rs12025031 | chr1 | 177855868 | + | 0.941 | 0.924 | 0.905 | 3449 | rs718043 | chr21 | 41017618 | + | 0.933 | 0.938 | 0.946 |
| 411 | rs10913839 | chr1 | 177859789 | + | 0.942 | 0.927 | 0.905 | 3450 | rs17000253 | chr21 | 41017802 | + | 0.933 | 0.939 | 0.929 |
| 412 | rs6704505 | chr1 | 177866624 | + | 0.942 | 0.927 | 0.905 | 3451 | rs17000254 | chr21 | 41018129 | + | 0.933 | 0.939 | 0.929 |
| 413 | rs11448814 | chr1 | 178089737 | + | 0.922 | 0.914 | 0.907 | 3452 | rs9980087 | chr21 | 44936883 | + | 0.925 | 0.935 | 0.901 |
| 414 | rs1758143 | chr1 | 178116475 | + | 0.082 | 0.077 | 0.094 | 3453 | rs9978932 | chr21 | 44948974 | + | 0.921 | 0.944 | 0.927 |
| 415 | rs1290274 | chr1 | 178128418 | + | 0.07 | 0.071 | 0.082 | 3454 | rs9977407 | chr21 | 44996653 | + | 0.925 | 0.921 | 0.914 |
| 416 | rs12140076 | chr1 | 178503147 | + | 0.942 | 0.927 | 0.938 | 3455 | rs9979409 | chr21 | 44996785 | + | 0.94 | 0.924 | 0.915 |
| 417 | rs173721421 | chr1 | 178505065 | + | 0.917 | 0.909 | 0.914 | 3456 | rs690279 | chr21 | 44997657 | + | 0.925 | 0.916 | 0.941 |
| 418 | rs2278944 | chr1 | 178506341 | + | 0.925 | 0.921 | 0.928 | 3457 | rs2838711 | chr21 | 45101264 | + | 0.917 | 0.95 | 0.91 |
| 419 | rs1575710 | chr1 | 178547601 | + | 0.933 | 0.911 | 0.922 | 3458 | rs2838712 | chr21 | 45102204 | + | 0.917 | 0.944 | 0.905 |

Fig. 9 Cont. 12

| | | | | | | | | | | | |
|---|---|---|---|---|---|---|---|---|---|---|---|
| 420 | rs7514062 | chr1 | 178797705 | + | 0.092 | 0.084 | 0.056 | 3459 | rs2838713 | chr21 | 45102396 | + | 0.917 | 0.949 | 0.91 |
| 421 | rs4652610 | chr1 | 179456805 | + | 0.95 | 0.92 | 0.92 | 3460 | rs9637167 | chr21 | 45584314 | + | 0.91 | 0.935 | 0.918 |
| 422 | rs17375436 | chr1 | 179475312 | + | 0.95 | 0.92 | 0.92 | 3461 | rs6518229 | chr21 | 45599929 | + | 0.058 | 0.056 | 0.095 |
| 423 | rs4651098 | chr1 | 179480020 | + | 0.95 | 0.92 | 0.943 | 3462 | rs2183593 | chr21 | 45616530 | + | 0.092 | 0.073 | 0.095 |
| 424 | rs4652623 | chr1 | 179480335 | + | 0.95 | 0.906 | 0.927 | 3463 | rs4818774 | chr21 | 45631718 | + | 0.062 | 0.06 | 0.07 |
| 425 | rs4652624 | chr1 | 179481197 | + | 0.949 | 0.906 | 0.918 | 3464 | rs7276092 | chr21 | 46888163 | + | 0.074 | 0.094 | 0.085 |
| 426 | rs4651099 | chr1 | 179494284 | + | 0.917 | 0.906 | 0.909 | 3465 | rs11700505 | chr21 | 46910997 | + | 0.07 | 0.08 | 0.067 |
| 427 | rs4652634 | chr1 | 179496234 | + | 0.917 | 0.906 | 0.92 | 3466 | rs8131044 | chr21 | 46912274 | + | 0.059 | 0.077 | 0.082 |
| 428 | rs17375519 | chr1 | 179499648 | + | 0.95 | 0.928 | 0.914 | 3467 | rs5746965 | chr22 | 15881980 | + | 0.904 | 0.92 | 0.945 |
| 429 | rs4652645 | chr1 | 179524375 | + | 0.95 | 0.927 | 0.914 | 3468 | rs366148 | chr22 | 18421609 | + | 0.908 | 0.933 | 0.935 |
| 430 | rs6698747 | chr1 | 179526821 | + | 0.942 | 0.92 | 0.926 | 3469 | rs446059 | chr22 | 18439763 | + | 0.924 | 0.933 | 0.937 |
| 431 | rs6674511 | chr1 | 179526838 | + | 0.95 | 0.928 | 0.909 | 3470 | rs2286931 | chr22 | 18508881 | + | 0.95 | 0.933 | 0.946 |
| 432 | rs17375625 | chr1 | 179529448 | + | 0.949 | 0.933 | 0.927 | 3471 | rs5760515 | chr22 | 19071060 | + | 0.922 | 0.926 | 0.917 |
| 433 | rs471910 | chr1 | 180741327 | + | 0.052 | 0.069 | 0.095 | 3472 | rs6004060 | chr22 | 19410404 | + | 0.95 | 0.938 | 0.932 |
| 434 | rs16860810 | chr1 | 181566597 | + | 0.942 | 0.939 | 0.919 | 3473 | rs5760338 | chr22 | 19432393 | + | 0.95 | 0.939 | 0.938 |
| 435 | rs120343392 | chr1 | 181570066 | + | 0.949 | 0.944 | 0.944 | 3474 | rs5760343 | chr22 | 19432830 | + | 0.95 | 0.938 | 0.945 |
| 436 | rs12032353 | chr1 | 181662689 | + | 0.942 | 0.939 | 0.938 | 3475 | rs16988764 | chr22 | 19435255 | + | 0.946 | 0.938 | 0.925 |
| 437 | rs12123812 | chr1 | 189219800 | + | 0.942 | 0.922 | 0.946 | 3476 | rs12162703 | chr22 | 19576902 | + | 0.933 | 0.939 | 0.932 |
| 438 | rs12139999 | chr1 | 189332590 | + | 0.941 | 0.938 | 0.941 | 3477 | rs5761433 | chr22 | 19244414 | + | 0.942 | 0.938 | 0.932 |
| 439 | rs1340203 | chr1 | 190129174 | + | 0.908 | 0.922 | 0.914 | 3478 | rs9610631 | chr22 | 20611243 | + | 0.942 | 0.933 | 0.907 |
| 440 | rs17586172 | chr1 | 191021919 | + | 0.938 | 0.926 | 0.936 | 3479 | rs5759371 | chr22 | 21366000 | + | 0.935 | 0.927 | 0.943 |
| 441 | rs17646713 | chr1 | 191022617 | + | 0.95 | 0.922 | 0.932 | 3480 | rs5759373 | chr22 | 21366105 | + | 0.93 | 0.928 | 0.95 |
| 442 | rs17646785 | chr1 | 191023029 | + | 0.95 | 0.926 | 0.938 | 3481 | rs9608043 | chr22 | 21393840 | + | 0.924 | 0.943 | 0.933 |
| 443 | rs17550167 | chr1 | 192306641 | + | 0.95 | 0.944 | 0.945 | 3482 | rs2298375 | chr22 | 22436448 | + | 0.941 | 0.927 | 0.927 |
| 444 | rs17615584 | chr1 | 192310863 | + | 0.917 | 0.944 | 0.946 | 3483 | rs9608196 | chr22 | 22493081 | + | 0.917 | 0.933 | 0.905 |
| 445 | rs17615608 | chr1 | 192310961 | + | 0.917 | 0.944 | 0.946 | 3484 | rs9608199 | chr22 | 22496230 | + | 0.904 | 0.938 | 0.907 |
| 446 | rs17615887 | chr1 | 192315739 | + | 0.917 | 0.933 | 0.946 | 3485 | rs9612481 | chr22 | 22504510 | + | 0.949 | 0.942 | 0.91 |
| 447 | rs10494695 | chr1 | 192320706 | + | 0.917 | 0.933 | 0.95 | 3486 | rs16978651 | chr22 | 23275361 | + | 0.918 | 0.943 | 0.929 |
| 448 | rs17551005 | chr1 | 192324383 | + | 0.917 | 0.944 | 0.946 | 3487 | rs12168578 | chr22 | 23903431 | + | 0.907 | 0.911 | 0.914 |
| 449 | rs11589052 | chr1 | 192324896 | + | 0.917 | 0.944 | 0.946 | 3488 | rs16980979 | chr22 | 24614669 | + | 0.924 | 0.947 | 0.917 |
| 450 | rs17615638 | chr1 | 192327708 | + | 0.917 | 0.944 | 0.946 | 3489 | rs12485050 | chr22 | 24721634 | + | 0.942 | 0.917 | 0.926 |
| 451 | rs17551424 | chr1 | 192329982 | + | 0.907 | 0.948 | 0.945 | 3490 | rs9608466 | chr22 | 24891478 | + | 0.917 | 0.916 | 0.923 |
| 452 | rs7528590 | chr1 | 193065351 | + | 0.917 | 0.917 | 0.938 | 3491 | rs2049988 | chr22 | 24892140 | + | 0.925 | 0.938 | 0.923 |
| 453 | rs6688883 | chr1 | 193092365 | + | 0.917 | 0.917 | 0.941 | 3492 | rs11913750 | chr22 | 25171390 | + | 0.925 | 0.917 | 0.95 |
| 454 | rs6658670 | chr1 | 194420284 | + | 0.069 | 0.078 | 0.055 | 3493 | rs16982107 | chr22 | 25171643 | + | 0.925 | 0.917 | 0.946 |

Fig. 9 Cont. 13

| | | | | | | | | | | |
|---|---|---|---|---|---|---|---|---|---|---|
| 455 | rs6658892 | chr1 | 194420699 | + | 0.071 | 0.074 | 0.055 | 3494 | rs3213582 | chr22 | 25172061 | + | 0.925 | 0.926 | 0.95 |
| 456 | rs12142118 | chr1 | 196336854 | + | 0.933 | 0.95 | 0.95 | 3495 | rs9608549 | chr22 | 25713140 | + | 0.902 | 0.941 | 0.928 |
| 457 | rs10494777 | chr1 | 196756080 | + | 0.925 | 0.921 | 0.927 | 3496 | rs12170239 | chr22 | 25892201 | + | 0.917 | 0.906 | 0.905 |
| 458 | rs16845389 | chr1 | 197901744 | + | 0.948 | 0.911 | 0.927 | 3497 | rs6005451 | chr22 | 26182183 | + | 0.933 | 0.91 | 0.901 |
| 459 | rs17653369 | chr1 | 197926402 | + | 0.941 | 0.938 | 0.932 | 3498 | rs16984925 | chr22 | 26244576 | + | 0.933 | 0.911 | 0.929 |
| 460 | rs12074649 | chr1 | 198105670 | + | 0.92 | 0.939 | 0.95 | 3499 | rs6005498 | chr22 | 26250961 | + | 0.925 | 0.933 | 0.919 |
| 461 | rs12404756 | chr1 | 198989600 | + | 0.942 | 0.904 | 0.926 | 3500 | rs12484213 | chr22 | 26330527 | + | 0.915 | 0.927 | 0.905 |
| 462 | rs6697899 | chr1 | 199058577 | + | 0.942 | 0.904 | 0.914 | 3501 | rs5997363 | chr22 | 27124069 | + | 0.933 | 0.933 | 0.95 |
| 463 | rs16847242 | chr1 | 199063734 | + | 0.942 | 0.906 | 0.914 | 3502 | rs1076807 | chr22 | 27432335 | + | 0.933 | 0.906 | 0.938 |
| 464 | rs831749 | chr1 | 199408406 | + | 0.917 | 0.933 | 0.946 | 3503 | rs3788418 | chr22 | 28610162 | + | 0.914 | 0.902 | 0.91 |
| 465 | rs831773 | chr1 | 199412273 | + | 0.932 | 0.928 | 0.946 | 3504 | rs737905 | chr22 | 28697490 | + | 0.917 | 0.904 | 0.929 |
| 466 | rs831763 | chr1 | 199417622 | + | 0.942 | 0.926 | 0.946 | 3505 | rs7285242 | chr22 | 30993153 | + | 0.925 | 0.949 | 0.937 |
| 467 | rs831759 | chr1 | 199420934 | + | 0.933 | 0.927 | 0.946 | 3506 | rs12167840 | chr22 | 31219558 | + | 0.942 | 0.917 | 0.914 |
| 468 | rs831752 | chr1 | 199423769 | + | 0.933 | 0.931 | 0.928 | 3507 | rs756481 | chr22 | 31435227 | + | 0.917 | 0.949 | 0.937 |
| 469 | rs12564284 | chr1 | 199586805 | + | 0.941 | 0.928 | 0.905 | 3508 | rs5749498 | chr22 | 31436947 | + | 0.925 | 0.95 | 0.937 |
| 470 | rs17426255 | chr1 | 199588399 | + | 0.939 | 0.935 | 0.907 | 3509 | rs130293 | chr22 | 31551939 | + | 0.092 | 0.09 | 0.086 |
| 471 | rs2275860 | chr1 | 199600326 | + | 0.933 | 0.928 | 0.905 | 3510 | rs11912964 | chr22 | 32512108 | + | 0.95 | 0.916 | 0.937 |
| 472 | rs4414100 | chr1 | 202267806 | + | 0.074 | 0.078 | 0.066 | 3511 | rs11915257C | chr22 | 32519746 | + | 0.95 | 0.917 | 0.927 |
| 473 | rs12125386 | chr1 | 203873453 | + | 0.924 | 0.938 | 0.911 | 3512 | rs17808744 | chr22 | 32553033 | + | 0.933 | 0.922 | 0.929 |
| 474 | rs12126801 | chr1 | 203882777 | + | 0.933 | 0.949 | 0.926 | 3513 | rs5995126 | chr22 | 34327222 | + | 0.939 | 0.949 | 0.934 |
| 475 | rs12565564 | chr1 | 203887792 | + | 0.933 | 0.938 | 0.936 | 3514 | rs1056680 | chr22 | 34332999 | + | 0.917 | 0.95 | 0.91 |
| 476 | rs7366689 | chr1 | 204154895 | + | 0.092 | 0.089 | 0.086 | 3515 | rs5755950 | chr22 | 34513934 | + | 0.942 | 0.944 | 0.919 |
| 477 | rs12759719 | chr1 | 204157302 | + | 0.075 | 0.089 | 0.09 | 3516 | rs5750208 | chr22 | 34708397 | + | 0.908 | 0.939 | 0.938 |
| 478 | rs2251465 | chr1 | 206000621 | + | 0.95 | 0.922 | 0.946 | 3517 | rs2413458 | chr22 | 35971187 | + | 0.941 | 0.921 | 0.937 |
| 479 | rs10494912 | chr1 | 207180845 | + | 0.942 | 0.933 | 0.905 | 3518 | rs12484031 | chr22 | 35979216 | + | 0.941 | 0.915 | 0.917 |
| 480 | rs4430327 | chr1 | 208566017 | + | 0.915 | 0.95 | 0.928 | 3519 | rs11089873 | chr22 | 36944879 | + | 0.057 | 0.052 | 0.086 |
| 481 | rs12120216 | chr1 | 208836218 | + | 0.931 | 0.911 | 0.929 | 3520 | rs12158968 | chr22 | 37714298 | + | 0.924 | 0.939 | 0.92 |
| 482 | rs12121937 | chr1 | 210166731 | + | 0.933 | 0.95 | 0.939 | 3521 | rs9941927 | chr22 | 38539121 | + | 0.933 | 0.949 | 0.914 |
| 483 | rs11119872 | chr1 | 210422934 | + | 0.908 | 0.917 | 0.917 | 3522 | rs8137779 | chr22 | 38542305 | + | 0.95 | 0.949 | 0.903 |
| 484 | rs12086905 | chr1 | 210424732 | + | 0.908 | 0.917 | 0.923 | 3523 | rs7287193 | chr22 | 38556737 | + | 0.95 | 0.949 | 0.91 |
| 485 | rs6656122 | chr1 | 212120324 | + | 0.926 | 0.916 | 0.941 | 3524 | rs10427892 | chr22 | 38570749 | + | 0.917 | 0.95 | 0.914 |
| 486 | rs11120227 | chr1 | 212154441 | + | 0.907 | 0.928 | 0.946 | 3525 | rs4822056 | chr22 | 40549800 | + | 0.942 | 0.944 | 0.936 |
| 487 | rs12407415 | chr1 | 212508277 | + | 0.942 | 0.922 | 0.909 | 3526 | rs139105 | chr22 | 42900679 | + | 0.947 | 0.941 | 0.917 |
| 488 | rs12406647 | chr1 | 212576593 | + | 0.932 | 0.944 | 0.941 | 3527 | rs7292668 | chr22 | 43140684 | + | 0.925 | 0.933 | 0.905 |
| 489 | rs17732074 | chr1 | 212665147 | + | 0.95 | 0.95 | 0.901 | 3528 | rs5765426 | chr22 | 44271320 | + | 0.94 | 0.937 | 0.95 |

Fig. 9  Cont. 14

| | | | | | | | | | | | | | |
|---|---|---|---|---|---|---|---|---|---|---|---|---|---|
| 490 | rs12043579 | chr1 | 215010642 | + | 0.915 | 0.949 | 0.944 | 3529 | rs17654028 | chr22 | 44614169 | + | 0.95 | 0.928 | 0.902 |

| # | SNP | chr | position | str | v1 | v2 | v3 | # | SNP | chr | position | str | v1 | v2 | v3 |
|---|---|---|---|---|---|---|---|---|---|---|---|---|---|---|---|
| 490 | rs12043579 | chr1 | 215010642 | + | 0.915 | 0.949 | 0.944 | 3529 | rs17654028 | chr22 | 44614169 | + | 0.95 | 0.928 | 0.902 |
| 491 | rs9970445 | chr1 | 215017127 | + | 0.917 | 0.95 | 0.95 | 3530 | rs2097429 | chr22 | 44635144 | + | 0.917 | 0.927 | 0.923 |
| 492 | rs10495035 | chr1 | 215024225 | + | 0.933 | 0.949 | 0.938 | 3531 | rs3788688 | chr22 | 45224264 | + | 0.933 | 0.906 | 0.946 |
| 493 | rs12048695 | chr1 | 215029516 | + | 0.933 | 0.95 | 0.95 | 3532 | rs5767668 | chr22 | 46086408 | + | 0.931 | 0.938 | 0.905 |
| 494 | rs17698444 | chr1 | 215483178 | + | 0.942 | 0.95 | 0.92 | 3533 | rs13056034 | chr22 | 46362768 | + | 0.941 | 0.921 | 0.904 |
| 495 | rs1466 | chr1 | 215502804 | + | 0.933 | 0.911 | 0.911 | 3534 | rs9615633 | chr22 | 46558713 | + | 0.908 | 0.915 | 0.938 |
| 496 | rs6674869 | chr1 | 215503999 | + | 0.925 | 0.911 | 0.911 | 3535 | rs9615638 | chr22 | 46565874 | + | 0.95 | 0.944 | 0.945 |
| 497 | rs6692462 | chr1 | 215504086 | + | 0.925 | 0.911 | 0.911 | 3536 | rs720441 | chr22 | 46569391 | + | 0.933 | 0.938 | 0.928 |
| 498 | rs7541360 | chr1 | 215504961 | + | 0.925 | 0.911 | 0.911 | 3537 | rs5768106 | chr22 | 46654442 | + | 0.95 | 0.928 | 0.946 |
| 499 | rs4335431 | chr1 | 216624232 | + | 0.941 | 0.903 | 0.905 | 3538 | rs738728 | chr22 | 46664655 | + | 0.95 | 0.921 | 0.946 |
| 500 | rs10495106 | chr1 | 217017809 | + | 0.925 | 0.916 | 0.95 | 3539 | rs5768239 | chr22 | 46763888 | + | 0.942 | 0.944 | 0.932 |
| 501 | rs11585361 | chr1 | 217126283 | + | 0.95 | 0.922 | 0.945 | 3540 | rs5768251 | chr22 | 46769328 | + | 0.942 | 0.944 | 0.938 |
| 502 | rs17516447 | chr1 | 217132795 | + | 0.95 | 0.933 | 0.938 | 3541 | rs135284 | chr22 | 46850865 | + | 0.93 | 0.912 | 0.91 |
| 503 | rs4846515 | chr1 | 217134232 | + | 0.95 | 0.93 | 0.936 | 3542 | rs133599 | chr22 | 47053440 | + | 0.933 | 0.949 | 0.92 |
| 504 | rs17516637 | chr1 | 217139354 | + | 0.949 | 0.932 | 0.938 | 3543 | rs7291555 | chr22 | 47954205 | + | 0.95 | 0.926 | 0.911 |
| 505 | rs17575959 | chr1 | 217140810 | + | 0.95 | 0.928 | 0.941 | 3544 | rs7285514 | chr22 | 47954656 | + | 0.95 | 0.926 | 0.901 |
| 506 | rs4846301 | chr1 | 217658571 | + | 0.917 | 0.939 | 0.927 | 3545 | rs745936 | chr22 | 47964413 | + | 0.95 | 0.925 | 0.911 |
| 507 | rs17527722 | chr1 | 217662455 | + | 0.917 | 0.933 | 0.911 | 3546 | rs2253008 | chr22 | 47990098 | + | 0.05 | 0.097 | 0.055 |
| 508 | rs12742106 | chr1 | 217683598 | + | 0.915 | 0.933 | 0.936 | 3547 | rs2688148 | chr22 | 48022067 | + | 0.05 | 0.072 | 0.089 |
| 509 | rs12752115 | chr1 | 217685025 | + | 0.929 | 0.936 | 0.945 | 3548 | rs5770112 | chr22 | 48022263 | + | 0.067 | 0.078 | 0.089 |
| 510 | rs17006249 | chr1 | 217895974 | + | 0.95 | 0.91 | 0.95 | 3549 | rs739088 | chr22 | 48022757 | + | 0.067 | 0.068 | 0.089 |
| 511 | rs7547631 | chr1 | 217952314 | + | 0.902 | 0.942 | 0.931 | 3550 | rs7287492 | chr22 | 48042967 | + | 0.931 | 0.935 | 0.931 |
| 512 | rs1933449 | chr1 | 217956370 | + | 0.917 | 0.944 | 0.944 | 3551 | rs6009837 | chr22 | 48488974 | + | 0.927 | 0.928 | 0.946 |
| 513 | rs12077296 | chr1 | 218189551 | + | 0.941 | 0.938 | 0.907 | 3552 | rs760753 | chr22 | 48939672 | + | 0.092 | 0.062 | 0.09 |
| 514 | rs17008315 | chr1 | 218951097 | + | 0.933 | 0.917 | 0.92 | 3553 | rs2129995 | chr3 | 1979442 | + | 0.921 | 0.947 | 0.929 |
| 515 | rs17011846 | chr1 | 221175677 | + | 0.949 | 0.91 | 0.927 | 3554 | rs4622887 | chr3 | 2093533 | + | 0.911 | 0.903 | 0.941 |
| 516 | rs6701453 | chr1 | 221632299 | + | 0.929 | 0.925 | 0.946 | 3555 | rs17018135 | chr3 | 2676890 | + | 0.941 | 0.95 | 0.923 |
| 517 | rs1037952 | chr1 | 222137182 | + | 0.905 | 0.943 | 0.946 | 3556 | rs17018141 | chr3 | 2677454 | + | 0.917 | 0.943 | 0.919 |
| 518 | rs4654023 | chr1 | 222584766 | + | 0.085 | 0.089 | 0.055 | 3557 | rs970826 | chr3 | 2808597 | + | 0.932 | 0.936 | 0.927 |
| 519 | rs4233235 | chr1 | 222587070 | + | 0.092 | 0.083 | 0.055 | 3558 | rs10510247 | chr3 | 3023016 | + | 0.931 | 0.909 | 0.91 |
| 520 | rs17571353 | chr1 | 222813200 | + | 0.921 | 0.92 | 0.931 | 3559 | rs3749363 | chr3 | 3054127 | + | 0.935 | 0.926 | 0.901 |
| 521 | rs10915829 | chr1 | 223708164 | + | 0.907 | 0.904 | 0.923 | 3560 | rs17659192 | chr3 | 3083711 | + | 0.908 | 0.944 | 0.901 |
| 522 | rs12022013 | chr1 | 223758043 | + | 0.917 | 0.906 | 0.914 | 3561 | rs17036228 | chr3 | 3759734 | + | 0.95 | 0.911 | 0.946 |
| 523 | rs3766931 | chr1 | 223758827 | + | 0.917 | 0.904 | 0.929 | 3562 | rs17362851 | chr3 | 3761517 | + | 0.908 | 0.939 | 0.946 |
| 524 | rs2184778 | chr1 | 223766304 | + | 0.917 | 0.904 | 0.91 | 3563 | rs3821790 | chr3 | 5157427 | + | 0.95 | 0.906 | 0.937 |

Fig. 9 Cont. 15

| | | | | | | | | | | |
|---|---|---|---|---|---|---|---|---|---|---|
| 525 | rs12031651 | chr1 | 223792908 | + | 0.915 | 0.906 | 0.929 | 3564 | rs1369404 | chr3 | 5876230 | + | 0.95 | 0.917 | 0.905 |
| 526 | rs2769686 | chr1 | 223938658 | + | 0.917 | 0.95 | 0.946 | 3565 | rs9830536 | chr3 | 6035965 | + | 0.95 | 0.906 | 0.911 |
| 527 | rs10915943 | chr1 | 224382238 | + | 0.914 | 0.915 | 0.946 | 3566 | rs17288121 | chr3 | 6377036 | + | 0.933 | 0.911 | 0.95 |
| 528 | rs650932 | chr1 | 224807499 | + | 0.1 | 0.072 | 0.098 | 3567 | rs1400286 | chr3 | 6836715 | + | 0.942 | 0.927 | 0.923 |
| 529 | rs2997438 | chr1 | 225245981 | + | 0.089 | 0.1 | 0.099 | 3568 | rs162779 | chr3 | 7709742 | + | 0.927 | 0.94 | 0.937 |
| 530 | rs1298652 | chr1 | 225257079 | + | 0.052 | 0.05 | 0.098 | 3569 | rs326426 | chr3 | 7842059 | + | 0.05 | 0.1 | 0.062 |
| 531 | rs7538126 | chr1 | 228330685 | + | 0.917 | 0.939 | 0.923 | 3570 | rs162716 | chr3 | 7843343 | + | 0.085 | 0.073 | 0.062 |
| 532 | rs3761952 | chr1 | 228850898 | + | 0.933 | 0.933 | 0.945 | 3571 | rs1488496 | chr3 | 7833883 | + | 0.068 | 0.073 | 0.063 |
| 533 | rs16856806 | chr1 | 230521253 | + | 0.925 | 0.922 | 0.945 | 3572 | rs2629229 | chr3 | 8400136 | + | 0.908 | 0.922 | 0.911 |
| 534 | rs12081587 | chr1 | 230521819 | + | 0.908 | 0.922 | 0.928 | 3573 | rs924364 | chr3 | 8400372 | + | 0.938 | 0.922 | 0.92 |
| 535 | rs66911007 | chr1 | 231329590 | + | 0.942 | 0.938 | 0.932 | 3574 | rs2292250 | chr3 | 9064178 | + | 0.925 | 0.903 | 0.95 |
| 536 | rs10797455 | chr1 | 231645911 | + | 0.092 | 0.08 | 0.077 | 3575 | rs901029 | chr3 | 10920374 | + | 0.942 | 0.939 | 0.95 |
| 537 | rs10797457 | chr1 | 231649791 | + | 0.092 | 0.08 | 0.089 | 3576 | rs2133064 | chr3 | 11873859 | + | 0.917 | 0.903 | 0.95 |
| 538 | rs4415516 | chr1 | 231653758 | + | 0.092 | 0.079 | 0.089 | 3577 | rs6777876 | chr3 | 11931598 | + | 0.908 | 0.933 | 0.91 |
| 539 | rs6659880 | chr1 | 231743800 | + | 0.908 | 0.91 | 0.909 | 3578 | rs6805619 | chr3 | 14956566 | + | 0.915 | 0.917 | 0.941 |
| 540 | rs12565388 | chr1 | 231755708 | + | 0.942 | 0.926 | 0.936 | 3579 | rs9867224 | chr3 | 15125801 | + | 0.917 | 0.917 | 0.937 |
| 541 | rs4920188 | chr1 | 232885014 | + | 0.908 | 0.944 | 0.936 | 3580 | rs9875977 | chr3 | 18070294 | + | 0.949 | 0.928 | 0.932 |
| 542 | rs11587639 | chr1 | 232900755 | + | 0.942 | 0.939 | 0.941 | 3581 | rs13076354 | chr3 | 18180487 | + | 0.942 | 0.938 | 0.918 |
| 543 | rs6684582 | chr1 | 233191574 | + | 0.925 | 0.922 | 0.946 | 3582 | rs9831811 | chr3 | 18264408 | + | 0.925 | 0.918 | 0.92 |
| 544 | rs6696218 | chr1 | 233917539 | + | 0.942 | 0.95 | 0.901 | 3583 | rs2165399 | chr3 | 18623485 | + | 0.95 | 0.904 | 0.91 |
| 545 | rs3768051 | chr1 | 233926337 | + | 0.942 | 0.949 | 0.901 | 3584 | rs9310573 | chr3 | 18765214 | + | 0.92 | 0.912 | 0.92 |
| 546 | rs12735189 | chr1 | 234930454 | + | 0.905 | 0.931 | 0.932 | 3585 | rs6789997 | chr3 | 18872429 | + | 0.948 | 0.944 | 0.909 |
| 547 | rs3738543 | chr1 | 234974470 | + | 0.95 | 0.903 | 0.928 | 3586 | rs17006078 | chr3 | 19598041 | + | 0.941 | 0.917 | 0.936 |
| 548 | rs10802560 | chr1 | 234983235 | + | 0.075 | 0.067 | 0.081 | 3587 | rs17006125 | chr3 | 19659185 | + | 0.912 | 0.921 | 0.925 |
| 549 | rs9428722 | chr1 | 236569908 | + | 0.059 | 0.064 | 0.066 | 3588 | rs17006126 | chr3 | 19660032 | + | 0.908 | 0.928 | 0.936 |
| 550 | rs7538546 | chr1 | 236578966 | + | 0.093 | 0.074 | 0.08 | 3589 | rs10510493 | chr3 | 19692203 | + | 0.933 | 0.928 | 0.941 |
| 551 | rs1577574 | chr1 | 236585352 | + | 0.092 | 0.074 | 0.072 | 3590 | rs2062976 | chr3 | 19730423 | + | 0.933 | 0.91 | 0.941 |
| 552 | rs10737824 | chr1 | 236586031 | + | 0.088 | 0.082 | 0.083 | 3591 | rs1506103 | chr3 | 19732620 | + | 0.933 | 0.91 | 0.927 |
| 553 | rs6702470 | chr1 | 236586841 | + | 0.086 | 0.075 | 0.091 | 3592 | rs1506102 | chr3 | 19732898 | + | 0.933 | 0.91 | 0.929 |
| 554 | rs1456659 | chr1 | 238475412 | + | 0.915 | 0.944 | 0.902 | 3593 | rs17006195 | chr3 | 19747191 | + | 0.933 | 0.906 | 0.941 |
| 555 | rs4559489 | chr1 | 238764761 | + | 0.083 | 0.051 | 0.082 | 3594 | rs17006199 | chr3 | 19747464 | + | 0.933 | 0.906 | 0.941 |
| 556 | rs4587552 | chr1 | 238764868 | + | 0.067 | 0.05 | 0.072 | 3595 | rs11128936 | chr3 | 20108603 | + | 0.925 | 0.938 | 0.901 |
| 557 | rs11583779 | chr1 | 239489359 | + | 0.927 | 0.907 | 0.936 | 3596 | rs7630411 | chr3 | 20773218 | + | 0.933 | 0.95 | 0.946 |
| 558 | rs10489352 | chr1 | 240051218 | + | 0.908 | 0.916 | 0.935 | 3597 | rs17811881 | chr3 | 20905471 | + | 0.925 | 0.933 | 0.909 |
| 559 | rs4149855 | chr1 | 240079229 | + | 0.925 | 0.908 | 0.927 | 3598 | rs17413483 | chr3 | 20971264 | + | 0.933 | 0.933 | 0.92 |

Fig. 9 Cont. 16

| | | | | | | | | | | | | |
|---|---|---|---|---|---|---|---|---|---|---|---|---|
| 560 | rs10926622 | chr1 | 240350060 | + | 0.917 | 0.928 | 0.918 | 3599 | rs13324110 | chr3 | 21737873 | + | 0.942 | 0.939 | 0.945 |
| 561 | rs2880314 | chr1 | 240601698 | + | 0.917 | 0.917 | 0.928 | 3600 | rs17619837 | chr3 | 21738243 | + | 0.942 | 0.944 | 0.938 |
| 562 | rs12133424 | chr1 | 240659717 | + | 0.95 | 0.903 | 0.909 | 3601 | rs7643485 | chr3 | 21808989 | + | 0.908 | 0.928 | 0.929 |
| 563 | rs11804678 | chr1 | 240768190 | + | 0.925 | 0.944 | 0.91 | 3602 | rs17009653 | chr3 | 21843084 | + | 0.908 | 0.933 | 0.946 |
| 564 | rs7536797 | chr1 | 240895285 | + | 0.942 | 0.944 | 0.936 | 3603 | rs716736 | chr3 | 22574916 | + | 0.942 | 0.91 | 0.905 |
| 565 | rs7517167 | chr1 | 240901393 | + | 0.942 | 0.944 | 0.944 | 3604 | rs2089848 | chr3 | 24081651 | + | 0.917 | 0.911 | 0.929 |
| 566 | rs7534025 | chr1 | 240901821 | + | 0.941 | 0.948 | 0.934 | 3605 | rs11714770 | chr3 | 24091053 | + | 0.95 | 0.927 | 0.935 |
| 567 | rs10927396 | chr1 | 243345536 | + | 0.907 | 0.933 | 0.92 | 3606 | rs11721182 | chr3 | 24102176 | + | 0.939 | 0.909 | 0.935 |
| 568 | rs12134117 | chr1 | 243703033 | + | 0.947 | 0.924 | 0.911 | 3607 | rs11705746 | chr3 | 24132943 | + | 0.908 | 0.911 | 0.929 |
| 569 | rs4654179 | chr1 | 244211059 | + | 0.942 | 0.911 | 0.914 | 3608 | rs12496664 | chr3 | 24197566 | + | 0.95 | 0.939 | 0.914 |
| 570 | rs7548294 | chr1 | 244223222 | + | 0.948 | 0.92 | 0.905 | 3609 | rs17014447 | chr3 | 24250387 | + | 0.949 | 0.95 | 0.935 |
| 571 | rs2105158 | chr1 | 244228879 | + | 0.941 | 0.911 | 0.909 | 3610 | rs17194919 | chr3 | 24320284 | + | 0.908 | 0.928 | 0.927 |
| 572 | rs6668455 | chr1 | 244731065 | + | 0.915 | 0.944 | 0.918 | 3611 | rs5014281 | chr3 | 24451890 | + | 0.067 | 0.089 | 0.063 |
| 573 | rs12040557 | chr1 | 246334436 | + | 0.905 | 0.907 | 0.938 | 3612 | rs6763228 | chr3 | 24752589 | + | 0.908 | 0.933 | 0.938 |
| 574 | rs6692816 | chr1 | 246389865 | + | 0.942 | 0.911 | 0.946 | 3613 | rs13433781 | chr3 | 24757705 | + | 0.914 | 0.95 | 0.911 |
| 575 | rs12255619 | chr10 | 88481 | + | 0.909 | 0.947 | 0.941 | 3614 | rs4404390 | chr3 | 24809789 | + | 0.935 | 0.937 | 0.923 |
| 576 | rs11599483 | chr10 | 1012147 | + | 0.947 | 0.935 | 0.923 | 3615 | rs13086347 | chr3 | 24815015 | + | 0.949 | 0.932 | 0.904 |
| 577 | rs2387650 | chr10 | 1370128 | + | 0.056 | 0.098 | 0.063 | 3616 | rs9826689 | chr3 | 24841056 | + | 0.908 | 0.91 | 0.941 |
| 578 | rs2820602 | chr10 | 1478339 | + | 0.068 | 0.078 | 0.077 | 3617 | rs9853652 | chr3 | 25288713 | + | 0.942 | 0.928 | 0.945 |
| 579 | rs11816776 | chr10 | 1612660 | + | 0.948 | 0.927 | 0.928 | 3618 | rs9867006 | chr3 | 25336856 | + | 0.908 | 0.922 | 0.919 |
| 580 | rs10437532 | chr10 | 1635568 | + | 0.1 | 0.061 | 0.05 | 3619 | rs9871002 | chr3 | 25455129 | + | 0.935 | 0.909 | 0.918 |
| 581 | rs10437529 | chr10 | 1637114 | + | 0.1 | 0.061 | 0.054 | 3620 | rs1435705 | chr3 | 25543875 | + | 0.908 | 0.91 | 0.905 |
| 582 | rs11251320 | chr10 | 2563796 | + | 0.946 | 0.92 | 0.905 | 3621 | rs1992005 | chr3 | 25551869 | + | 0.927 | 0.929 | 0.919 |
| 583 | rs1808116 | chr10 | 3633563 | + | 0.942 | 0.906 | 0.902 | 3622 | rs1357244 | chr3 | 27028134 | + | 0.933 | 0.91 | 0.946 |
| 584 | rs7909115 | chr10 | 3633713 | + | 0.942 | 0.906 | 0.936 | 3623 | rs3856675 | chr3 | 27523271 | + | 0.95 | 0.917 | 0.901 |
| 585 | rs17135445 | chr10 | 3634678 | + | 0.942 | 0.906 | 0.945 | 3624 | rs1461810 | chr3 | 28709777 | + | 0.95 | 0.928 | 0.902 |
| 586 | rs11251973 | chr10 | 3654150 | + | 0.94 | 0.909 | 0.934 | 3625 | rs9865738 | chr3 | 29320185 | + | 0.933 | 0.939 | 0.914 |
| 587 | rs17135579 | chr10 | 3690438 | + | 0.917 | 0.925 | 0.938 | 3626 | rs4334600 | chr3 | 29464611 | + | 0.058 | 0.056 | 0.062 |
| 588 | rs11252061 | chr10 | 3764779 | + | 0.908 | 0.944 | 0.95 | 3627 | rs9823737 | chr3 | 29465553 | + | 0.059 | 0.067 | 0.054 |
| 589 | rs2094179 | chr10 | 3910818 | + | 0.942 | 0.917 | 0.918 | 3628 | rs12490145 | chr3 | 30402083 | + | 0.948 | 0.943 | 0.915 |
| 590 | rs11252155 | chr10 | 3916536 | + | 0.95 | 0.917 | 0.928 | 3629 | rs17643248 | chr3 | 31178991 | + | 0.917 | 0.949 | 0.928 |
| 591 | rs10795138 | chr10 | 4162732 | + | 0.1 | 0.056 | 0.071 | 3630 | rs1866260 | chr3 | 32337429 | + | 0.933 | 0.933 | 0.928 |
| 592 | rs11252374 | chr10 | 4176228 | + | 0.917 | 0.921 | 0.941 | 3631 | rs1438182 | chr3 | 32340792 | + | 0.942 | 0.938 | 0.927 |
| 593 | rs7078830 | chr10 | 4261663 | + | 0.925 | 0.939 | 0.918 | 3632 | rs2342366 | chr3 | 32343577 | + | 0.932 | 0.922 | 0.923 |
| 594 | rs17373443 | chr10 | 4817569 | + | 0.941 | 0.928 | 0.909 | 3633 | rs9810960 | chr3 | 32440753 | + | 0.942 | 0.917 | 0.932 |

Fig. 9 Cont. 17

| | | | | | | | | | | |
|---|---|---|---|---|---|---|---|---|---|---|
| 595 rs17155721 chr10 | 4832546 | + | 0.933 | 0.911 | 0.938 | 3634 rs6809257 chr3 | 32722648 | + | 0.915 | 0.942 | 0.937 |
| 596 rs11252747 chr10 | 4832901 | + | 0.933 | 0.911 | 0.91 | 3635 rs6784341 chr3 | 32726044 | + | 0.924 | 0.937 | 0.93 |
| 597 rs10904347 chr10 | 4835520 | + | 0.933 | 0.922 | 0.938 | 3636 rs7431578 chr3 | 32728377 | + | 0.917 | 0.933 | 0.937 |
| 598 rs9423934 chr10 | 5773466 | + | 0.074 | 0.06 | 0.073 | 3637 rs6785966 chr3 | 32775326 | + | 0.917 | 0.933 | 0.937 |
| 599 rs1418739 chr10 | 5793743 | + | 0.058 | 0.053 | 0.068 | 3638 rs6781308 chr3 | 32779189 | + | 0.915 | 0.933 | 0.937 |
| 600 rs2669138 chr10 | 5834481 | + | 0.067 | 0.051 | 0.068 | 3639 rs12486515 chr3 | 33344969 | + | 0.924 | 0.933 | 0.911 |
| 601 rs10906504 chr10 | 6500512 | + | 0.076 | 0.096 | 0.064 | 3640 rs1780585C chr3 | 33391144 | + | 0.95 | 0.939 | 0.914 |
| 602 rs10795408 chr10 | 6778565 | + | 0.922 | 0.908 | 0.934 | 3641 rs7613545 chr3 | 33484765 | + | 0.908 | 0.917 | 0.905 |
| 603 rs2387755 chr10 | 6981309 | + | 0.071 | 0.097 | 0.093 | 3642 rs17030742 chr3 | 33510415 | + | 0.933 | 0.95 | 0.914 |
| 604 rs2892351 chr10 | 6981316 | + | 0.05 | 0.074 | 0.095 | 3643 rs2299 chr3 | 35013255 | + | 0.933 | 0.927 | 0.91 |
| 605 rs2248474 chr10 | 7325638 | + | 0.067 | 0.096 | 0.099 | 3644 rs2359209 chr3 | 35014865 | + | 0.929 | 0.928 | 0.938 |
| 606 rs10795568 chr10 | 7833820 | + | 0.1 | 0.056 | 0.081 | 3645 rs1703333C chr3 | 35529934 | + | 0.908 | 0.939 | 0.946 |
| 607 rs1981015 chr10 | 7879231 | + | 0.917 | 0.939 | 0.929 | 3646 rs17033335 chr3 | 35530698 | + | 0.908 | 0.938 | 0.946 |
| 608 rs7904875 chr10 | 7892634 | + | 0.92 | 0.933 | 0.946 | 3647 rs17033337 chr3 | 35535975 | + | 0.908 | 0.939 | 0.946 |
| 609 rs10508336 chr10 | 7916836 | + | 0.925 | 0.92 | 0.927 | 3648 rs7374633 chr3 | 38702618 | + | 0.942 | 0.922 | 0.914 |
| 610 rs10905236 chr10 | 7924582 | + | 0.908 | 0.938 | 0.95 | 3649 rs7374030 chr3 | 38772932 | + | 0.905 | 0.909 | 0.926 |
| 611 rs11255616 chr10 | 8355112 | + | 0.948 | 0.942 | 0.918 | 3650 rs13063658 chr3 | 39053665 | + | 0.921 | 0.904 | 0.906 |
| 612 rs10905341 chr10 | 8387278 | + | 0.908 | 0.904 | 0.92 | 3651 rs7613342 chr3 | 40271633 | + | 0.917 | 0.933 | 0.932 |
| 613 rs17136612 chr10 | 8700652 | + | 0.915 | 0.901 | 0.919 | 3652 rs7649848 chr3 | 40316715 | + | 0.95 | 0.933 | 0.932 |
| 614 rs17413004 chr10 | 8989186 | + | 0.942 | 0.944 | 0.902 | 3653 rs13098354 chr3 | 40317848 | + | 0.948 | 0.937 | 0.907 |
| 615 rs17145253 chr10 | 9185562 | + | 0.906 | 0.903 | 0.944 | 3654 rs33916626 chr3 | 41469622 | + | 0.933 | 0.944 | 0.928 |
| 616 rs11257104 chr10 | 11538136 | + | 0.926 | 0.944 | 0.929 | 3655 rs1449362 chr3 | 42323072 | + | 0.922 | 0.931 | 0.906 |
| 617 rs11257105 chr10 | 11538492 | + | 0.917 | 0.935 | 0.926 | 3656 rs12490234 chr3 | 42447032 | + | 0.939 | 0.916 | 0.919 |
| 618 rs7922799 chr10 | 12733766 | + | 0.941 | 0.926 | 0.943 | 3657 rs17320695 chr3 | 43264842 | + | 0.95 | 0.917 | 0.91 |
| 619 rs11258130 chr10 | 13100798 | + | 0.907 | 0.939 | 0.906 | 3658 rs718779 chr3 | 44048839 | + | 0.95 | 0.91 | 0.927 |
| 620 rs11259060 chr10 | 14479283 | + | 0.933 | 0.944 | 0.946 | 3659 rs4682747 chr3 | 44594138 | + | 0.057 | 0.096 | 0.08 |
| 621 rs17253915 chr10 | 14492675 | + | 0.95 | 0.933 | 0.938 | 3660 rs17282175 chr3 | 46148646 | + | 0.921 | 0.949 | 0.909 |
| 622 rs1547219 chr10 | 14507356 | + | 0.942 | 0.927 | 0.913 | 3661 rs1306245C chr3 | 46202175 | + | 0.925 | 0.938 | 0.929 |
| 623 rs6602749 chr10 | 14723487 | + | 0.911 | 0.936 | 0.92 | 3662 rs3136673 chr3 | 46217620 | + | 0.924 | 0.939 | 0.919 |
| 624 rs11595229 chr10 | 14748595 | + | 0.917 | 0.933 | 0.92 | 3663 rs17053453 chr3 | 53754816 | + | 0.915 | 0.933 | 0.946 |
| 625 rs11599834 chr10 | 14748696 | + | 0.917 | 0.933 | 0.92 | 3664 rs3774560 chr3 | 53760443 | + | 0.908 | 0.933 | 0.946 |
| 626 rs11259309 chr10 | 14835634 | + | 0.933 | 0.92 | 0.928 | 3665 rs1705489C chr3 | 55174307 | + | 0.908 | 0.906 | 0.941 |
| 627 rs10508482 chr10 | 14835794 | + | 0.917 | 0.906 | 0.939 | 3666 rs12632515 chr3 | 55185110 | + | 0.904 | 0.949 | 0.919 |
| 628 rs11259496 chr10 | 15196615 | + | 0.933 | 0.933 | 0.95 | 3667 rs13083875 chr3 | 55297493 | + | 0.922 | 0.927 | 0.923 |
| 629 rs11259499 chr10 | 15198449 | + | 0.917 | 0.932 | 0.95 | 3668 rs9857104 chr3 | 55838899 | + | 0.933 | 0.921 | 0.929 |

Fig. 9 Cont. 18

| | | | | | | | | | | | |
|---|---|---|---|---|---|---|---|---|---|---|---|
| 630 | rs70080831 | chr10 | 16215963 | + | 0.1 | 0.051 | 0.099 | 3669 | rs9850057 | chr3 | 55849805 | + | 0.933 | 0.916 | 0.935 |
| 631 | rs10752068 | chr10 | 17204075 | + | 0.083 | 0.052 | 0.056 | 3670 | rs13082740 | chr3 | 59673425 | + | 0.942 | 0.928 | 0.938 |
| 632 | rs942773 | chr10 | 17810946 | + | 0.93 | 0.937 | 0.906 | 3671 | rs3772460 | chr3 | 59918572 | + | 0.95 | 0.917 | 0.91 |
| 633 | rs1779244 | chr10 | 18517631 | + | 0.058 | 0.05 | 0.077 | 3672 | rs6796003 | chr3 | 60707230 | + | 0.052 | 0.083 | 0.071 |
| 634 | rs11816378 | chr10 | 18569652 | + | 0.95 | 0.933 | 0.91 | 3673 | rs1763793 | chr3 | 61117481 | + | 0.917 | 0.917 | 0.901 |
| 635 | rs11812617 | chr10 | 18572235 | + | 0.95 | 0.933 | 0.91 | 3674 | rs745830 | chr3 | 61242456 | + | 0.904 | 0.906 | 0.901 |
| 636 | rs10828679 | chr10 | 18751294 | + | 0.068 | 0.061 | 0.099 | 3675 | rs815699 | chr3 | 61246144 | + | 0.908 | 0.906 | 0.92 |
| 637 | rs6415973 | chr10 | 18755174 | + | 0.055 | 0.052 | 0.098 | 3676 | rs815700 | chr3 | 61246242 | + | 0.917 | 0.904 | 0.92 |
| 638 | rs107410S8 | chr10 | 18756151 | + | 0.066 | 0.083 | 0.099 | 3677 | rs1209099 | chr3 | 61818379 | + | 0.902 | 0.929 | 0.925 |
| 639 | rs10764483 | chr10 | 18756352 | + | 0.058 | 0.056 | 0.099 | 3678 | rs7647422 | chr3 | 62001628 | + | 0.917 | 0.944 | 0.901 |
| 640 | rs7923938 | chr10 | 18784725 | + | 0.925 | 0.928 | 0.91 | 3679 | rs7611626 | chr3 | 62377935 | + | 0.933 | 0.95 | 0.923 |
| 641 | rs16918827 | chr10 | 19806061 | + | 0.939 | 0.933 | 0.937 | 3680 | rs17066673 | chr3 | 62553376 | + | 0.925 | 0.95 | 0.945 |
| 642 | rs16918840 | chr10 | 19816612 | + | 0.946 | 0.928 | 0.937 | 3681 | rs9861880 | chr3 | 62597372 | + | 0.058 | 0.087 | 0.096 |
| 643 | rs10494868 | chr10 | 19847881 | + | 0.95 | 0.931 | 0.911 | 3682 | rs4688316 | chr3 | 62663151 | + | 0.948 | 0.906 | 0.946 |
| 644 | rs4748598 | chr10 | 19901191 | + | 0.933 | 0.922 | 0.929 | 3683 | rs9849009 | chr3 | 63459530 | + | 0.908 | 0.95 | 0.918 |
| 645 | rs3844359 | chr10 | 19935038 | + | 0.078 | 0.096 | 0.1 | 3684 | rs704428 | chr3 | 64815440 | + | 0.908 | 0.938 | 0.946 |
| 646 | rs1831047 | chr10 | 19994935 | + | 0.075 | 0.1 | 0.072 | 3685 | rs2583718 | chr3 | 64820775 | + | 0.917 | 0.922 | 0.932 |
| 647 | rs1326247 | chr10 | 20221637 | + | 0.083 | 0.072 | 0.077 | 3686 | rs997448 | chr3 | 64935253 | + | 0.942 | 0.944 | 0.914 |
| 648 | rs10827903 | chr10 | 20252577 | + | 0.083 | 0.08 | 0.081 | 3687 | rs12107001 | chr3 | 64937270 | + | 0.942 | 0.944 | 0.914 |
| 649 | rs10764178 | chr10 | 20259274 | + | 0.083 | 0.078 | 0.077 | 3688 | rs9311941 | chr3 | 65293452 | + | 0.95 | 0.922 | 0.91 |
| 650 | rs6482071 | chr10 | 20269755 | + | 0.092 | 0.079 | 0.072 | 3689 | rs9861361 | chr3 | 65295974 | + | 0.95 | 0.917 | 0.911 |
| 651 | rs2461943 | chr10 | 20439185 | + | 0.062 | 0.062 | 0.072 | 3690 | rs13078969 | chr3 | 65379690 | + | 0.942 | 0.944 | 0.905 |
| 652 | rs2460589 | chr10 | 20441991 | + | 0.093 | 0.062 | 0.089 | 3691 | rs4547637 | chr3 | 66710211 | + | 0.908 | 0.916 | 0.946 |
| 653 | rs2461924 | chr10 | 20464962 | + | 0.061 | 0.057 | 0.068 | 3692 | rs11128434 | chr3 | 67294399 | + | 0.092 | 0.079 | 0.063 |
| 654 | rs4575163 | chr10 | 20531608 | + | 0.075 | 0.067 | 0.072 | 3693 | rs11922554 | chr3 | 67525374 | + | 0.905 | 0.928 | 0.911 |
| 655 | rs7915493 | chr10 | 20813815 | + | 0.917 | 0.944 | 0.909 | 3694 | rs17046411 | chr3 | 67525645 | + | 0.947 | 0.929 | 0.91 |
| 656 | rs12572139 | chr10 | 20841599 | + | 0.917 | 0.91 | 0.901 | 3695 | rs7652000 | chr3 | 67532616 | + | 0.95 | 0.928 | 0.914 |
| 657 | rs10508628 | chr10 | 20916620 | + | 0.939 | 0.921 | 0.941 | 3696 | rs7642811 | chr3 | 67532855 | + | 0.95 | 0.928 | 0.911 |
| 658 | rs16920689 | chr10 | 20917501 | + | 0.942 | 0.95 | 0.941 | 3697 | rs17047216 | chr3 | 68283056 | + | 0.95 | 0.911 | 0.941 |
| 659 | rs12219682 | chr10 | 20919877 | + | 0.935 | 0.949 | 0.944 | 3698 | rs17047218 | chr3 | 68287042 | + | 0.949 | 0.911 | 0.936 |
| 660 | rs16921795 | chr10 | 21723283 | + | 0.944 | 0.931 | 0.917 | 3699 | rs9826468 | chr3 | 68403369 | + | 0.942 | 0.904 | 0.95 |
| 661 | rs16924724 | chr10 | 24724060 | + | 0.917 | 0.904 | 0.946 | 3700 | rs9848101 | chr3 | 69509485 | + | 0.1 | 0.05 | 0.062 |
| 662 | rs12241251 | chr10 | 24738341 | + | 0.925 | 0.933 | 0.945 | 3701 | rs1733504 | chr3 | 71455487 | + | 0.917 | 0.939 | 0.932 |
| 663 | rs12220461 | chr10 | 27084466 | + | 0.931 | 0.926 | 0.933 | 3702 | rs1300170 | chr3 | 71471832 | + | 0.908 | 0.915 | 0.928 |
| 664 | rs1998633 | chr10 | 27087646 | + | 0.933 | 0.914 | 0.946 | 3703 | rs1288702 | chr3 | 71474560 | + | 0.908 | 0.916 | 0.932 |

Fig. 9 Cont. 19

| # | rsID | chr | pos | str | v1 | v2 | v3 | # | rsID | chr | pos | str | v4 | v5 | v6 |
|---|---|---|---|---|---|---|---|---|---|---|---|---|---|---|---|
| 665 | rs11015277 | chr10 | 27099642 | + | 0.933 | 0.911 | 0.929 | 3704 | rs1290499 | chr3 | 71476030 | + | 0.908 | 0.911 | 0.91 |
| 666 | rs3802616 | chr10 | 27100816 | + | 0.933 | 0.917 | 0.929 | 3705 | rs13058906 | chr3 | 72118527 | + | 0.933 | 0.939 | 0.95 |
| 667 | rs11015278 | chr10 | 27103503 | + | 0.933 | 0.916 | 0.932 | 3706 | rs13083056 | chr3 | 73089457 | + | 0.924 | 0.939 | 0.938 |
| 668 | rs11015299 | chr10 | 27134582 | + | 0.933 | 0.917 | 0.929 | 3707 | rs13060181 | chr3 | 73089578 | + | 0.924 | 0.939 | 0.938 |
| 669 | rs12220354 | chr10 | 27167288 | + | 0.933 | 0.917 | 0.929 | 3708 | rs13060515 | chr3 | 73089764 | + | 0.938 | 0.949 | 0.938 |
| 670 | rs7898888 | chr10 | 28680238 | + | 0.908 | 0.928 | 0.932 | 3709 | rs13071429 | chr3 | 73091291 | + | 0.925 | 0.944 | 0.938 |
| 671 | rs1495672 | chr10 | 29175611 | + | 0.908 | 0.906 | 0.928 | 3710 | rs17691949 | chr3 | 73093053 | + | 0.924 | 0.939 | 0.932 |
| 672 | rs7088136 | chr10 | 29199496 | + | 0.917 | 0.911 | 0.928 | 3711 | rs13081583 | chr3 | 73105391 | + | 0.925 | 0.914 | 0.938 |
| 673 | rs16930212 | chr10 | 29750794 | + | 0.908 | 0.95 | 0.919 | 3712 | rs17742965 | chr3 | 73106311 | + | 0.925 | 0.916 | 0.941 |
| 674 | rs16930216 | chr10 | 29754342 | + | 0.908 | 0.95 | 0.945 | 3713 | rs11917479 | chr3 | 73110001 | + | 0.941 | 0.933 | 0.938 |
| 675 | rs16930217 | chr10 | 29754454 | + | 0.908 | 0.95 | 0.911 | 3714 | rs4499540 | chr3 | 73742150 | + | 0.051 | 0.083 | 0.089 |
| 676 | rs12770852 | chr10 | 29755448 | + | 0.908 | 0.95 | 0.911 | 3715 | rs11714985 | chr3 | 74368910 | + | 0.908 | 0.918 | 0.912 |
| 677 | rs16930246 | chr10 | 29798352 | + | 0.908 | 0.95 | 0.918 | 3716 | rs7430041 | chr3 | 74611916 | + | 0.918 | 0.913 | 0.943 |
| 678 | rs16930249 | chr10 | 29798825 | + | 0.908 | 0.95 | 0.919 | 3717 | rs7427367 | chr3 | 74678509 | + | 0.1 | 0.068 | 0.071 |
| 679 | rs16930268 | chr10 | 29814448 | + | 0.908 | 0.95 | 0.907 | 3718 | rs6807299 | chr3 | 74684215 | + | 0.093 | 0.061 | 0.086 |
| 680 | rs2480286 | chr10 | 30708967 | + | 0.909 | 0.93 | 0.917 | 3719 | rs9850402 | chr3 | 74688681 | + | 0.1 | 0.062 | 0.071 |
| 681 | rs12770855 | chr10 | 31160204 | + | 0.95 | 0.904 | 0.914 | 3720 | rs9814354 | chr3 | 74688913 | + | 0.1 | 0.062 | 0.073 |
| 682 | rs11008367 | chr10 | 31482842 | + | 0.915 | 0.903 | 0.902 | 3721 | rs4677414 | chr3 | 74689710 | + | 0.1 | 0.061 | 0.091 |
| 683 | rs2124533 | chr10 | 33919351 | + | 0.925 | 0.91 | 0.919 | 3722 | rs9828844 | chr3 | 75411524 | + | 0.92 | 0.948 | 0.912 |
| 684 | rs2167712 | chr10 | 33927881 | + | 0.924 | 0.91 | 0.927 | 3723 | rs11127662 | chr3 | 79854677 | + | 0.092 | 0.078 | 0.089 |
| 685 | rs7907596 | chr10 | 33988001 | + | 0.942 | 0.943 | 0.937 | 3724 | rs6548649 | chr3 | 79858019 | + | 0.092 | 0.078 | 0.089 |
| 686 | rs1412116 | chr10 | 34113154 | + | 0.942 | 0.948 | 0.905 | 3725 | rs6548651 | chr3 | 79867106 | + | 0.092 | 0.079 | 0.099 |
| 687 | rs7078774 | chr10 | 35260157 | + | 0.908 | 0.939 | 0.91 | 3726 | rs6548652 | chr3 | 79869811 | + | 0.092 | 0.079 | 0.089 |
| 688 | rs11011095 | chr10 | 37630649 | + | 0.907 | 0.944 | 0.914 | 3727 | rs2011569 | chr3 | 80440718 | + | 0.942 | 0.91 | 0.929 |
| 689 | rs11011109 | chr10 | 37630690 | + | 0.907 | 0.944 | 0.914 | 3728 | rs17407422 | chr3 | 81358320 | + | 0.941 | 0.944 | 0.92 |
| 690 | rs11011098 | chr10 | 37630845 | + | 0.921 | 0.944 | 0.914 | 3729 | rs727824 | chr3 | 81366052 | + | 0.933 | 0.944 | 0.91 |
| 691 | rs7069858 | chr10 | 37632716 | + | 0.905 | 0.944 | 0.909 | 3730 | rs12107246 | chr3 | 81400006 | + | 0.915 | 0.927 | 0.92 |
| 692 | rs11011095 | chr10 | 37635016 | + | 0.907 | 0.944 | 0.909 | 3731 | rs12107255 | chr3 | 81400092 | + | 0.917 | 0.927 | 0.92 |
| 693 | rs11011101 | chr10 | 37635518 | + | 0.907 | 0.944 | 0.914 | 3732 | rs1482617 | chr3 | 83095002 | + | 0.1 | 0.084 | 0.099 |
| 694 | rs11011102 | chr10 | 37635675 | + | 0.907 | 0.944 | 0.909 | 3733 | rs11127801 | chr3 | 83112842 | + | 0.942 | 0.91 | 0.941 |
| 695 | rs11011103 | chr10 | 37635796 | + | 0.907 | 0.944 | 0.909 | 3734 | rs17020418 | chr3 | 83117334 | + | 0.94 | 0.909 | 0.933 |
| 696 | rs7093790 | chr10 | 37636395 | + | 0.907 | 0.944 | 0.909 | 3735 | rs12233488 | chr3 | 85006628 | + | 0.932 | 0.927 | 0.946 |
| 697 | rs7097277 | chr10 | 37636731 | + | 0.908 | 0.949 | 0.914 | 3736 | rs12493342 | chr3 | 85010495 | + | 0.933 | 0.928 | 0.932 |
| 698 | rs11011105 | chr10 | 37637053 | + | 0.908 | 0.944 | 0.909 | 3737 | rs17022126 | chr3 | 85099250 | + | 0.942 | 0.947 | 0.925 |
| 699 | rs11011106 | chr10 | 37637192 | + | 0.908 | 0.944 | 0.911 | 3738 | rs12495727 | chr3 | 87901533 | + | 0.938 | 0.909 | 0.944 |

Fig. 9  Cont. 20

| # | SNP chr | pos1 | | | | SNP chr | pos2 | | | |
|---|---|---|---|---|---|---|---|---|---|---|
| 700 | rs10827768 chr10 | 37638301 | + | 0.908 | 0.949 | 0.909 | 3739 rs119161S1 chr3 | 88363366 | + | 0.942 | 0.933 | 0.928 |
| 701 | rs12356232 chr10 | 37638865 | + | 0.907 | 0.943 | 0.914 | 3740 rs12496388 chr3 | 88446391 | + | 0.932 | 0.929 | 0.942 |
| 702 | rs11011107 chr10 | 37638959 | + | 0.908 | 0.948 | 0.911 | 3741 rs7641881 chr3 | 88864824 | + | 0.95 | 0.921 | 0.909 |
| 703 | rs11011108 chr10 | 37639428 | + | 0.908 | 0.949 | 0.911 | 3742 rs13059845 chr3 | 88867444 | + | 0.907 | 0.928 | 0.911 |
| 704 | rs12356772 chr10 | 37640592 | + | 0.908 | 0.944 | 0.914 | 3743 rs6774956 chr3 | 89015844 | + | 0.948 | 0.92 | 0.937 |
| 705 | rs12358359 chr10 | 37640660 | + | 0.908 | 0.949 | 0.911 | 3744 rs4392452 chr3 | 100633580 | + | 0.933 | 0.917 | 0.938 |
| 706 | rs11011112 chr10 | 37642770 | + | 0.907 | 0.948 | 0.906 | 3745 rs4544654 chr3 | 100633635 | + | 0.933 | 0.921 | 0.938 |
| 707 | rs11011114 chr10 | 37642893 | + | 0.907 | 0.949 | 0.911 | 3746 rs12486853 chr3 | 100722480 | + | 0.942 | 0.933 | 0.936 |
| 708 | rs2296592 chr10 | 37643445 | + | 0.908 | 0.95 | 0.911 | 3747 rs17777354 chr3 | 100859910 | + | 0.942 | 0.938 | 0.923 |
| 709 | rs2296593 chr10 | 37644417 | + | 0.908 | 0.95 | 0.914 | 3748 rs6774706 chr3 | 100863079 | + | 0.942 | 0.939 | 0.929 |
| 710 | rs11011116 chr10 | 37645503 | + | 0.908 | 0.95 | 0.911 | 3749 rs13089811 chr3 | 100878596 | + | 0.941 | 0.939 | 0.929 |
| 711 | rs7081873 chr10 | 37646066 | + | 0.908 | 0.95 | 0.934 | 3750 rs13066932 chr3 | 100878843 | + | 0.942 | 0.939 | 0.929 |
| 712 | rs1926123 chr10 | 37650801 | + | 0.908 | 0.95 | 0.914 | 3751 rs13095226 chr3 | 100878962 | + | 0.942 | 0.939 | 0.923 |
| 713 | rs10827775 chr10 | 37669696 | + | 0.908 | 0.95 | 0.911 | 3752 rs13067276 chr3 | 100879014 | + | 0.942 | 0.939 | 0.929 |
| 714 | rs11011137 chr10 | 37674688 | + | 0.915 | 0.95 | 0.911 | 3753 rs13059876 chr3 | 100880846 | + | 0.942 | 0.939 | 0.923 |
| 715 | rs6482034 chr10 | 37681554 | + | 0.908 | 0.949 | 0.911 | 3754 rs6808963 chr3 | 100887003 | + | 0.942 | 0.939 | 0.929 |
| 716 | rs11815830 chr10 | 37682424 | + | 0.908 | 0.95 | 0.911 | 3755 rs4535264 chr3 | 100895644 | + | 0.942 | 0.933 | 0.925 |
| 717 | rs11819714 chr10 | 37682483 | + | 0.908 | 0.95 | 0.911 | 3756 rs6779634 chr3 | 100901234 | + | 0.942 | 0.928 | 0.929 |
| 718 | rs11511137 chr10 | 37683144 | + | 0.908 | 0.949 | 0.911 | 3757 rs9878198 chr3 | 104610168 | + | 0.907 | 0.95 | 0.902 |
| 719 | rs7096318 chr10 | 37684214 | + | 0.908 | 0.95 | 0.911 | 3758 rs1511627 chr3 | 104821906 | + | 0.95 | 0.933 | 0.932 |
| 720 | rs7920176 chr10 | 37684581 | + | 0.908 | 0.95 | 0.918 | 3759 rs4856184 chr3 | 104836971 | + | 0.95 | 0.933 | 0.932 |
| 721 | rs11011144 chr10 | 37685740 | + | 0.908 | 0.95 | 0.911 | 3760 rs16849953 chr3 | 105588276 | + | 0.917 | 0.95 | 0.91 |
| 722 | rs12769884 chr10 | 37692421 | + | 0.907 | 0.947 | 0.907 | 3761 rs11710356 chr3 | 106034568 | + | 0.925 | 0.944 | 0.946 |
| 723 | rs11011153 chr10 | 37695880 | + | 0.905 | 0.95 | 0.914 | 3762 rs3772550 chr3 | 106744170 | + | 0.942 | 0.928 | 0.937 |
| 724 | rs11011154 chr10 | 37696038 | + | 0.908 | 0.95 | 0.914 | 3763 rs12493268 chr3 | 107381448 | + | 0.938 | 0.94 | 0.926 |
| 725 | rs10827776 chr10 | 37697591 | + | 0.908 | 0.95 | 0.911 | 3764 rs6437661 chr3 | 107536100 | + | 0.079 | 0.071 | 0.075 |
| 726 | rs12783534 chr10 | 37703406 | + | 0.908 | 0.95 | 0.914 | 3765 rs6437662 chr3 | 107546653 | + | 0.083 | 0.073 | 0.072 |
| 727 | rs11011157 chr10 | 37703658 | + | 0.908 | 0.95 | 0.911 | 3766 rs2399082 chr3 | 107552207 | + | 0.083 | 0.074 | 0.072 |
| 728 | rs11693746 chr10 | 37706224 | + | 0.908 | 0.949 | 0.923 | 3767 rs1596694 chr3 | 107746963 | + | 0.917 | 0.928 | 0.905 |
| 729 | rs12356503 chr10 | 37715447 | + | 0.908 | 0.95 | 0.919 | 3768 rs1867557 chr3 | 107751913 | + | 0.917 | 0.927 | 0.901 |
| 730 | rs17417815 chr10 | 42379710 | + | 0.905 | 0.947 | 0.926 | 3769 rs2117761 chr3 | 109352829 | + | 0.931 | 0.939 | 0.902 |
| 731 | rs7912057 chr10 | 42395657 | + | 0.92 | 0.944 | 0.917 | 3770 rs11920797 chr3 | 109355355 | + | 0.925 | 0.938 | 0.902 |
| 732 | rs7067919 chr10 | 43769123 | + | 0.902 | 0.926 | 0.944 | 3771 rs11926978 chr3 | 109359057 | + | 0.925 | 0.939 | 0.902 |
| 733 | rs11239019 chr10 | 44183340 | + | 0.924 | 0.943 | 0.938 | 3772 rs11919348 chr3 | 109359122 | + | 0.922 | 0.938 | 0.902 |
| 734 | rs11239020 chr10 | 44183999 | + | 0.932 | 0.943 | 0.945 | 3773 rs9860418 chr3 | 109364391 | + | 0.917 | 0.938 | 0.902 |

Fig. 9 Cont. 21

| | | | | | | | | | |
|---|---|---|---|---|---|---|---|---|---|
| 735 | rs12239021 | chr10 | 44184638 | + | 0.94 | 0.947 | 0.938 | 3774 | rs9860587 | chr3 | 109364486 | + | 0.922 | 0.948 | 0.902 |
| 736 | rs1090003C | chr10 | 44185273 | + | 0.93 | 0.936 | 0.935 | 3775 | rs13325340 | chr3 | 109366220 | + | 0.917 | 0.938 | 0.902 |
| 737 | rs1804430 | chr10 | 44185745 | + | 0.925 | 0.939 | 0.938 | 3776 | rs13318436 | chr3 | 109366458 | + | 0.915 | 0.943 | 0.904 |
| 738 | rs1804429 | chr10 | 44185847 | + | 0.925 | 0.939 | 0.946 | 3777 | rs9838360 | chr3 | 109367515 | + | 0.917 | 0.944 | 0.902 |
| 739 | rs1065297 | chr10 | 44185982 | + | 0.917 | 0.938 | 0.946 | 3778 | rs9852283 | chr3 | 109367795 | + | 0.917 | 0.938 | 0.902 |
| 740 | rs2839696 | chr10 | 44186634 | + | 0.925 | 0.938 | 0.946 | 3779 | rs11928732 | chr3 | 109372751 | + | 0.917 | 0.938 | 0.902 |
| 741 | rs2522 | chr10 | 44187310 | + | 0.925 | 0.939 | 0.946 | 3780 | rs1192109C | chr3 | 109373150 | + | 0.915 | 0.939 | 0.902 |
| 742 | rs12258838 | chr10 | 44188471 | + | 0.925 | 0.939 | 0.941 | 3781 | rs10514751 | chr3 | 109375839 | + | 0.917 | 0.938 | 0.902 |
| 743 | rs4948878 | chr10 | 44194827 | + | 0.95 | 0.939 | 0.946 | 3782 | rs9844904 | chr3 | 109376794 | + | 0.917 | 0.944 | 0.902 |
| 744 | rs11239032 | chr10 | 44210553 | + | 0.942 | 0.944 | 0.938 | 3783 | rs723272 | chr3 | 109377530 | + | 0.925 | 0.938 | 0.902 |
| 745 | rs17156688 | chr10 | 44438955 | + | 0.943 | 0.918 | 0.902 | 3784 | rs9822625 | chr3 | 109378186 | + | 0.917 | 0.938 | 0.902 |
| 746 | rs3814160 | chr10 | 47991283 | + | 0.942 | 0.944 | 0.902 | 3785 | rs1982435 | chr3 | 109378861 | + | 0.915 | 0.943 | 0.902 |
| 747 | rs4838484 | chr10 | 50152258 | + | 0.917 | 0.91 | 0.946 | 3786 | rs9883627 | chr3 | 109379401 | + | 0.915 | 0.944 | 0.909 |
| 748 | rs1700988C | chr10 | 50156166 | + | 0.942 | 0.949 | 0.929 | 3787 | rs11922835 | chr3 | 109379929 | + | 0.922 | 0.948 | 0.907 |
| 749 | rs1085747C | chr10 | 50203469 | + | 0.941 | 0.938 | 0.907 | 3788 | rs11915212 | chr3 | 109379984 | + | 0.917 | 0.939 | 0.909 |
| 750 | rs11101094 | chr10 | 50203847 | + | 0.941 | 0.938 | 0.907 | 3789 | rs11915231 | chr3 | 109380235 | + | 0.908 | 0.938 | 0.902 |
| 751 | rs1991393 | chr10 | 53757111 | + | 0.938 | 0.905 | 0.905 | 3790 | rs9818755 | chr3 | 109381283 | + | 0.917 | 0.938 | 0.902 |
| 752 | rs2384205 | chr10 | 54764849 | + | 0.917 | 0.944 | 0.918 | 3791 | rs7622938 | chr3 | 109382348 | + | 0.917 | 0.938 | 0.902 |
| 753 | rs1909426 | chr10 | 54778135 | + | 0.932 | 0.902 | 0.914 | 3792 | rs7647452 | chr3 | 109382651 | + | 0.925 | 0.938 | 0.902 |
| 754 | rs12762435 | chr10 | 55302380 | + | 0.95 | 0.944 | 0.938 | 3793 | rs17829536 | chr3 | 109383755 | + | 0.925 | 0.939 | 0.902 |
| 755 | rs12781255 | chr10 | 55323173 | + | 0.908 | 0.911 | 0.935 | 3794 | rs10511268 | chr3 | 109384773 | + | 0.917 | 0.938 | 0.902 |
| 756 | rs12412902 | chr10 | 55355079 | + | 0.933 | 0.933 | 0.938 | 3795 | rs13323383 | chr3 | 109385154 | + | 0.907 | 0.939 | 0.902 |
| 757 | rs12259237 | chr10 | 58212517 | + | 0.922 | 0.902 | 0.927 | 3796 | rs13323413 | chr3 | 109385283 | + | 0.915 | 0.938 | 0.902 |
| 758 | rs71100774 | chr10 | 59012258 | + | 0.95 | 0.939 | 0.929 | 3797 | rs10511265 | chr3 | 109385691 | + | 0.917 | 0.938 | 0.902 |
| 759 | rs7909485 | chr10 | 59013798 | + | 0.95 | 0.939 | 0.936 | 3798 | rs10514752 | chr3 | 109385765 | + | 0.917 | 0.938 | 0.902 |
| 760 | rs2393335 | chr10 | 59020458 | + | 0.95 | 0.939 | 0.919 | 3799 | rs13433942 | chr3 | 109388029 | + | 0.917 | 0.939 | 0.902 |
| 761 | rs12773089 | chr10 | 59028725 | + | 0.95 | 0.939 | 0.927 | 3800 | rs9832007 | chr3 | 109390216 | + | 0.917 | 0.939 | 0.909 |
| 762 | rs7088834 | chr10 | 59032532 | + | 0.95 | 0.939 | 0.919 | 3801 | rs9288861 | chr3 | 109390508 | + | 0.917 | 0.938 | 0.902 |
| 763 | rs10763513 | chr10 | 59170426 | + | 0.059 | 0.098 | 0.056 | 3802 | rs9816413 | chr3 | 109390614 | + | 0.917 | 0.939 | 0.902 |
| 764 | rs12359064 | chr10 | 59567591 | + | 0.941 | 0.922 | 0.905 | 3803 | rs9288862 | chr3 | 109390664 | + | 0.917 | 0.938 | 0.902 |
| 765 | rs6479679 | chr10 | 61424719 | + | 0.917 | 0.935 | 0.926 | 3804 | rs9859807 | chr3 | 109391939 | + | 0.917 | 0.944 | 0.909 |
| 766 | rs16916356 | chr10 | 63028400 | + | 0.925 | 0.939 | 0.937 | 3805 | rs9871169 | chr3 | 109394360 | + | 0.917 | 0.937 | 0.902 |
| 767 | rs1933443 | chr10 | 63038076 | + | 0.925 | 0.939 | 0.938 | 3806 | rs12152431 | chr3 | 109394655 | + | 0.917 | 0.938 | 0.902 |
| 768 | rs10509152 | chr10 | 63039167 | + | 0.905 | 0.938 | 0.938 | 3807 | rs9863548 | chr3 | 109397887 | + | 0.917 | 0.943 | 0.902 |
| 769 | rs16916385 | chr10 | 63039258 | + | 0.908 | 0.939 | 0.936 | 3808 | rs11918055 | chr3 | 109419388 | + | 0.925 | 0.939 | 0.902 |

Fig. 9 Cont. 22

| | | | | | | | | | | | |
|---|---|---|---|---|---|---|---|---|---|---|---|
| 770 | rs12258095 | chr10 | 63043175 | + | 0.908 | 0.939 | 0.937 | 3809 | rs11924878 | chr3 | 111215577 | + | 0.933 | 0.939 | 0.918 |
| 771 | rs1456293 | chr10 | 63048055 | + | 0.908 | 0.939 | 0.937 | 3810 | rs1015582 | chr3 | 111355997 | + | 0.908 | 0.933 | 0.902 |
| 772 | rs10994843 | chr10 | 63066046 | + | 0.902 | 0.934 | 0.938 | 3811 | rs16856531 | chr3 | 1114445744 | + | 0.933 | 0.922 | 0.946 |
| 773 | rs11497865 | chr10 | 63079627 | + | 0.914 | 0.944 | 0.945 | 3812 | rs10511291 | chr3 | 1121556188 | + | 0.942 | 0.938 | 0.946 |
| 774 | rs10994852 | chr10 | 63080172 | + | 0.914 | 0.938 | 0.932 | 3813 | rs4450776 | chr3 | 112905819 | + | 0.067 | 0.073 | 0.054 |
| 775 | rs10994853 | chr10 | 63080361 | + | 0.908 | 0.943 | 0.936 | 3814 | rs1282963 | chr3 | 113128484 | + | 0.093 | 0.061 | 0.074 |
| 776 | rs2588949 | chr10 | 63265208 | + | 0.933 | 0.906 | 0.946 | 3815 | rs33940464 | chr3 | 114179120 | + | 0.908 | 0.911 | 0.95 |
| 777 | rs2675653 | chr10 | 63276569 | + | 0.933 | 0.917 | 0.946 | 3816 | rs7614288 | chr3 | 114457844 | + | 0.925 | 0.939 | 0.919 |
| 778 | rs10995933 | chr10 | 66045964 | + | 0.925 | 0.944 | 0.932 | 3817 | rs16860739 | chr3 | 114461868 | + | 0.95 | 0.939 | 0.922 |
| 779 | rs7903020 | chr10 | 66046735 | + | 0.925 | 0.944 | 0.938 | 3818 | rs3814401 | chr3 | 114479831 | + | 0.917 | 0.944 | 0.919 |
| 780 | rs2139911 | chr10 | 66112829 | + | 0.05 | 0.051 | 0.054 | 3819 | rs2247225 | chr3 | 115035412 | + | 0.942 | 0.949 | 0.923 |
| 781 | rs10740161 | chr10 | 66131263 | + | 0.051 | 0.05 | 0.054 | 3820 | rs12492484 | chr3 | 115205834 | + | 0.925 | 0.933 | 0.928 |
| 782 | rs1915608 | chr10 | 66145239 | + | 0.076 | 0.051 | 0.055 | 3821 | rs9869187 | chr3 | 115250036 | + | 0.906 | 0.902 | 0.901 |
| 783 | rs1082261C | chr10 | 67143423 | + | 0.948 | 0.922 | 0.95 | 3822 | rs13314266 | chr3 | 115279807 | + | 0.917 | 0.933 | 0.901 |
| 784 | rs1462829 | chr10 | 67648356 | + | 0.908 | 0.944 | 0.92 | 3823 | rs11920885 | chr3 | 115719669 | + | 0.939 | 0.943 | 0.931 |
| 785 | rs17247353 | chr10 | 67668342 | + | 0.908 | 0.944 | 0.919 | 3824 | rs16823178 | chr3 | 115948790 | + | 0.95 | 0.933 | 0.92 |
| 786 | rs1911473 | chr10 | 67679992 | + | 0.95 | 0.943 | 0.926 | 3825 | rs4831217 | chr3 | 116477430 | + | 0.942 | 0.933 | 0.941 |
| 787 | rs2254849 | chr10 | 70985384 | + | 0.069 | 0.093 | 0.09 | 3826 | rs9876009 | chr3 | 118931999 | + | 0.909 | 0.907 | 0.915 |
| 788 | rs17591282 | chr10 | 71356421 | + | 0.942 | 0.95 | 0.923 | 3827 | rs9858155 | chr3 | 118957425 | + | 0.917 | 0.933 | 0.91 |
| 789 | rs12241227 | chr10 | 71361700 | + | 0.922 | 0.911 | 0.946 | 3828 | rs939316 | chr3 | 119712060 | + | 0.917 | 0.916 | 0.905 |
| 790 | rs3750764 | chr10 | 71753841 | + | 0.912 | 0.949 | 0.929 | 3829 | rs4687920 | chr3 | 119786462 | + | 0.95 | 0.95 | 0.911 |
| 791 | rs4747142 | chr10 | 72693389 | + | 0.076 | 0.052 | 0.05 | 3830 | rs4687922 | chr3 | 119786820 | + | 0.95 | 0.95 | 0.911 |
| 792 | rs11598330 | chr10 | 72704959 | + | 0.907 | 0.944 | 0.941 | 3831 | rs7626927 | chr3 | 119787854 | + | 0.95 | 0.95 | 0.911 |
| 793 | rs2394789 | chr10 | 72706397 | + | 0.083 | 0.094 | 0.05 | 3832 | rs7638484 | chr3 | 119787909 | + | 0.95 | 0.949 | 0.941 |
| 794 | rs6480503 | chr10 | 72714960 | + | 0.093 | 0.096 | 0.073 | 3833 | rs4687817 | chr3 | 119789208 | + | 0.95 | 0.949 | 0.941 |
| 795 | rs6480504 | chr10 | 72716105 | + | 0.085 | 0.094 | 0.05 | 3834 | rs4687923 | chr3 | 119803092 | + | 0.95 | 0.95 | 0.911 |
| 796 | rs780680 | chr10 | 72792474 | + | 0.931 | 0.928 | 0.914 | 3835 | rs6771892 | chr3 | 119810276 | + | 0.95 | 0.95 | 0.909 |
| 797 | rs115977662 | chr10 | 72880499 | + | 0.912 | 0.923 | 0.902 | 3836 | rs17455252 | chr3 | 120019769 | + | 0.95 | 0.928 | 0.938 |
| 798 | rs11591454 | chr10 | 72880507 | + | 0.915 | 0.94 | 0.917 | 3837 | rs17455281 | chr3 | 120019795 | + | 0.95 | 0.928 | 0.937 |
| 799 | rs4747171 | chr10 | 73041044 | + | 0.908 | 0.933 | 0.946 | 3838 | rs16829649 | chr3 | 120478069 | + | 0.907 | 0.939 | 0.901 |
| 800 | rs11001230 | chr10 | 76403774 | + | 0.95 | 0.944 | 0.923 | 3839 | rs1388755 | chr3 | 121430401 | + | 0.1 | 0.05 | 0.072 |
| 801 | rs11001239 | chr10 | 76427413 | + | 0.925 | 0.944 | 0.919 | 3840 | rs1464099 | chr3 | 122807333 | + | 0.083 | 0.056 | 0.099 |
| 802 | rs12218784 | chr10 | 76427497 | + | 0.925 | 0.944 | 0.927 | 3841 | rs4676761 | chr3 | 123082801 | + | 0.075 | 0.078 | 0.099 |
| 803 | rs3781252 | chr10 | 76430637 | + | 0.908 | 0.944 | 0.914 | 3842 | rs7625960 | chr3 | 123085312 | + | 0.055 | 0.053 | 0.078 |
| 804 | rs1649988 | chr10 | 79717424 | + | 0.95 | 0.917 | 0.914 | 3843 | rs2293613 | chr3 | 123125026 | + | 0.933 | 0.933 | 0.923 |

Fig. 9 Cont. 23

| # | rs | chr | pos | strand | v1 | v2 | v3 | # | rs | chr | pos | strand | v1 | v2 | v3 |
|---|---|---|---|---|---|---|---|---|---|---|---|---|---|---|---|
| 805 | rs16935935 | chr10 | 79866558 | + | 0.942 | 0.927 | 0.918 | 3844 | rs1920310 | chr3 | 123145090 | + | 0.925 | 0.925 | 0.923 |
| 806 | rs11002586 | chr10 | 79940075 | + | 0.917 | 0.904 | 0.901 | 3845 | rs4602434 | chr3 | 123171325 | + | 0.925 | 0.933 | 0.923 |
| 807 | rs7078982 | chr10 | 80316227 | + | 0.917 | 0.922 | 0.919 | 3846 | rs9835545 | chr3 | 123809268 | + | 0.908 | 0.95 | 0.905 |
| 808 | rs10882499 | chr10 | 82759279 | + | 0.907 | 0.908 | 0.92 | 3847 | rs9823535 | chr3 | 123810640 | + | 0.908 | 0.95 | 0.914 |
| 809 | rs10882541 | chr10 | 82803658 | + | 0.914 | 0.917 | 0.912 | 3848 | rs16833457 | chr3 | 123922733 | + | 0.95 | 0.917 | 0.923 |
| 810 | rs17712426 | chr10 | 83553627 | + | 0.942 | 0.944 | 0.923 | 3849 | rs13095775 | chr3 | 123987164 | + | 0.924 | 0.917 | 0.923 |
| 811 | rs17712988 | chr10 | 83579114 | + | 0.942 | 0.944 | 0.923 | 3850 | rs10511415 | chr3 | 124011725 | + | 0.917 | 0.916 | 0.923 |
| 812 | rs10509439 | chr10 | 83591904 | + | 0.947 | 0.914 | 0.941 | 3851 | rs1318840 | chr3 | 124030872 | + | 0.925 | 0.92 | 0.923 |
| 813 | rs10883976 | chr10 | 83710211 | + | 0.95 | 0.904 | 0.937 | 3852 | rs7647458 | chr3 | 124060357 | + | 0.925 | 0.922 | 0.923 |
| 814 | rs2162629 | chr10 | 83940783 | + | 0.95 | 0.939 | 0.946 | 3853 | rs16833750 | chr3 | 124196931 | + | 0.95 | 0.933 | 0.95 |
| 815 | rs11592457 | chr10 | 85145754 | + | 0.907 | 0.938 | 0.946 | 3854 | rs2061085 | chr3 | 126487275 | + | 0.95 | 0.95 | 0.919 |
| 816 | rs17104368 | chr10 | 86667508 | + | 0.915 | 0.911 | 0.945 | 3855 | rs9852389 | chr3 | 126488221 | + | 0.95 | 0.949 | 0.918 |
| 817 | rs1933958 | chr10 | 86686451 | + | 0.924 | 0.921 | 0.946 | 3856 | rs4679460 | chr3 | 126927729 | + | 0.073 | 0.079 | 0.096 |
| 818 | rs11201313 | chr10 | 86687142 | + | 0.908 | 0.92 | 0.946 | 3857 | rs2971270 | chr3 | 126932304 | + | 0.911 | 0.924 | 0.943 |
| 819 | rs1338860 | chr10 | 86689035 | + | 0.908 | 0.906 | 0.946 | 3858 | rs4679325 | chr3 | 128224168 | + | 0.95 | 0.916 | 0.901 |
| 820 | rs1933941 | chr10 | 86701009 | + | 0.908 | 0.91 | 0.946 | 3859 | rs13070949 | chr3 | 128649509 | + | 0.915 | 0.906 | 0.905 |
| 821 | rs17104445 | chr10 | 86705793 | + | 0.925 | 0.906 | 0.946 | 3860 | rs6777714 | chr3 | 128667459 | + | 0.95 | 0.91 | 0.905 |
| 822 | rs12569712 | chr10 | 86716466 | + | 0.925 | 0.911 | 0.946 | 3861 | rs6764517 | chr3 | 129230531 | + | 0.054 | 0.085 | 0.071 |
| 823 | rs7907234 | chr10 | 88165186 | + | 0.938 | 0.902 | 0.918 | 3862 | rs9855048 | chr3 | 129646580 | + | 0.924 | 0.933 | 0.932 |
| 824 | rs11597669 | chr10 | 88639156 | + | 0.941 | 0.939 | 0.941 | 3863 | rs17747964 | chr3 | 1318 29406 | + | 0.95 | 0.944 | 0.941 |
| 825 | rs647416 | chr10 | 89736548 | + | 0.933 | 0.904 | 0.911 | 3864 | rs6805937 | chr3 | 1331 22301 | + | 0.92 | 0.905 | 0.935 |
| 826 | rs809368 | chr10 | 89786797 | + | 0.94 | 0.93 | 0.935 | 3865 | rs4462908 | chr3 | 1413 09441 | + | 0.933 | 0.939 | 0.946 |
| 827 | rs4592343 | chr10 | 91197655 | + | 0.907 | 0.931 | 0.917 | 3866 | rs349552 | chr3 | 141742735 | + | 0.95 | 0.916 | 0.932 |
| 828 | rs12571183 | chr10 | 92085645 | + | 0.947 | 0.903 | 0.92 | 3867 | rs3816690 | chr3 | 144049720 | + | 0.927 | 0.925 | 0.941 |
| 829 | rs11188388 | chr10 | 97350493 | + | 0.908 | 0.944 | 0.932 | 3868 | rs11926631 | chr3 | 144113737 | + | 0.917 | 0.932 | 0.928 |
| 830 | rs11188410 | chr10 | 97386551 | + | 0.931 | 0.943 | 0.932 | 3869 | rs9859012 | chr3 | 144464313 | + | 0.933 | 0.935 | 0.917 |
| 831 | rs11188415 | chr10 | 97398766 | + | 0.932 | 0.939 | 0.945 | 3870 | rs1355476 | chr3 | 147919806 | + | 0.942 | 0.95 | 0.929 |
| 832 | rs11188431 | chr10 | 97429280 | + | 0.925 | 0.939 | 0.946 | 3871 | rs6440487 | chr3 | 148788481 | + | 0.933 | 0.944 | 0.918 |
| 833 | rs3818833 | chr10 | 97432298 | + | 0.925 | 0.949 | 0.937 | 3872 | rs6765573 | chr3 | 148790793 | + | 0.933 | 0.944 | 0.919 |
| 834 | rs12358517 | chr10 | 97438391 | + | 0.925 | 0.939 | 0.946 | 3873 | rs16859608 | chr3 | 148842762 | + | 0.933 | 0.944 | 0.929 |
| 835 | rs11188846 | chr10 | 97498997 | + | 0.925 | 0.939 | 0.946 | 3874 | rs275690 | chr3 | 149828216 | + | 0.942 | 0.944 | 0.923 |
| 836 | rs11188469 | chr10 | 97501891 | + | 0.925 | 0.939 | 0.937 | 3875 | rs13095262 | chr3 | 150397852 | + | 0.95 | 0.949 | 0.914 |
| 837 | rs11188475 | chr10 | 97514924 | + | 0.94 | 0.938 | 0.946 | 3876 | rs13075891 | chr3 | 150398264 | + | 0.95 | 0.95 | 0.92 |
| 838 | rs7093453 | chr10 | 97561565 | + | 0.925 | 0.939 | 0.936 | 3877 | rs13075921 | chr3 | 150398318 | + | 0.95 | 0.95 | 0.923 |
| 839 | rs3181121 | chr10 | 97608570 | + | 0.925 | 0.949 | 0.937 | 3878 | rs3816893 | chr3 | 150410401 | + | 0.95 | 0.949 | 0.914 |

Fig. 9 Cont. 24

| | | | | | | | | | | | | |
|---|---|---|---|---|---|---|---|---|---|---|---|---|
| 840 | rs3176882 | chr10 | 97613997 | + | 0.925 | 0.949 | 0.919 | 3879 | rs16861954 | chr3 | 150737390 | + | 0.908 | 0.933 | 0.91 |
| 841 | rs7100644 | chr10 | 97618428 | + | 0.925 | 0.939 | 0.946 | 3880 | rs2903688 | chr3 | 151397480 | + | 0.917 | 0.943 | 0.905 |
| 842 | rs11188705 | chr10 | 98066200 | + | 0.947 | 0.947 | 0.923 | 3881 | rs10804776 | chr3 | 158210022 | + | 0.907 | 0.928 | 0.936 |
| 843 | rs2181324 | chr10 | 98135274 | + | 0.945 | 0.947 | 0.95 | 3882 | rs2362248 | chr3 | 159427678 | + | 0.939 | 0.902 | 0.938 |
| 844 | rs11189425 | chr10 | 99649364 | + | 0.908 | 0.917 | 0.941 | 3883 | rs17742826 | chr3 | 160734333 | + | 0.908 | 0.911 | 0.905 |
| 845 | rs11189426 | chr10 | 99649457 | + | 0.902 | 0.908 | 0.941 | 3884 | rs890914 | chr3 | 161184501 | + | 0.933 | 0.928 | 0.911 |
| 846 | rs7914222 | chr10 | 99656265 | + | 0.941 | 0.91 | 0.941 | 3885 | rs2243136 | chr3 | 161195781 | + | 0.941 | 0.937 | 0.95 |
| 847 | rs12219837 | chr10 | 99666393 | + | 0.94 | 0.919 | 0.95 | 3886 | rs4635753 | chr3 | 161842405 | + | 0.068 | 0.057 | 0.087 |
| 848 | rs3793702 | chr10 | 99668856 | + | 0.908 | 0.904 | 0.95 | 3887 | rs1947498 | chr3 | 161936112 | + | 0.933 | 0.916 | 0.907 |
| 849 | rs11189431 | chr10 | 99669134 | + | 0.908 | 0.906 | 0.95 | 3888 | rs16832548 | chr3 | 162701699 | + | 0.915 | 0.944 | 0.94 |
| 850 | rs11189572 | chr10 | 100108255 | + | 0.908 | 0.927 | 0.934 | 3889 | rs17421292 | chr3 | 162748261 | + | 0.942 | 0.911 | 0.938 |
| 851 | rs1462140 | chr10 | 100355999 | + | 0.95 | 0.901 | 0.906 | 3890 | rs1347625 | chr3 | 163005093 | + | 0.908 | 0.944 | 0.936 |
| 852 | rs17722574 | chr10 | 101814651 | + | 0.932 | 0.928 | 0.938 | 3891 | rs4273381 | chr3 | 163005580 | + | 0.924 | 0.944 | 0.936 |
| 853 | rs12769818 | chr10 | 101905619 | + | 0.907 | 0.928 | 0.946 | 3892 | rs1436739 | chr3 | 163006637 | + | 0.908 | 0.944 | 0.936 |
| 854 | rs7923115 | chr10 | 101990210 | + | 0.912 | 0.928 | 0.936 | 3893 | rs9859426 | chr3 | 163006553 | + | 0.908 | 0.95 | 0.936 |
| 855 | rs12763385 | chr10 | 101991221 | + | 0.914 | 0.933 | 0.938 | 3894 | rs7641571 | chr3 | 164232530 | + | 0.912 | 0.928 | 0.926 |
| 856 | rs7896703 | chr10 | 102008621 | + | 0.922 | 0.929 | 0.936 | 3895 | rs2872065 | chr3 | 167239267 | + | 0.942 | 0.927 | 0.946 |
| 857 | rs1393492 | chr10 | 102117376 | + | 0.917 | 0.915 | 0.937 | 3896 | rs6778008 | chr3 | 167249226 | + | 0.945 | 0.943 | 0.936 |
| 858 | rs685397 | chr10 | 102133198 | + | 0.933 | 0.921 | 0.938 | 3897 | rs16850003 | chr3 | 167264114 | + | 0.942 | 0.927 | 0.927 |
| 859 | rs11191937 | chr10 | 105923310 | + | 0.946 | 0.923 | 0.917 | 3898 | rs9860703 | chr3 | 167499191 | + | 0.93 | 0.948 | 0.946 |
| 860 | rs11191946 | chr10 | 105952281 | + | 0.924 | 0.912 | 0.918 | 3899 | rs9810972 | chr3 | 167500506 | + | 0.915 | 0.949 | 0.946 |
| 861 | rs7099278 | chr10 | 107015790 | + | 0.95 | 0.95 | 0.905 | 3900 | rs9981427 | chr3 | 167533110 | + | 0.908 | 0.944 | 0.936 |
| 862 | rs7916802 | chr10 | 107027011 | + | 0.908 | 0.95 | 0.905 | 3901 | rs9875627 | chr3 | 167561754 | + | 0.908 | 0.949 | 0.941 |
| 863 | rs2926457 | chr10 | 107245337 | + | 0.067 | 0.079 | 0.059 | 3902 | rs9876002 | chr3 | 167561997 | + | 0.908 | 0.949 | 0.946 |
| 864 | rs2926456 | chr10 | 107245461 | + | 0.067 | 0.08 | 0.08 | 3903 | rs9826385 | chr3 | 167563408 | + | 0.932 | 0.944 | 0.946 |
| 865 | rs11192687 | chr10 | 107799986 | + | 0.949 | 0.922 | 0.946 | 3904 | rs9810572 | chr3 | 167563631 | + | 0.941 | 0.949 | 0.946 |
| 866 | rs11192688 | chr10 | 107800240 | + | 0.942 | 0.922 | 0.937 | 3905 | rs9871837 | chr3 | 167578828 | + | 0.908 | 0.944 | 0.941 |
| 867 | rs11192690 | chr10 | 107801245 | + | 0.941 | 0.921 | 0.946 | 3906 | rs9844810 | chr3 | 167580709 | + | 0.933 | 0.944 | 0.941 |
| 868 | rs11192691 | chr10 | 107801403 | + | 0.942 | 0.921 | 0.945 | 3907 | rs9839126 | chr3 | 167641401 | + | 0.931 | 0.944 | 0.937 |
| 869 | rs11192698 | chr10 | 107811288 | + | 0.933 | 0.922 | 0.937 | 3908 | rs9827437 | chr3 | 167655147 | + | 0.907 | 0.949 | 0.937 |
| 870 | rs11192695 | chr10 | 107814026 | + | 0.933 | 0.922 | 0.946 | 3909 | rs17251311 | chr3 | 170499068 | + | 0.941 | 0.933 | 0.932 |
| 871 | rs11192704 | chr10 | 107819451 | + | 0.95 | 0.922 | 0.946 | 3910 | rs16853574 | chr3 | 170562457 | + | 0.917 | 0.917 | 0.946 |
| 872 | rs7907139 | chr10 | 107823630 | + | 0.939 | 0.927 | 0.945 | 3911 | rs17559919 | chr3 | 170666137 | + | 0.933 | 0.938 | 0.928 |
| 873 | rs4244265 | chr10 | 108957520 | + | 0.092 | 0.05 | 0.068 | 3912 | rs9831990 | chr3 | 172415672 | + | 0.915 | 0.944 | 0.946 |
| 874 | rs11193818 | chr10 | 109718131 | + | 0.942 | 0.944 | 0.923 | 3913 | rs9838981 | chr3 | 172431394 | + | 0.922 | 0.944 | 0.907 |

Fig. 9 Cont. 25

| | | | | | | | | | |
|---|---|---|---|---|---|---|---|---|---|
| 875 rs10509987 chr10 | 110013826 | + | 0.942 | 0.939 | 0.914 | 3914 rs7355905 chr3 | 172431970 | + | 0.917 0.949 0.91 |
| 876 rs1415555 chr10 | 110492172 | + | 0.933 | 0.944 | 0.918 | 3915 rs4521259 chr3 | 174794654 | + | 0.075 0.067 0.054 |
| 877 rs1415554 chr10 | 110492537 | + | 0.948 | 0.944 | 0.923 | 3916 rs3853388 chr3 | 174799756 | + | 0.05 0.067 0.098 |
| 878 rs3887904 chr10 | 110571798 | + | 0.933 | 0.944 | 0.938 | 3917 rs3866707 chr3 | 174800804 | + | 0.092 0.067 0.098 |
| 879 rs11195124 chr10 | 112166291 | + | 0.949 | 0.935 | 0.945 | 3918 rs10513714 chr3 | 174806202 | + | 0.941 0.948 0.911 |
| 880 rs11195321 chr10 | 112539411 | + | 0.942 | 0.944 | 0.905 | 3919 rs7638716 chr3 | 174896213 | + | 0.907 0.904 0.946 |
| 881 rs6585034 chr10 | 112813413 | + | 0.95 | 0.922 | 0.902 | 3920 rs11920792 chr3 | 174945349 | + | 0.942 0.95 0.905 |
| 882 rs7080792 chr10 | 112819094 | + | 0.95 | 0.921 | 0.902 | 3921 rs2193844 chr3 | 176696223 | + | 0.904 0.92 0.944 |
| 883 rs17186196 chr10 | 112821777 | + | 0.95 | 0.922 | 0.914 | 3922 rs4429642 chr3 | 176811107 | + | 0.067 0.094 0.072 |
| 884 rs7096359 chr10 | 112823551 | + | 0.933 | 0.915 | 0.914 | 3923 rs4434155 chr3 | 176811190 | + | 0.05 0.094 0.072 |
| 885 rs105009933 chr10 | 112855333 | + | 0.949 | 0.938 | 0.905 | 3924 rs4459913 chr3 | 176815917 | + | 0.05 0.094 0.062 |
| 886 rs17128458 chr10 | 112885850 | + | 0.95 | 0.944 | 0.946 | 3925 rs14888883 chr3 | 178053039 | + | 0.052 0.062 0.054 |
| 887 rs11195475 chr10 | 112955850 | + | 0.942 | 0.949 | 0.902 | 3926 rs9861424 chr3 | 178055951 | + | 0.059 0.064 0.056 |
| 888 rs12258397 chr10 | 112958769 | + | 0.908 | 0.949 | 0.914 | 3927 rs17553377 chr3 | 178237805 | + | 0.942 0.95 0.92 |
| 889 rs17189569 chr10 | 112960941 | + | 0.95 | 0.944 | 0.929 | 3928 rs2862644 chr3 | 178253094 | + | 0.942 0.949 0.91 |
| 890 rs17775480 chr10 | 112969072 | + | 0.95 | 0.95 | 0.928 | 3929 rs7651265 chr3 | 180375723 | + | 0.904 0.92 0.905 |
| 891 rs12780993 chr10 | 112999248 | + | 0.95 | 0.95 | 0.938 | 3930 rs2177591 chr3 | 181079498 | + | 0.092 0.09 0.077 |
| 892 rs115993394 chr10 | 113004127 | + | 0.948 | 0.949 | 0.934 | 3931 rs3821798 chr3 | 181121893 | + | 0.075 0.09 0.077 |
| 893 rs105009938 chr10 | 113018607 | + | 0.925 | 0.95 | 0.928 | 3932 rs6414498 chr3 | 184353908 | + | 0.1 0.083 0.09 |
| 894 rs3125455 chr10 | 113257756 | + | 0.085 | 0.05 | 0.054 | 3933 rs12163540 chr3 | 184755823 | + | 0.933 0.922 0.946 |
| 895 rs9645581 chr10 | 113967283 | + | 0.924 | 0.901 | 0.932 | 3934 rs12493550 chr3 | 185235467 | + | 0.917 0.922 0.928 |
| 896 rs4917633 chr10 | 114080315 | + | 0.075 | 0.067 | 0.09 | 3935 rs12696534 chr3 | 185886997 | + | 0.1 0.056 0.098 |
| 897 rs17129824 chr10 | 114218901 | + | 0.913 | 0.914 | 0.933 | 3936 rs7651025 chr3 | 185890905 | + | 0.05 0.056 0.098 |
| 898 rs2240877 chr10 | 115333576 | + | 0.908 | 0.927 | 0.91 | 3937 rs7619914 chr3 | 186320739 | + | 0.067 0.062 0.054 |
| 899 rs11593766 chr10 | 115447254 | + | 0.907 | 0.91 | 0.919 | 3938 rs16861384 chr3 | 188167205 | + | 0.942 0.95 0.945 |
| 900 rs3124738 chr10 | 115461763 | + | 0.1 | 0.094 | 0.081 | 3939 rs9866953 chr3 | 188381472 | + | 0.908 0.932 0.938 |
| 901 rs111196447 chr10 | 115462902 | + | 0.947 | 0.932 | 0.917 | 3940 rs12485777 chr3 | 188743727 | + | 0.931 0.903 0.905 |
| 902 rs17090895 chr10 | 115464026 | + | 0.942 | 0.906 | 0.938 | 3941 rs568066 chr3 | 189161679 | + | 0.075 0.067 0.081 |
| 903 rs12569537 chr10 | 115468116 | + | 0.93 | 0.908 | 0.935 | 3942 rs11923721 chr3 | 189582882 | + | 0.949 0.908 0.936 |
| 904 rs17090907 chr10 | 115468667 | + | 0.941 | 0.906 | 0.944 | 3943 rs9821596 chr3 | 190580499 | + | 0.925 0.921 0.928 |
| 905 rs17090911 chr10 | 115468970 | + | 0.942 | 0.906 | 0.919 | 3944 rs1516496 chr3 | 192982194 | + | 0.942 0.916 0.914 |
| 906 rs111196473 chr10 | 115502483 | + | 0.917 | 0.911 | 0.92 | 3945 rs6803696 chr3 | 192988865 | + | 0.924 0.917 0.907 |
| 907 rs17653278 chr10 | 115728492 | + | 0.942 | 0.933 | 0.946 | 3946 rs2293147 chr3 | 193402670 | + | 0.908 0.949 0.91 |
| 908 rs17574901 chr10 | 115729399 | + | 0.949 | 0.944 | 0.946 | 3947 rs1773176 chr3 | 195797527 | + | 0.058 0.062 0.08 |
| 909 rs17653713 chr10 | 115736409 | + | 0.95 | 0.922 | 0.945 | 3948 rs9288751 chr3 | 195797583 | + | 0.051 0.056 0.086 |

Fig. 9 Cont. 26

| | | | | | | | | | | |
|---|---|---|---|---|---|---|---|---|---|---|
| 910 | rs10160168 | chr10 | 115964818 | + | 0.941 | 0.922 | 0.936 | 3949 | rs708632 | chr3 | 195806614 | + | 0.061 | 0.086 | 0.069 |
| 911 | rs10160173 | chr10 | 115965055 | + | 0.933 | 0.921 | 0.929 | 3950 | rs789850 | chr3 | 195806785 | + | 0.05 | 0.078 | 0.081 |
| 912 | rs12253699 | chr10 | 115965447 | + | 0.933 | 0.921 | 0.929 | 3951 | rs789852 | chr3 | 195808387 | + | 0.05 | 0.056 | 0.081 |
| 913 | rs10159905 | chr10 | 115967055 | + | 0.933 | 0.921 | 0.929 | 3952 | rs6437416 | chr3 | 195981661 | + | 0.907 | 0.916 | 0.937 |
| 914 | rs12266538 | chr10 | 115981735 | + | 0.95 | 0.936 | 0.901 | 3953 | rs6793035 | chr3 | 196543309 | + | 0.093 | 0.054 | 0.089 |
| 915 | rs10749199 | chr10 | 117926346 | + | 0.083 | 0.094 | 0.054 | 3954 | rs3773844 | chr3 | 198297441 | + | 0.092 | 0.056 | 0.068 |
| 916 | rs10749200 | chr10 | 117926361 | + | 0.083 | 0.094 | 0.054 | 3955 | rs1741950 | chr3 | 198491097 | + | 0.05 | 0.079 | 0.068 |
| 917 | rs4751580 | chr10 | 117934730 | + | 0.052 | 0.069 | 0.057 | 3956 | rs2242235 | chr4 | 745210 | + | 0.949 | 0.932 | 0.905 |
| 918 | rs12770865 | chr10 | 119513025 | + | 0.932 | 0.927 | 0.941 | 3957 | rs1811560 | chr4 | 753229 | + | 0.946 | 0.925 | 0.929 |
| 919 | rs1925256 | chr10 | 119559734 | + | 0.058 | 0.062 | 0.054 | 3958 | rs11934423 | chr4 | 4962213 | + | 0.907 | 0.907 | 0.923 |
| 920 | rs912741 | chr10 | 119563460 | + | 0.058 | 0.062 | 0.063 | 3959 | rs11946368 | chr4 | 4990324 | + | 0.94 | 0.917 | 0.91 |
| 921 | rs17097692 | chr10 | 120208179 | + | 0.941 | 0.928 | 0.92 | 3960 | rs1046322 | chr4 | 6353349 | + | 0.925 | 0.917 | 0.905 |
| 922 | rs4751702 | chr10 | 120969739 | + | 0.067 | 0.1 | 0.081 | 3961 | rs9654057 | chr4 | 6597514 | + | 0.92 | 0.924 | 0.947 |
| 923 | rs17098586 | chr10 | 120996217 | + | 0.95 | 0.917 | 0.941 | 3962 | rs4586932 | chr4 | 8985469 | + | 0.058 | 0.061 | 0.071 |
| 924 | rs11199047 | chr10 | 121366007 | + | 0.927 | 0.942 | 0.923 | 3963 | rs2127797 | chr4 | 9092441 | + | 0.083 | 0.091 | 0.062 |
| 925 | rs11199399 | chr10 | 122305913 | + | 0.95 | 0.922 | 0.945 | 3964 | rs11722581 | chr4 | 9093860 | + | 0.083 | 0.07 | 0.062 |
| 926 | rs4752487 | chr10 | 122726411 | + | 0.932 | 0.909 | 0.932 | 3965 | rs12647851 | chr4 | 9333617 | + | 0.925 | 0.95 | 0.95 |
| 927 | rs11200091 | chr10 | 123470616 | + | 0.912 | 0.938 | 0.946 | 3966 | rs11729012 | chr4 | 10309851 | + | 0.069 | 0.052 | 0.054 |
| 928 | rs11597291 | chr10 | 123509970 | + | 0.939 | 0.903 | 0.943 | 3967 | rs12646691 | chr4 | 10316911 | + | 0.931 | 0.921 | 0.929 |
| 929 | rs10159583 | chr10 | 123742659 | + | 0.945 | 0.907 | 0.906 | 3968 | rs4452425 | chr4 | 10320566 | + | 0.908 | 0.916 | 0.929 |
| 930 | rs12241688 | chr10 | 123908925 | + | 0.908 | 0.946 | 0.95 | 3969 | rs7695689 | chr4 | 10323871 | + | 0.915 | 0.917 | 0.946 |
| 931 | rs9423334 | chr10 | 125109613 | + | 0.908 | 0.92 | 0.919 | 3970 | rs9997174 | chr4 | 10422066 | + | 0.908 | 0.904 | 0.927 |
| 932 | rs7902179 | chr10 | 126047531 | + | 0.949 | 0.907 | 0.904 | 3971 | rs6843978 | chr4 | 10859239 | + | 0.906 | 0.901 | 0.902 |
| 933 | rs11245199 | chr10 | 126172611 | + | 0.945 | 0.91 | 0.901 | 3972 | rs4697875 | chr4 | 10949638 | + | 0.087 | 0.096 | 0.074 |
| 934 | rs12572285 | chr10 | 126266577 | + | 0.932 | 0.902 | 0.943 | 3973 | rs1590059 | chr4 | 10971605 | + | 0.078 | 0.079 | 0.061 |
| 935 | rs4962487 | chr10 | 127424824 | + | 0.058 | 0.051 | 0.086 | 3974 | rs2058360 | chr4 | 10988383 | + | 0.06 | 0.07 | 0.068 |
| 936 | rs7903058 | chr10 | 127669154 | + | 0.083 | 0.078 | 0.098 | 3975 | rs1528081 | chr4 | 11007980 | + | 0.059 | 0.068 | 0.068 |
| 937 | rs12413049 | chr10 | 127755987 | + | 0.904 | 0.931 | 0.92 | 3976 | rs4305508 | chr4 | 11011606 | + | 0.067 | 0.072 | 0.068 |
| 938 | rs1380436 | chr10 | 127757991 | + | 0.933 | 0.926 | 0.92 | 3977 | rs1382752 | chr4 | 11752465 | + | 0.933 | 0.95 | 0.914 |
| 939 | rs17154276 | chr10 | 127781262 | + | 0.948 | 0.91 | 0.932 | 3978 | rs17331012 | chr4 | 11753753 | + | 0.933 | 0.95 | 0.91 |
| 940 | rs2804427 | chr10 | 128278719 | + | 0.932 | 0.911 | 0.945 | 3979 | rs1397622 | chr4 | 13492251 | + | 0.942 | 0.916 | 0.901 |
| 941 | rs2842164 | chr10 | 128281427 | + | 0.925 | 0.904 | 0.937 | 3980 | rs16889409 | chr4 | 13513401 | + | 0.933 | 0.933 | 0.928 |
| 942 | rs7921079 | chr10 | 128326463 | + | 0.942 | 0.917 | 0.905 | 3981 | rs16889439 | chr4 | 13527526 | + | 0.915 | 0.928 | 0.927 |
| 943 | rs4564243 | chr10 | 128327342 | + | 0.94 | 0.919 | 0.905 | 3982 | rs726056 | chr4 | 13532702 | + | 0.942 | 0.938 | 0.914 |
| 944 | rs7069588 | chr10 | 128328085 | + | 0.917 | 0.921 | 0.91 | 3983 | rs11944910 | chr4 | 13727049 | + | 0.092 | 0.084 | 0.089 |

Fig. 9 Cont. 27

| | | | | | | | | | | | |
|---|---|---|---|---|---|---|---|---|---|---|---|
| 945 | rs4751179 | chr10 | 128699635 | + | 0.093 | 0.067 | 0.077 | 3984 | rs16889755 chr4 | 13750341 | + | 0.949 | 0.917 | 0.901 |
| 946 | rs7068941 | chr10 | 128718078 | + | 0.058 | 0.062 | 0.081 | 3985 | rs16889769 chr4 | 13768095 | + | 0.915 | 0.917 | 0.902 |
| 947 | rs7079472 | chr10 | 128721993 | + | 0.06 | 0.057 | 0.096 | 3986 | rs16891486 chr4 | 14759075 | + | 0.925 | 0.921 | 0.946 |
| 948 | rs880272 | chr10 | 128730832 | + | 0.067 | 0.061 | 0.082 | 3987 | rs10008462 chr4 | 14807034 | + | 0.933 | 0.916 | 0.946 |
| 949 | rs1538788 | chr10 | 128735637 | + | 0.059 | 0.061 | 0.077 | 3988 | rs6851785 chr4 | 15886589 | + | 0.942 | 0.922 | 0.91 |
| 950 | rs7923722 | chr10 | 128744069 | + | 0.075 | 0.072 | 0.082 | 3989 | rs2215639 chr4 | 15949608 | + | 0.95 | 0.921 | 0.91 |
| 951 | rs988521 | chr10 | 129949288 | + | 0.905 | 0.906 | 0.936 | 3990 | rs10489060 chr4 | 15961647 | + | 0.95 | 0.921 | 0.902 |
| 952 | rs2244286 | chr10 | 131753694 | + | 0.076 | 0.061 | 0.08 | 3991 | rs10489059 chr4 | 15965196 | + | 0.908 | 0.921 | 0.902 |
| 953 | rs1186085 | chr10 | 131755311 | + | 0.083 | 0.062 | 0.08 | 3992 | rs16893385 chr4 | 15965932 | + | 0.908 | 0.927 | 0.91 |
| 954 | rs12255434 | chr10 | 131969078 | + | 0.918 | 0.929 | 0.938 | 3993 | rs16893387 chr4 | 15967510 | + | 0.908 | 0.922 | 0.91 |
| 955 | rs430345 | chr10 | 132171228 | + | 0.076 | 0.086 | 0.055 | 3994 | rs1501129 chr4 | 15995671 | + | 0.908 | 0.916 | 0.919 |
| 956 | rs2484234 | chr10 | 132173810 | + | 0.058 | 0.08 | 0.081 | 3995 | rs2312947 chr4 | 15999441 | + | 0.925 | 0.91 | 0.92 |
| 957 | rs12356074 | chr10 | 133248004 | + | 0.949 | 0.921 | 0.902 | 3996 | rs16893441 chr4 | 16000072 | + | 0.905 | 0.911 | 0.923 |
| 958 | rs2995307 | chr10 | 134929778 | + | 0.092 | 0.083 | 0.081 | 3997 | rs4698486 chr4 | 16027497 | + | 0.933 | 0.904 | 0.937 |
| 959 | rs2995308 | chr10 | 134929852 | + | 0.092 | 0.083 | 0.083 | 3998 | rs16893682 chr4 | 16218899 | + | 0.917 | 0.938 | 0.941 |
| 960 | rs2995310 | chr10 | 134932800 | + | 0.056 | 0.051 | 0.086 | 3999 | rs17443775 chr4 | 16585517 | + | 0.95 | 0.95 | 0.936 |
| 961 | rs3008324 | chr10 | 134936370 | + | 0.092 | 0.085 | 0.081 | 4000 | rs9291654 chr4 | 16735794 | + | 0.933 | 0.949 | 0.91 |
| 962 | rs2275725 | chr10 | 134939025 | + | 0.059 | 0.084 | 0.093 | 4001 | rs4698169 chr4 | 16744441 | + | 0.914 | 0.901 | 0.932 |
| 963 | rs3008328 | chr10 | 134942580 | + | 0.092 | 0.083 | 0.081 | 4002 | rs16895779 chr4 | 17418943 | + | 0.93 | 0.945 | 0.928 |
| 964 | rs10857729 | chr10 | 135171764 | + | 0.942 | 0.931 | 0.938 | 4003 | rs2302211 chr4 | 17428233 | + | 0.942 | 0.938 | 0.902 |
| 965 | rs7103978 | chr11 | 1078815 | + | 0.933 | 0.95 | 0.914 | 4004 | rs10939761 chr4 | 17429615 | + | 0.942 | 0.938 | 0.902 |
| 966 | rs10768675 | chr11 | 1590237 | + | 0.922 | 0.907 | 0.932 | 4005 | rs10489040 chr4 | 17437343 | + | 0.942 | 0.938 | 0.902 |
| 967 | rs11038260 | chr11 | 1630292 | + | 0.947 | 0.923 | 0.93 | 4006 | rs16895838 chr4 | 17441516 | + | 0.942 | 0.939 | 0.902 |
| 968 | rs12808620 | chr11 | 2564426 | + | 0.924 | 0.947 | 0.914 | 4007 | rs16895845 chr4 | 17444819 | + | 0.942 | 0.944 | 0.909 |
| 969 | rs231845 | chr11 | 2693259 | + | 0.915 | 0.948 | 0.908 | 4008 | rs2286536 chr4 | 17450718 | + | 0.908 | 0.939 | 0.928 |
| 970 | rs12362694 | chr11 | 3674705 | + | 0.942 | 0.917 | 0.937 | 4009 | rs16895877 chr4 | 17455620 | + | 0.908 | 0.938 | 0.928 |
| 971 | rs12284835 | chr11 | 3975604 | + | 0.907 | 0.943 | 0.91 | 4010 | rs16895878 chr4 | 17456379 | + | 0.942 | 0.939 | 0.928 |
| 972 | rs10498198 | chr11 | 4081307 | + | 0.933 | 0.921 | 0.946 | 4011 | rs16895883 chr4 | 17458012 | + | 0.942 | 0.939 | 0.902 |
| 973 | rs2268166 | chr11 | 4082585 | + | 0.917 | 0.922 | 0.941 | 4012 | rs16895884 chr4 | 17462824 | + | 0.908 | 0.939 | 0.928 |
| 974 | rs232045 | chr11 | 4100268 | + | 0.092 | 0.072 | 0.071 | 4013 | rs16895895 chr4 | 17463866 | + | 0.942 | 0.939 | 0.927 |
| 975 | rs10835678 | chr11 | 4123992 | + | 0.092 | 0.072 | 0.072 | 4014 | rs13144223 chr4 | 17481805 | + | 0.942 | 0.933 | 0.923 |
| 976 | rs1430404 | chr11 | 4489414 | + | 0.94 | 0.934 | 0.94 | 4015 | rs13113107 chr4 | 17526288 | + | 0.933 | 0.933 | 0.919 |
| 977 | rs1228285C | chr11 | 4507305 | + | 0.933 | 0.935 | 0.927 | 4016 | rs13102976 chr4 | 17588927 | + | 0.942 | 0.933 | 0.927 |
| 978 | rs12788743 | chr11 | 4923162 | + | 0.918 | 0.921 | 0.92 | 4017 | rs6449369 chr4 | 17873677 | + | 0.058 | 0.062 | 0.085 |
| 979 | rs12786696 | chr11 | 4923426 | + | 0.918 | 0.925 | 0.923 | 4018 | rs2192519 chr4 | 17874850 | + | 0.055 | 0.069 | 0.091 |

Fig. 9 Cont. 28

| | | | | | | | | | | | | |
|---|---|---|---|---|---|---|---|---|---|---|---|---|
| 980 | rs952667 | chr11 | 5412659 | + | 0.931 | 0.949 | 0.95 | 4019 | rs13149698 | chr4 | 18433922 | + | 0.95 | 0.904 | 0.917 |
| 981 | rs4910793 | chr11 | 5419637 | + | 0.933 | 0.943 | 0.95 | 4020 | rs12645759 | chr4 | 19570649 | + | 0.923 | 0.924 | 0.946 |
| 982 | rs4910794 | chr11 | 5426377 | + | 0.925 | 0.948 | 0.929 | 4021 | rs12507133 | chr4 | 19771800 | + | 0.95 | 0.906 | 0.914 |
| 983 | rs11040876 | chr11 | 6350752 | + | 0.908 | 0.95 | 0.923 | 4022 | rs13117394 | chr4 | 19778654 | + | 0.917 | 0.926 | 0.905 |
| 984 | rs4758429 | chr11 | 6552996 | + | 0.066 | 0.072 | 0.059 | 4023 | rs13120431 | chr4 | 20921125 | + | 0.946 | 0.93 | 0.945 |
| 985 | rs12364405 | chr11 | 7088070 | + | 0.93 | 0.925 | 0.923 | 4024 | rs16871243 | chr4 | 21110787 | + | 0.932 | 0.944 | 0.929 |
| 986 | rs11041205 | chr11 | 7100789 | + | 0.917 | 0.917 | 0.923 | 4025 | rs17539073 | chr4 | 22999259 | + | 0.917 | 0.944 | 0.919 |
| 987 | rs1858281 | chr11 | 7910420 | + | 0.067 | 0.067 | 0.081 | 4026 | rs17551181 | chr4 | 24025994 | + | 0.95 | 0.95 | 0.932 |
| 988 | rs1528128 | chr11 | 8111720 | + | 0.933 | 0.921 | 0.946 | 4027 | rs1089070 | chr4 | 24397001 | + | 0.915 | 0.917 | 0.938 |
| 989 | rs3812761 | chr11 | 8117499 | + | 0.933 | 0.921 | 0.938 | 4028 | rs16876811 | chr4 | 24711168 | + | 0.929 | 0.911 | 0.946 |
| 990 | rs11820921 | chr11 | 8130972 | + | 0.907 | 0.922 | 0.944 | 4029 | rs10014227 | chr4 | 24892262 | + | 0.924 | 0.906 | 0.95 |
| 991 | rs4758298 | chr11 | 8138538 | + | 0.933 | 0.922 | 0.95 | 4030 | rs1033103 | chr4 | 24903317 | + | 0.925 | 0.904 | 0.95 |
| 992 | rs11825426 | chr11 | 8145822 | + | 0.933 | 0.921 | 0.936 | 4031 | rs13128106 | chr4 | 24934362 | + | 0.95 | 0.95 | 0.929 |
| 993 | rs4758301 | chr11 | 8147559 | + | 0.908 | 0.938 | 0.95 | 4032 | rs16877042 | chr4 | 24953689 | + | 0.925 | 0.938 | 0.95 |
| 994 | rs16937236 | chr11 | 8220926 | + | 0.908 | 0.949 | 0.946 | 4033 | rs10032586 | chr4 | 25009566 | + | 0.931 | 0.92 | 0.95 |
| 995 | rs11606051 | chr11 | 8306585 | + | 0.931 | 0.928 | 0.928 | 4034 | rs2276950 | chr4 | 25370042 | + | 0.942 | 0.933 | 0.941 |
| 996 | rs10840606 | chr11 | 11148897 | + | 0.917 | 0.906 | 0.902 | 4035 | rs4692073 | chr4 | 25709884 | + | 0.05 | 0.079 | 0.086 |
| 997 | rs12364306 | chr11 | 11149646 | + | 0.948 | 0.91 | 0.914 | 4036 | rs946346 | chr4 | 26040484 | + | 0.05 | 0.061 | 0.088 |
| 998 | rs7121637 | chr11 | 11547589 | + | 0.059 | 0.078 | 0.054 | 4037 | rs4692322 | chr4 | 28064971 | + | 0.067 | 0.067 | 0.067 |
| 999 | rs9919632 | chr11 | 11549686 | + | 0.087 | 0.072 | 0.078 | 4038 | rs292037 | chr4 | 28076672 | + | 0.067 | 0.062 | 0.08 |
| 1000 | rs2306729 | chr11 | 12194691 | + | 0.925 | 0.911 | 0.91 | 4039 | rs11930458 | chr4 | 28478702 | + | 0.904 | 0.91 | 0.912 |
| 1001 | rs12294434 | chr11 | 12221659 | + | 0.942 | 0.939 | 0.914 | 4040 | rs7680112 | chr4 | 29257700 | + | 0.947 | 0.943 | 0.936 |
| 1002 | rs4757389 | chr11 | 12333636 | + | 0.075 | 0.067 | 0.08 | 4041 | rs11930330 | chr4 | 29282607 | + | 0.907 | 0.926 | 0.918 |
| 1003 | rs7113072 | chr11 | 12334622 | + | 0.082 | 0.062 | 0.065 | 4042 | rs16882208 | chr4 | 29351154 | + | 0.949 | 0.939 | 0.945 |
| 1004 | rs10734193 | chr11 | 12354210 | + | 0.9 | 0.094 | 0.095 | 4043 | rs16883118 | chr4 | 29847400 | + | 0.908 | 0.928 | 0.946 |
| 1005 | rs12098918 | chr11 | 12434991 | + | 0.93 | 0.92 | 0.927 | 4044 | rs16883126 | chr4 | 29848078 | + | 0.908 | 0.928 | 0.932 |
| 1006 | rs7124398 | chr11 | 13022995 | + | 0.922 | 0.933 | 0.932 | 4045 | rs17080793 | chr4 | 31647397 | + | 0.908 | 0.922 | 0.937 |
| 1007 | rs16913313 | chr11 | 13860753 | + | 0.95 | 0.944 | 0.946 | 4046 | rs6825247 | chr4 | 31738900 | + | 0.066 | 0.087 | 0.073 |
| 1008 | rs2615027 | chr11 | 15870567 | + | 0.1 | 0.089 | 0.05 | 4047 | rs11113320 | chr4 | 31939303 | + | 0.067 | 0.056 | 0.077 |
| 1009 | rs17703528 | chr11 | 17480050 | + | 0.942 | 0.944 | 0.91 | 4048 | rs4862925 | chr4 | 32069709 | + | 0.933 | 0.933 | 0.95 |
| 1010 | rs7107406 | chr11 | 17490989 | + | 0.924 | 0.944 | 0.919 | 4049 | rs4862927 | chr4 | 32090655 | + | 0.933 | 0.906 | 0.944 |
| 1011 | rs17714673 | chr11 | 17491427 | + | 0.925 | 0.944 | 0.919 | 4050 | rs4862931 | chr4 | 32100805 | + | 0.933 | 0.944 | 0.95 |
| 1012 | rs16934376 | chr11 | 17499779 | + | 0.942 | 0.95 | 0.923 | 4051 | rs16990009 | chr4 | 34252180 | + | 0.933 | 0.939 | 0.95 |
| 1013 | rs12793095 | chr11 | 17769116 | + | 0.939 | 0.935 | 0.95 | 4052 | rs12503828 | chr4 | 34362133 | + | 0.942 | 0.939 | 0.945 |
| 1014 | rs2721126 | chr11 | 18412757 | + | 0.058 | 0.05 | 0.098 | 4053 | rs12500647 | chr4 | 34362185 | + | 0.941 | 0.943 | 0.946 |

Fig. 9  Cont. 29

| | | | | | | | | | | | |
|---|---|---|---|---|---|---|---|---|---|---|---|
| 1015 | rs116059580 chr11 | 18691956 | + | 0.925 | 0.926 | 0.946 | 4054 | rs125058380 chr4 | 34363844 | + | 0.942 | 0.939 | 0.946 |
| 1016 | rs111606142 chr11 | 19139146 | + | 0.949 | 0.95 | 0.932 | 4055 | rs12501135 chr4 | 34364003 | + | 0.942 | 0.939 | 0.946 |
| 1017 | rs107665430 chr11 | 19310510 | + | 0.1 | 0.061 | 0.095 | 4056 | rs12501139 chr4 | 34364019 | + | 0.942 | 0.939 | 0.946 |
| 1018 | rs169373440 chr11 | 19980715 | + | 0.932 | 0.917 | 0.905 | 4057 | rs12510531 chr4 | 34371087 | + | 0.942 | 0.939 | 0.946 |
| 1019 | rs116052750 chr11 | 19988441 | + | 0.942 | 0.927 | 0.905 | 4058 | rs125070100 chr4 | 34371135 | + | 0.942 | 0.939 | 0.946 |
| 1020 | rs116057040 chr11 | 19988672 | + | 0.941 | 0.926 | 0.905 | 4059 | rs12512872 chr4 | 34381166 | + | 0.942 | 0.938 | 0.94 |
| 1021 | rs110254470 chr11 | 20199046 | + | 0.95 | 0.933 | 0.945 | 4060 | rs1912843 chr4 | 34387076 | + | 0.942 | 0.938 | 0.946 |
| 1022 | rs113227850 chr11 | 20284646 | + | 0.917 | 0.938 | 0.95 | 4061 | rs124998550 chr4 | 34389443 | + | 0.942 | 0.938 | 0.946 |
| 1023 | rs1914984 chr11 | 20807913 | + | 0.943 | 0.949 | 0.917 | 4062 | rs124999140 chr4 | 34389596 | + | 0.942 | 0.939 | 0.946 |
| 1024 | rs118245800 chr11 | 21202600 | + | 0.917 | 0.904 | 0.911 | 4063 | rs16990198 chr4 | 34392506 | + | 0.942 | 0.939 | 0.95 |
| 1025 | rs110265870 chr11 | 22472783 | + | 0.915 | 0.91 | 0.938 | 4064 | rs16990202 chr4 | 34392617 | + | 0.924 | 0.939 | 0.946 |
| 1026 | rs118223380 chr11 | 23564641 | + | 0.927 | 0.948 | 0.927 | 4065 | rs16990205 chr4 | 34392703 | + | 0.942 | 0.939 | 0.95 |
| 1027 | rs169120940 chr11 | 24088825 | + | 0.917 | 0.917 | 0.932 | 4066 | rs1511859 chr4 | 34392989 | + | 0.94 | 0.938 | 0.95 |
| 1028 | rs127916230 chr11 | 24234500 | + | 0.932 | 0.906 | 0.905 | 4067 | rs126438650 chr4 | 34396612 | + | 0.942 | 0.939 | 0.946 |
| 1029 | rs169124250 chr11 | 24300986 | + | 0.917 | 0.911 | 0.945 | 4068 | rs126438870 chr4 | 34396712 | + | 0.942 | 0.939 | 0.946 |
| 1030 | rs110290900 chr11 | 25995147 | + | 0.925 | 0.911 | 0.932 | 4069 | rs1511855 chr4 | 34397251 | + | 0.942 | 0.949 | 0.95 |
| 1031 | rs293958 chr11 | 26573775 | + | 0.908 | 0.911 | 0.909 | 4070 | rs1511856 chr4 | 34397322 | + | 0.945 | 0.938 | 0.945 |
| 1032 | rs110297450 chr11 | 26923678 | + | 0.95 | 0.922 | 0.914 | 4071 | rs16990214 chr4 | 34398852 | + | 0.942 | 0.938 | 0.946 |
| 1033 | rs79426500 chr11 | 26935696 | + | 0.925 | 0.922 | 0.914 | 4072 | rs6851590 chr4 | 35725354 | + | 0.935 | 0.904 | 0.937 |
| 1034 | rs18386160 chr11 | 26937198 | + | 0.925 | 0.922 | 0.911 | 4073 | rs2175323 chr4 | 35733511 | + | 0.05 | 0.051 | 0.054 |
| 1035 | rs21662590 chr11 | 26939939 | + | 0.924 | 0.922 | 0.914 | 4074 | rs119390510 chr4 | 35753851 | + | 0.075 | 0.052 | 0.073 |
| 1036 | rs769272 chr11 | 26952670 | + | 0.925 | 0.921 | 0.911 | 4075 | rs117271100 chr4 | 40645356 | + | 0.948 | 0.938 | 0.945 |
| 1037 | rs107677601 chr11 | 27055319 | + | 0.058 | 0.097 | 0.065 | 4076 | rs6832948 chr4 | 40653125 | + | 0.917 | 0.91 | 0.919 |
| 1038 | rs118212660 chr11 | 29582304 | + | 0.95 | 0.949 | 0.945 | 4077 | rs10938466 chr4 | 40656950 | + | 0.917 | 0.91 | 0.938 |
| 1039 | rs21228360 chr11 | 29662418 | + | 0.917 | 0.949 | 0.946 | 4078 | rs4607257 chr4 | 41116805 | + | 0.904 | 0.933 | 0.946 |
| 1040 | rs169196880 chr11 | 29663884 | + | 0.95 | 0.944 | 0.946 | 4079 | rs17590698 chr4 | 41518372 | + | 0.933 | 0.938 | 0.919 |
| 1041 | rs118205750 chr11 | 29696722 | + | 0.922 | 0.943 | 0.945 | 4080 | rs3103204 chr4 | 42067408 | + | 0.92 | 0.949 | 0.909 |
| 1042 | rs118264740 chr11 | 29704069 | + | 0.95 | 0.938 | 0.946 | 4081 | rs23473450 chr4 | 43455970 | + | 0.933 | 0.921 | 0.95 |
| 1043 | rs118218360 chr11 | 29704373 | + | 0.95 | 0.943 | 0.935 | 4082 | rs2162128 chr4 | 43470268 | + | 0.942 | 0.939 | 0.91 |
| 1044 | rs169197310 chr11 | 29705316 | + | 0.915 | 0.939 | 0.946 | 4083 | rs976283 chr4 | 43504518 | + | 0.942 | 0.933 | 0.905 |
| 1045 | rs584452 chr11 | 30398992 | + | 0.093 | 0.051 | 0.089 | 4084 | rs168515050 chr4 | 43622613 | + | 0.917 | 0.95 | 0.941 |
| 1046 | rs633171 chr11 | 30734761 | + | 0.933 | 0.909 | 0.914 | 4085 | rs7660283 chr4 | 44697281 | + | 0.938 | 0.948 | 0.923 |
| 1047 | rs10408540 chr11 | 30799276 | + | 0.924 | 0.921 | 0.901 | 4086 | rs100271180 chr4 | 44876501 | + | 0.95 | 0.921 | 0.932 |
| 1048 | rs14489440 chr11 | 30799489 | + | 0.925 | 0.917 | 0.901 | 4087 | rs176408930 chr4 | 46534890 | + | 0.95 | 0.933 | 0.944 |
| 1049 | rs273586 chr11 | 30843822 | + | 0.925 | 0.904 | 0.901 | 4088 | rs175986360 chr4 | 46547971 | + | 0.95 | 0.933 | 0.941 |

Fig. 9 Cont. 30

| | | | | | | | | | |
|---|---|---|---|---|---|---|---|---|---|
| 1050 | rs273574 | chr11 | 30867230 | + | 0.947 | 0.912 | 0.92 | 4089 | rs17653240 chr4 | 46972055 | + | 0.925 | 0.911 | 0.901 |
| 1051 | rs158633 | chr11 | 30930691 | + | 0.929 | 0.914 | 0.905 | 4090 | rs1886044C chr4 | 47298612 | + | 0.95 | 0.911 | 0.91 |
| 1052 | rs17668735 | chr11 | 32153896 | + | 0.95 | 0.944 | 0.905 | 4091 | rs4864779 chr4 | 54077831 | + | 0.917 | 0.906 | 0.905 |
| 1053 | rs7113149 | chr11 | 32474646 | + | 0.908 | 0.95 | 0.901 | 4092 | rs9918031 chr4 | 54984228 | + | 0.942 | 0.928 | 0.946 |
| 1054 | rs7126059 | chr11 | 32649292 | + | 0.942 | 0.906 | 0.928 | 4093 | rs17084392 chr4 | 55035339 | + | 0.908 | 0.928 | 0.946 |
| 1055 | rs7107642 | chr11 | 32739569 | + | 0.933 | 0.906 | 0.928 | 4094 | rs17086939 chr4 | 57085407 | + | 0.95 | 0.926 | 0.905 |
| 1056 | rs286891 | chr11 | 34636976 | + | 0.933 | 0.933 | 0.92 | 4095 | rs4865117 chr4 | 57093058 | + | 0.925 | 0.911 | 0.908 |
| 1057 | rs17435465 | chr11 | 34937118 | + | 0.908 | 0.92 | 0.95 | 4096 | rs3755901 chr4 | 57470753 | + | 0.925 | 0.903 | 0.946 |
| 1058 | rs10488800 | chr11 | 34962478 | + | 0.908 | 0.921 | 0.95 | 4097 | rs17087484 chr4 | 57630662 | + | 0.914 | 0.949 | 0.929 |
| 1059 | rs10488881 | chr11 | 35169954 | + | 0.933 | 0.944 | 0.901 | 4098 | rs17769765 chr4 | 58021797 | + | 0.917 | 0.95 | 0.938 |
| 1060 | rs4083482 | chr11 | 35308215 | + | 0.95 | 0.911 | 0.95 | 4099 | rs13129428 chr4 | 58031289 | + | 0.924 | 0.95 | 0.945 |
| 1061 | rs1997118 | chr11 | 36158256 | + | 0.95 | 0.933 | 0.932 | 4100 | rs7664064 chr4 | 58033766 | + | 0.95 | 0.949 | 0.938 |
| 1062 | rs7119512 | chr11 | 37741578 | + | 0.058 | 0.097 | 0.098 | 4101 | rs17088981 chr4 | 58510014 | + | 0.907 | 0.933 | 0.946 |
| 1063 | rs176802 | chr11 | 37787578 | + | 0.949 | 0.921 | 0.933 | 4102 | rs269833 chr4 | 58534261 | + | 0.917 | 0.921 | 0.95 |
| 1064 | rs7935185 | chr11 | 38994888 | + | 0.942 | 0.949 | 0.923 | 4103 | rs17089004 chr4 | 58540378 | + | 0.924 | 0.92 | 0.929 |
| 1065 | rs11035068 | chr11 | 39045380 | + | 0.931 | 0.944 | 0.923 | 4104 | rs4860341 chr4 | 60933701 | + | 0.1 | 0.089 | 0.055 |
| 1066 | rs11035200 | chr11 | 39245244 | + | 0.95 | 0.906 | 0.902 | 4105 | rs17085407 chr4 | 65380291 | + | 0.933 | 0.926 | 0.927 |
| 1067 | rs12422132 | chr11 | 39680451 | + | 0.933 | 0.939 | 0.945 | 4106 | rs34801717 chr4 | 65402266 | + | 0.933 | 0.91 | 0.914 |
| 1068 | rs16933730 | chr11 | 39690118 | + | 0.925 | 0.944 | 0.946 | 4107 | rs17085449 chr4 | 65419204 | + | 0.925 | 0.911 | 0.928 |
| 1069 | rs16933754 | chr11 | 39697112 | + | 0.925 | 0.944 | 0.95 | 4108 | rs17085470 chr4 | 65426988 | + | 0.933 | 0.917 | 0.91 |
| 1070 | rs16933776 | chr11 | 39703380 | + | 0.925 | 0.944 | 0.95 | 4109 | rs11131681 chr4 | 67721476 | + | 0.949 | 0.926 | 0.911 |
| 1071 | rs2927204 | chr11 | 40122200 | + | 0.092 | 0.083 | 0.081 | 4110 | rs7661050 chr4 | 69762604 | + | 0.915 | 0.92 | 0.931 |
| 1072 | rs10501220 | chr11 | 40104412 | + | 0.95 | 0.944 | 0.936 | 4111 | rs17147073 chr4 | 70337029 | + | 0.949 | 0.903 | 0.901 |
| 1073 | rs11035717 | chr11 | 40130309 | + | 0.938 | 0.938 | 0.906 | 4112 | rs11573763 chr4 | 70753626 | + | 0.917 | 0.904 | 0.928 |
| 1074 | rs4756579 | chr11 | 40149503 | + | 0.908 | 0.944 | 0.901 | 4113 | rs11941079 chr4 | 72156309 | + | 0.925 | 0.916 | 0.901 |
| 1075 | rs12273790 | chr11 | 41107932 | + | 0.904 | 0.916 | 0.95 | 4114 | rs1603131 chr4 | 75581500 | + | 0.915 | 0.921 | 0.95 |
| 1076 | rs11036673 | chr11 | 42039592 | + | 0.942 | 0.922 | 0.905 | 4115 | rs1039011 chr4 | 75588305 | + | 0.907 | 0.922 | 0.95 |
| 1077 | rs1463541 | chr11 | 42466497 | + | 0.058 | 0.087 | 0.054 | 4116 | rs3113925 chr4 | 75588921 | + | 0.908 | 0.922 | 0.95 |
| 1078 | rs2169544 | chr11 | 42471540 | + | 0.067 | 0.094 | 0.086 | 4117 | rs3113927 chr4 | 75589079 | + | 0.908 | 0.92 | 0.932 |
| 1079 | rs2862573 | chr11 | 42479942 | + | 0.075 | 0.09 | 0.086 | 4118 | rs17250403 chr4 | 76172919 | + | 0.933 | 0.922 | 0.932 |
| 1080 | rs11604500 | chr11 | 42606114 | + | 0.908 | 0.95 | 0.914 | 4119 | rs11731905 chr4 | 76640053 | + | 0.925 | 0.933 | 0.928 |
| 1081 | rs12272023 | chr11 | 43071502 | + | 0.941 | 0.91 | 0.901 | 4120 | rs4594746 chr4 | 78408995 | + | 0.941 | 0.903 | 0.934 |
| 1082 | rs12285206 | chr11 | 43073276 | + | 0.931 | 0.909 | 0.92 | 4121 | rs4859778 chr4 | 78444616 | + | 0.939 | 0.901 | 0.935 |
| 1083 | rs12225970 | chr11 | 43113494 | + | 0.941 | 0.907 | 0.946 | 4122 | rs17401714 chr4 | 78457748 | + | 0.941 | 0.903 | 0.944 |
| 1084 | rs2162168 | chr11 | 43136959 | + | 0.949 | 0.903 | 0.945 | 4123 | rs12644366 chr4 | 81660186 | + | 0.933 | 0.911 | 0.946 |

Fig. 9 Cont. 31

| | | | | | | | | | | |
|---|---|---|---|---|---|---|---|---|---|---|
| 1085 | rs12226058 | chr11 | 43147205 | + | 0.947 | 0.914 | 0.945 | 4124 | rs12650756 | chr4 | 81672407 | + | 0.932 | 0.917 | 0.941 |
| 1086 | rs2201615 | chr11 | 43152977 | + | 0.925 | 0.906 | 0.946 | 4125 | rs13146627 | chr4 | 81673239 | + | 0.932 | 0.909 | 0.936 |
| 1087 | rs2220956 | chr11 | 43153232 | + | 0.95 | 0.906 | 0.946 | 4126 | rs13129636 | chr4 | 81673760 | + | 0.925 | 0.911 | 0.941 |
| 1088 | rs11037313 | chr11 | 43155164 | + | 0.93 | 0.906 | 0.936 | 4127 | rs13129104 | chr4 | 81675781 | + | 0.925 | 0.911 | 0.938 |
| 1089 | rs11037314 | chr11 | 43155260 | + | 0.912 | 0.904 | 0.927 | 4128 | rs12639952 | chr4 | 81712638 | + | 0.924 | 0.91 | 0.911 |
| 1090 | rs11037315 | chr11 | 43156022 | + | 0.931 | 0.924 | 0.932 | 4129 | rs13131230 | chr4 | 81846530 | + | 0.907 | 0.91 | 0.92 |
| 1091 | rs11037317 | chr11 | 43156111 | + | 0.925 | 0.906 | 0.932 | 4130 | rs17005046 | chr4 | 82222811 | + | 0.917 | 0.933 | 0.936 |
| 1092 | rs11037320 | chr11 | 43160139 | + | 0.924 | 0.913 | 0.946 | 4131 | rs7683827 | chr4 | 82847591 | + | 0.914 | 0.95 | 0.923 |
| 1093 | rs12282705 | chr11 | 44817767 | + | 0.94 | 0.938 | 0.933 | 4132 | rs17006171 | chr4 | 83866085 | + | 0.907 | 0.91 | 0.905 |
| 1094 | rs11038215 | chr11 | 44903228 | + | 0.906 | 0.95 | 0.906 | 4133 | rs17006263 | chr4 | 83888005 | + | 0.924 | 0.917 | 0.946 |
| 1095 | rs11038515 | chr11 | 45510559 | + | 0.917 | 0.938 | 0.927 | 4134 | rs6844363 | chr4 | 87403190 | + | 0.912 | 0.928 | 0.905 |
| 1096 | rs3809047 | chr11 | 46324278 | + | 0.95 | 0.903 | 0.919 | 4135 | rs17013280 | chr4 | 88981320 | + | 0.925 | 0.933 | 0.928 |
| 1097 | rs17197116 | chr11 | 46476878 | + | 0.924 | 0.931 | 0.919 | 4136 | rs6835557 | chr4 | 91689876 | + | 0.942 | 0.933 | 0.928 |
| 1098 | rs12576839 | chr11 | 47039040 | + | 0.942 | 0.939 | 0.901 | 4137 | rs2158193 | chr4 | 92258219 | + | 0.069 | 0.084 | 0.089 |
| 1099 | rs17790306 | chr11 | 47046266 | + | 0.942 | 0.939 | 0.901 | 4138 | rs10031846 | chr4 | 92263344 | + | 0.093 | 0.084 | 0.08 |
| 1100 | rs4572092 | chr11 | 47051122 | + | 0.942 | 0.938 | 0.901 | 4139 | rs12642555 | chr4 | 92660239 | + | 0.949 | 0.938 | 0.914 |
| 1101 | rs17790336 | chr11 | 47084125 | + | 0.924 | 0.938 | 0.905 | 4140 | rs17019750 | chr4 | 93825786 | + | 0.941 | 0.916 | 0.928 |
| 1102 | rs17197619 | chr11 | 47089336 | + | 0.925 | 0.939 | 0.911 | 4141 | rs16996358 | chr4 | 93826080 | + | 0.917 | 0.916 | 0.928 |
| 1103 | rs17790390 | chr11 | 47108473 | + | 0.925 | 0.939 | 0.901 | 4142 | rs17019760 | chr4 | 93831121 | + | 0.917 | 0.917 | 0.932 |
| 1104 | rs12573896 | chr11 | 49237057 | + | 0.932 | 0.906 | 0.909 | 4143 | rs17019782 | chr4 | 93833900 | + | 0.925 | 0.917 | 0.902 |
| 1105 | rs10769580 | chr11 | 49424784 | + | 0.1 | 0.065 | 0.07 | 4144 | rs13133845 | chr4 | 95813639 | + | 0.933 | 0.95 | 0.902 |
| 1106 | rs12223248 | chr11 | 55644209 | + | 0.936 | 0.903 | 0.904 | 4145 | rs16996515 | chr4 | 96978471 | + | 0.907 | 0.943 | 0.928 |
| 1107 | rs17150088 | chr11 | 55651438 | + | 0.942 | 0.905 | 0.917 | 4146 | rs7677817 | chr4 | 96983000 | + | 0.1 | 0.067 | 0.059 |
| 1108 | rs11227702 | chr11 | 55791350 | + | 0.94 | 0.901 | 0.908 | 4147 | rs1816557 | chr4 | 97003108 | + | 0.1 | 0.067 | 0.062 |
| 1109 | rs10896353 | chr11 | 55940950 | + | 0.051 | 0.1 | 0.083 | 4148 | rs12648161 | chr4 | 97927848 | + | 0.941 | 0.949 | 0.919 |
| 1110 | rs12418771 | chr11 | 56031958 | + | 0.94 | 0.902 | 0.923 | 4149 | rs1018951 | chr4 | 98151170 | + | 0.942 | 0.933 | 0.927 |
| 1111 | rs3758919 | chr11 | 57119379 | + | 0.915 | 0.935 | 0.905 | 4150 | rs6837816 | chr4 | 98293276 | + | 0.942 | 0.903 | 0.902 |
| 1112 | rs10501372 | chr11 | 58160409 | + | 0.933 | 0.911 | 0.91 | 4151 | rs11942542 | chr4 | 98319074 | + | 0.908 | 0.91 | 0.919 |
| 1113 | rs7114773 | chr11 | 59320057 | + | 0.907 | 0.942 | 0.936 | 4152 | rs11935004 | chr4 | 98348071 | + | 0.925 | 0.906 | 0.902 |
| 1114 | rs7951717 | chr11 | 59870717 | + | 0.92 | 0.927 | 0.945 | 4153 | rs17027530 | chr4 | 99522656 | + | 0.941 | 0.95 | 0.943 |
| 1115 | rs17154838 | chr11 | 59882016 | + | 0.95 | 0.93 | 0.92 | 4154 | rs17027533 | chr4 | 99523046 | + | 0.933 | 0.95 | 0.95 |
| 1116 | rs2073588 | chr11 | 61492987 | + | 0.917 | 0.904 | 0.941 | 4155 | rs17027552 | chr4 | 99533644 | + | 0.941 | 0.95 | 0.95 |
| 1117 | rs1300836 | chr11 | 64588605 | + | 0.1 | 0.05 | 0.062 | 4156 | rs7667212 | chr4 | 100537122 | + | 0.92 | 0.948 | 0.917 |
| 1118 | rs527039 | chr11 | 64589072 | + | 0.1 | 0.05 | 0.072 | 4157 | rs1994634 | chr4 | 106067195 | + | 0.908 | 0.917 | 0.932 |
| 1119 | rs907629 | chr11 | 64596273 | + | 0.1 | 0.05 | 0.072 | 4158 | rs10032763 | chr4 | 106079450 | + | 0.907 | 0.916 | 0.932 |

Fig. 9  Cont. 32

| | | | | | | | | | |
|---|---|---|---|---|---|---|---|---|---|
| 1120 | rs1196051 | chr11 | 64626907 | + | 0.1 | 0.052 | 0.064 | 4159 | rs7660636 | chr4 | 106089432 | + | 0.908 | 0.915 | 0.945 |
| 1121 | rs3896078 | chr11 | 64630838 | + | 0.1 | 0.05 | 0.073 | 4160 | rs2726145 | chr4 | 108764483 | + | 0.908 | 0.922 | 0.95 |
| 1122 | rs3819049 | chr11 | 64648911 | + | 0.914 | 0.95 | 0.938 | 4161 | rs3805348 | chr4 | 108821736 | + | 0.1 | 0.079 | 0.075 |
| 1123 | rs11228296 | chr11 | 68147773 | + | 0.94 | 0.926 | 0.936 | 4162 | rs7665258 | chr4 | 111193605 | + | 0.949 | 0.911 | 0.911 |
| 1124 | rs11228303 | chr11 | 68156745 | + | 0.942 | 0.938 | 0.911 | 4163 | rs3796879 | chr4 | 116696150 | + | 0.949 | 0.916 | 0.933 |
| 1125 | rs10791997 | chr11 | 68301561 | + | 0.1 | 0.079 | 0.092 | 4164 | rs1562640 | chr4 | 117711818 | + | 0.092 | 0.062 | 0.081 |
| 1126 | rs3017493 | chr11 | 70343169 | + | 0.083 | 0.053 | 0.086 | 4165 | rs1554467 | chr4 | 113346031 | + | 0.933 | 0.91 | 0.946 |
| 1127 | rs11233358 | chr11 | 70757050 | + | 0.942 | 0.942 | 0.943 | 4166 | rs17046034 | chr4 | 114574305 | + | 0.942 | 0.939 | 0.92 |
| 1128 | rs11233373 | chr11 | 70761385 | + | 0.933 | 0.944 | 0.928 | 4167 | rs7684418 | chr4 | 114581335 | + | 0.942 | 0.944 | 0.914 |
| 1129 | rs11233512 | chr11 | 70788137 | + | 0.907 | 0.938 | 0.946 | 4168 | rs17620581 | chr4 | 115046824 | + | 0.939 | 0.904 | 0.909 |
| 1130 | rs12576621 | chr11 | 70877314 | + | 0.93 | 0.901 | 0.941 | 4169 | rs17677130 | chr4 | 115047674 | + | 0.932 | 0.904 | 0.911 |
| 1131 | rs12286616 | chr11 | 70887601 | + | 0.924 | 0.902 | 0.941 | 4170 | rs6822455 | chr4 | 115050404 | + | 0.925 | 0.91 | 0.901 |
| 1132 | rs7950584 | chr11 | 70897403 | + | 0.075 | 0.096 | 0.054 | 4171 | rs17677317 | chr4 | 115075766 | + | 0.942 | 0.906 | 0.918 |
| 1133 | rs2155430 | chr11 | 71007283 | + | 0.076 | 0.085 | 0.055 | 4172 | rs7673354 | chr4 | 115996582 | + | 0.917 | 0.917 | 0.929 |
| 1134 | rs7124841 | chr11 | 73248345 | + | 0.933 | 0.933 | 0.936 | 4173 | rs17679144 | chr4 | 116027258 | + | 0.938 | 0.906 | 0.937 |
| 1135 | rs17244695 | chr11 | 73349433 | + | 0.936 | 0.933 | 0.933 | 4174 | rs13129545 | chr4 | 118608698 | + | 0.908 | 0.91 | 0.946 |
| 1136 | rs603290 | chr11 | 75079083 | + | 0.922 | 0.943 | 0.909 | 4175 | rs17861955 | chr4 | 118613059 | + | 0.917 | 0.909 | 0.941 |
| 1137 | rs675028 | chr11 | 75086714 | + | 0.942 | 0.944 | 0.91 | 4176 | rs17861965 | chr4 | 118618785 | + | 0.933 | 0.909 | 0.941 |
| 1138 | rs590550 | chr11 | 75101865 | + | 0.949 | 0.944 | 0.91 | 4177 | rs1193233C | chr4 | 122099524 | + | 0.93 | 0.933 | 0.919 |
| 1139 | rs11237734 | chr11 | 78548669 | + | 0.917 | 0.949 | 0.909 | 4178 | rs10518306 | chr4 | 124955655 | + | 0.95 | 0.933 | 0.927 |
| 1140 | rs17755323 | chr11 | 78598130 | + | 0.931 | 0.932 | 0.936 | 4179 | rs17007499 | chr4 | 124986545 | + | 0.95 | 0.933 | 0.902 |
| 1141 | rs11237888 | chr11 | 78917180 | + | 0.927 | 0.93 | 0.912 | 4180 | rs17007781 | chr4 | 125196764 | + | 0.942 | 0.933 | 0.941 |
| 1142 | rs22998668 | chr11 | 82241942 | + | 0.925 | 0.949 | 0.92 | 4181 | rs1390079 | chr4 | 125742492 | + | 0.942 | 0.936 | 0.905 |
| 1143 | rs11233495 | chr11 | 82548125 | + | 0.933 | 0.949 | 0.95 | 4182 | rs7686429 | chr4 | 126034105 | + | 0.075 | 0.056 | 0.059 |
| 1144 | rs17144761 | chr11 | 82576049 | + | 0.917 | 0.95 | 0.95 | 4183 | rs1120767 | chr4 | 126036233 | + | 0.075 | 0.057 | 0.059 |
| 1145 | rs12226394 | chr11 | 82584059 | + | 0.908 | 0.904 | 0.95 | 4184 | rs13121227 | chr4 | 127526584 | + | 0.917 | 0.906 | 0.92 |
| 1146 | rs10501549 | chr11 | 83230041 | + | 0.95 | 0.938 | 0.937 | 4185 | rs17014446 | chr4 | 130347853 | + | 0.917 | 0.935 | 0.937 |
| 1147 | rs11234007 | chr11 | 83778931 | + | 0.924 | 0.938 | 0.096 | 4186 | rs4276290 | chr4 | 130424381 | + | 0.925 | 0.938 | 0.902 |
| 1148 | rs7929161 | chr11 | 83922417 | + | 0.067 | 0.056 | 0.096 | 4187 | rs13435332 | chr4 | 130994003 | + | 0.921 | 0.946 | 0.943 |
| 1149 | rs12574324 | chr11 | 85796157 | + | 0.942 | 0.922 | 0.929 | 4188 | rs13103836 | chr4 | 132298868 | + | 0.941 | 0.902 | 0.911 |
| 1150 | rs11234849 | chr11 | 86264967 | + | 0.914 | 0.911 | 0.941 | 4189 | rs6848554 | chr4 | 133181322 | + | 0.915 | 0.945 | 0.913 |
| 1151 | rs10501644 | chr11 | 87124860 | + | 0.917 | 0.922 | 0.919 | 4190 | rs6849829 | chr4 | 133181940 | + | 0.907 | 0.942 | 0.931 |
| 1152 | rs12786604 | chr11 | 87201589 | + | 0.925 | 0.933 | 0.946 | 4191 | rs12500825 | chr4 | 133642221 | + | 0.933 | 0.906 | 0.938 |
| 1153 | rs12793270 | chr11 | 87201828 | + | 0.925 | 0.933 | 0.946 | 4192 | rs12505254 | chr4 | 133642452 | + | 0.933 | 0.906 | 0.946 |
| 1154 | rs1784016 | chr11 | 87307740 | + | 0.1 | 0.056 | 0.09 | 4193 | rs7657767 | chr4 | 133645157 | + | 0.933 | 0.906 | 0.946 |

Fig. 9   Cont. 33

| | | | | | | | | |
|---|---|---|---|---|---|---|---|---|
| 1155 | rs593775 | chr11 | 87440844 | + | 0.918 | 0.932 | 0.912 | 4194 | rs955987 | chr4 | 133646952 | + | 0.94 | 0.906 | 0.935 |
| 1156 | rs2129419 | chr11 | 87449915 | + | 0.925 | 0.927 | 0.909 | 4195 | rs2420159 | chr4 | 134375866 | + | 0.914 | 0.924 | 0.95 |
| 1157 | rs523225 | chr11 | 87452223 | + | 0.918 | 0.933 | 0.912 | 4196 | rs17025316 | chr4 | 134628871 | + | 0.917 | 0.922 | 0.945 |
| 1158 | rs1386330 | chr11 | 87459075 | + | 0.942 | 0.933 | 0.901 | 4197 | rs7657696 | chr4 | 136050626 | + | 0.905 | 0.948 | 0.946 |
| 1159 | rs17770561 | chr11 | 88011202 | + | 0.925 | 0.938 | 0.926 | 4198 | rs10049602 | chr4 | 136052645 | + | 0.935 | 0.948 | 0.909 |
| 1160 | rs17770573 | chr11 | 88012356 | + | 0.924 | 0.938 | 0.909 | 4199 | rs13435865 | chr4 | 136055638 | + | 0.925 | 0.944 | 0.911 |
| 1161 | rs17832888 | chr11 | 88025809 | + | 0.942 | 0.933 | 0.902 | 4200 | rs12505219 | chr4 | 136298790 | + | 0.944 | 0.907 | 0.902 |
| 1162 | rs17770948 | chr11 | 88025948 | + | 0.942 | 0.933 | 0.91 | 4201 | rs1905461 | chr4 | 136535637 | + | 0.917 | 0.918 | 0.923 |
| 1163 | rs16914447 | chr11 | 88027987 | + | 0.925 | 0.933 | 0.914 | 4202 | rs2634888 | chr4 | 137933620 | + | 0.058 | 0.067 | 0.071 |
| 1164 | rs2387405 | chr11 | 88277854 | + | 0.933 | 0.949 | 0.901 | 4203 | rs1517949 | chr4 | 138118972 | + | 0.949 | 0.938 | 0.928 |
| 1165 | rs316115 | chr11 | 88261957 | + | 0.092 | 0.083 | 0.071 | 4204 | rs298481 | chr4 | 139474769 | + | 0.092 | 0.094 | 0.089 |
| 1166 | rs563012 | chr11 | 88432234 | + | 0.051 | 0.062 | 0.072 | 4205 | rs3208941 | chr4 | 140407544 | + | 0.949 | 0.927 | 0.946 |
| 1167 | rs10765188 | chr11 | 88498127 | + | 0.05 | 0.072 | 0.068 | 4206 | rs12639667 | chr4 | 140463272 | + | 0.95 | 0.933 | 0.937 |
| 1168 | rs10437757 | chr11 | 90684754 | + | 0.917 | 0.944 | 0.946 | 4207 | rs1453136 | chr4 | 140799401 | + | 0.924 | 0.933 | 0.906 |
| 1169 | rs11019405 | chr11 | 90717719 | + | 0.95 | 0.944 | 0.938 | 4208 | rs4147586 | chr4 | 140806892 | + | 0.942 | 0.921 | 0.944 |
| 1170 | rs7112868 | chr11 | 90725362 | + | 0.95 | 0.944 | 0.946 | 4209 | rs6818155 | chr4 | 141611318 | + | 0.907 | 0.933 | 0.901 |
| 1171 | rs12575757 | chr11 | 90730402 | + | 0.95 | 0.927 | 0.941 | 4210 | rs12504457 | chr4 | 141635465 | + | 0.905 | 0.928 | 0.92 |
| 1172 | rs12360807 | chr11 | 93717338 | + | 0.95 | 0.916 | 0.932 | 4211 | rs16998469 | chr4 | 141680620 | + | 0.934 | 0.927 | 0.918 |
| 1173 | rs1255533 | chr11 | 94950625 | + | 0.917 | 0.932 | 0.919 | 4212 | rs9308131 | chr4 | 141930698 | + | 0.942 | 0.929 | 0.91 |
| 1174 | rs7943282 | chr11 | 97672003 | + | 0.914 | 0.938 | 0.923 | 4213 | rs336361 | chr4 | 143164901 | + | 0.092 | 0.094 | 0.086 |
| 1175 | rs4754503 | chr11 | 97729886 | + | 0.925 | 0.933 | 0.923 | 4214 | rs17015882 | chr4 | 143445946 | + | 0.942 | 0.917 | 0.932 |
| 1176 | rs4754504 | chr11 | 97730873 | + | 0.925 | 0.933 | 0.914 | 4215 | rs13104265 | chr4 | 143558155 | + | 0.908 | 0.91 | 0.937 |
| 1177 | rs1386411 | chr11 | 98311546 | + | 0.08 | 0.089 | 0.068 | 4216 | rs13140375 | chr4 | 143857327 | + | 0.907 | 0.944 | 0.92 |
| 1178 | rs17134173 | chr11 | 99044338 | + | 0.917 | 0.922 | 0.908 | 4217 | rs986081 | chr4 | 143874624 | + | 0.908 | 0.944 | 0.914 |
| 1179 | rs17134252 | chr11 | 99093340 | + | 0.933 | 0.928 | 0.927 | 4218 | rs11723869 | chr4 | 145115700 | + | 0.941 | 0.933 | 0.902 |
| 1180 | rs11603633 | chr11 | 99329859 | + | 0.941 | 0.921 | 0.918 | 4219 | rs13109195 | chr4 | 146589206 | + | 0.908 | 0.933 | 0.92 |
| 1181 | rs11222274 | chr11 | 99474024 | + | 0.942 | 0.917 | 0.909 | 4220 | rs13130076 | chr4 | 146770882 | + | 0.908 | 0.949 | 0.91 |
| 1182 | rs10894564 | chr11 | 99550910 | + | 0.915 | 0.95 | 0.905 | 4221 | rs12640509 | chr4 | 146774740 | + | 0.95 | 0.949 | 0.909 |
| 1183 | rs17094597 | chr11 | 99573389 | + | 0.941 | 0.931 | 0.918 | 4222 | rs1874571 | chr4 | 146804392 | + | 0.95 | 0.95 | 0.927 |
| 1184 | rs17094600 | chr11 | 99573474 | + | 0.933 | 0.933 | 0.914 | 4223 | rs7689436 | chr4 | 147793138 | + | 0.95 | 0.944 | 0.914 |
| 1185 | rs17094604 | chr11 | 99573973 | + | 0.95 | 0.927 | 0.909 | 4224 | rs7673393 | chr4 | 148852440 | + | 0.908 | 0.944 | 0.919 |
| 1186 | rs11223252 | chr11 | 99589030 | + | 0.94 | 0.933 | 0.92 | 4225 | rs11725360 | chr4 | 149317493 | + | 0.915 | 0.916 | 0.935 |
| 1187 | rs10894664 | chr11 | 99624917 | + | 0.925 | 0.938 | 0.905 | 4226 | rs901207 | chr4 | 153023590 | + | 0.933 | 0.911 | 0.901 |
| 1188 | rs11224706 | chr11 | 100683810 | + | 0.925 | 0.95 | 0.938 | 4227 | rs2406810 | chr4 | 153109000 | + | 0.917 | 0.938 | 0.901 |
| 1189 | rs11224819 | chr11 | 100906062 | + | 0.931 | 0.901 | 0.915 | 4228 | rs10434142 | chr4 | 155837437 | + | 0.907 | 0.906 | 0.945 |

Fig. 9 Cont. 34

| | | | | | | | | | |
|---|---|---|---|---|---|---|---|---|---|
| 1190 | rs12363710 | chr11 | 103382521 | + | 0.94 | 0.924 | 0.907 | 4229 | rs17031914 chr4 | 155847419 | + | 0.918 | 0.91 | 0.946 |
| 1191 | rs11603920 | chr11 | 104595018 | + | 0.908 | 0.95 | 0.946 | 4230 | rs3806781 chr4 | 156807106 | + | 0.925 | 0.92 | 0.911 |
| 1192 | rs11600433 | chr11 | 104595506 | + | 0.908 | 0.939 | 0.946 | 4231 | rs1483026 chr4 | 156832264 | + | 0.915 | 0.944 | 0.945 |
| 1193 | rs2510165 | chr11 | 104921016 | + | 0.083 | 0.1 | 0.054 | 4232 | rs10024268 chr4 | 156973552 | + | 0.941 | 0.944 | 0.931 |
| 1194 | rs12574588 | chr11 | 106345993 | + | 0.905 | 0.907 | 0.919 | 4233 | rs13106367 chr4 | 157126306 | + | 0.922 | 0.92 | 0.946 |
| 1195 | rs12801961 | chr11 | 107164234 | + | 0.933 | 0.916 | 0.939 | 4234 | rs13141045 chr4 | 157582795 | + | 0.938 | 0.947 | 0.925 |
| 1196 | rs2016916 | chr11 | 107166562 | + | 0.933 | 0.911 | 0.945 | 4235 | rs13130184 chr4 | 157623486 | + | 0.908 | 0.939 | 0.914 |
| 1197 | rs12808838 | chr11 | 107189581 | + | 0.927 | 0.949 | 0.941 | 4236 | rs13113997 chr4 | 157633828 | + | 0.917 | 0.939 | 0.926 |
| 1198 | rs11823735 | chr11 | 107197765 | + | 0.932 | 0.944 | 0.941 | 4237 | rs6816593 chr4 | 157658854 | + | 0.907 | 0.938 | 0.914 |
| 1199 | rs11212883 | chr11 | 108424992 | + | 0.942 | 0.906 | 0.92 | 4238 | rs7672387 chr4 | 157771848 | + | 0.915 | 0.904 | 0.921 |
| 1200 | rs11212884 | chr11 | 108425012 | + | 0.925 | 0.904 | 0.91 | 4239 | rs12507707 chr4 | 157774702 | + | 0.914 | 0.904 | 0.923 |
| 1201 | rs11212886 | chr11 | 108425255 | + | 0.925 | 0.906 | 0.91 | 4240 | rs4691377 chr4 | 157914101 | + | 0.912 | 0.938 | 0.906 |
| 1202 | rs11212887 | chr11 | 108425457 | + | 0.924 | 0.903 | 0.918 | 4241 | rs9992249 chr4 | 159457861 | + | 0.944 | 0.906 | 0.946 |
| 1203 | rs10502108 | chr11 | 108425691 | + | 0.942 | 0.906 | 0.91 | 4242 | rs11100161 chr4 | 159462016 | + | 0.95 | 0.909 | 0.946 |
| 1204 | rs17109048 | chr11 | 108426505 | + | 0.932 | 0.914 | 0.92 | 4243 | rs11100162 chr4 | 159463323 | + | 0.942 | 0.911 | 0.941 |
| 1205 | rs11605310 | chr11 | 108427884 | + | 0.907 | 0.91 | 0.92 | 4244 | rs924678 chr4 | 160732251 | + | 0.1 | 0.067 | 0.05 |
| 1206 | rs10890942 | chr11 | 108428172 | + | 0.914 | 0.909 | 0.917 | 4245 | rs4690963 chr4 | 161036784 | + | 0.076 | 0.051 | 0.063 |
| 1207 | rs11212938 | chr11 | 108511038 | + | 0.921 | 0.922 | 0.946 | 4246 | rs2348997 chr4 | 161041441 | + | 0.051 | 0.061 | 0.063 |
| 1208 | rs11212953 | chr11 | 108517646 | + | 0.932 | 0.947 | 0.941 | 4247 | rs4691655 chr4 | 161563820 | + | 0.917 | 0.927 | 0.936 |
| 1209 | rs17461656 | chr11 | 110580638 | + | 0.95 | 0.944 | 0.946 | 4248 | rs7681545 chr4 | 161661695 | + | 0.933 | 0.935 | 0.91 |
| 1210 | rs10502138 | chr11 | 110584705 | + | 0.95 | 0.944 | 0.923 | 4249 | rs7681094 chr4 | 161661776 | + | 0.942 | 0.922 | 0.914 |
| 1211 | rs7106333 | chr11 | 111957704 | + | 0.925 | 0.911 | 0.902 | 4250 | rs17040351 chr4 | 162018850 | + | 0.933 | 0.933 | 0.91 |
| 1212 | rs7106735 | chr11 | 111958007 | + | 0.925 | 0.911 | 0.911 | 4251 | rs34018667 chr4 | 162455468 | + | 0.925 | 0.911 | 0.923 |
| 1213 | rs11214944 | chr11 | 136697673 | + | 0.917 | 0.908 | 0.95 | 4252 | rs2314105 chr4 | 162540870 | + | 0.939 | 0.95 | 0.929 |
| 1214 | rs7924722 | chr11 | 133755781 | + | 0.908 | 0.944 | 0.927 | 4253 | rs10016590 chr4 | 163580977 | + | 0.933 | 0.939 | 0.946 |
| 1215 | rs1712839 | chr11 | 114076454 | + | 0.075 | 0.067 | 0.063 | 4254 | rs6536698 chr4 | 164176383 | + | 0.95 | 0.933 | 0.938 |
| 1216 | rs1712840 | chr11 | 114081588 | + | 0.06 | 0.057 | 0.059 | 4255 | rs17473171 chr4 | 164694041 | + | 0.917 | 0.927 | 0.929 |
| 1217 | rs1792428 | chr11 | 114089910 | + | 0.069 | 0.067 | 0.071 | 4256 | rs17678924 chr4 | 165911269 | + | 0.917 | 0.906 | 0.941 |
| 1218 | rs1631482 | chr11 | 114092755 | + | 0.05 | 0.067 | 0.063 | 4257 | rs17679574 chr4 | 166008125 | + | 0.925 | 0.949 | 0.941 |
| 1219 | rs1792439 | chr11 | 114099314 | + | 0.05 | 0.072 | 0.062 | 4258 | rs17623248 chr4 | 166020521 | + | 0.924 | 0.95 | 0.941 |
| 1220 | rs1792438 | chr11 | 114099397 | + | 0.051 | 0.073 | 0.059 | 4259 | rs6816264 chr4 | 167446168 | + | 0.925 | 0.92 | 0.946 |
| 1221 | rs11215187 | chr11 | 114131837 | + | 0.908 | 0.944 | 0.928 | 4260 | rs10019607 chr4 | 168057827 | + | 0.941 | 0.944 | 0.929 |
| 1222 | rs2366356 | chr11 | 114169194 | + | 0.92 | 0.924 | 0.923 | 4261 | rs12649447 chr4 | 168058589 | + | 0.941 | 0.944 | 0.901 |
| 1223 | rs17117512 | chr11 | 114170068 | + | 0.927 | 0.92 | 0.942 | 4262 | rs13106418 chr4 | 168136690 | + | 0.949 | 0.916 | 0.902 |
| 1224 | rs4936302 | chr11 | 114203464 | + | 0.925 | 0.906 | 0.92 | 4263 | rs13116056 chr4 | 168453407 | + | 0.948 | 0.931 | 0.907 |

Fig. 9 Cont. 35

| | | | | | | | | | | |
|---|---|---|---|---|---|---|---|---|---|---|
| 1225 | rs4936305 | chr11 | 114223242 | + | 0.933 | 0.927 | 0.92 | 4264 | rs7685882 | chr4 | 169842947 | + | 0.925 | 0.938 | 0.937 |
| 1226 | rs1711840C | chr11 | 114918214 | + | 0.907 | 0.931 | 0.942 | 4265 | rs17054448C | chr4 | 169845365 | + | 0.924 | 0.933 | 0.94 |
| 1227 | rs7102312 | chr11 | 114923160 | + | 0.933 | 0.922 | 0.92 | 4266 | rs1875297 | chr4 | 169961584 | + | 0.05 | 0.051 | 0.095 |
| 1228 | rs12283886 | chr11 | 115599681 | + | 0.933 | 0.949 | 0.937 | 4267 | rs2660416 | chr4 | 170370486 | + | 0.917 | 0.949 | 0.946 |
| 1229 | rs1899052 | chr11 | 115730174 | + | 0.933 | 0.927 | 0.945 | 4268 | rs4591556 | chr4 | 171830962 | + | 0.907 | 0.933 | 0.919 |
| 1230 | rs1160038C | chr11 | 116175392 | + | 0.942 | 0.928 | 0.941 | 4269 | rs2177183 | chr4 | 171891312 | + | 0.922 | 0.939 | 0.935 |
| 1231 | rs12227943 | chr11 | 116253431 | + | 0.925 | 0.927 | 0.946 | 4270 | rs17730489 | chr4 | 171895336 | + | 0.95 | 0.939 | 0.928 |
| 1232 | rs2044426 | chr11 | 116261393 | + | 0.925 | 0.917 | 0.945 | 4271 | rs13132576 | chr4 | 171900103 | + | 0.925 | 0.939 | 0.928 |
| 1233 | rs12242020C | chr11 | 116503516 | + | 0.941 | 0.904 | 0.95 | 4272 | rs11731157 | chr4 | 1721120073 | + | 0.933 | 0.906 | 0.914 |
| 1234 | rs3802877 | chr11 | 116920158 | + | 0.942 | 0.904 | 0.928 | 4273 | rs11731120C | chr4 | 1721120229 | + | 0.941 | 0.91 | 0.918 |
| 1235 | rs7110219 | chr11 | 116925546 | + | 0.942 | 0.904 | 0.932 | 4274 | rs7668065 | chr4 | 1721120605 | + | 0.933 | 0.916 | 0.911 |
| 1236 | rs3863317 | chr11 | 117309319 | + | 0.914 | 0.943 | 0.905 | 4275 | rs7663393 | chr4 | 1721120772 | + | 0.933 | 0.904 | 0.911 |
| 1237 | rs10892306 | chr11 | 118256536 | + | 0.052 | 0.061 | 0.06 | 4276 | rs7685060 | chr4 | 1721121043 | + | 0.933 | 0.906 | 0.911 |
| 1238 | rs11600793 | chr11 | 119363717 | + | 0.95 | 0.933 | 0.929 | 4277 | rs7674250 | chr4 | 1721125132 | + | 0.933 | 0.906 | 0.911 |
| 1239 | rs3758893 | chr11 | 120480600 | + | 0.917 | 0.91 | 0.941 | 4278 | rs7674455 | chr4 | 1721125231 | + | 0.933 | 0.91 | 0.914 |
| 1240 | rs7108166 | chr11 | 120506473 | + | 0.924 | 0.926 | 0.902 | 4279 | rs7679704 | chr4 | 1721125362 | + | 0.933 | 0.906 | 0.911 |
| 1241 | rs7950536 | chr11 | 120593328 | + | 0.924 | 0.924 | 0.943 | 4280 | rs7656121 | chr4 | 1721126491 | + | 0.933 | 0.915 | 0.911 |
| 1242 | rs7128433 | chr11 | 120661965 | + | 0.929 | 0.906 | 0.92 | 4281 | rs7658356 | chr4 | 1721126873 | + | 0.933 | 0.906 | 0.914 |
| 1243 | rs7928868 | chr11 | 120670708 | + | 0.925 | 0.906 | 0.92 | 4282 | rs1097441 | chr4 | 1733351950 | + | 0.05 | 0.083 | 0.068 |
| 1244 | rs727422 | chr11 | 120673388 | + | 0.925 | 0.906 | 0.923 | 4283 | rs11723864 | chr4 | 1748810981 | + | 0.95 | 0.928 | 0.932 |
| 1245 | rs7942396 | chr11 | 120684759 | + | 0.924 | 0.903 | 0.914 | 4284 | rs1706043 | chr4 | 1754421413 | + | 0.925 | 0.911 | 0.946 |
| 1246 | rs12290188 | chr11 | 120771229 | + | 0.925 | 0.933 | 0.946 | 4285 | rs17066321 | chr4 | 1797707752 | + | 0.918 | 0.907 | 0.926 |
| 1247 | rs4936641 | chr11 | 121089654 | + | 0.95 | 0.939 | 0.941 | 4286 | rs1378545 | chr4 | 1805570676 | + | 0.933 | 0.933 | 0.929 |
| 1248 | rs1996354 | chr11 | 121969880 | + | 0.92 | 0.946 | 0.943 | 4287 | rs6419926 | chr4 | 1807768308 | + | 0.075 | 0.094 | 0.08 |
| 1249 | rs11218996 | chr11 | 122498526 | + | 0.904 | 0.901 | 0.906 | 4288 | rs10032248 | chr4 | 1808825875 | + | 0.067 | 0.089 | 0.077 |
| 1250 | rs1557423 | chr11 | 122958657 | + | 0.914 | 0.901 | 0.915 | 4289 | rs1020237 | chr4 | 1808856402 | + | 0.096 | 0.092 | 0.095 |
| 1251 | rs1975922 | chr11 | 123052720 | + | 0.907 | 0.925 | 0.929 | 4290 | rs17090639 | chr4 | 1809902470 | + | 0.922 | 0.948 | 0.902 |
| 1252 | rs4372466 | chr11 | 123067773 | + | 0.905 | 0.915 | 0.927 | 4291 | rs10520433 | chr4 | 180906412 | + | 0.942 | 0.933 | 0.91 |
| 1253 | rs1275055 | chr11 | 123076941 | + | 0.1 | 0.09 | 0.071 | 4292 | rs6829907 | chr4 | 181199068 | + | 0.942 | 0.944 | 0.923 |
| 1254 | rs2512271 | chr11 | 123570132 | + | 0.934 | 0.912 | 0.943 | 4293 | rs7673020 | chr4 | 181199279 | + | 0.925 | 0.939 | 0.914 |
| 1255 | rs2508889 | chr11 | 123590256 | + | 0.933 | 0.916 | 0.91 | 4294 | rs11943526 | chr4 | 1816686349 | + | 0.925 | 0.906 | 0.937 |
| 1256 | rs1121966C | chr11 | 123818245 | + | 0.942 | 0.904 | 0.923 | 4295 | rs17069621 | chr4 | 1816689284 | + | 0.908 | 0.904 | 0.936 |
| 1257 | rs1078278 | chr11 | 123823917 | + | 0.942 | 0.904 | 0.914 | 4296 | rs4861929 | chr4 | 1824401509 | + | 0.942 | 0.904 | 0.941 |
| 1258 | rs4936931 | chr11 | 123837345 | + | 0.947 | 0.901 | 0.936 | 4297 | rs17072892 | chr4 | 1833378784 | + | 0.925 | 0.944 | 0.941 |
| 1259 | rs12798584 | chr11 | 125567971 | + | 0.946 | 0.927 | 0.936 | 4298 | rs10224627 | chr4 | 1833383244 | + | 0.93 | 0.93 | 0.937 |

Fig. 9 Cont. 36

| | | | | | | | | | |
|---|---|---|---|---|---|---|---|---|---|
| 1260 | rs2243883 | chr11 | 126612691 | + | 0.924 | 0.921 | 0.946 | 4299 | rs12503428 chr4 | 183925422 | + | 0.905 | 0.938 | 0.937 |
| 1261 | rs11221055 | chr11 | 127179747 | + | 0.923 | 0.906 | 0.911 | 4300 | rs17264314 chr4 | 183928473 | + | 0.914 | 0.921 | 0.928 |
| 1262 | rs7950582 | chr11 | 127684286 | + | 0.05 | 0.067 | 0.054 | 4301 | rs11931238 chr4 | 184716958 | + | 0.934 | 0.908 | 0.928 |
| 1263 | rs4144897 | chr11 | 127686401 | + | 0.075 | 0.062 | 0.05 | 4302 | rs1217944 chr4 | 185430417 | + | 0.059 | 0.074 | 0.063 |
| 1264 | rs12792710 | chr11 | 127710703 | + | 0.925 | 0.95 | 0.946 | 4303 | rs793778 chr4 | 185549854 | + | 0.067 | 0.056 | 0.054 |
| 1265 | rs11221267 | chr11 | 127750541 | + | 0.908 | 0.906 | 0.919 | 4304 | rs4862378 chr4 | 185704258 | + | 0.915 | 0.943 | 0.945 |
| 1266 | rs11824786 | chr11 | 128639852 | + | 0.933 | 0.95 | 0.937 | 4305 | rs4862379 chr4 | 185711552 | + | 0.908 | 0.95 | 0.937 |
| 1267 | rs12286754 | chr11 | 130480604 | + | 0.915 | 0.939 | 0.935 | 4306 | rs4256264 chr4 | 186112200 | + | 0.058 | 0.061 | 0.095 |
| 1268 | rs2511767 | chr11 | 130623702 | + | 0.098 | 0.072 | 0.095 | 4307 | rs6854741 chr4 | 186114023 | + | 0.058 | 0.056 | 0.083 |
| 1269 | rs1793573 | chr11 | 130662520 | + | 0.067 | 0.089 | 0.05 | 4308 | rs4407549 chr4 | 186836345 | + | 0.075 | 0.076 | 0.062 |
| 1270 | rs11222289 | chr11 | 131430324 | + | 0.908 | 0.924 | 0.935 | 4309 | rs4862561 chr4 | 186839024 | + | 0.05 | 0.079 | 0.062 |
| 1271 | rs1793288 | chr11 | 132079999 | + | 0.917 | 0.933 | 0.911 | 4310 | rs4376189 chr4 | 186849669 | + | 0.058 | 0.073 | 0.077 |
| 1272 | rs11223297 | chr11 | 132336504 | + | 0.907 | 0.921 | 0.934 | 4311 | rs7688359 chr4 | 186852448 | + | 0.054 | 0.067 | 0.062 |
| 1273 | rs11223525 | chr11 | 132971529 | + | 0.925 | 0.933 | 0.95 | 4312 | rs10471184 chr4 | 187359898 | + | 0.083 | 0.067 | 0.095 |
| 1274 | rs16928563 | chr12 | 1544549 | + | 0.924 | 0.917 | 0.937 | 4313 | rs2102575 chr4 | 187368498 | + | 0.058 | 0.062 | 0.09 |
| 1275 | rs2108639 | chr12 | 1843645 | + | 0.089 | 0.083 | 0.099 | 4314 | rs6842047 chr4 | 187370570 | + | 0.067 | 0.067 | 0.095 |
| 1276 | rs3794292 | chr12 | 2634253 | + | 0.932 | 0.921 | 0.911 | 4315 | rs3087505 chr4 | 187416480 | + | 0.092 | 0.078 | 0.095 |
| 1277 | rs2302727 | chr12 | 2644862 | + | 0.942 | 0.916 | 0.932 | 4316 | rs6839415 chr4 | 187474299 | + | 0.917 | 0.911 | 0.946 |
| 1278 | rs4409904 | chr12 | 2756390 | + | 0.921 | 0.948 | 0.905 | 4317 | rs7699670 chr4 | 187674309 | + | 0.925 | 0.904 | 0.939 |
| 1279 | rs12822834 | chr12 | 3333070 | + | 0.931 | 0.944 | 0.946 | 4318 | rs7697693 chr4 | 188240362 | + | 0.95 | 0.944 | 0.946 |
| 1280 | rs7305595 | chr12 | 3432495 | + | 0.95 | 0.928 | 0.901 | 4319 | rs6553052 chr4 | 188427213 | + | 0.058 | 0.084 | 0.09 |
| 1281 | rs4551842 | chr12 | 4192879 | + | 0.95 | 0.933 | 0.946 | 4320 | rs4478239 chr4 | 188428300 | + | 0.058 | 0.079 | 0.09 |
| 1282 | rs4765795 | chr12 | 4969037 | + | 0.942 | 0.922 | 0.902 | 4321 | rs4478240 chr4 | 188428510 | + | 0.058 | 0.084 | 0.086 |
| 1283 | rs11836278 | chr12 | 4977474 | + | 0.942 | 0.922 | 0.902 | 4322 | rs13139935 chr4 | 189041622 | + | 0.939 | 0.949 | 0.913 |
| 1284 | rs4766327 | chr12 | 4981093 | + | 0.942 | 0.927 | 0.911 | 4323 | rs6842546 chr4 | 189839901 | + | 0.92 | 0.902 | 0.929 |
| 1285 | rs10849191 | chr12 | 4984558 | + | 0.942 | 0.927 | 0.911 | 4324 | rs10020429 chr4 | 190187391 | + | 0.083 | 0.065 | 0.068 |
| 1286 | rs11063463 | chr12 | 4991618 | + | 0.942 | 0.922 | 0.918 | 4325 | rs11721411 chr4 | 190586038 | + | 0.907 | 0.938 | 0.913 |
| 1287 | rs11063464 | chr12 | 4993591 | + | 0.925 | 0.95 | 0.914 | 4326 | rs10064055 chr5 | 476698 | + | 0.938 | 0.913 | 0.932 |
| 1288 | rs758605 | chr12 | 4994427 | + | 0.083 | 0.062 | 0.098 | 4327 | rs10079709 chr5 | 1997308 | + | 0.905 | 0.91 | 0.938 |
| 1289 | rs11063465 | chr12 | 4995241 | + | 0.917 | 0.944 | 0.902 | 4328 | rs10040471 chr5 | 2386521 | + | 0.905 | 0.906 | 0.938 |
| 1290 | rs2854871 | chr12 | 6003340 | + | 0.926 | 0.94 | 0.908 | 4329 | rs998700 chr5 | 2615663 | + | 0.922 | 0.95 | 0.901 |
| 1291 | rs7962629 | chr12 | 7037031 | + | 0.941 | 0.904 | 0.932 | 4330 | rs10065088 chr5 | 2622438 | + | 0.946 | 0.948 | 0.918 |
| 1292 | rs11064497 | chr12 | 7039922 | + | 0.941 | 0.906 | 0.923 | 4331 | rs13181184 chr5 | 2704220 | + | 0.917 | 0.928 | 0.92 |
| 1293 | rs12146727 | chr12 | 7040597 | + | 0.95 | 0.906 | 0.937 | 4332 | rs9313010 chr5 | 2705235 | + | 0.917 | 0.928 | 0.932 |
| 1294 | rs16933078 | chr12 | 7041599 | + | 0.95 | 0.92 | 0.936 | 4333 | rs7705712 chr5 | 2706554 | + | 0.917 | 0.928 | 0.932 |

Fig. 9 Cont. 37

| | | | | | | | | | | | |
|---|---|---|---|---|---|---|---|---|---|---|---|
| 1295 | rs17802485 | chr12 | 8907932 | + | 0.933 | 0.917 | 0.905 | 4334 | rs10042330 | chr5 | 2721187 | + | 0.917 | 0.933 | 0.946 |
| 1296 | rs4764015 | chr12 | 9882363 | + | 0.908 | 0.933 | 0.914 | 4335 | rs17571538 | chr5 | 3325039 | + | 0.933 | 0.944 | 0.902 |
| 1297 | rs4764017 | chr12 | 9882427 | + | 0.908 | 0.933 | 0.914 | 4336 | rs11738731 | chr5 | 3916152 | + | 0.908 | 0.911 | 0.938 |
| 1298 | rs11053415 | chr12 | 9884719 | + | 0.925 | 0.933 | 0.914 | 4337 | rs6893637 | chr5 | 4298119 | + | 0.924 | 0.928 | 0.938 |
| 1299 | rs11829144 | chr12 | 10241300 | + | 0.925 | 0.917 | 0.936 | 4338 | rs16873305 | chr5 | 4386446 | + | 0.942 | 0.91 | 0.943 |
| 1300 | rs2951782 | chr12 | 11478163 | + | 0.927 | 0.918 | 0.948 | 4339 | rs1346461 | chr5 | 5251616 | + | 0.083 | 0.083 | 0.1 |
| 1301 | rs11610477 | chr12 | 11545297 | + | 0.95 | 0.939 | 0.901 | 4340 | rs246763 | chr5 | 5634140 | + | 0.075 | 0.051 | 0.055 |
| 1302 | rs2724632 | chr12 | 11701550 | + | 0.925 | 0.939 | 0.946 | 4341 | rs246765 | chr5 | 5634548 | + | 0.075 | 0.05 | 0.073 |
| 1303 | rs6488468 | chr12 | 11989315 | + | 0.077 | 0.053 | 0.082 | 4342 | rs26424 | chr5 | 5641539 | + | 0.075 | 0.05 | 0.074 |
| 1304 | rs17303178 | chr12 | 12376618 | + | 0.933 | 0.906 | 0.911 | 4343 | rs26426 | chr5 | 5641699 | + | 0.075 | 0.056 | 0.089 |
| 1305 | rs3759217 | chr12 | 12759719 | + | 0.95 | 0.938 | 0.932 | 4344 | rs436704 | chr5 | 5642465 | + | 0.075 | 0.05 | 0.091 |
| 1306 | rs10772637 | chr12 | 13284168 | + | 0.083 | 0.057 | 0.054 | 4345 | rs372208 | chr5 | 5642918 | + | 0.075 | 0.05 | 0.091 |
| 1307 | rs10734860 | chr12 | 13284461 | + | 0.083 | 0.067 | 0.068 | 4346 | rs16876028 | chr5 | 5756521 | + | 0.95 | 0.938 | 0.941 |
| 1308 | rs4763948 | chr12 | 13284875 | + | 0.083 | 0.067 | 0.054 | 4347 | rs12110025 | chr5 | 5762270 | + | 0.942 | 0.938 | 0.941 |
| 1309 | rs7979618 | chr12 | 13289406 | + | 0.092 | 0.067 | 0.068 | 4348 | rs12110260 | chr5 | 5764184 | + | 0.932 | 0.933 | 0.941 |
| 1310 | rs1600285 | chr12 | 13290059 | + | 0.078 | 0.062 | 0.068 | 4349 | rs13355112 | chr5 | 6557090 | + | 0.904 | 0.949 | 0.92 |
| 1311 | rs2417264 | chr12 | 13294489 | + | 0.092 | 0.067 | 0.054 | 4350 | rs11740531 | chr5 | 6898811 | + | 0.908 | 0.911 | 0.901 |
| 1312 | rs4763952 | chr12 | 13296923 | + | 0.092 | 0.062 | 0.072 | 4351 | rs6898011 | chr5 | 7072207 | + | 0.927 | 0.921 | 0.912 |
| 1313 | rs4763953 | chr12 | 13297163 | + | 0.092 | 0.067 | 0.054 | 4352 | rs16882260 | chr5 | 9439310 | + | 0.908 | 0.944 | 0.911 |
| 1314 | rs2900308 | chr12 | 13297393 | + | 0.075 | 0.067 | 0.072 | 4353 | rs10513007 | chr5 | 9448453 | + | 0.942 | 0.939 | 0.914 |
| 1315 | rs2417261 | chr12 | 13305406 | + | 0.082 | 0.07 | 0.05 | 4354 | rs788470 | chr5 | 9450771 | + | 0.927 | 0.901 | 0.935 |
| 1316 | rs1542480 | chr12 | 15440261 | + | 0.925 | 0.938 | 0.927 | 4355 | rs16883903 | chr5 | 10009290 | + | 0.917 | 0.928 | 0.923 |
| 1317 | rs7294417 | chr12 | 18260348 | + | 0.912 | 0.926 | 0.927 | 4356 | rs16883905 | chr5 | 10009338 | + | 0.915 | 0.928 | 0.923 |
| 1318 | rs16913962 | chr12 | 18262311 | + | 0.914 | 0.904 | 0.926 | 4357 | rs1399830 | chr5 | 10605667 | + | 0.95 | 0.939 | 0.928 |
| 1319 | rs11044072 | chr12 | 18437911 | + | 0.902 | 0.931 | 0.911 | 4358 | rs2673886 | chr5 | 10608321 | + | 0.95 | 0.944 | 0.929 |
| 1320 | rs16914359 | chr12 | 18698844 | + | 0.917 | 0.944 | 0.922 | 4359 | rs7718186 | chr5 | 10631881 | + | 0.05 | 0.056 | 0.09 |
| 1321 | rs16915104 | chr12 | 19179105 | + | 0.931 | 0.91 | 0.92 | 4360 | rs4701873 | chr5 | 10644698 | + | 0.08 | 0.058 | 0.062 |
| 1322 | rs17322468 | chr12 | 19240190 | + | 0.942 | 0.928 | 0.919 | 4361 | rs4702707 | chr5 | 10646755 | + | 0.092 | 0.051 | 0.099 |
| 1323 | rs1552750 | chr12 | 19247772 | + | 0.949 | 0.927 | 0.088 | 4362 | rs2128760 | chr5 | 10650986 | + | 0.083 | 0.056 | 0.099 |
| 1324 | rs10083161 | chr12 | 19537583 | + | 0.051 | 0.085 | 0.911 | 4363 | rs2170698 | chr5 | 10655050 | + | 0.075 | 0.057 | 0.062 |
| 1325 | rs12824186 | chr12 | 19537841 | + | 0.925 | 0.95 | 0.935 | 4364 | rs10474916 | chr5 | 11346094 | + | 0.907 | 0.915 | 0.914 |
| 1326 | rs7486638 | chr12 | 19652424 | + | 0.915 | 0.91 | 0.941 | 4365 | rs31885 | chr5 | 11475057 | + | 0.908 | 0.916 | 0.946 |
| 1327 | rs7136028 | chr12 | 19662552 | + | 0.923 | 0.929 | 0.059 | 4366 | rs10080088 | chr5 | 11483815 | + | 0.942 | 0.932 | 0.95 |
| 1328 | rs7487108 | chr12 | 19665429 | + | 0.092 | 0.08 | 0.063 | 4367 | rs10075848 | chr5 | 11488767 | + | 0.95 | 0.92 | 0.937 |
| 1329 | rs7956585 | chr12 | 19669784 | + | 0.075 | 0.094 | | 4368 | rs12523633 | chr5 | 11571704 | + | 0.95 | 0.949 | 0.936 |

Fig. 9 Cont. 38

| | | | | | | | | | |
|---|---|---|---|---|---|---|---|---|---|
| 1330 | rs12580173 | chr12 | 20680350 | + | 0.908 | 0.91 | 0.904 | 4369 rs795509 chr5 | 13923582 | + | 0.067 | 0.051 | 0.099 |
| 1331 | rs1863656 | chr12 | 22892283 | + | 0.907 | 0.925 | 0.946 | 4370 rs17232390 chr5 | 14178733 | + | 0.95 | 0.933 | 0.936 |
| 1332 | rs11047215 | chr12 | 24070989 | + | 0.95 | 0.933 | 0.941 | 4371 rs17298767 chr5 | 14210376 | + | 0.95 | 0.933 | 0.905 |
| 1333 | rs1498884 | chr12 | 24144596 | + | 0.941 | 0.938 | 0.95 | 4372 rs10513185 chr5 | 14818010 | + | 0.942 | 0.939 | 0.923 |
| 1334 | rs16927193 | chr12 | 24160074 | + | 0.942 | 0.944 | 0.938 | 4373 rs10064209 chr5 | 14852788 | + | 0.915 | 0.933 | 0.936 |
| 1335 | rs7132878 | chr12 | 25468046 | + | 0.053 | 0.083 | 0.054 | 4374 rs4702149 chr5 | 16557763 | + | 0.067 | 0.083 | 0.072 |
| 1336 | rs7960064 | chr12 | 25474467 | + | 0.075 | 0.082 | 0.054 | 4375 rs12514745 chr5 | 17055503 | + | 0.936 | 0.926 | 0.92 |
| 1337 | rs16929850 | chr12 | 26036116 | + | 0.939 | 0.91 | 0.919 | 4376 rs17658678 chr5 | 17458816 | + | 0.924 | 0.934 | 0.945 |
| 1338 | rs4963645 | chr12 | 26078662 | + | 0.908 | 0.923 | 0.934 | 4377 rs7708009 chr5 | 17820536 | + | 0.058 | 0.05 | 0.055 |
| 1339 | rs16933302 | chr12 | 28845601 | + | 0.917 | 0.944 | 0.938 | 4378 rs2380159 chr5 | 17924872 | + | 0.083 | 0.074 | 0.054 |
| 1340 | rs12228134 | chr12 | 29050065 | + | 0.94 | 0.928 | 0.923 | 4379 rs2120247 chr5 | 17925481 | + | 0.076 | 0.073 | 0.054 |
| 1341 | rs1122176 | chr12 | 29053621 | + | 0.948 | 0.928 | 0.929 | 4380 rs1542128 chr5 | 17926883 | + | 0.083 | 0.073 | 0.081 |
| 1342 | rs12300735 | chr12 | 29108512 | + | 0.908 | 0.928 | 0.926 | 4381 rs4866334 chr5 | 18519408 | + | 0.05 | 0.083 | 0.068 |
| 1343 | rs10843302 | chr12 | 29112988 | + | 0.932 | 0.927 | 0.927 | 4382 rs4866335 chr5 | 18519791 | + | 0.05 | 0.084 | 0.089 |
| 1344 | rs12823627 | chr12 | 29752395 | + | 0.925 | 0.922 | 0.945 | 4383 rs4866336 chr5 | 18519862 | + | 0.051 | 0.06 | 0.089 |
| 1345 | rs11050595 | chr12 | 30028101 | + | 0.908 | 0.911 | 0.932 | 4384 rs4302587 chr5 | 18520485 | + | 0.05 | 0.084 | 0.089 |
| 1346 | rs7955127 | chr12 | 30033789 | + | 0.912 | 0.909 | 0.904 | 4385 rs10063324 chr5 | 19445197 | + | 0.908 | 0.907 | 0.948 |
| 1347 | rs33157 | chr12 | 30879244 | + | 0.925 | 0.906 | 0.928 | 4386 rs11959007 chr5 | 22992727 | + | 0.933 | 0.95 | 0.927 |
| 1348 | rs12822239 | chr12 | 31086539 | + | 0.942 | 0.933 | 0.937 | 4387 rs16892093 chr5 | 23245937 | + | 0.941 | 0.933 | 0.941 |
| 1349 | rs7133392 | chr12 | 31774740 | + | 0.925 | 0.922 | 0.932 | 4388 rs17312807 chr5 | 23361189 | + | 0.917 | 0.938 | 0.936 |
| 1350 | rs17554204 | chr12 | 33131311 | + | 0.941 | 0.939 | 0.918 | 4389 rs16899423 chr5 | 24131448 | + | 0.934 | 0.921 | 0.941 |
| 1351 | rs871915 | chr12 | 37785319 | + | 0.925 | 0.92 | 0.928 | 4390 rs17445636 chr5 | 24197491 | + | 0.925 | 0.939 | 0.911 |
| 1352 | rs7955590 | chr12 | 37992012 | + | 0.933 | 0.92 | 0.938 | 4391 rs17445670 chr5 | 24197963 | + | 0.925 | 0.939 | 0.905 |
| 1353 | rs11180331 | chr12 | 39897315 | + | 0.942 | 0.928 | 0.902 | 4392 rs7732219 chr5 | 24199648 | + | 0.925 | 0.939 | 0.905 |
| 1354 | rs7311069 | chr12 | 39898091 | + | 0.939 | 0.926 | 0.902 | 4393 rs1012757 chr5 | 24201673 | + | 0.933 | 0.938 | 0.907 |
| 1355 | rs17091117 | chr12 | 41052980 | + | 0.933 | 0.933 | 0.941 | 4394 rs1366919 chr5 | 24703885 | + | 0.911 | 0.937 | 0.946 |
| 1356 | rs1037401 | chr12 | 41152976 | + | 0.948 | 0.921 | 0.95 | 4395 rs13436065 chr5 | 24736668 | + | 0.932 | 0.922 | 0.946 |
| 1357 | rs11182653 | chr12 | 43443040 | + | 0.932 | 0.939 | 0.901 | 4396 rs10520906 chr5 | 24761800 | + | 0.912 | 0.946 | 0.946 |
| 1358 | rs11183497 | chr12 | 45142487 | + | 0.942 | 0.922 | 0.919 | 4397 rs1888268 chr5 | 26236885 | + | 0.1 | 0.072 | 0.055 |
| 1359 | rs12579089 | chr12 | 45297375 | + | 0.95 | 0.933 | 0.914 | 4398 rs16895993 chr5 | 26758542 | + | 0.908 | 0.928 | 0.927 |
| 1360 | rs12582476 | chr12 | 45308841 | + | 0.95 | 0.933 | 0.929 | 4399 rs6878604 chr5 | 26763901 | + | 0.904 | 0.939 | 0.934 |
| 1361 | rs17611638 | chr12 | 45311571 | + | 0.948 | 0.933 | 0.936 | 4400 rs13157739 chr5 | 30221768 | + | 0.914 | 0.948 | 0.906 |
| 1362 | rs766794 | chr12 | 45333004 | + | 0.95 | 0.933 | 0.929 | 4401 rs12655405 chr5 | 31801198 | + | 0.075 | 0.05 | 0.063 |
| 1363 | rs17594275 | chr12 | 45374775 | + | 0.95 | 0.944 | 0.914 | 4402 rs10037691 chr5 | 31967392 | + | 0.051 | 0.085 | 0.054 |
| 1364 | rs12317057 | chr12 | 45377685 | + | 0.917 | 0.944 | 0.92 | 4403 rs4703508 chr5 | 35224559 | + | 0.917 | 0.939 | 0.91 |

Fig. 9 Cont. 39

| | | | | | | | | | |
|---|---|---|---|---|---|---|---|---|---|
| 1365 | rs11183569 | chr12 | 45390124 | + | 0.925 | 0.949 | 0.928 | 4404 | rs2455275 chr5 | 36492065 | + | 0.925 | 0.933 | 0.938 |
| 1366 | rs2051827 | chr12 | 46242298 | + | 0.932 | 0.933 | 0.941 | 4405 | rs2455280 chr5 | 36496182 | + | 0.925 | 0.933 | 0.937 |
| 1367 | rs4768158 | chr12 | 46242734 | + | 0.933 | 0.933 | 0.938 | 4406 | rs12653677 chr5 | 36766468 | + | 0.942 | 0.933 | 0.95 |
| 1368 | rs11830037 | chr12 | 46443638 | + | 0.933 | 0.938 | 0.946 | 4407 | rs16903304 chr5 | 36766982 | + | 0.933 | 0.933 | 0.95 |
| 1369 | rs11830537 | chr12 | 46443970 | + | 0.933 | 0.937 | 0.928 | 4408 | rs16903305 chr5 | 36767642 | + | 0.939 | 0.94 | 0.948 |
| 1370 | rs6580833 | chr12 | 50093066 | + | 0.092 | 0.068 | 0.069 | 4409 | rs11743146 chr5 | 36844388 | + | 0.917 | 0.933 | 0.914 |
| 1371 | rs10876176 | chr12 | 50098099 | + | 0.092 | 0.056 | 0.068 | 4410 | rs12521488 chr5 | 36861839 | + | 0.933 | 0.933 | 0.944 |
| 1372 | rs2135829 | chr12 | 50100662 | + | 0.092 | 0.061 | 0.068 | 4411 | rs12513653 chr5 | 36875687 | + | 0.95 | 0.933 | 0.946 |
| 1373 | rs1850709 | chr12 | 50101969 | + | 0.093 | 0.062 | 0.071 | 4412 | rs11743833 chr5 | 36969704 | + | 0.927 | 0.933 | 0.915 |
| 1374 | rs10876177 | chr12 | 50102407 | + | 0.092 | 0.061 | 0.069 | 4413 | rs16903403 chr5 | 36970595 | + | 0.925 | 0.927 | 0.948 |
| 1375 | rs10747613 | chr12 | 50103802 | + | 0.092 | 0.061 | 0.068 | 4414 | rs16903413 chr5 | 36981291 | + | 0.933 | 0.933 | 0.928 |
| 1376 | rs7300910 | chr12 | 50110704 | + | 0.085 | 0.056 | 0.068 | 4415 | rs10941319 chr5 | 36988447 | + | 0.929 | 0.93 | 0.945 |
| 1377 | rs870814 | chr12 | 50121527 | + | 0.092 | 0.062 | 0.09 | 4416 | rs16903427 chr5 | 37013238 | + | 0.933 | 0.933 | 0.928 |
| 1378 | rs1995690 | chr12 | 50131962 | + | 0.092 | 0.062 | 0.068 | 4417 | rs16903429 chr5 | 37018720 | + | 0.933 | 0.933 | 0.946 |
| 1379 | rs4761817 | chr12 | 50133185 | + | 0.085 | 0.061 | 0.068 | 4418 | rs3776588 chr5 | 37019399 | + | 0.933 | 0.933 | 0.905 |
| 1380 | rs4491281 | chr12 | 50149910 | + | 0.092 | 0.061 | 0.068 | 4419 | rs3822471 chr5 | 37021060 | + | 0.933 | 0.933 | 0.905 |
| 1381 | rs79961653 | chr12 | 50161967 | + | 0.085 | 0.052 | 0.059 | 4420 | rs16903442 chr5 | 37034044 | + | 0.933 | 0.938 | 0.905 |
| 1382 | rs10783445 | chr12 | 50166093 | + | 0.092 | 0.061 | 0.068 | 4421 | rs12187383 chr5 | 37063015 | + | 0.931 | 0.933 | 0.927 |
| 1383 | rs4761974 | chr12 | 50166712 | + | 0.092 | 0.061 | 0.068 | 4422 | rs12153359 chr5 | 37055642 | + | 0.94 | 0.933 | 0.905 |
| 1384 | rs2292221 | chr12 | 50188262 | + | 0.092 | 0.062 | 0.071 | 4423 | rs12188075 chr5 | 37087003 | + | 0.917 | 0.933 | 0.934 |
| 1385 | rs3926616 | chr12 | 50191126 | + | 0.092 | 0.061 | 0.068 | 4424 | rs2910721 chr5 | 37791094 | + | 0.949 | 0.939 | 0.95 |
| 1386 | rs1493193 | chr12 | 50192616 | + | 0.092 | 0.062 | 0.068 | 4425 | rs17331676 chr5 | 38032744 | + | 0.933 | 0.95 | 0.902 |
| 1387 | rs7302923 | chr12 | 50202853 | + | 0.092 | 0.062 | 0.068 | 4426 | rs270548 chr5 | 38083604 | + | 0.922 | 0.931 | 0.905 |
| 1388 | rs1992294 | chr12 | 50443754 | + | 0.941 | 0.91 | 0.927 | 4427 | rs10045133 chr5 | 38386859 | + | 0.908 | 0.915 | 0.937 |
| 1389 | rs1402594 | chr12 | 51438591 | + | 0.1 | 0.083 | 0.054 | 4428 | rs13159944 chr5 | 39145162 | + | 0.917 | 0.922 | 0.914 |
| 1390 | rs1521350 | chr12 | 51444127 | + | 0.1 | 0.083 | 0.054 | 4429 | rs2962478 chr5 | 39575032 | + | 0.908 | 0.928 | 0.946 |
| 1391 | rs2056375 | chr12 | 51445999 | + | 0.059 | 0.084 | 0.054 | 4430 | rs16870171 chr5 | 40643917 | + | 0.908 | 0.928 | 0.946 |
| 1392 | rs10876558 | chr12 | 53088357 | + | 0.941 | 0.917 | 0.907 | 4431 | rs7714031 chr5 | 41512104 | + | 0.933 | 0.928 | 0.937 |
| 1393 | rs11170895 | chr12 | 53097975 | + | 0.95 | 0.921 | 0.91 | 4432 | rs16880442 chr5 | 52221452 | + | 0.932 | 0.944 | 0.941 |
| 1394 | rs17115701 | chr12 | 53365621 | + | 0.942 | 0.944 | 0.95 | 4433 | rs6450228 chr5 | 53973383 | + | 0.908 | 0.094 | 0.1 |
| 1395 | rs937758 | chr12 | 53679657 | + | 0.925 | 0.935 | 0.902 | 4434 | rs4593230 chr5 | 53973993 | + | 0.075 | 0.091 | 0.072 |
| 1396 | rs10876558 | chr12 | 55709201 | + | 0.95 | 0.908 | 0.923 | 4435 | rs1876680 chr5 | 54370181 | + | 0.083 | 0.906 | 0.937 |
| 1397 | rs1059513 | chr12 | 55775976 | + | 0.949 | 0.904 | 0.914 | 4436 | rs17707459 chr5 | 55784499 | + | 0.917 | 0.95 | 0.901 |
| 1398 | rs12368658 | chr12 | 57732758 | + | 0.925 | 0.944 | 0.911 | 4437 | rs16885555 chr5 | 55825237 | + | 0.933 | 0.917 | 0.937 |
| 1399 | rs17120243 | chr12 | 58492903 | + | 0.917 | 0.944 | 0.91 | 4438 | rs3852142 chr5 | 55832725 | + | 0.922 | 0.911 | 0.946 |

Fig. 9 Cont. 40

| | | | | | | | | | | | | | |
|---|---|---|---|---|---|---|---|---|---|---|---|---|---|
| 1400 | rs4131430 | chr12 | 58520213 | + | 0.917 | 0.949 | 0.905 | 4439 | rs12054839 | chr5 | 57254238 | + | 0.95 | 0.933 | 0.931 |
| 1401 | rs7303705 | chr12 | 58539264 | + | 0.917 | 0.95 | 0.905 | 4440 | rs6450453 | chr5 | 57304424 | + | 0.075 | 0.062 | 0.083 |
| 1402 | rs17123263 | chr12 | 58740562 | + | 0.95 | 0.95 | 0.929 | 4441 | rs995443 | chr5 | 57308680 | + | 0.075 | 0.062 | 0.098 |
| 1403 | rs12318268 | chr12 | 59205387 | + | 0.907 | 0.938 | 0.938 | 4442 | rs1489796 | chr5 | 57309335 | + | 0.075 | 0.062 | 0.098 |
| 1404 | rs12307407 | chr12 | 59233662 | + | 0.925 | 0.933 | 0.919 | 4443 | rs10080109 | chr5 | 57315992 | + | 0.05 | 0.057 | 0.098 |
| 1405 | rs1604717 | chr12 | 59345316 | + | 0.921 | 0.944 | 0.909 | 4444 | rs4279298 | chr5 | 57376901 | + | 0.922 | 0.938 | 0.905 |
| 1406 | rs17311257 | chr12 | 59474268 | + | 0.942 | 0.922 | 0.918 | 4445 | rs13185082 | chr5 | 57441016 | + | 0.908 | 0.922 | 0.941 |
| 1407 | rs10083195 | chr12 | 59487245 | + | 0.924 | 0.922 | 0.911 | 4446 | rs2910569 | chr5 | 57490085 | + | 0.075 | 0.1 | 0.089 |
| 1408 | rs11174503 | chr12 | 61162980 | + | 0.941 | 0.944 | 0.918 | 4447 | rs13187650 | chr5 | 57498803 | + | 0.075 | 0.1 | 0.081 |
| 1409 | rs7302781 | chr12 | 61190571 | + | 0.904 | 0.931 | 0.911 | 4448 | rs10472035 | chr5 | 57499887 | + | 0.075 | 0.1 | 0.091 |
| 1410 | rs11174561 | chr12 | 61294203 | + | 0.925 | 0.938 | 0.91 | 4449 | rs10472036 | chr5 | 57499922 | + | 0.075 | 0.1 | 0.091 |
| 1411 | rs17098092 | chr12 | 61295232 | + | 0.933 | 0.933 | 0.923 | 4450 | rs2962016 | chr5 | 57503956 | + | 0.068 | 0.083 | 0.091 |
| 1412 | rs12229932 | chr12 | 61318710 | + | 0.942 | 0.922 | 0.902 | 4451 | rs2964177 | chr5 | 57504555 | + | 0.075 | 0.1 | 0.089 |
| 1413 | rs10877903 | chr12 | 61333499 | + | 0.908 | 0.939 | 0.938 | 4452 | rs1035475 | chr5 | 57505530 | + | 0.065 | 0.091 | 0.07 |
| 1414 | rs2272521 | chr12 | 61347473 | + | 0.917 | 0.921 | 0.906 | 4453 | rs1981838 | chr5 | 57510605 | + | 0.075 | 0.1 | 0.081 |
| 1415 | rs7296442 | chr12 | 61681768 | + | 0.922 | 0.928 | 0.93 | 4454 | rs2962009 | chr5 | 57510781 | + | 0.068 | 0.079 | 0.098 |
| 1416 | rs7308855 | chr12 | 61834323 | + | 0.933 | 0.944 | 0.914 | 4455 | rs2964184 | chr5 | 57513873 | + | 0.075 | 0.1 | 0.089 |
| 1417 | rs1390033 | chr12 | 61889795 | + | 0.925 | 0.95 | 0.914 | 4456 | rs2910601 | chr5 | 57519118 | + | 0.075 | 0.1 | 0.081 |
| 1418 | rs11176243 | chr12 | 65199258 | + | 0.933 | 0.933 | 0.945 | 4457 | rs2910594 | chr5 | 57528876 | + | 0.075 | 0.1 | 0.089 |
| 1419 | rs12320846 | chr12 | 65433711 | + | 0.943 | 0.92 | 0.941 | 4458 | rs2910577 | chr5 | 57568114 | + | 0.061 | 0.09 | 0.083 |
| 1420 | rs9776714 | chr12 | 65489547 | + | 0.925 | 0.904 | 0.902 | 4459 | rs2675390 | chr5 | 58201132 | + | 0.06 | 0.054 | 0.065 |
| 1421 | rs7955073 | chr12 | 65621547 | + | 0.917 | 0.928 | 0.938 | 4460 | rs538776 | chr5 | 58218944 | + | 0.942 | 0.922 | 0.91 |
| 1422 | rs2870805 | chr12 | 66200187 | + | 0.908 | 0.92 | 0.928 | 4461 | rs12655332 | chr5 | 58293409 | + | 0.926 | 0.944 | 0.919 |
| 1423 | rs7485119 | chr12 | 67874801 | + | 0.917 | 0.944 | 0.938 | 4462 | rs12657171 | chr5 | 58326965 | + | 0.95 | 0.904 | 0.932 |
| 1424 | rs7962703 | chr12 | 67879862 | + | 0.917 | 0.944 | 0.918 | 4463 | rs17449821 | chr5 | 59509124 | + | 0.95 | 0.95 | 0.911 |
| 1425 | rs4072257 | chr12 | 67884017 | + | 0.933 | 0.944 | 0.919 | 4464 | rs17449877 | chr5 | 59509457 | + | 0.949 | 0.95 | 0.911 |
| 1426 | rs4761277 | chr12 | 68657388 | + | 0.908 | 0.909 | 0.902 | 4465 | rs409912 | chr5 | 60954520 | + | 0.917 | 0.916 | 0.905 |
| 1427 | rs3782384 | chr12 | 69065821 | + | 0.932 | 0.933 | 0.946 | 4466 | rs10214403 | chr5 | 61483255 | + | 0.933 | 0.937 | 0.936 |
| 1428 | rs10785032 | chr12 | 72108495 | + | 0.051 | 0.078 | 0.07 | 4467 | rs10057846 | chr5 | 61492526 | + | 0.943 | 0.938 | 0.914 |
| 1429 | rs12299583 | chr12 | 73012239 | + | 0.908 | 0.939 | 0.945 | 4468 | rs16893555 | chr5 | 64579272 | + | 0.933 | 0.903 | 0.927 |
| 1430 | rs12313269 | chr12 | 73012783 | + | 0.917 | 0.944 | 0.945 | 4469 | rs16893578 | chr5 | 64582921 | + | 0.917 | 0.906 | 0.929 |
| 1431 | rs7964349 | chr12 | 73210778 | + | 0.925 | 0.939 | 0.946 | 4470 | rs16893582 | chr5 | 64583344 | + | 0.917 | 0.904 | 0.919 |
| 1432 | rs10785206 | chr12 | 74371102 | + | 0.067 | 0.097 | 0.077 | 4471 | rs10514980 | chr5 | 64643686 | + | 0.95 | 0.904 | 0.941 |
| 1433 | rs12310537 | chr12 | 74549756 | + | 0.91 | 0.916 | 0.941 | 4472 | rs4700677 | chr5 | 64701981 | + | 0.939 | 0.904 | 0.941 |
| 1434 | rs12227679 | chr12 | 76319198 | + | 0.917 | 0.91 | 0.937 | 4473 | rs16893764 | chr5 | 64718984 | + | 0.908 | 0.904 | 0.929 |

Fig. 9 Cont. 41

| | | | | | | | | | | | |
|---|---|---|---|---|---|---|---|---|---|---|---|
| 1435 | rs11105098 | chr12 | 76319306 | + | 0.917 | 0.91 | 0.932 | 4474 | rs16893787 chr5 | 64724770 | + | 0.925 | 0.911 | 0.941 |
| 1436 | rs300483 | chr12 | 77004724 | + | 0.925 | 0.939 | 0.932 | 4475 | rs13165273 chr5 | 64728807 | + | 0.925 | 0.911 | 0.935 |
| 1437 | rs300486 | chr12 | 77008252 | + | 0.907 | 0.933 | 0.937 | 4476 | rs6877731 chr5 | 64731473 | + | 0.931 | 0.918 | 0.927 |
| 1438 | rs300487 | chr12 | 77008621 | + | 0.915 | 0.939 | 0.938 | 4477 | rs2367534 chr5 | 64819746 | + | 0.912 | 0.943 | 0.94 |
| 1439 | rs12321427 | chr12 | 77252345 | + | 0.941 | 0.922 | 0.937 | 4478 | rs17828812 chr5 | 64886188 | + | 0.912 | 0.933 | 0.928 |
| 1440 | rs1510888 | chr12 | 77252840 | + | 0.925 | 0.909 | 0.929 | 4479 | rs17828842 chr5 | 64886234 | + | 0.905 | 0.933 | 0.927 |
| 1441 | rs10860314 | chr12 | 77255375 | + | 0.925 | 0.917 | 0.929 | 4480 | rs17830337 chr5 | 64961309 | + | 0.945 | 0.928 | 0.927 |
| 1442 | rs2037406 | chr12 | 79811443 | + | 0.95 | 0.927 | 0.937 | 4481 | rs17241952 chr5 | 65039962 | + | 0.924 | 0.924 | 0.931 |
| 1443 | rs17766600 | chr12 | 81137845 | + | 0.917 | 0.917 | 0.911 | 4482 | rs2113030 chr5 | 65221177 | + | 0.941 | 0.922 | 0.928 |
| 1444 | rs17766762 | chr12 | 81143125 | + | 0.917 | 0.917 | 0.911 | 4483 | rs253287 chr5 | 65547728 | + | 0.908 | 0.91 | 0.946 |
| 1445 | rs17766804 | chr12 | 81143332 | + | 0.917 | 0.917 | 0.911 | 4484 | rs253218 chr5 | 65559086 | + | 0.908 | 0.904 | 0.938 |
| 1446 | rs17766846 | chr12 | 81143430 | + | 0.914 | 0.917 | 0.913 | 4485 | rs6869587 chr5 | 66812640 | + | 0.924 | 0.949 | 0.919 |
| 1447 | rs7316792 | chr12 | 81538305 | + | 0.905 | 0.937 | 0.923 | 4486 | rs4607305 chr5 | 67046294 | + | 0.917 | 0.911 | 0.901 |
| 1448 | rs11115636 | chr12 | 82108504 | + | 0.95 | 0.922 | 0.946 | 4487 | rs16897840 chr5 | 67769297 | + | 0.942 | 0.95 | 0.95 |
| 1449 | rs12426701 | chr12 | 82157215 | + | 0.921 | 0.906 | 0.936 | 4488 | rs403031 chr5 | 73252218 | + | 0.942 | 0.926 | 0.927 |
| 1450 | rs2130635 | chr12 | 82372409 | + | 0.908 | 0.928 | 0.905 | 4489 | rs386852 chr5 | 73251475 | + | 0.942 | 0.917 | 0.911 |
| 1451 | rs12230777 | chr12 | 86386818 | + | 0.933 | 0.939 | 0.945 | 4490 | rs405063 chr5 | 73251691 | + | 0.942 | 0.917 | 0.911 |
| 1452 | rs11104527 | chr12 | 86427076 | + | 0.942 | 0.944 | 0.95 | 4491 | rs4703656 chr5 | 74490823 | + | 0.92 | 0.936 | 0.901 |
| 1453 | rs990400 | chr12 | 86788829 | + | 0.942 | 0.912 | 0.919 | 4492 | rs16872528 chr5 | 74712039 | + | 0.95 | 0.911 | 0.931 |
| 1454 | rs10745465 | chr12 | 86871331 | + | 0.092 | 0.056 | 0.081 | 4493 | rs7733891 chr5 | 75135366 | + | 0.917 | 0.95 | 0.946 |
| 1455 | rs7969969 | chr12 | 88186014 | + | 0.935 | 0.907 | 0.94 | 4494 | rs6887093 chr5 | 75491007 | + | 0.931 | 0.941 | 0.931 |
| 1456 | rs11105230 | chr12 | 88187440 | + | 0.939 | 0.928 | 0.918 | 4495 | rs2431352 chr5 | 75959050 | + | 0.053 | 0.07 | 0.054 |
| 1457 | rs12809787 | chr12 | 90838893 | + | 0.949 | 0.928 | 0.937 | 4496 | rs2909892 chr5 | 75965105 | + | 0.079 | 0.071 | 0.054 |
| 1458 | rs4761580 | chr12 | 93043590 | + | 0.096 | 0.086 | 0.093 | 4497 | rs2242991 chr5 | 76150615 | + | 0.95 | 0.944 | 0.92 |
| 1459 | rs2054724 | chr12 | 93166996 | + | 0.908 | 0.911 | 0.923 | 4498 | rs11740813 chr5 | 76262501 | + | 0.917 | 0.95 | 0.928 |
| 1460 | rs10507042 | chr12 | 93584361 | + | 0.067 | 0.092 | 0.08 | 4499 | rs10942805 chr5 | 76267859 | + | 0.949 | 0.95 | 0.946 |
| 1461 | rs2134129 | chr12 | 93591955 | + | 0.067 | 0.09 | 0.099 | 4500 | rs10058100 chr5 | 76346154 | + | 0.908 | 0.933 | 0.932 |
| 1462 | rs6538525 | chr12 | 93594443 | + | 0.069 | 0.099 | 0.099 | 4501 | rs17226802 chr5 | 78424694 | + | 0.917 | 0.944 | 0.95 |
| 1463 | rs20036382 | chr12 | 93658449 | + | 0.05 | 0.08 | 0.08 | 4502 | rs2278240 chr5 | 79069147 | + | 0.942 | 0.91 | 0.945 |
| 1464 | rs12320082 | chr12 | 93658628 | + | 0.05 | 0.074 | 0.08 | 4503 | rs16877206 chr5 | 79127270 | + | 0.94 | 0.906 | 0.925 |
| 1465 | rs1019980 | chr12 | 93670498 | + | 0.058 | 0.062 | 0.068 | 4504 | rs2042980 chr5 | 80728943 | + | 0.95 | 0.927 | 0.938 |
| 1466 | rs2117322 | chr12 | 93695096 | + | 0.092 | 0.079 | 0.05 | 4505 | rs7736398 chr5 | 82344884 | + | 0.942 | 0.922 | 0.928 |
| 1467 | rs10859776 | chr12 | 93783324 | + | 0.067 | 0.078 | 0.05 | 4506 | rs4364367 chr5 | 83259929 | + | 0.915 | 0.944 | 0.91 |
| 1468 | rs7312459 | chr12 | 95079533 | + | 0.933 | 0.916 | 0.923 | 4507 | rs4920674 chr5 | 84587486 | + | 0.949 | 0.933 | 0.92 |
| 1469 | rs11108802 | chr12 | 96017296 | + | 0.917 | 0.944 | 0.923 | 4508 | rs4602659 chr5 | 84592032 | + | 0.95 | 0.927 | 0.941 |

Fig. 9  Cont. 42

| # | RS | chr | pos | strand | v1 | v2 | v3 | # | RS | chr | pos | strand | v1 | v2 | v3 |
|---|---|---|---|---|---|---|---|---|---|---|---|---|---|---|---|
| 1470 | rs11108813 | chr12 | 96025191 | + | 0.93 | 0.937 | 0.935 | | 4509 rs4244384 | chr5 | 84593941 | + | 0.949 | 0.928 | 0.92 |
| 1471 | rs10860148 | chr12 | 96040015 | + | 0.917 | 0.944 | 0.923 | | 4510 rs4244385 | chr5 | 84594012 | + | 0.95 | 0.927 | 0.92 |
| 1472 | rs759571 | chr12 | 96074344 | + | 0.075 | 0.1 | 0.054 | | 4511 rs4920772 | chr5 | 84594166 | + | 0.949 | 0.928 | 0.92 |
| 1473 | rs7974139 | chr12 | 96087610 | + | 0.933 | 0.95 | 0.92 | | 4512 rs4920781 | chr5 | 84606937 | + | 0.95 | 0.927 | 0.941 |
| 1474 | rs2111027 | chr12 | 96209188 | + | 0.933 | 0.921 | 0.923 | | 4513 rs37241 | chr5 | 89889098 | + | 0.942 | 0.938 | 0.946 |
| 1475 | rs12426600 | chr12 | 96375870 | + | 0.933 | 0.916 | 0.946 | | 4514 rs100045071 | chr5 | 90163715 | + | 0.933 | 0.946 | 0.926 |
| 1476 | rs4762390 | chr12 | 96410872 | + | 0.925 | 0.917 | 0.913 | | 4515 rs16869562 | chr5 | 90521470 | + | 0.941 | 0.938 | 0.937 |
| 1477 | rs11109148 | chr12 | 96569025 | + | 0.938 | 0.92 | 0.92 | | 4516 rs1827818 | chr5 | 90967243 | + | 0.932 | 0.92 | 0.946 |
| 1478 | rs7973118 | chr12 | 96576245 | + | 0.933 | 0.921 | 0.92 | | 4517 rs1380646 | chr5 | 93635771 | + | 0.075 | 0.094 | 0.059 |
| 1479 | rs1420396 | chr12 | 96586016 | + | 0.932 | 0.917 | 0.928 | | 4518 rs2081863 | chr5 | 93642605 | + | 0.076 | 0.083 | 0.055 |
| 1480 | rs11109163 | chr12 | 96599570 | + | 0.932 | 0.927 | 0.923 | | 4519 rs12513728 | chr5 | 95187501 | + | 0.906 | 0.94 | 0.941 |
| 1481 | rs7136455 | chr12 | 97141605 | + | 0.05 | 0.067 | 0.071 | | 4520 rs17087180 | chr5 | 96280057 | + | 0.912 | 0.914 | 0.926 |
| 1482 | rs11109456 | chr12 | 97294794 | + | 0.915 | 0.907 | 0.914 | | 4521 rs7714122 | chr5 | 96280773 | + | 0.908 | 0.914 | 0.941 |
| 1483 | rs7965231 | chr12 | 99005657 | + | 0.925 | 0.939 | 0.911 | | 4522 rs7721014 | chr5 | 96284496 | + | 0.926 | 0.906 | 0.909 |
| 1484 | rs17029981 | chr12 | 99015682 | + | 0.925 | 0.939 | 0.925 | | 4523 rs7733301 | chr5 | 96289346 | + | 0.908 | 0.91 | 0.941 |
| 1485 | rs989964 | chr12 | 100473868 | + | 0.942 | 0.943 | 0.937 | | 4524 rs31008 | chr5 | 96511042 | + | 0.917 | 0.944 | 0.902 |
| 1486 | rs1603818 | chr12 | 101913368 | + | 0.05 | 0.05 | 0.054 | | 4525 rs31007 | chr5 | 96511131 | + | 0.931 | 0.949 | 0.902 |
| 1487 | rs1574503 | chr12 | 102274239 | + | 0.908 | 0.921 | 0.937 | | 4526 rs30998 | chr5 | 96521945 | + | 0.933 | 0.933 | 0.928 |
| 1488 | rs12813302 | chr12 | 102381038 | + | 0.95 | 0.922 | 0.946 | | 4527 rs6896160 | chr5 | 96540738 | + | 0.067 | 0.061 | 0.072 |
| 1489 | rs9645789 | chr12 | 102449259 | + | 0.95 | 0.922 | 0.941 | | 4528 rs2431140 | chr5 | 96546024 | + | 0.068 | 0.051 | 0.098 |
| 1490 | rs17034433 | chr12 | 102648148 | + | 0.948 | 0.943 | 0.946 | | 4529 rs1485470 | chr5 | 96774421 | + | 0.092 | 0.099 | 0.09 |
| 1491 | rs12425719 | chr12 | 102650816 | + | 0.95 | 0.931 | 0.946 | | 4530 rs291816 | chr5 | 96776642 | + | 0.078 | 0.096 | 0.089 |
| 1492 | rs17812685 | chr12 | 103468941 | + | 0.95 | 0.911 | 0.914 | | 4531 rs291818 | chr5 | 96777120 | + | 0.085 | 0.1 | 0.089 |
| 1493 | rs10861443 | chr12 | 104428655 | + | 0.942 | 0.902 | 0.905 | | 4532 rs17414873 | chr5 | 99288167 | + | 0.925 | 0.95 | 0.937 |
| 1494 | rs3741786 | chr12 | 106211020 | + | 0.933 | 0.944 | 0.941 | | 4533 rs3811976 | chr5 | 101598135 | + | 0.914 | 0.906 | 0.901 |
| 1495 | rs2058823 | chr12 | 106637681 | + | 0.933 | 0.944 | 0.941 | | 4534 rs17155558 | chr5 | 102973423 | + | 0.942 | 0.95 | 0.928 |
| 1496 | rs3741791 | chr12 | 106677701 | + | 0.942 | 0.916 | 0.941 | | 4535 rs11948851 | chr5 | 102986181 | + | 0.942 | 0.92 | 0.928 |
| 1497 | rs11113957 | chr12 | 107426887 | + | 0.915 | 0.941 | 0.936 | | 4536 rs6596650 | chr5 | 105206356 | + | 0.067 | 0.067 | 0.08 |
| 1498 | rs7975814 | chr12 | 110139253 | + | 0.917 | 0.947 | 0.905 | | 4537 rs1388136 | chr5 | 107061430 | + | 0.925 | 0.938 | 0.919 |
| 1499 | rs16941541 | chr12 | 110438087 | + | 0.907 | 0.933 | 0.923 | | 4538 rs1388135 | chr5 | 107065815 | + | 0.925 | 0.939 | 0.92 |
| 1500 | rs1859194 | chr12 | 111697129 | + | 0.924 | 0.916 | 0.934 | | 4539 rs1352726 | chr5 | 107065959 | + | 0.933 | 0.939 | 0.919 |
| 1501 | rs10850226 | chr12 | 112779732 | + | 0.927 | 0.915 | 0.923 | | 4540 rs7444469 | chr5 | 107066250 | + | 0.933 | 0.938 | 0.919 |
| 1502 | rs7975774 | chr12 | 112847548 | + | 0.949 | 0.92 | 0.938 | | 4541 rs13161312 | chr5 | 107260981 | + | 0.908 | 0.933 | 0.913 |
| 1503 | rs10850293 | chr12 | 113160874 | + | 0.941 | 0.935 | 0.932 | | 4542 rs10515394 | chr5 | 108272675 | + | 0.917 | 0.916 | 0.94 |
| 1504 | rs1920569 | chr12 | 113166045 | + | 0.925 | 0.904 | 0.923 | | 4543 rs17534807 | chr5 | 108472327 | + | 0.941 | 0.926 | 0.903 |

Fig. 9 Cont. 43

| | | | | | | | | | |
|---|---|---|---|---|---|---|---|---|---|
| 1505 | rs4259873 | chr12 | 113219162 | + | 0.918 | 0.938 | 0.949 | 4544 | rs3814066 | chr5 | 108517843 | + | 0.948 | 0.927 | 0.905 |
| 1506 | rs12227415 | chr12 | 113349645 | + | 0.917 | 0.939 | 0.946 | 4545 | rs36807 | chr5 | 109299381 | + | 0.933 | 0.91 | 0.938 |
| 1507 | rs110671112 | chr12 | 113353155 | + | 0.917 | 0.933 | 0.946 | 4546 | rs12654231 | chr5 | 109704605 | + | 0.942 | 0.949 | 0.945 |
| 1508 | rs17676517 | chr12 | 113372692 | + | 0.917 | 0.944 | 0.923 | 4547 | rs12187994 | chr5 | 109978880 | + | 0.917 | 0.938 | 0.927 |
| 1509 | rs12426009 | chr12 | 113871505 | + | 0.933 | 0.95 | 0.92 | 4548 | rs12186893 | chr5 | 109980882 | + | 0.924 | 0.904 | 0.905 |
| 1510 | rs17740223 | chr12 | 118748855 | + | 0.933 | 0.949 | 0.92 | 4549 | rs100669111 | chr5 | 109991089 | + | 0.933 | 0.916 | 0.929 |
| 1511 | rs35458 | chr12 | 114020549 | + | 0.925 | 0.927 | 0.95 | 4550 | rs1422495 | chr5 | 110001801 | + | 0.921 | 0.918 | 0.913 |
| 1512 | rs16945151 | chr12 | 114124295 | + | 0.942 | 0.922 | 0.937 | 4551 | rs1579298 | chr5 | 110009221 | + | 0.083 | 0.073 | 0.062 |
| 1513 | rs16945585 | chr12 | 114395788 | + | 0.924 | 0.911 | 0.95 | 4552 | rs34929 | chr5 | 111335459 | + | 0.075 | 0.067 | 0.089 |
| 1514 | rs108505592 | chr12 | 114932518 | + | 0.1 | 0.08 | 0.098 | 4553 | rs173900 | chr5 | 111348486 | + | 0.1 | 0.056 | 0.089 |
| 1515 | rs10850758 | chr12 | 116019090 | + | 0.917 | 0.932 | 0.901 | 4554 | rs7731748 | chr5 | 111863295 | + | 0.083 | 0.083 | 0.054 |
| 1516 | rs864641 | chr12 | 116173353 | + | 0.938 | 0.912 | 0.923 | 4555 | rs10515452 | chr5 | 112323863 | + | 0.915 | 0.947 | 0.919 |
| 1517 | rs4767684 | chr12 | 117446376 | + | 0.947 | 0.932 | 0.901 | 4556 | rs882755 | chr5 | 112634326 | + | 0.942 | 0.944 | 0.95 |
| 1518 | rs12322165 | chr12 | 118347888 | + | 0.95 | 0.916 | 0.917 | 4557 | rs4440352 | chr5 | 114248155 | + | 0.917 | 0.944 | 0.932 |
| 1519 | rs7967638 | chr12 | 118354518 | + | 0.95 | 0.911 | 0.923 | 4558 | rs3805594 | chr5 | 145503673 | + | 0.917 | 0.933 | 0.941 |
| 1520 | rs2293495 | chr12 | 118355649 | + | 0.933 | 0.904 | 0.921 | 4559 | rs17137771 | chr5 | 114778601 | + | 0.95 | 0.922 | 0.905 |
| 1521 | rs1464374 | chr12 | 118370008 | + | 0.941 | 0.921 | 0.93 | 4560 | rs1422498 | chr5 | 115590049 | + | 0.921 | 0.904 | 0.926 |
| 1522 | rs12426170 | chr12 | 119997971 | + | 0.938 | 0.947 | 0.946 | 4561 | rs6861198 | chr5 | 115803067 | + | 0.908 | 0.933 | 0.945 |
| 1523 | rs618201 | chr12 | 120039181 | + | 0.075 | 0.089 | 0.077 | 4562 | rs924454 | chr5 | 116152174 | + | 0.95 | 0.922 | 0.919 |
| 1524 | rs7315108 | chr12 | 122904020 | + | 0.942 | 0.933 | 0.95 | 4563 | rs4585482 | chr5 | 120518563 | + | 0.915 | 0.933 | 0.901 |
| 1525 | rs12318786 | chr12 | 124557695 | + | 0.949 | 0.904 | 0.936 | 4564 | rs6876223 | chr5 | 1228816501 | + | 0.904 | 0.904 | 0.928 |
| 1526 | rs12367685 | chr12 | 124999363 | + | 0.933 | 0.944 | 0.914 | 4565 | rs4836018 | chr5 | 1228834456 | + | 0.924 | 0.903 | 0.932 |
| 1527 | rs12425458 | chr12 | 125804819 | + | 0.95 | 0.928 | 0.921 | 4566 | rs4085308 | chr5 | 123141397 | + | 0.925 | 0.906 | 0.946 |
| 1528 | rs11058945 | chr12 | 126091792 | + | 0.924 | 0.904 | 0.936 | 4567 | rs255243 | chr5 | 123201346 | + | 0.914 | 0.938 | 0.946 |
| 1529 | rs6489148 | chr12 | 126107307 | + | 0.069 | 0.094 | 0.071 | 4568 | rs1501763 | chr5 | 123268328 | + | 0.942 | 0.916 | 0.923 |
| 1530 | rs1713614 | chr12 | 127521651 | + | 0.908 | 0.927 | 0.937 | 4569 | rs6595498 | chr5 | 123402156 | + | 0.068 | 0.081 | 0.068 |
| 1531 | rs12809589 | chr12 | 127699609 | + | 0.95 | 0.922 | 0.91 | 4570 | rs1984601 | chr5 | 123402744 | + | 0.058 | 0.084 | 0.054 |
| 1532 | rs563311 | chr12 | 127902544 | + | 0.907 | 0.927 | 0.917 | 4571 | rs6595499 | chr5 | 123403331 | + | 0.067 | 0.09 | 0.055 |
| 1533 | rs560526 | chr12 | 127902839 | + | 0.907 | 0.927 | 0.919 | 4572 | rs12332605 | chr5 | 123409709 | + | 0.052 | 0.053 | 0.068 |
| 1534 | rs9316686 | chr13 | 21472007 | + | 0.95 | 0.933 | 0.902 | 4573 | rs9327393 | chr5 | 125523737 | + | 0.932 | 0.907 | 0.927 |
| 1535 | rs9510726 | chr13 | 22885829 | + | 0.925 | 0.906 | 0.938 | 4574 | rs11957746 | chr5 | 125561908 | + | 0.949 | 0.95 | 0.91 |
| 1536 | rs7986530 | chr13 | 25051596 | + | 0.924 | 0.92 | 0.925 | 4575 | rs3749830 | chr5 | 126168421 | + | 0.95 | 0.949 | 0.932 |
| 1537 | rs1409268 | chr13 | 25272832 | + | 0.95 | 0.933 | 0.946 | 4576 | rs7737871 | chr5 | 126806749 | + | 0.95 | 0.906 | 0.95 |
| 1538 | rs11840279 | chr13 | 25793252 | + | 0.92 | 0.924 | 0.931 | 4577 | rs2291628 | chr5 | 127637532 | + | 0.95 | 0.927 | 0.932 |
| 1539 | rs17083596 | chr13 | 25847454 | + | 0.95 | 0.916 | 0.921 | 4578 | rs11955288 | chr5 | 127666658 | + | 0.925 | 0.928 | 0.927 |

Fig. 9 Cont. 44

| | | | | | | | | | | |
|---|---|---|---|---|---|---|---|---|---|---|
| 1540 | rs9670785 | chr13 | 26368188 | + | 0.902 | 0.935 | 0.927 | 4579 | rs17676538 | chr5 | 127667962 | + | 0.925 | 0.928 | 0.923 |
| 1541 | rs3759430 | chr13 | 27091422 | + | 0.942 | 0.915 | 0.946 | 4580 | rs1716539C | chr5 | 129936268 | + | 0.925 | 0.944 | 0.919 |
| 1542 | rs2296187 | chr13 | 27791341 | + | 0.942 | 0.917 | 0.95 | 4581 | rs6888605 | chr5 | 132774962 | + | 0.908 | 0.903 | 0.923 |
| 1543 | rs1927836 | chr13 | 28607309 | + | 0.075 | 0.067 | 0.081 | 4582 | rs7712156 | chr5 | 133167937 | + | 0.941 | 0.929 | 0.928 |
| 1544 | rs7982169 | chr13 | 28615757 | + | 0.083 | 0.078 | 0.08 | 4583 | rs2431551 | chr5 | 133257492 | + | 0.942 | 0.933 | 0.902 |
| 1545 | rs1927827 | chr13 | 28634982 | + | 0.05 | 0.079 | 0.086 | 4584 | rs244692 | chr5 | 133480434 | + | 0.075 | 0.079 | 0.081 |
| 1546 | rs12583304 | chr13 | 28865568 | + | 0.925 | 0.928 | 0.902 | 4585 | rs6889807 | chr5 | 133854426 | + | 0.941 | 0.911 | 0.905 |
| 1547 | rs9550508 | chr13 | 29371418 | + | 0.947 | 0.912 | 0.923 | 4586 | rs3756366 | chr5 | 134724667 | + | 0.95 | 0.911 | 0.923 |
| 1548 | rs11841168 | chr13 | 29772638 | + | 0.949 | 0.943 | 0.939 | 4587 | rs11738689 | chr5 | 134975216 | + | 0.933 | 0.913 | 0.935 |
| 1549 | rs2031724 | chr13 | 30500261 | + | 0.933 | 0.949 | 0.91 | 4588 | rs7725225 | chr5 | 134987865 | + | 0.948 | 0.909 | 0.923 |
| 1550 | rs17075352 | chr13 | 30558123 | + | 0.949 | 0.917 | 0.914 | 4589 | rs11742182 | chr5 | 138922912 | + | 0.941 | 0.939 | 0.913 |
| 1551 | rs12864549 | chr13 | 30581514 | + | 0.939 | 0.941 | 0.949 | 4590 | rs355158 | chr5 | 138945560 | + | 0.915 | 0.943 | 0.914 |
| 1552 | rs364 | chr13 | 31377297 | + | 0.1 | 0.089 | 0.0059 | 4591 | rs355159 | chr5 | 138947692 | + | 0.908 | 0.944 | 0.911 |
| 1553 | rs17732441 | chr13 | 33215471 | + | 0.942 | 0.939 | 0.914 | 4592 | rs355148 | chr5 | 138955008 | + | 0.908 | 0.943 | 0.914 |
| 1554 | rs2322115 | chr13 | 33985891 | + | 0.942 | 0.917 | 0.923 | 4593 | rs403583 | chr5 | 138960558 | + | 0.908 | 0.944 | 0.914 |
| 1555 | rs1980203 | chr13 | 36158371 | + | 0.908 | 0.921 | 0.95 | 4594 | rs356463 | chr5 | 138991693 | + | 0.908 | 0.944 | 0.914 |
| 1556 | rs9547952 | chr13 | 37036689 | + | 0.908 | 0.938 | 0.95 | 4595 | rs260733 | chr5 | 139076089 | + | 0.085 | 0.078 | 0.058 |
| 1557 | rs4399429 | chr13 | 37233339 | + | 0.949 | 0.938 | 0.923 | 4596 | rs260735 | chr5 | 139084065 | + | 0.091 | 0.089 | 0.095 |
| 1558 | rs17058375 | chr13 | 38117859 | + | 0.917 | 0.933 | 0.928 | 4597 | rs260727 | chr5 | 139120893 | + | 0.058 | 0.094 | 0.086 |
| 1559 | rs53125306 | chr13 | 38237345 | + | 0.914 | 0.929 | 0.92 | 4598 | rs12519544 | chr5 | 139207177 | + | 0.907 | 0.943 | 0.919 |
| 1560 | rs17446005 | chr13 | 39607752 | + | 0.942 | 0.95 | 0.911 | 4599 | rs6877423 | chr5 | 139418290 | + | 0.925 | 0.95 | 0.918 |
| 1561 | rs9566518 | chr13 | 39853427 | + | 0.908 | 0.922 | 0.922 | 4600 | rs4912924 | chr5 | 142905945 | + | 0.933 | 0.949 | 0.911 |
| 1562 | rs9566856 | chr13 | 41285973 | + | 0.94 | 0.911 | 0.935 | 4601 | rs246425 | chr5 | 142966688 | + | 0.925 | 0.927 | 0.905 |
| 1563 | rs2121528 | chr13 | 41470463 | + | 0.948 | 0.926 | 0.914 | 4602 | rs374379 | chr5 | 142976334 | + | 0.908 | 0.938 | 0.911 |
| 1564 | rs346583 | chr13 | 42016425 | + | 0.95 | 0.917 | 0.946 | 4603 | rs17107349 | chr5 | 147221297 | + | 0.924 | 0.922 | 0.932 |
| 1565 | rs17064492 | chr13 | 42860622 | + | 0.95 | 0.939 | 0.941 | 4604 | rs17108911 | chr5 | 148263515 | + | 0.915 | 0.921 | 0.937 |
| 1566 | rs17064752 | chr13 | 43060561 | + | 0.917 | 0.933 | 0.95 | 4605 | rs11740002 | chr5 | 149058822 | + | 0.948 | 0.91 | 0.911 |
| 1567 | rs4942278 | chr13 | 43579950 | + | 0.092 | 0.061 | 0.091 | 4606 | rs17110375 | chr5 | 149104421 | + | 0.95 | 0.933 | 0.946 |
| 1568 | rs17065665 | chr13 | 43760358 | + | 0.908 | 0.928 | 0.945 | 4607 | rs6884015 | chr5 | 149692429 | + | 0.95 | 0.933 | 0.914 |
| 1569 | rs9567474 | chr13 | 44242585 | + | 0.942 | 0.944 | 0.928 | 4608 | rs1107239 | chr5 | 150434799 | + | 0.906 | 0.929 | 0.943 |
| 1570 | rs9567478 | chr13 | 44254685 | + | 0.917 | 0.944 | 0.946 | 4609 | rs10072803 | chr5 | 150522414 | + | 0.945 | 0.939 | 0.925 |
| 1571 | rs9595206 | chr13 | 44258761 | + | 0.917 | 0.944 | 0.928 | 4610 | rs10476763 | chr5 | 150528477 | + | 0.933 | 0.944 | 0.934 |
| 1572 | rs17294691 | chr13 | 44518771 | + | 0.942 | 0.928 | 0.937 | 4611 | rs6888953 | chr5 | 151498251 | + | 0.918 | 0.926 | 0.914 |
| 1573 | rs17066406 | chr13 | 44522623 | + | 0.95 | 0.911 | 0.95 | 4612 | rs296182 | chr5 | 152575555 | + | 0.95 | 0.939 | 0.902 |
| 1574 | rs12585422 | chr13 | 44943088 | + | 0.941 | 0.915 | 0.902 | 4613 | rs2161393 | chr5 | 153571213 | + | 0.083 | 0.089 | 0.095 |

Fig. 9 Cont. 45

| | | | | | | | | | | | |
|---|---|---|---|---|---|---|---|---|---|---|---|
| 1575 | rs17066929 | chr13 | 45046097 | + | 0.922 | 0.916 | 0.932 | 4614 | rs13160265 | chr5 | 153759838 | + | 0.925 | 0.911 | 0.946 |
| 1576 | rs7321658 | chr13 | 46111173 | + | 0.95 | 0.939 | 0.919 | 4615 | rs13183515 | chr5 | 153864296 | + | 0.95 | 0.95 | 0.937 |
| 1577 | rs7328175 | chr13 | 46221456 | + | 0.908 | 0.95 | 0.911 | 4616 | rs17116417 | chr5 | 154125667 | + | 0.932 | 0.95 | 0.921 |
| 1578 | rs6561355 | chr13 | 46612458 | + | 0.912 | 0.95 | 0.932 | 4617 | rs12188498 | chr5 | 154144897 | + | 0.925 | 0.95 | 0.923 |
| 1579 | rs7982925 | chr13 | 47098219 | + | 0.1 | 0.05 | 0.054 | 4618 | rs7710000 | chr5 | 154952180 | + | 0.917 | 0.95 | 0.946 |
| 1580 | rs9591243 | chr13 | 48657628 | + | 0.95 | 0.928 | 0.928 | 4619 | rs10051752 | chr5 | 154966485 | + | 0.915 | 0.938 | 0.932 |
| 1581 | rs9316430 | chr13 | 48674081 | + | 0.95 | 0.933 | 0.928 | 4620 | rs6864938 | chr5 | 155945932 | + | 0.908 | 0.906 | 0.932 |
| 1582 | rs9568315 | chr13 | 49206963 | + | 0.94 | 0.932 | 0.946 | 4621 | rs6893385 | chr5 | 155946265 | + | 0.907 | 0.906 | 0.936 |
| 1583 | rs706615 | chr13 | 49604552 | + | 0.902 | 0.919 | 0.928 | 4622 | rs2194036 | chr5 | 155972329 | + | 0.933 | 0.906 | 0.932 |
| 1584 | rs2687935 | chr13 | 49630287 | + | 0.912 | 0.928 | 0.937 | 4623 | rs10214374 | chr5 | 156000706 | + | 0.908 | 0.911 | 0.946 |
| 1585 | rs2687936 | chr13 | 49630514 | + | 0.927 | 0.931 | 0.937 | 4624 | rs6890836 | chr5 | 157694134 | + | 0.931 | 0.914 | 0.938 |
| 1586 | rs17074055 | chr13 | 49744749 | + | 0.94 | 0.949 | 0.905 | 4625 | rs10476265 | chr5 | 158111730 | + | 0.917 | 0.944 | 0.905 |
| 1587 | rs10459378 | chr13 | 52396015 | + | 0.922 | 0.95 | 0.923 | 4626 | rs11747112 | chr5 | 158707187 | + | 0.933 | 0.906 | 0.911 |
| 1588 | rs2208989 | chr13 | 52425974 | + | 0.067 | 0.051 | 0.099 | 4627 | rs34618866 | chr5 | 158938017 | + | 0.942 | 0.944 | 0.937 |
| 1589 | rs1418616 | chr13 | 52830716 | + | 0.949 | 0.908 | 0.946 | 4628 | rs4429888 | chr5 | 159431165 | + | 0.949 | 0.903 | 0.95 |
| 1590 | rs11620178 | chr13 | 53783864 | + | 0.927 | 0.95 | 0.905 | 4629 | rs2421535 | chr5 | 160089731 | + | 0.942 | 0.944 | 0.905 |
| 1591 | rs9569275 | chr13 | 54767596 | + | 0.925 | 0.927 | 0.935 | 4630 | rs6882493 | chr5 | 161627067 | + | 0.905 | 0.948 | 0.944 |
| 1592 | rs4444226 | chr13 | 57172173 | + | 0.942 | 0.949 | 0.914 | 4631 | rs17060196 | chr5 | 161629753 | + | 0.95 | 0.917 | 0.91 |
| 1593 | rs17266038 | chr13 | 57372272 | + | 0.95 | 0.933 | 0.911 | 4632 | rs299316 | chr5 | 162849006 | + | 0.067 | 0.067 | 0.092 |
| 1594 | rs9597633 | chr13 | 57376811 | + | 0.95 | 0.933 | 0.911 | 4633 | rs2860891 | chr5 | 163483256 | + | 0.933 | 0.928 | 0.938 |
| 1595 | rs10162191 | chr13 | 57382032 | + | 0.95 | 0.916 | 0.911 | 4634 | rs7736271 | chr5 | 163707558 | + | 0.915 | 0.927 | 0.946 |
| 1596 | rs13378355 | chr13 | 57392119 | + | 0.95 | 0.922 | 0.907 | 4635 | rs10516022 | chr5 | 166086976 | + | 0.933 | 0.915 | 0.911 |
| 1597 | rs9597639 | chr13 | 57396810 | + | 0.95 | 0.933 | 0.907 | 4636 | rs17067490 | chr5 | 166087659 | + | 0.941 | 0.948 | 0.937 |
| 1598 | rs9597640 | chr13 | 57399320 | + | 0.95 | 0.933 | 0.918 | 4637 | rs17067512 | chr5 | 166099976 | + | 0.904 | 0.917 | 0.932 |
| 1599 | rs9597642 | chr13 | 57421309 | + | 0.948 | 0.933 | 0.911 | 4638 | rs17068169 | chr5 | 166603287 | + | 0.95 | 0.913 | 0.919 |
| 1600 | rs9597643 | chr13 | 57430906 | + | 0.95 | 0.929 | 0.917 | 4639 | rs12657611 | chr5 | 166639850 | + | 0.942 | 0.906 | 0.927 |
| 1601 | rs9597649 | chr13 | 57464265 | + | 0.944 | 0.933 | 0.911 | 4640 | rs12655415 | chr5 | 166639861 | + | 0.942 | 0.91 | 0.938 |
| 1602 | rs9597650 | chr13 | 57467703 | + | 0.95 | 0.933 | 0.911 | 4641 | rs7700457 | chr5 | 166640141 | + | 0.942 | 0.904 | 0.938 |
| 1603 | rs9597653 | chr13 | 57474444 | + | 0.95 | 0.933 | 0.911 | 4642 | rs7700378 | chr5 | 166640291 | + | 0.942 | 0.904 | 0.927 |
| 1604 | rs9597655 | chr13 | 57485290 | + | 0.95 | 0.936 | 0.926 | 4643 | rs17068240 | chr5 | 166642581 | + | 0.94 | 0.91 | 0.938 |
| 1605 | rs12018907 | chr13 | 57509161 | + | 0.95 | 0.928 | 0.911 | 4644 | rs12658750 | chr5 | 166643564 | + | 0.942 | 0.909 | 0.938 |
| 1606 | rs9597661 | chr13 | 57516991 | + | 0.949 | 0.926 | 0.911 | 4645 | rs7709569 | chr5 | 166911384 | + | 0.924 | 0.931 | 0.902 |
| 1607 | rs9597662 | chr13 | 57518452 | + | 0.95 | 0.928 | 0.911 | 4646 | rs2059090 | chr5 | 167717202 | + | 0.942 | 0.911 | 0.932 |
| 1608 | rs9597663 | chr13 | 57518473 | + | 0.95 | 0.928 | 0.911 | 4647 | rs1864951 | chr5 | 168071847 | + | 0.939 | 0.94 | 0.95 |
| 1609 | rs9597664 | chr13 | 57520030 | + | 0.95 | 0.927 | 0.932 | 4648 | rs9313435 | chr5 | 168327584 | + | 0.925 | 0.948 | 0.919 |

Fig. 9 Cont. 46

| | | | | | | | | | | | |
|---|---|---|---|---|---|---|---|---|---|---|---|
| 1610 | rs9591849 | chr13 | 57533038 | + | 0.949 | 0.927 | 0.932 | 4649 | rs100538858 | chr5 | 168328797 | + | 0.925 | 0.95 | 0.919 |
| 1611 | rs9591853 | chr13 | 57547387 | + | 0.95 | 0.928 | 0.911 | 4650 | rs100539973 | chr5 | 168329003 | + | 0.925 | 0.95 | 0.919 |
| 1612 | rs9597671 | chr13 | 57560265 | + | 0.942 | 0.928 | 0.911 | 4651 | rs100576359 | chr5 | 168569868 | + | 0.925 | 0.944 | 0.946 |
| 1613 | rs9597673 | chr13 | 57565143 | + | 0.94 | 0.926 | 0.911 | 4652 | rs104440703 | chr5 | 168825580 | + | 0.933 | 0.917 | 0.948 |
| 1614 | rs11840733 | chr13 | 57570375 | + | 0.942 | 0.927 | 0.911 | 4653 | rs126544354 | chr5 | 169475949 | + | 0.933 | 0.944 | 0.914 |
| 1615 | rs9597674 | chr13 | 57571626 | + | 0.949 | 0.932 | 0.911 | 4654 | rs126569595 | chr5 | 169476207 | + | 0.948 | 0.944 | 0.918 |
| 1616 | rs11843934 | chr13 | 57583968 | + | 0.95 | 0.927 | 0.911 | 4655 | rs6888770 | chr5 | 169673087 | + | 0.942 | 0.917 | 0.931 |
| 1617 | rs11841255 | chr13 | 57587237 | + | 0.949 | 0.93 | 0.909 | 4656 | rs117423395 | chr5 | 169995236 | + | 0.917 | 0.904 | 0.911 |
| 1618 | rs6561955 | chr13 | 57600933 | + | 0.083 | 0.083 | 0.08 | 4657 | rs33865 | chr5 | 171100266 | + | 0.092 | 0.056 | 0.1 |
| 1619 | rs171837146 | chr13 | 57630474 | + | 0.933 | 0.944 | 0.914 | 4658 | rs254901 | chr5 | 171101363 | + | 0.092 | 0.056 | 0.099 |
| 1620 | rs172276133 | chr13 | 57664373 | + | 0.932 | 0.949 | 0.923 | 4659 | rs2116794 | chr5 | 171194965 | + | 0.092 | 0.083 | 0.062 |
| 1621 | rs4886066 | chr13 | 57666111 | + | 0.93 | 0.95 | 0.929 | 4660 | rs7721845 | chr5 | 171670344 | + | 0.932 | 0.911 | 0.919 |
| 1622 | rs171915950 | chr13 | 57675414 | + | 0.942 | 0.95 | 0.91 | 4661 | rs177157850 | chr5 | 172178674 | + | 0.941 | 0.924 | 0.92 |
| 1623 | rs9538178 | chr13 | 58196631 | + | 0.933 | 0.909 | 0.92 | 4662 | rs4868306 | chr5 | 173071128 | + | 0.933 | 0.939 | 0.946 |
| 1624 | rs170554486 | chr13 | 58223245 | + | 0.908 | 0.939 | 0.937 | 4663 | rs2594831 | chr5 | 173132360 | + | 0.915 | 0.928 | 0.907 |
| 1625 | rs9569993 | chr13 | 58311680 | + | 0.083 | 0.061 | 0.072 | 4664 | rs2546760 | chr5 | 173133075 | + | 0.926 | 0.941 | 0.912 |
| 1626 | rs9538228 | chr13 | 58314120 | + | 0.067 | 0.061 | 0.077 | 4665 | rs2561761 | chr5 | 173133577 | + | 0.941 | 0.932 | 0.909 |
| 1627 | rs9538366 | chr13 | 58752360 | + | 0.917 | 0.922 | 0.941 | 4666 | rs117454100 | chr5 | 173348840 | + | 0.902 | 0.949 | 0.909 |
| 1628 | rs177066330 | chr13 | 58833601 | + | 0.908 | 0.95 | 0.911 | 4667 | rs171396 | chr5 | 173606766 | + | 0.075 | 0.1 | 0.098 |
| 1629 | rs170566570 | chr13 | 58983162 | + | 0.931 | 0.944 | 0.945 | 4668 | rs7731281 | chr5 | 175931521 | + | 0.926 | 0.91 | 0.929 |
| 1630 | rs170582900 | chr13 | 60072932 | + | 0.942 | 0.917 | 0.902 | 4669 | rs100370255 | chr5 | 177584604 | + | 0.932 | 0.933 | 0.936 |
| 1631 | rs170582959 | chr13 | 60075299 | + | 0.942 | 0.917 | 0.91 | 4670 | rs100624211 | chr5 | 177585490 | + | 0.925 | 0.928 | 0.938 |
| 1632 | rs170582995 | chr13 | 60075670 | + | 0.942 | 0.917 | 0.902 | 4671 | rs100539299 | chr5 | 177586789 | + | 0.925 | 0.933 | 0.938 |
| 1633 | rs9570491 | chr13 | 60647525 | + | 0.912 | 0.93 | 0.936 | 4672 | rs100630940 | chr5 | 177587062 | + | 0.92 | 0.925 | 0.923 |
| 1634 | rs8001207 | chr13 | 61203800 | + | 0.922 | 0.943 | 0.949 | 4673 | rs6881428 | chr5 | 178189623 | + | 0.934 | 0.905 | 0.928 |
| 1635 | rs9592141 | chr13 | 61248042 | + | 0.922 | 0.903 | 0.919 | 4674 | rs734674 | chr6 | 224695 | + | 0.908 | 0.938 | 0.936 |
| 1636 | rs9598357 | chr13 | 61248391 | + | 0.908 | 0.906 | 0.919 | 4675 | rs2797312 | chr6 | 229215 | + | 0.058 | 0.062 | 0.1 |
| 1637 | rs6562343 | chr13 | 63636527 | + | 0.95 | 0.944 | 0.938 | 4676 | rs2788235 | chr6 | 688488 | + | 0.094 | 0.083 | 0.089 |
| 1638 | rs7330611 | chr13 | 63766310 | + | 0.917 | 0.949 | 0.946 | 4677 | rs1538325 | chr6 | 688995 | + | 0.086 | 0.085 | 0.063 |
| 1639 | rs170847259 | chr13 | 63780952 | + | 0.925 | 0.95 | 0.929 | 4678 | rs1890363 | chr6 | 691486 | + | 0.092 | 0.083 | 0.098 |
| 1640 | rs128688180 | chr13 | 64068334 | + | 0.908 | 0.922 | 0.927 | 4679 | rs2788239 | chr6 | 694182 | + | 0.085 | 0.079 | 0.091 |
| 1641 | rs4344607 | chr13 | 64627874 | + | 0.917 | 0.922 | 0.911 | 4680 | rs2788241 | chr6 | 696037 | + | 0.092 | 0.083 | 0.098 |
| 1642 | rs9529109 | chr13 | 66115781 | + | 0.921 | 0.908 | 0.934 | 4681 | rs2788197 | chr6 | 701884 | + | 0.05 | 0.088 | 0.088 |
| 1643 | rs9540860 | chr13 | 66130414 | + | 0.942 | 0.916 | 0.914 | 4682 | rs9503612 | chr6 | 3475720 | + | 0.092 | 0.079 | 0.056 |
| 1644 | rs9571611 | chr13 | 66139668 | + | 0.942 | 0.928 | 0.914 | 4683 | rs2810793 | chr6 | 4173048 | + | 0.922 | 0.921 | 0.914 |

Fig. 9 Cont. 47

| | | | | | | | | | | |
|---|---|---|---|---|---|---|---|---|---|---|
| 1645 | rs124311268 | chr13 | 66893721 | + | 0.95 | 0.95 | 0.92 | 4684 | rs1330800 | chr6 | 4308388 | + | 0.908 | 0.906 | 0.923 |
| 1646 | rs116163363 | chr13 | 66894513 | + | 0.948 | 0.95 | 0.92 | 4685 | rs17138106 | chr6 | 4311380 | + | 0.917 | 0.906 | 0.927 |
| 1647 | rs116186632 | chr13 | 66894915 | + | 0.915 | 0.949 | 0.907 | 4686 | rs17138105 | chr6 | 4311478 | + | 0.917 | 0.906 | 0.923 |
| 1648 | rs116162265 | chr13 | 66897434 | + | 0.948 | 0.95 | 0.911 | 4687 | rs6928621 | chr6 | 4660324 | + | 0.915 | 0.944 | 0.95 |
| 1649 | rs1335954 | chr13 | 67204859 | + | 0.942 | 0.939 | 0.92 | 4688 | rs233480 | chr6 | 4730248 | + | 0.056 | 0.071 | 0.087 |
| 1650 | rs1335955 | chr13 | 67205507 | + | 0.942 | 0.939 | 0.92 | 4689 | rs6926191 | chr6 | 4809002 | + | 0.942 | 0.921 | 0.919 |
| 1651 | rs2786262 | chr13 | 67215592 | + | 0.942 | 0.939 | 0.918 | 4690 | rs465481 | chr6 | 5075154 | + | 0.055 | 0.071 | 0.059 |
| 1652 | rs2251640 | chr13 | 67235571 | + | 0.942 | 0.939 | 0.919 | 4691 | rs6904616 | chr6 | 5362142 | + | 0.931 | 0.908 | 0.945 |
| 1653 | rs2784464 | chr13 | 67234780 | + | 0.941 | 0.943 | 0.918 | 4692 | rs5987 | chr6 | 6097139 | + | 0.942 | 0.91 | 0.946 |
| 1654 | rs1023329 | chr13 | 67237228 | + | 0.942 | 0.939 | 0.919 | 4693 | rs13200015 | chr6 | 6101326 | + | 0.908 | 0.906 | 0.918 |
| 1655 | rs2784465 | chr13 | 67239281 | + | 0.941 | 0.939 | 0.918 | 4694 | rs2774510 | chr6 | 6359049 | + | 0.914 | 0.933 | 0.92 |
| 1656 | rs17664927 | chr13 | 67289647 | + | 0.947 | 0.914 | 0.929 | 4695 | rs2774511 | chr6 | 6378910 | + | 0.917 | 0.933 | 0.916 |
| 1657 | rs17664993 | chr13 | 67292999 | + | 0.95 | 0.911 | 0.92 | 4696 | rs201018 | chr6 | 6611843 | + | 0.907 | 0.95 | 0.919 |
| 1658 | rs9572036 | chr13 | 68341847 | + | 0.917 | 0.95 | 0.92 | 4697 | rs12207764 | chr6 | 6556926 | + | 0.917 | 0.939 | 0.946 |
| 1659 | rs9572062 | chr13 | 68442428 | + | 0.948 | 0.912 | 0.909 | 4698 | rs12206627 | chr6 | 6936303 | + | 0.925 | 0.95 | 0.932 |
| 1660 | rs9564681 | chr13 | 69763946 | + | 0.938 | 0.906 | 0.928 | 4699 | rs12197730 | chr6 | 6942449 | + | 0.942 | 0.95 | 0.932 |
| 1661 | rs9572447 | chr13 | 69911677 | + | 0.941 | 0.937 | 0.946 | 4700 | rs3823108 | chr6 | 8359340 | + | 0.942 | 0.916 | 0.937 |
| 1662 | rs9572451 | chr13 | 69913311 | + | 0.95 | 0.906 | 0.946 | 4701 | rs7762389 | chr6 | 8501366 | + | 0.95 | 0.911 | 0.932 |
| 1663 | rs9542499 | chr13 | 70241938 | + | 0.917 | 0.933 | 0.914 | 4702 | rs10456225 | chr6 | 10313172 | + | 0.908 | 0.944 | 0.941 |
| 1664 | rs10492536 | chr13 | 71316320 | + | 0.95 | 0.922 | 0.946 | 4703 | rs7745093 | chr6 | 10348360 | + | 0.917 | 0.917 | 0.911 |
| 1665 | rs17833163 | chr13 | 71999616 | + | 0.942 | 0.95 | 0.946 | 4704 | rs10484886 | chr6 | 10477661 | + | 0.933 | 0.91 | 0.946 |
| 1666 | rs118400561 | chr13 | 72787351 | + | 0.915 | 0.939 | 0.935 | 4705 | rs4713332 | chr6 | 11378623 | + | 0.942 | 0.933 | 0.946 |
| 1667 | rs17090131 | chr13 | 72863610 | + | 0.911 | 0.938 | 0.935 | 4706 | rs4711221 | chr6 | 11385190 | + | 0.942 | 0.938 | 0.938 |
| 1668 | rs17090132 | chr13 | 72864360 | + | 0.911 | 0.939 | 0.936 | 4707 | rs16871253 | chr6 | 11430622 | + | 0.942 | 0.932 | 0.919 |
| 1669 | rs17061703 | chr13 | 73414526 | + | 0.932 | 0.939 | 0.936 | 4708 | rs16872098 | chr6 | 12054465 | + | 0.933 | 0.922 | 0.938 |
| 1670 | rs17071090 | chr13 | 73415393 | + | 0.932 | 0.939 | 0.92 | 4709 | rs1205886 | chr6 | 12056064 | + | 0.075 | 0.052 | 0.062 |
| 1671 | rs4883960 | chr13 | 73420062 | + | 0.931 | 0.937 | 0.932 | 4710 | rs9357250 | chr6 | 12092833 | + | 0.907 | 0.917 | 0.911 |
| 1672 | rs17062027 | chr13 | 73514955 | + | 0.917 | 0.949 | 0.92 | 4711 | rs9296237 | chr6 | 12141237 | + | 0.925 | 0.922 | 0.946 |
| 1673 | rs2025532 | chr13 | 73515965 | + | 0.917 | 0.944 | 0.92 | 4712 | rs9394473 | chr6 | 12141282 | + | 0.925 | 0.921 | 0.938 |
| 1674 | rs17062696 | chr13 | 73904894 | + | 0.949 | 0.944 | 0.918 | 4713 | rs6933280 | chr6 | 12167304 | + | 0.933 | 0.911 | 0.941 |
| 1675 | rs9600325 | chr13 | 73909953 | + | 0.917 | 0.944 | 0.928 | 4714 | rs9366970 | chr6 | 12185758 | + | 0.948 | 0.942 | 0.929 |
| 1676 | rs17062728 | chr13 | 73919504 | + | 0.95 | 0.917 | 0.937 | 4715 | rs9369070 | chr6 | 12187179 | + | 0.941 | 0.933 | 0.929 |
| 1677 | rs9600328 | chr13 | 73924265 | + | 0.95 | 0.917 | 0.929 | 4716 | rs6910959 | chr6 | 12187742 | + | 0.94 | 0.933 | 0.929 |
| 1678 | rs9600329 | chr13 | 73929126 | + | 0.925 | 0.917 | 0.937 | 4717 | rs9394517 | chr6 | 12188635 | + | 0.941 | 0.933 | 0.941 |
| 1679 | rs9318272 | chr13 | 73930265 | + | 0.917 | 0.917 | 0.937 | 4718 | rs9349095 | chr6 | 12188749 | + | 0.941 | 0.933 | 0.929 |

Fig. 9 Cont. 48

| | | | | | | | | | | | | | |
|---|---|---|---|---|---|---|---|---|---|---|---|---|---|
| 1680 | rs9530645 | chr13 | 76860767 | + | 0.083 | 0.1 | 0.09 | 4719 | rs9369072 | chr6 | 12189132 | + | 0.925 | 0.933 | 0.929 |
| 1681 | rs624474 | chr13 | 77037920 | + | 0.05 | 0.051 | 0.059 | 4720 | rs10498679 | chr6 | 12189887 | + | 0.932 | 0.933 | 0.929 |
| 1682 | rs488942 | chr13 | 77038048 | + | 0.05 | 0.05 | 0.059 | 4721 | rs9380764 | chr6 | 12190200 | + | 0.933 | 0.933 | 0.941 |
| 1683 | rs17828304 | chr13 | 78157247 | + | 0.905 | 0.922 | 0.914 | 4722 | rs9296253 | chr6 | 12190675 | + | 0.933 | 0.933 | 0.929 |
| 1684 | rs12428698 | chr13 | 78260806 | + | 0.95 | 0.911 | 0.938 | 4723 | rs9366972 | chr6 | 12190824 | + | 0.933 | 0.933 | 0.941 |
| 1685 | rs7997459 | chr13 | 78411048 | + | 0.917 | 0.944 | 0.91 | 4724 | rs9394520 | chr6 | 12191426 | + | 0.942 | 0.95 | 0.929 |
| 1686 | rs17072133 | chr13 | 79501183 | + | 0.95 | 0.922 | 0.909 | 4725 | rs9462724 | chr6 | 12485379 | + | 0.924 | 0.911 | 0.936 |
| 1687 | rs12857898 | chr13 | 79743931 | + | 0.909 | 0.936 | 0.944 | 4726 | rs9462725 | chr6 | 12485617 | + | 0.902 | 0.915 | 0.945 |
| 1688 | rs12865196 | chr13 | 79774400 | + | 0.907 | 0.943 | 0.946 | 4727 | rs7356888 | chr6 | 12503708 | + | 0.917 | 0.933 | 0.929 |
| 1689 | rs12866240 | chr13 | 79774594 | + | 0.931 | 0.938 | 0.946 | 4728 | rs4715168 | chr6 | 13328394 | + | 0.917 | 0.927 | 0.946 |
| 1690 | rs12870466 | chr13 | 79775663 | + | 0.908 | 0.928 | 0.946 | 4729 | rs7765972 | chr6 | 13335983 | + | 0.917 | 0.922 | 0.946 |
| 1691 | rs17072637 | chr13 | 79833544 | + | 0.905 | 0.926 | 0.91 | 4730 | rs534449 | chr6 | 13369658 | + | 0.942 | 0.933 | 0.946 |
| 1692 | rs17072638 | chr13 | 79834815 | + | 0.95 | 0.928 | 0.946 | 4731 | rs6941522 | chr6 | 13763318 | + | 0.925 | 0.949 | 0.928 |
| 1693 | rs11842853 | chr13 | 79835860 | + | 0.908 | 0.928 | 0.936 | 4732 | rs7742765 | chr6 | 14566356 | + | 0.05 | 0.094 | 0.098 |
| 1694 | rs11840723 | chr13 | 79837484 | + | 0.908 | 0.925 | 0.946 | 4733 | rs12211278 | chr6 | 15462991 | + | 0.933 | 0.939 | 0.938 |
| 1695 | rs17073080 | chr13 | 80125467 | + | 0.933 | 0.939 | 0.905 | 4734 | rs13220654 | chr6 | 17726484 | + | 0.95 | 0.939 | 0.928 |
| 1696 | rs17071496 | chr13 | 80375886 | + | 0.925 | 0.939 | 0.938 | 4735 | rs1006066 | chr6 | 17788094 | + | 0.95 | 0.939 | 0.928 |
| 1697 | rs11619772 | chr13 | 80376050 | + | 0.925 | 0.938 | 0.938 | 4736 | rs13217969 | chr6 | 17808530 | + | 0.95 | 0.939 | 0.938 |
| 1698 | rs17073553 | chr13 | 80377853 | + | 0.925 | 0.938 | 0.946 | 4737 | rs2057539 | chr6 | 17811623 | + | 0.95 | 0.939 | 0.938 |
| 1699 | rs17073727 | chr13 | 80521991 | + | 0.95 | 0.95 | 0.941 | 4738 | rs13219815 | chr6 | 17814383 | + | 0.938 | 0.939 | 0.914 |
| 1700 | rs105079155 | chr13 | 80558592 | + | 0.933 | 0.949 | 0.918 | 4739 | rs2876476 | chr6 | 18265947 | + | 0.093 | 0.092 | 0.097 |
| 1701 | rs105079166 | chr13 | 80558774 | + | 0.95 | 0.949 | 0.928 | 4740 | rs1886330 | chr6 | 18270208 | + | 0.083 | 0.09 | 0.064 |
| 1702 | rs12865047 | chr13 | 80686305 | + | 0.948 | 0.906 | 0.936 | 4741 | rs7744132 | chr6 | 18278451 | + | 0.083 | 0.084 | 0.08 |
| 1703 | rs9546210 | chr13 | 82142435 | + | 0.076 | 0.051 | 0.073 | 4742 | rs13214665 | chr6 | 19718745 | + | 0.942 | 0.911 | 0.95 |
| 1704 | rs6563303 | chr13 | 82143138 | + | 0.067 | 0.051 | 0.08 | 4743 | rs1209816 | chr6 | 19850222 | + | 0.075 | 0.056 | 0.051 |
| 1705 | rs1855352 | chr13 | 82143862 | + | 0.05 | 0.051 | 0.09 | 4744 | rs17549422 | chr6 | 19902023 | + | 0.95 | 0.944 | 0.901 |
| 1706 | rs1333567 | chr13 | 82146185 | + | 0.067 | 0.05 | 0.08 | 4745 | rs16883406 | chr6 | 20243536 | + | 0.933 | 0.911 | 0.938 |
| 1707 | rs1333569 | chr13 | 82146862 | + | 0.067 | 0.051 | 0.08 | 4746 | rs12197794 | chr6 | 22516806 | + | 0.924 | 0.938 | 0.923 |
| 1708 | rs1333570 | chr13 | 82148112 | + | 0.076 | 0.051 | 0.08 | 4747 | rs12211595 | chr6 | 22517175 | + | 0.924 | 0.938 | 0.946 |
| 1709 | rs1333571 | chr13 | 82158113 | + | 0.068 | 0.05 | 0.08 | 4748 | rs16886351 | chr6 | 22621987 | + | 0.917 | 0.95 | 0.938 |
| 1710 | rs2329247 | chr13 | 82160171 | + | 0.058 | 0.051 | 0.1 | 4749 | rs16886628 | chr6 | 22741720 | + | 0.948 | 0.909 | 0.937 |
| 1711 | rs1537485 | chr13 | 82161746 | + | 0.051 | 0.051 | 0.099 | 4750 | rs9358721 | chr6 | 24023754 | + | 0.917 | 0.939 | 0.946 |
| 1712 | rs1998691 | chr13 | 82169993 | + | 0.058 | 0.05 | 0.071 | 4751 | rs9393510 | chr6 | 24032210 | + | 0.917 | 0.938 | 0.946 |
| 1713 | rs1577067 | chr13 | 82175629 | + | 0.067 | 0.051 | 0.099 | 4752 | rs13211695 | chr6 | 24119353 | + | 0.917 | 0.95 | 0.914 |
| 1714 | rs9546367 | chr13 | 82859915 | + | 0.933 | 0.938 | 0.927 | 4753 | rs13215261 | chr6 | 24222573 | + | 0.904 | 0.933 | 0.928 |

Fig. 9 Cont. 49

| | | | | | | | | | | | |
|---|---|---|---|---|---|---|---|---|---|---|---|
| 1715 | rs9318939 | chr13 | 82853650 | + | 0.933 | 0.939 | 0.909 | 4754 | rs1995675 | chr6 | 25522807 | + | 0.95 | 0.949 | 0.946 |
| 1716 | rs9575613 | chr13 | 84081505 | + | 0.949 | 0.938 | 0.909 | 4755 | rs17693877 | chr6 | 27815025 | + | 0.95 | 0.922 | 0.92 |
| 1717 | rs1446792 | chr13 | 84089937 | + | 0.949 | 0.938 | 0.902 | 4756 | rs9348782 | chr6 | 28090511 | + | 0.925 | 0.921 | 0.946 |
| 1718 | rs9575621 | chr13 | 84102404 | + | 0.949 | 0.944 | 0.914 | 4757 | rs17313276 | chr6 | 28445728 | + | 0.933 | 0.906 | 0.946 |
| 1719 | rs9602525 | chr13 | 84114641 | + | 0.942 | 0.944 | 0.902 | 4758 | rs2232438 | chr6 | 28458458 | + | 0.933 | 0.906 | 0.946 |
| 1720 | rs9575636 | chr13 | 84142066 | + | 0.915 | 0.944 | 0.919 | 4759 | rs17314224 | chr6 | 28462925 | + | 0.933 | 0.904 | 0.946 |
| 1721 | rs12100200 | chr13 | 84143232 | + | 0.917 | 0.949 | 0.919 | 4760 | rs17392982 | chr6 | 28468550 | + | 0.933 | 0.906 | 0.946 |
| 1722 | rs9575638 | chr13 | 84147159 | + | 0.932 | 0.95 | 0.902 | 4761 | rs7738990 | chr6 | 29209100 | + | 0.917 | 0.931 | 0.938 |
| 1723 | rs9565967 | chr13 | 84169399 | + | 0.933 | 0.949 | 0.902 | 4762 | rs2223363 | chr6 | 29212651 | + | 0.917 | 0.933 | 0.91 |
| 1724 | rs7319590 | chr13 | 84181912 | + | 0.068 | 0.051 | 0.077 | 4763 | rs17343045 | chr6 | 29215633 | + | 0.917 | 0.933 | 0.938 |
| 1725 | rs10507945 | chr13 | 84407313 | + | 0.908 | 0.938 | 0.929 | 4764 | rs7745785 | chr6 | 29218757 | + | 0.917 | 0.933 | 0.938 |
| 1726 | rs17078933 | chr13 | 84453974 | + | 0.909 | 0.916 | 0.917 | 4765 | rs7763908 | chr6 | 29218817 | + | 0.917 | 0.933 | 0.938 |
| 1727 | rs17079004 | chr13 | 84474502 | + | 0.905 | 0.915 | 0.945 | 4766 | rs6904165 | chr6 | 29299368 | + | 0.917 | 0.938 | 0.91 |
| 1728 | rs4502116 | chr13 | 84767462 | + | 0.083 | 0.056 | 0.095 | 4767 | rs2024680 | chr6 | 29336225 | + | 0.908 | 0.932 | 0.946 |
| 1729 | rs12585502 | chr13 | 85775322 | + | 0.923 | 0.907 | 0.943 | 4768 | rs10484545 | chr6 | 29342489 | + | 0.908 | 0.933 | 0.946 |
| 1730 | rs10492619 | chr13 | 90976896 | + | 0.917 | 0.906 | 0.928 | 4769 | rs6904130 | chr6 | 29343172 | + | 0.908 | 0.933 | 0.919 |
| 1731 | rs17429394 | chr13 | 91726146 | + | 0.95 | 0.911 | 0.932 | 4770 | rs6924127 | chr6 | 29343212 | + | 0.908 | 0.933 | 0.946 |
| 1732 | rs16947826 | chr13 | 92079129 | + | 0.924 | 0.949 | 0.946 | 4771 | rs17344111 | chr6 | 29344567 | + | 0.908 | 0.922 | 0.946 |
| 1733 | rs17188711 | chr13 | 92361912 | + | 0.925 | 0.938 | 0.923 | 4772 | rs6921498 | chr6 | 29345753 | + | 0.908 | 0.922 | 0.946 |
| 1734 | rs1323988 | chr13 | 92864558 | + | 0.922 | 0.943 | 0.901 | 4773 | rs6942318 | chr6 | 29345994 | + | 0.908 | 0.922 | 0.919 |
| 1735 | rs1933780 | chr13 | 93177060 | + | 0.05 | 0.09 | 0.05 | 4774 | rs2523448 | chr6 | 29642570 | + | 0.925 | 0.939 | 0.938 |
| 1736 | rs6492735 | chr13 | 94161618 | + | 0.925 | 0.904 | 0.92 | 4775 | rs740883 | chr6 | 29683384 | + | 0.933 | 0.911 | 0.919 |
| 1737 | rs16950384 | chr13 | 94410103 | + | 0.925 | 0.95 | 0.908 | 4776 | rs740882 | chr6 | 29683435 | + | 0.933 | 0.909 | 0.919 |
| 1738 | rs4148456 | chr13 | 94686105 | + | 0.925 | 0.917 | 0.905 | 4777 | rs740881 | chr6 | 29683546 | + | 0.933 | 0.911 | 0.902 |
| 1739 | rs16951448 | chr13 | 95512279 | + | 0.907 | 0.933 | 0.914 | 4778 | rs29229 | chr6 | 29683837 | + | 0.933 | 0.911 | 0.902 |
| 1740 | rs1763703 | chr13 | 96077097 | + | 0.1 | 0.09 | 0.098 | 4779 | rs881284 | chr6 | 29684026 | + | 0.933 | 0.911 | 0.919 |
| 1741 | rs7997549 | chr13 | 97551280 | + | 0.917 | 0.928 | 0.911 | 4780 | rs29261 | chr6 | 29684177 | + | 0.933 | 0.921 | 0.913 |
| 1742 | rs11069292 | chr13 | 97552079 | + | 0.933 | 0.926 | 0.911 | 4781 | rs29262 | chr6 | 29684571 | + | 0.933 | 0.914 | 0.919 |
| 1743 | rs9517192 | chr13 | 97559580 | + | 0.929 | 0.948 | 0.908 | 4782 | rs29258 | chr6 | 29685596 | + | 0.939 | 0.91 | 0.919 |
| 1744 | rs9557513 | chr13 | 100275665 | + | 0.95 | 0.933 | 0.945 | 4783 | rs29257 | chr6 | 29686009 | + | 0.939 | 0.91 | 0.902 |
| 1745 | rs9585612 | chr13 | 100515413 | + | 0.917 | 0.917 | 0.909 | 4784 | rs29253 | chr6 | 29688415 | + | 0.933 | 0.909 | 0.919 |
| 1746 | rs9518299 | chr13 | 100533682 | + | 0.933 | 0.933 | 0.909 | 4785 | rs29227 | chr6 | 29688567 | + | 0.939 | 0.91 | 0.919 |
| 1747 | rs9513850 | chr13 | 100542783 | + | 0.925 | 0.939 | 0.932 | 4786 | rs29226 | chr6 | 29688990 | + | 0.933 | 0.915 | 0.919 |
| 1748 | rs9518302 | chr13 | 100544658 | + | 0.933 | 0.939 | 0.909 | 4787 | rs29225 | chr6 | 29689020 | + | 0.932 | 0.91 | 0.919 |
| 1749 | rs9518303 | chr13 | 100544971 | + | 0.933 | 0.939 | 0.909 | 4788 | rs29224 | chr6 | 29689322 | + | 0.933 | 0.91 | 0.919 |

Fig. 9 Cont. 50

| | | | | | | | | | | |
|---|---|---|---|---|---|---|---|---|---|---|
| 1750 | rs9513851 | chr13 | 100545985 | + | 0.941 | 0.939 | 0.909 | 4789 | rs1686769C chr6 | 29693362 | + | 0.92 | 0.911 | 0.919 |
| 1751 | rs12019631 | chr13 | 100549900 | + | 0.925 | 0.939 | 0.909 | 4790 | rs17842396 chr6 | 29694363 | + | 0.933 | 0.911 | 0.919 |
| 1752 | rs9518307 | chr13 | 100552162 | + | 0.933 | 0.939 | 0.928 | 4791 | rs6919973 chr6 | 29695853 | + | 0.933 | 0.915 | 0.919 |
| 1753 | rs12430805 | chr13 | 101410771 | + | 0.942 | 0.909 | 0.938 | 4792 | rs29223 chr6 | 29696523 | + | 0.939 | 0.91 | 0.919 |
| 1754 | rs12430821 | chr13 | 101410824 | + | 0.949 | 0.914 | 0.938 | 4793 | rs2021749 chr6 | 29706098 | + | 0.933 | 0.914 | 0.919 |
| 1755 | rs16961268 | chr13 | 102513784 | + | 0.942 | 0.922 | 0.941 | 4794 | rs2734924 chr6 | 29990153 | + | 0.1 | 0.068 | 0.08 |
| 1756 | rs16961281 | chr13 | 102516825 | + | 0.908 | 0.944 | 0.928 | 4795 | rs9261132 chr6 | 30089042 | + | 0.941 | 0.939 | 0.929 |
| 1757 | rs12583004 | chr13 | 102878193 | + | 0.95 | 0.924 | 0.91 | 4796 | rs17475879 chr6 | 30472487 | + | 0.95 | 0.933 | 0.919 |
| 1758 | rs4328300 | chr13 | 103113375 | + | 0.092 | 0.089 | 0.05 | 4797 | rs17476793 chr6 | 30518967 | + | 0.95 | 0.933 | 0.911 |
| 1759 | rs1360478 | chr13 | 103113530 | + | 0.092 | 0.089 | 0.05 | 4798 | rs11753326 chr6 | 31033964 | + | 0.907 | 0.938 | 0.923 |
| 1760 | rs3908674 | chr13 | 103114292 | + | 0.092 | 0.096 | 0.05 | 4799 | rs7768644 chr6 | 31110080 | + | 0.933 | 0.95 | 0.95 |
| 1761 | rs1772552 | chr13 | 103135853 | + | 0.059 | 0.089 | 0.054 | 4800 | rs9264672 chr6 | 31347745 | + | 0.912 | 0.934 | 0.915 |
| 1762 | rs9300900 | chr13 | 103620347 | + | 0.948 | 0.935 | 0.92 | 4801 | rs2844596 chr6 | 31365355 | + | 0.922 | 0.919 | 0.939 |
| 1763 | rs9519246 | chr13 | 103627866 | + | 0.95 | 0.928 | 0.92 | 4802 | rs9264849 chr6 | 31379205 | + | 0.936 | 0.94 | 0.923 |
| 1764 | rs9519248 | chr13 | 103628083 | + | 0.949 | 0.926 | 0.906 | 4803 | rs4327724 chr6 | 31440667 | + | 0.926 | 0.909 | 0.929 |
| 1765 | rs9300901 | chr13 | 103629393 | + | 0.95 | 0.928 | 0.92 | 4804 | rs4711314 chr6 | 33193925 | + | 0.925 | 0.906 | 0.902 |
| 1766 | rs9519251 | chr13 | 103637496 | + | 0.942 | 0.933 | 0.901 | 4805 | rs493932 chr6 | 33689514 | + | 0.929 | 0.931 | 0.915 |
| 1767 | rs9558317 | chr13 | 103961597 | + | 0.933 | 0.915 | 0.941 | 4806 | rs12192035 chr6 | 33828043 | + | 0.933 | 0.933 | 0.902 |
| 1768 | rs9558334 | chr13 | 103990758 | + | 0.933 | 0.904 | 0.938 | 4807 | rs2495958 chr6 | 34025191 | + | 0.067 | 0.09 | 0.098 |
| 1769 | rs9301010 | chr13 | 104700276 | + | 0.933 | 0.917 | 0.911 | 4808 | rs7761629 chr6 | 38801339 | + | 0.917 | 0.933 | 0.95 |
| 1770 | rs101161652 | chr13 | 104700371 | + | 0.933 | 0.917 | 0.911 | 4809 | rs9942541 chr6 | 39232660 | + | 0.925 | 0.939 | 0.909 |
| 1771 | rs116200002 | chr13 | 106244325 | + | 0.933 | 0.933 | 0.937 | 4810 | rs9394632 chr6 | 39967080 | + | 0.938 | 0.921 | 0.95 |
| 1772 | rs116189951 | chr13 | 106279755 | + | 0.95 | 0.933 | 0.937 | 4811 | rs1408977 chr6 | 40355100 | + | 0.05 | 0.062 | 0.05 |
| 1773 | rs12560665 | chr13 | 106403715 | + | 0.95 | 0.928 | 0.938 | 4812 | rs7743422 chr6 | 40360718 | + | 0.075 | 0.061 | 0.05 |
| 1774 | rs12430847 | chr13 | 106813272 | + | 0.914 | 0.949 | 0.946 | 4813 | rs987065 chr6 | 40535559 | + | 0.933 | 0.922 | 0.932 |
| 1775 | rs12430738 | chr13 | 107604907 | + | 0.915 | 0.928 | 0.909 | 4814 | rs9394740 chr6 | 40932394 | + | 0.933 | 0.939 | 0.927 |
| 1776 | rs12855465 | chr13 | 107678142 | + | 0.925 | 0.928 | 0.946 | 4815 | rs9367085 chr6 | 40955991 | + | 0.917 | 0.938 | 0.932 |
| 1777 | rs12856208 | chr13 | 107678245 | + | 0.925 | 0.928 | 0.946 | 4816 | rs673537 chr6 | 41391341 | + | 0.083 | 0.062 | 0.098 |
| 1778 | rs12874414 | chr13 | 107699553 | + | 0.95 | 0.928 | 0.946 | 4817 | rs7765789 chr6 | 41528120 | + | 0.917 | 0.927 | 0.95 |
| 1779 | rs1285607C | chr13 | 107701109 | + | 0.949 | 0.927 | 0.946 | 4818 | rs7763360 chr6 | 42147550 | + | 0.918 | 0.927 | 0.928 |
| 1780 | rs9301294 | chr13 | 107851114 | + | 0.908 | 0.922 | 0.902 | 4819 | rs11754445 chr6 | 42210996 | + | 0.941 | 0.932 | 0.926 |
| 1781 | rs9587570 | chr13 | 107857202 | + | 0.914 | 0.932 | 0.917 | 4820 | rs6911790 chr6 | 45998769 | + | 0.924 | 0.933 | 0.946 |
| 1782 | rs11842722 | chr13 | 107871916 | + | 0.908 | 0.922 | 0.902 | 4821 | rs16875982 chr6 | 47562354 | + | 0.927 | 0.924 | 0.944 |
| 1783 | rs9587580 | chr13 | 107882158 | + | 0.907 | 0.926 | 0.946 | 4822 | rs2105005 chr6 | 47570530 | + | 0.932 | 0.921 | 0.94 |
| 1784 | rs9587583 | chr13 | 107887617 | + | 0.907 | 0.922 | 0.91 | 4823 | rs12523687 chr6 | 47577095 | + | 0.931 | 0.918 | 0.932 |

Fig. 9 Cont. 51

| | | | | | | | | | |
|---|---|---|---|---|---|---|---|---|---|
| 1785 | rs7320126 | chr13 | 109430936 | + | 0.908 | 0.949 | 0.931 | 4824 | rs12525335 chr6 | 47598742 | + | 0.931 | 0.917 | 0.92 |
| 1786 | rs3742209 | chr13 | 109436361 | + | 0.933 | 0.943 | 0.923 | 4825 | rs18876602 chr6 | 47912395 | + | 0.908 | 0.939 | 0.914 |
| 1787 | rs7320027 | chr13 | 109664904 | + | 0.902 | 0.948 | 0.931 | 4826 | rs6911556 chr6 | 47913528 | + | 0.908 | 0.939 | 0.929 |
| 1788 | rs9521776 | chr13 | 109905938 | + | 0.914 | 0.927 | 0.914 | 4827 | rs16876627 chr6 | 47928323 | + | 0.914 | 0.939 | 0.914 |
| 1789 | rs9521777 | chr13 | 109906132 | + | 0.912 | 0.91 | 0.914 | 4828 | rs1328981 chr6 | 47949031 | + | 0.908 | 0.933 | 0.932 |
| 1790 | rs9559826 | chr13 | 109943780 | + | 0.947 | 0.92 | 0.939 | 4829 | rs1219606 chr6 | 48139953 | + | 0.95 | 0.95 | 0.937 |
| 1791 | rs167890 | chr13 | 110247116 | + | 0.917 | 0.91 | 0.928 | 4830 | rs17289986 chr6 | 48893230 | + | 0.917 | 0.936 | 0.931 |
| 1792 | rs1555754 | chr13 | 110692672 | + | 0.942 | 0.933 | 0.913 | 4831 | rs11970308 chr6 | 49014693 | + | 0.949 | 0.926 | 0.926 |
| 1793 | rs13378156 | chr13 | 110695443 | + | 0.942 | 0.933 | 0.936 | 4832 | rs16881244 chr6 | 51256487 | + | 0.908 | 0.938 | 0.928 |
| 1794 | rs2182064 | chr13 | 110702035 | + | 0.092 | 0.1 | 0.095 | 4833 | rs764184 chr6 | 51281754 | + | 0.933 | 0.904 | 0.902 |
| 1795 | rs942649 | chr13 | 110752557 | + | 0.083 | 0.08 | 0.062 | 4834 | rs7759159 chr6 | 51282205 | + | 0.932 | 0.906 | 0.909 |
| 1796 | rs2391932 | chr13 | 110769001 | + | 0.905 | 0.931 | 0.932 | 4835 | rs6927969 chr6 | 51289995 | + | 0.933 | 0.906 | 0.902 |
| 1797 | rs9560137 | chr13 | 111064640 | + | 0.936 | 0.94 | 0.927 | 4836 | rs10484409 chr6 | 52939744 | + | 0.908 | 0.933 | 0.923 |
| 1798 | rs9549867 | chr13 | 111881373 | + | 0.95 | 0.933 | 0.918 | 4837 | rs3734431 chr6 | 52951388 | + | 0.907 | 0.938 | 0.923 |
| 1799 | rs9549459 | chr13 | 111957516 | + | 0.95 | 0.922 | 0.911 | 4838 | rs12524274 chr6 | 52952282 | + | 0.933 | 0.938 | 0.91 |
| 1800 | rs9549460 | chr13 | 111957690 | + | 0.949 | 0.922 | 0.914 | 4839 | rs7739196 chr6 | 54027983 | + | 0.908 | 0.906 | 0.931 |
| 1801 | rs9549912 | chr13 | 111958520 | + | 0.95 | 0.922 | 0.909 | 4840 | rs12660631 chr6 | 55855392 | + | 0.942 | 0.938 | 0.95 |
| 1802 | rs12877054 | chr13 | 111960045 | + | 0.947 | 0.92 | 0.907 | 4841 | rs16887361 chr6 | 55867901 | + | 0.925 | 0.921 | 0.95 |
| 1803 | rs11842542 | chr13 | 111960315 | + | 0.949 | 0.922 | 0.902 | 4842 | rs16887399 chr6 | 55895554 | + | 0.95 | 0.944 | 0.946 |
| 1804 | rs11841658 | chr13 | 111960707 | + | 0.949 | 0.922 | 0.913 | 4843 | rs6923551 chr6 | 55900206 | + | 0.95 | 0.944 | 0.946 |
| 1805 | rs9549916 | chr13 | 111962391 | + | 0.95 | 0.922 | 0.909 | 4844 | rs10498805 chr6 | 55902352 | + | 0.942 | 0.944 | 0.946 |
| 1806 | rs11839945 | chr13 | 113057171 | + | 0.917 | 0.922 | 0.938 | 4845 | rs16887409 chr6 | 55903570 | + | 0.95 | 0.944 | 0.945 |
| 1807 | rs11847223 | chr14 | 19437207 | + | 0.941 | 0.941 | 0.938 | 4846 | rs17683688 chr6 | 559106603 | + | 0.946 | 0.937 | 0.946 |
| 1808 | rs12888873 | chr14 | 19582973 | + | 0.948 | 0.916 | 0.906 | 4847 | rs12660477 chr6 | 56285975 | + | 0.946 | 0.949 | 0.91 |
| 1809 | rs17211264 | chr14 | 19761502 | + | 0.917 | 0.928 | 0.923 | 4848 | rs1993118 chr6 | 57005993 | + | 0.933 | 0.917 | 0.905 |
| 1810 | rs10140652 | chr14 | 19761728 | + | 0.908 | 0.928 | 0.919 | 4849 | rs9370559 chr6 | 57037768 | + | 0.933 | 0.921 | 0.922 |
| 1811 | rs9323693 | chr14 | 19761802 | + | 0.908 | 0.927 | 0.911 | 4850 | rs9464418 chr6 | 57081861 | + | 0.933 | 0.921 | 0.923 |
| 1812 | rs7157592 | chr14 | 20073565 | + | 0.917 | 0.949 | 0.946 | 4851 | rs16888316 chr6 | 57084903 | + | 0.933 | 0.917 | 0.911 |
| 1813 | rs8008670 | chr14 | 20906240 | + | 0.094 | 0.08 | 0.059 | 4852 | rs9370567 chr6 | 571463628 | + | 0.94 | 0.922 | 0.923 |
| 1814 | rs10143061 | chr14 | 20977684 | + | 0.05 | 0.089 | 0.054 | 4853 | rs1935268 chr6 | 58447977 | + | 0.942 | 0.91 | 0.931 |
| 1815 | rs10135603 | chr14 | 21113042 | + | 0.914 | 0.938 | 0.909 | 4854 | rs16990514 chr6 | 62669538 | + | 0.942 | 0.92 | 0.904 |
| 1816 | rs4982558 | chr14 | 21644214 | + | 0.068 | 0.056 | 0.09 | 4855 | rs16900602 chr6 | 62683938 | + | 0.941 | 0.925 | 0.901 |
| 1817 | rs10143357 | chr14 | 21858450 | + | 0.917 | 0.922 | 0.929 | 4856 | rs2134476 chr6 | 62814384 | + | 0.933 | 0.928 | 0.932 |
| 1818 | rs10483273 | chr14 | 21986886 | + | 0.917 | 0.91 | 0.941 | 4857 | rs17533836 chr6 | 62814829 | + | 0.922 | 0.932 | 0.927 |
| 1819 | rs1076861 | chr14 | 22012459 | + | 0.933 | 0.927 | 0.919 | 4858 | rs1048462C chr6 | 62833834 | + | 0.925 | 0.927 | 0.932 |

Fig. 9 Cont. 52

| | | | | | | | | | | | |
|---|---|---|---|---|---|---|---|---|---|---|---|
| 1820 | rs2055134 | chr14 | 22328029 | + | 0.925 | 0.939 | 0.91 | 4859 | rs10484619 | chr6 | 62917772 | + | 0.908 | 0.927 | 0.929 |
| 1821 | rs3764167 | chr14 | 22589815 | + | 0.908 | 0.917 | 0.914 | 4860 | rs2200104 | chr6 | 64673781 | + | 0.925 | 0.949 | 0.946 |
| 1822 | rs1950252 | chr14 | 22848538 | + | 0.067 | 0.05 | 0.081 | 4861 | rs7743334 | chr6 | 66323264 | + | 0.93 | 0.903 | 0.925 |
| 1823 | rs9323298 | chr14 | 22852609 | + | 0.078 | 0.056 | 0.071 | 4862 | rs9363590 | chr6 | 67155058 | + | 0.95 | 0.916 | 0.936 |
| 1824 | rs7142474 | chr14 | 22855445 | + | 0.075 | 0.057 | 0.081 | 4863 | rs6939140 | chr6 | 67397784 | + | 0.096 | 0.076 | 0.058 |
| 1825 | rs1955559 | chr14 | 22857807 | + | 0.075 | 0.061 | 0.064 | 4864 | rs4710623 | chr6 | 67456460 | + | 0.05 | 0.094 | 0.054 |
| 1826 | rs8020117 | chr14 | 22861859 | + | 0.067 | 0.051 | 0.081 | 4865 | rs17541229 | chr6 | 67962431 | + | 0.925 | 0.928 | 0.91 |
| 1827 | rs7161120 | chr14 | 22867041 | + | 0.075 | 0.05 | 0.073 | 4866 | rs10455635 | chr6 | 68360689 | + | 0.939 | 0.91 | 0.945 |
| 1828 | rs4981468 | chr14 | 22867359 | + | 0.075 | 0.05 | 0.05 | 4867 | rs9294846 | chr6 | 70436711 | + | 0.947 | 0.926 | 0.927 |
| 1829 | rs178637 | chr14 | 22924112 | + | 0.942 | 0.928 | 0.91 | 4868 | rs9454868 | chr6 | 70445531 | + | 0.95 | 0.928 | 0.909 |
| 1830 | rs17091434 | chr14 | 22930548 | + | 0.942 | 0.906 | 0.941 | 4869 | rs1457498 | chr6 | 70565589 | + | 0.95 | 0.927 | 0.91 |
| 1831 | rs10483285 | chr14 | 23869198 | + | 0.907 | 0.924 | 0.937 | 4870 | rs4707626 | chr6 | 70853842 | + | 0.908 | 0.906 | 0.932 |
| 1832 | rs1270756 | chr14 | 24415738 | + | 0.083 | 0.072 | 0.086 | 4871 | rs4707627 | chr6 | 70857338 | + | 0.95 | 0.95 | 0.932 |
| 1833 | rs1241643 | chr14 | 24420594 | + | 0.096 | 0.072 | 0.089 | 4872 | rs2747697 | chr6 | 71286004 | + | 0.1 | 0.096 | 0.098 |
| 1834 | rs10483296 | chr14 | 24652725 | + | 0.942 | 0.938 | 0.905 | 4873 | rs16880774 | chr6 | 71449132 | + | 0.932 | 0.928 | 0.941 |
| 1835 | rs8015722 | chr14 | 27092639 | + | 0.95 | 0.904 | 0.911 | 4874 | rs7750238 | chr6 | 71665770 | + | 0.922 | 0.948 | 0.914 |
| 1836 | rs17113053 | chr14 | 27234932 | + | 0.908 | 0.939 | 0.946 | 4875 | rs10943088 | chr6 | 74041441 | + | 0.933 | 0.944 | 0.919 |
| 1837 | rs12590946 | chr14 | 27273647 | + | 0.925 | 0.944 | 0.946 | 4876 | rs9442947 | chr6 | 74463698 | + | 0.908 | 0.925 | 0.928 |
| 1838 | rs7151440 | chr14 | 29024415 | + | 0.08 | 0.084 | 0.053 | 4877 | rs6935547 | chr6 | 74495369 | + | 0.925 | 0.917 | 0.95 |
| 1839 | rs10143362 | chr14 | 30114206 | + | 0.913 | 0.925 | 0.929 | 4878 | rs4708108 | chr6 | 74736106 | + | 0.925 | 0.944 | 0.911 |
| 1840 | rs10143215 | chr14 | 30181611 | + | 0.914 | 0.903 | 0.941 | 4879 | rs4708129 | chr6 | 74914816 | + | 0.095 | 0.06 | 0.076 |
| 1841 | rs11624441 | chr14 | 30217169 | + | 0.904 | 0.908 | 0.935 | 4880 | rs12525517 | chr6 | 74999820 | + | 0.93 | 0.922 | 0.911 |
| 1842 | rs7149528 | chr14 | 31834970 | + | 0.908 | 0.906 | 0.923 | 4881 | rs7755776 | chr6 | 75024125 | + | 0.925 | 0.928 | 0.95 |
| 1843 | rs8014419 | chr14 | 31967501 | + | 0.076 | 0.1 | 0.086 | 4882 | rs2756344 | chr6 | 75158402 | + | 0.058 | 0.096 | 0.063 |
| 1844 | rs12897888 | chr14 | 33247557 | + | 0.95 | 0.911 | 0.946 | 4883 | rs1203210 | chr6 | 75953792 | + | 0.093 | 0.061 | 0.089 |
| 1845 | rs7151397 | chr14 | 33261435 | + | 0.924 | 0.944 | 0.946 | 4884 | rs4527665 | chr6 | 77386332 | + | 0.933 | 0.944 | 0.918 |
| 1846 | rs7141142 | chr14 | 33262954 | + | 0.908 | 0.939 | 0.938 | 4885 | rs11755314 | chr6 | 77396867 | + | 0.932 | 0.944 | 0.917 |
| 1847 | rs797340 | chr14 | 33721254 | + | 0.942 | 0.922 | 0.901 | 4886 | rs4708278 | chr6 | 77410910 | + | 0.902 | 0.948 | 0.904 |
| 1848 | rs1244349 | chr14 | 33742521 | + | 0.942 | 0.922 | 0.909 | 4887 | rs9448057 | chr6 | 78068077 | + | 0.925 | 0.944 | 0.937 |
| 1849 | rs12164885 | chr14 | 35108794 | + | 0.917 | 0.906 | 0.901 | 4888 | rs9343725 | chr6 | 78858543 | + | 0.942 | 0.904 | 0.928 |
| 1850 | rs10133473 | chr14 | 35114168 | + | 0.915 | 0.906 | 0.905 | 4889 | rs9341723 | chr6 | 78891850 | + | 0.942 | 0.906 | 0.938 |
| 1851 | rs4982302 | chr14 | 35197105 | + | 0.908 | 0.904 | 0.905 | 4890 | rs9341729 | chr6 | 78990468 | + | 0.933 | 0.938 | 0.932 |
| 1852 | rs1951844 | chr14 | 35280825 | + | 0.907 | 0.906 | 0.927 | 4891 | rs2063044 | chr6 | 79277042 | + | 0.923 | 0.91 | 0.904 |
| 1853 | rs17836222 | chr14 | 35295011 | + | 0.907 | 0.906 | 0.905 | 4892 | rs10485132 | chr6 | 79333000 | + | 0.917 | 0.911 | 0.932 |
| 1854 | rs10152105 | chr14 | 35304962 | + | 0.908 | 0.906 | 0.912 | 4893 | rs1543482 | chr6 | 79485857 | + | 0.908 | 0.911 | 0.92 |

Fig. 9 Cont. 53

| | | | | | | | | | | | | | |
|---|---|---|---|---|---|---|---|---|---|---|---|---|---|
| 1855 | rs17103608 chr14 | 35422074 | + | 0.93 | 0.929 | 0.941 | 4894 | rs9352673 chr6 | 79659462 | + | 0.092 | 0.075 | 0.08 |
| 1856 | rs12590949 chr14 | 35523553 | + | 0.925 | 0.922 | 0.902 | 4895 | rs10943611 chr6 | 79747894 | + | 0.915 | 0.922 | 0.905 |
| 1857 | rs1535722 chr14 | 35872483 | + | 0.1 | 0.074 | 0.072 | 4896 | rs13214510 chr6 | 80074987 | + | 0.915 | 0.916 | 0.914 |
| 1858 | rs8007769 chr14 | 39078057 | + | 0.95 | 0.928 | 0.905 | 4897 | rs649647 chr6 | 80162946 | + | 0.092 | 0.061 | 0.09 |
| 1859 | rs10147884 chr14 | 39283220 | + | 0.933 | 0.906 | 0.92 | 4898 | rs6939506 chr6 | 80163711 | + | 0.95 | 0.933 | 0.938 |
| 1860 | rs12323926 chr14 | 39284587 | + | 0.933 | 0.906 | 0.92 | 4899 | rs3907329 chr6 | 80165056 | + | 0.924 | 0.927 | 0.92 |
| 1861 | rs10134852 chr14 | 39286500 | + | 0.933 | 0.906 | 0.92 | 4900 | rs6925847 chr6 | 80166966 | + | 0.917 | 0.928 | 0.929 |
| 1862 | rs10130625 chr14 | 39290467 | + | 0.941 | 0.92 | 0.92 | 4901 | rs196666 chr6 | 80167508 | + | 0.05 | 0.051 | 0.1 |
| 1863 | rs11846720 chr14 | 39322001 | + | 0.905 | 0.91 | 0.926 | 4902 | rs16890675 chr6 | 80175415 | + | 0.942 | 0.917 | 0.927 |
| 1864 | rs1547007 chr14 | 39652817 | + | 0.912 | 0.916 | 0.946 | 4903 | rs9343946 chr6 | 80622953 | + | 0.907 | 0.933 | 0.944 |
| 1865 | rs1952915 chr14 | 40015091 | + | 0.075 | 0.083 | 0.052 | 4904 | rs17254348 chr6 | 80804656 | + | 0.942 | 0.95 | 0.946 |
| 1866 | rs17110795 chr14 | 40027151 | + | 0.95 | 0.911 | 0.95 | 4905 | rs1561181 chr6 | 81149022 | + | 0.917 | 0.933 | 0.914 |
| 1867 | rs1176881 chr14 | 40337739 | + | 0.067 | 0.085 | 0.055 | 4906 | rs9344146 chr6 | 82072373 | + | 0.924 | 0.911 | 0.914 |
| 1868 | rs1185821 chr14 | 40358532 | + | 0.058 | 0.089 | 0.059 | 4907 | rs9352982 chr6 | 82074149 | + | 0.924 | 0.92 | 0.914 |
| 1869 | rs1176880 chr14 | 40363170 | + | 0.058 | 0.089 | 0.054 | 4908 | rs12203618 chr6 | 84407107 | + | 0.942 | 0.927 | 0.95 |
| 1870 | rs1176801 chr14 | 40366061 | + | 0.058 | 0.089 | 0.054 | 4909 | rs6940118 chr6 | 84222197 | + | 0.941 | 0.927 | 0.95 |
| 1871 | rs1176797 chr14 | 40368662 | + | 0.069 | 0.08 | 0.059 | 4910 | rs2273365 chr6 | 84423502 | + | 0.933 | 0.927 | 0.95 |
| 1872 | rs1666956 chr14 | 40379906 | + | 0.058 | 0.089 | 0.059 | 4911 | rs12194716 chr6 | 84462226 | + | 0.941 | 0.928 | 0.902 |
| 1873 | rs2899927 chr14 | 41127274 | + | 0.933 | 0.95 | 0.938 | 4912 | rs1928279 chr6 | 84810157 | + | 0.908 | 0.904 | 0.905 |
| 1874 | rs12433478 chr14 | 41945669 | + | 0.924 | 0.939 | 0.918 | 4913 | rs858738 chr6 | 85579854 | + | 0.918 | 0.915 | 0.923 |
| 1875 | rs17711301 chr14 | 41955344 | + | 0.917 | 0.939 | 0.914 | 4914 | rs13222863 chr6 | 85777044 | + | 0.95 | 0.906 | 0.923 |
| 1876 | rs1982750 chr14 | 41964490 | + | 0.917 | 0.939 | 0.914 | 4915 | rs16875501 chr6 | 85778095 | + | 0.95 | 0.906 | 0.944 |
| 1877 | rs11844346 chr14 | 41991989 | + | 0.915 | 0.95 | 0.914 | 4916 | rs17805597 chr6 | 86112439 | + | 0.94 | 0.949 | 0.935 |
| 1878 | rs11157293 chr14 | 42022286 | + | 0.942 | 0.933 | 0.914 | 4917 | rs12528012 chr6 | 87028180 | + | 0.939 | 0.914 | 0.904 |
| 1879 | rs10498369 chr14 | 42032706 | + | 0.942 | 0.938 | 0.92 | 4918 | rs6935746 chr6 | 87032213 | + | 0.942 | 0.921 | 0.926 |
| 1880 | rs10498370 chr14 | 42035467 | + | 0.942 | 0.937 | 0.92 | 4919 | rs12524252 chr6 | 87070986 | + | 0.904 | 0.916 | 0.91 |
| 1881 | rs17113115 chr14 | 42052684 | + | 0.942 | 0.933 | 0.919 | 4920 | rs12193445 chr6 | 87181104 | + | 0.925 | 0.935 | 0.902 |
| 1882 | rs2062469 chr14 | 42078679 | + | 0.948 | 0.944 | 0.926 | 4921 | rs11757848 chr6 | 87401099 | + | 0.93 | 0.928 | 0.927 |
| 1883 | rs12432241 chr14 | 42079403 | + | 0.942 | 0.933 | 0.92 | 4922 | rs6910863 chr6 | 88019291 | + | 0.908 | 0.911 | 0.923 |
| 1884 | rs12436309 chr14 | 42082332 | + | 0.942 | 0.937 | 0.927 | 4923 | rs6454601 chr6 | 88075181 | + | 0.908 | 0.911 | 0.938 |
| 1885 | rs12431970 chr14 | 42084287 | + | 0.942 | 0.933 | 0.92 | 4924 | rs12663251 chr6 | 88082653 | + | 0.908 | 0.911 | 0.901 |
| 1886 | rs11844350 chr14 | 42087052 | + | 0.949 | 0.938 | 0.934 | 4925 | rs2296133 chr6 | 88089051 | + | 0.907 | 0.91 | 0.938 |
| 1887 | rs17113152 chr14 | 42089428 | + | 0.942 | 0.933 | 0.92 | 4926 | rs9344704 chr6 | 88097075 | + | 0.92 | 0.916 | 0.938 |
| 1888 | rs11847898 chr14 | 42092193 | + | 0.942 | 0.943 | 0.919 | 4927 | rs9351127 chr6 | 88117103 | + | 0.942 | 0.91 | 0.938 |
| 1889 | rs12431425 chr14 | 42101416 | + | 0.941 | 0.933 | 0.92 | 4928 | rs7756440 chr6 | 88117410 | + | 0.939 | 0.908 | 0.938 |

Fig. 9 Cont. 54

| | | | | | | | | | | | |
|---|---|---|---|---|---|---|---|---|---|---|---|
| 1890 | rs12432206 | chr14 | 42101856 | + | 0.94 | 0.933 | 0.915 | 4929 | rs7745625 | chr6 | 88125564 | + | 0.942 | 0.911 | 0.938 |
| 1891 | rs11847495 | chr14 | 42104128 | + | 0.942 | 0.933 | 0.92 | 4930 | rs7745870 | chr6 | 88125987 | + | 0.933 | 0.911 | 0.901 |
| 1892 | rs10467780 | chr14 | 42269278 | + | 0.95 | 0.911 | 0.919 | 4931 | rs16879281 | chr6 | 88183142 | + | 0.95 | 0.928 | 0.929 |
| 1893 | rs8017512 | chr14 | 42644218 | + | 0.917 | 0.944 | 0.929 | 4932 | rs9342115 | chr6 | 88322538 | + | 0.908 | 0.932 | 0.938 |
| 1894 | rs17713412 | chr14 | 43016839 | + | 0.924 | 0.92 | 0.928 | 4933 | rs16879596 | chr6 | 88357886 | + | 0.949 | 0.933 | 0.929 |
| 1895 | rs2415810 | chr14 | 43020837 | + | 0.925 | 0.921 | 0.92 | 4934 | rs12662677 | chr6 | 88365330 | + | 0.925 | 0.922 | 0.945 |
| 1896 | rs4598805 | chr14 | 43021242 | + | 0.93 | 0.922 | 0.928 | 4935 | rs2787923 | chr6 | 88458081 | + | 0.95 | 0.933 | 0.914 |
| 1897 | rs8005320 | chr14 | 43029345 | + | 0.925 | 0.927 | 0.92 | 4936 | rs12665198 | chr6 | 89369462 | + | 0.95 | 0.906 | 0.92 |
| 1898 | rs1874052 | chr14 | 43029754 | + | 0.932 | 0.943 | 0.92 | 4937 | rs3778172 | chr6 | 89406157 | + | 0.925 | 0.916 | 0.932 |
| 1899 | rs4906516 | chr14 | 43629948 | + | 0.942 | 0.908 | 0.914 | 4938 | rs9353591 | chr6 | 89477308 | + | 0.91 | 0.949 | 0.93 |
| 1900 | rs2273387 | chr14 | 48594272 | + | 0.908 | 0.95 | 0.946 | 4939 | rs9359808 | chr6 | 89484453 | + | 0.902 | 0.935 | 0.917 |
| 1901 | rs10129635 | chr14 | 50568287 | + | 0.917 | 0.917 | 0.929 | 4940 | rs12200224 | chr6 | 89578841 | + | 0.917 | 0.933 | 0.905 |
| 1902 | rs10141612 | chr14 | 50570087 | + | 0.95 | 0.917 | 0.941 | 4941 | rs6924814 | chr6 | 91842708 | + | 0.909 | 0.909 | 0.945 |
| 1903 | rs7148279 | chr14 | 50601499 | + | 0.933 | 0.927 | 0.946 | 4942 | rs345731 | chr6 | 94024040 | + | 0.908 | 0.909 | 0.95 |
| 1904 | rs2356917 | chr14 | 50988310 | + | 0.058 | 0.056 | 0.062 | 4943 | rs345725 | chr6 | 94030290 | + | 0.908 | 0.913 | 0.95 |
| 1905 | rs7154230 | chr14 | 51130538 | + | 0.922 | 0.947 | 0.95 | 4944 | rs345724 | chr6 | 94030379 | + | 0.908 | 0.911 | 0.95 |
| 1906 | rs11622237 | chr14 | 51291137 | + | 0.931 | 0.939 | 0.901 | 4945 | rs2716073 | chr6 | 96015045 | + | 0.079 | 0.067 | 0.089 |
| 1907 | rs17126012 | chr14 | 52537610 | + | 0.942 | 0.928 | 0.919 | 4946 | rs2613552 | chr6 | 96022679 | + | 0.075 | 0.067 | 0.089 |
| 1908 | rs8005863 | chr14 | 52541779 | + | 0.942 | 0.916 | 0.92 | 4947 | rs9486307 | chr6 | 96045680 | + | 0.067 | 0.067 | 0.089 |
| 1909 | rs17831826 | chr14 | 52771193 | + | 0.942 | 0.95 | 0.902 | 4948 | rs6568531 | chr6 | 96063407 | + | 0.083 | 0.073 | 0.091 |
| 1910 | rs763328 | chr14 | 52776759 | + | 0.917 | 0.949 | 0.901 | 4949 | rs13218746 | chr6 | 96068774 | + | 0.917 | 0.933 | 0.911 |
| 1911 | rs4901374 | chr14 | 52777578 | + | 0.917 | 0.95 | 0.901 | 4950 | rs13202449 | chr6 | 96069781 | + | 0.95 | 0.928 | 0.911 |
| 1912 | rs10498447 | chr14 | 52788208 | + | 0.917 | 0.949 | 0.901 | 4951 | rs13193369 | chr6 | 96081133 | + | 0.95 | 0.917 | 0.911 |
| 1913 | rs2880178 | chr14 | 55024759 | + | 0.922 | 0.943 | 0.914 | 4952 | rs17712479 | chr6 | 96082595 | + | 0.95 | 0.917 | 0.911 |
| 1914 | rs242389 | chr14 | 55661860 | + | 0.058 | 0.094 | 0.063 | 4953 | rs13212001 | chr6 | 96086391 | + | 0.95 | 0.917 | 0.909 |
| 1915 | rs1959066 | chr14 | 56077259 | + | 0.925 | 0.95 | 0.91 | 4954 | rs13218324 | chr6 | 96086661 | + | 0.95 | 0.916 | 0.918 |
| 1916 | rs12885535 | chr14 | 56079634 | + | 0.925 | 0.95 | 0.929 | 4955 | rs9387043 | chr6 | 97569811 | + | 0.95 | 0.921 | 0.927 |
| 1917 | rs12589627 | chr14 | 56293359 | + | 0.917 | 0.95 | 0.941 | 4956 | rs12175747 | chr6 | 97573649 | + | 0.939 | 0.906 | 0.923 |
| 1918 | rs12888921 | chr14 | 57534571 | + | 0.95 | 0.933 | 0.918 | 4957 | rs9372321 | chr6 | 97600416 | + | 0.942 | 0.906 | 0.923 |
| 1919 | rs3783763 | chr14 | 61037921 | + | 0.912 | 0.919 | 0.92 | 4958 | rs9398813 | chr6 | 99042031 | + | 0.908 | 0.944 | 0.946 |
| 1920 | rs10143557 | chr14 | 61120343 | + | 0.949 | 0.931 | 0.939 | 4959 | rs12197025 | chr6 | 99653202 | + | 0.902 | 0.95 | 0.93 |
| 1921 | rs1583945 | chr14 | 61376625 | + | 0.95 | 0.933 | 0.919 | 4960 | rs9402564 | chr6 | 99786623 | + | 0.907 | 0.944 | 0.909 |
| 1922 | rs1583947 | chr14 | 61376977 | + | 0.95 | 0.933 | 0.919 | 4961 | rs6931919 | chr6 | 101134161 | + | 0.083 | 0.086 | 0.065 |
| 1923 | rs17099284 | chr14 | 61397051 | + | 0.925 | 0.933 | 0.914 | 4962 | rs10485268 | chr6 | 102010156 | + | 0.917 | 0.922 | 0.941 |
| 1924 | rs12878037 | chr14 | 63406383 | + | 0.917 | 0.939 | 0.92 | 4963 | rs2852537 | chr6 | 102054705 | + | 0.95 | 0.939 | 0.902 |

Fig. 9 Cont. 55

| | | | | | | | | | | | |
|---|---|---|---|---|---|---|---|---|---|---|---|
| 1925 | rs12884259 | chr14 | 63407583 | + | 0.942 | 0.932 | 0.944 | 4964 | rs2243889 | chr6 | 102066682 | + | 0.95 | 0.939 | 0.911 |
| 1926 | rs12882429 | chr14 | 63420812 | + | 0.95 | 0.939 | 0.92 | 4965 | rs2245817 | chr6 | 102109049 | + | 0.075 | 0.056 | 0.099 |
| 1927 | rs12889107 | chr14 | 63446795 | + | 0.917 | 0.95 | 0.946 | 4966 | rs11156144 | chr6 | 102155227 | + | 0.925 | 0.944 | 0.92 |
| 1928 | rs10138525 | chr14 | 64230971 | + | 0.948 | 0.95 | 0.927 | 4967 | rs2518296 | chr6 | 102233451 | + | 0.05 | 0.1 | 0.077 |
| 1929 | rs747860 | chr14 | 64309647 | + | 0.949 | 0.95 | 0.914 | 4968 | rs949395 | chr6 | 102238945 | + | 0.051 | 0.086 | 0.081 |
| 1930 | rs17180385 | chr14 | 64321204 | + | 0.917 | 0.95 | 0.946 | 4969 | rs2764234 | chr6 | 102273373 | + | 0.05 | 0.094 | 0.082 |
| 1931 | rs10129595 | chr14 | 64327025 | + | 0.942 | 0.95 | 0.936 | 4970 | rs6907134 | chr6 | 102758284 | + | 0.904 | 0.938 | 0.901 |
| 1932 | rs17180532 | chr14 | 64340471 | + | 0.917 | 0.95 | 0.919 | 4971 | rs17715923 | chr6 | 103718571 | + | 0.942 | 0.904 | 0.946 |
| 1933 | rs3819918 | chr14 | 64358485 | + | 0.908 | 0.922 | 0.932 | 4972 | rs46039362 | chr6 | 104409170 | + | 0.925 | 0.939 | 0.905 |
| 1934 | rs12436545 | chr14 | 64366294 | + | 0.917 | 0.917 | 0.938 | 4973 | rs13204815 | chr6 | 104410838 | + | 0.921 | 0.942 | 0.905 |
| 1935 | rs17102190 | chr14 | 64366988 | + | 0.949 | 0.933 | 0.935 | 4974 | rs1416039 | chr6 | 105102552 | + | 0.927 | 0.904 | 0.912 |
| 1936 | rs7494064 | chr14 | 65357663 | + | 0.088 | 0.068 | 0.063 | 4975 | rs12055433 | chr6 | 106137852 | + | 0.908 | 0.916 | 0.937 |
| 1937 | rs12431858 | chr14 | 65481988 | + | 0.942 | 0.95 | 0.928 | 4976 | rs6933284 | chr6 | 106475582 | + | 0.95 | 0.95 | 0.95 |
| 1938 | rs388642 | chr14 | 68295440 | + | 0.083 | 0.076 | 0.05 | 4977 | rs17699974 | chr6 | 106804026 | + | 0.92 | 0.95 | 0.929 |
| 1939 | rs2273419 | chr14 | 68420514 | + | 0.915 | 0.939 | 0.932 | 4978 | rs577707 | chr6 | 106893837 | + | 0.05 | 0.051 | 0.071 |
| 1940 | rs1045301 | chr14 | 68998060 | + | 0.925 | 0.91 | 0.921 | 4979 | rs783395 | chr6 | 107094683 | + | 0.083 | 0.051 | 0.071 |
| 1941 | rs2181130 | chr14 | 69446732 | + | 0.933 | 0.917 | 0.901 | 4980 | rs9398098 | chr6 | 107195754 | + | 0.942 | 0.928 | 0.929 |
| 1942 | rs12894731 | chr14 | 70427418 | + | 0.942 | 0.917 | 0.945 | 4981 | rs4946815 | chr6 | 107567039 | + | 0.942 | 0.938 | 0.905 |
| 1943 | rs17108694 | chr14 | 70427723 | + | 0.942 | 0.917 | 0.936 | 4982 | rs12208316 | chr6 | 107633770 | + | 0.95 | 0.928 | 0.95 |
| 1944 | rs17710873 | chr14 | 70467402 | + | 0.917 | 0.904 | 0.945 | 4983 | rs9486632 | chr6 | 107933084 | + | 0.933 | 0.91 | 0.936 |
| 1945 | rs80221632 | chr14 | 71560733 | + | 0.933 | 0.906 | 0.905 | 4984 | rs12197661 | chr6 | 108006689 | + | 0.947 | 0.927 | 0.902 |
| 1946 | rs80222416 | chr14 | 71568274 | + | 0.933 | 0.906 | 0.929 | 4985 | rs17585366 | chr6 | 108117082 | + | 0.925 | 0.917 | 0.914 |
| 1947 | rs2239280 | chr14 | 72006873 | + | 0.95 | 0.944 | 0.914 | 4986 | rs12153852 | chr6 | 108267804 | + | 0.943 | 0.905 | 0.909 |
| 1948 | rs17117164 | chr14 | 72077300 | + | 0.933 | 0.939 | 0.946 | 4987 | rs17069274 | chr6 | 108552716 | + | 0.946 | 0.948 | 0.941 |
| 1949 | rs12586654 | chr14 | 72629071 | + | 0.95 | 0.906 | 0.946 | 4988 | rs9486817 | chr6 | 108566703 | + | 0.917 | 0.927 | 0.95 |
| 1950 | rs17182111 | chr14 | 72632253 | + | 0.95 | 0.911 | 0.946 | 4989 | rs1252933 | chr6 | 108772625 | + | 0.914 | 0.927 | 0.936 |
| 1951 | rs764361 | chr14 | 73334265 | + | 0.948 | 0.926 | 0.928 | 4990 | rs12200544 | chr6 | 108971057 | + | 0.933 | 0.906 | 0.901 |
| 1952 | rs17103080 | chr14 | 74754776 | + | 0.933 | 0.904 | 0.928 | 4991 | rs7746906 | chr6 | 108985506 | + | 0.917 | 0.904 | 0.901 |
| 1953 | rs958729 | chr14 | 76061739 | + | 0.933 | 0.928 | 0.914 | 4992 | rs17598747 | chr6 | 109048086 | + | 0.908 | 0.917 | 0.91 |
| 1954 | rs748783 | chr14 | 76120854 | + | 0.908 | 0.921 | 0.937 | 4993 | rs17310525 | chr6 | 109064223 | + | 0.908 | 0.917 | 0.91 |
| 1955 | rs1676286 | chr14 | 76124766 | + | 0.082 | 0.073 | 0.05 | 4994 | rs12202209 | chr6 | 109066718 | + | 0.908 | 0.916 | 0.91 |
| 1956 | rs2540887 | chr14 | 76777388 | + | 0.925 | 0.933 | 0.902 | 4995 | rs12207868 | chr6 | 109071578 | + | 0.908 | 0.916 | 0.91 |
| 1957 | rs17106513 | chr14 | 77407874 | + | 0.917 | 0.928 | 0.914 | 4996 | rs12202049 | chr6 | 109075370 | + | 0.908 | 0.916 | 0.911 |
| 1958 | rs8016198 | chr14 | 78304064 | + | 0.917 | 0.906 | 0.911 | 4997 | rs12209092 | chr6 | 109077373 | + | 0.908 | 0.917 | 0.911 |
| 1959 | rs8012207 | chr14 | 78307117 | + | 0.925 | 0.906 | 0.941 | 4998 | rs12197634 | chr6 | 109078349 | + | 0.908 | 0.917 | 0.911 |

Fig. 9 Cont. 56

| # | RS ID | chr | pos | strand | v1 | v2 | v3 | # | RS ID | chr | pos | strand | v1 | v2 | v3 |
|---|---|---|---|---|---|---|---|---|---|---|---|---|---|---|---|
| 1960 | rs10141297 | chr14 | 79069418 | + | 0.05 | 0.067 | 0.054 | 4999 | rs111153120 | chr6 | 109081146 | + | 0.905 | 0.92 | 0.905 |
| 1961 | rs1364607 | chr14 | 79071220 | + | 0.05 | 0.072 | 0.054 | 5000 | rs121540031 | chr6 | 109081271 | + | 0.908 | 0.917 | 0.911 |
| 1962 | rs2223032 | chr14 | 79356960 | + | 0.085 | 0.05 | 0.083 | 5001 | rs121969996 | chr6 | 109090760 | + | 0.942 | 0.916 | 0.914 |
| 1963 | rs932261 | chr14 | 79357514 | + | 0.092 | 0.051 | 0.095 | 5002 | rs3800226 | chr6 | 109095288 | + | 0.942 | 0.921 | 0.92 |
| 1964 | rs932263 | chr14 | 79357598 | + | 0.093 | 0.051 | 0.089 | 5003 | rs13219760 | chr6 | 110867882 | + | 0.933 | 0.922 | 0.919 |
| 1965 | rs8017057 | chr14 | 79358419 | + | 0.092 | 0.05 | 0.095 | 5004 | rs9400489 | chr6 | 112093487 | + | 0.941 | 0.92 | 0.937 |
| 1966 | rs8003909 | chr14 | 79369951 | + | 0.092 | 0.05 | 0.09 | 5005 | rs2282855 | chr6 | 112098504 | + | 0.942 | 0.93 | 0.937 |
| 1967 | rs727106 | chr14 | 79370865 | + | 0.092 | 0.051 | 0.08 | 5006 | rs9374294 | chr6 | 112241800 | + | 0.942 | 0.909 | 0.938 |
| 1968 | rs6574526 | chr14 | 79372302 | + | 0.092 | 0.05 | 0.08 | 5007 | rs9374296 | chr6 | 112247958 | + | 0.933 | 0.902 | 0.936 |
| 1969 | rs2178886 | chr14 | 79372952 | + | 0.092 | 0.051 | 0.08 | 5008 | rs9372315 | chr6 | 112256610 | + | 0.942 | 0.906 | 0.938 |
| 1970 | rs171160019 | chr14 | 81377797 | + | 0.942 | 0.95 | 0.919 | 5009 | rs9398330 | chr6 | 113500683 | + | 0.925 | 0.933 | 0.937 |
| 1971 | rs11845778 | chr14 | 81401489 | + | 0.942 | 0.933 | 0.911 | 5010 | rs2502380 | chr6 | 113581923 | + | 0.05 | 0.096 | 0.059 |
| 1972 | rs11850511 | chr14 | 81405631 | + | 0.942 | 0.933 | 0.911 | 5011 | rs13208050 | chr6 | 113674685 | + | 0.95 | 0.927 | 0.91 |
| 1973 | rs171160667 | chr14 | 81407881 | + | 0.933 | 0.928 | 0.923 | 5012 | rs17074944 | chr6 | 113685557 | + | 0.95 | 0.928 | 0.92 |
| 1974 | rs171160082 | chr14 | 81416138 | + | 0.933 | 0.928 | 0.911 | 5013 | rs17074947 | chr6 | 113685775 | + | 0.95 | 0.928 | 0.92 |
| 1975 | rs7149815 | chr14 | 81417277 | + | 0.933 | 0.928 | 0.923 | 5014 | rs6568833 | chr6 | 114670392 | + | 0.092 | 0.057 | 0.095 |
| 1976 | rs171160087 | chr14 | 81419004 | + | 0.93 | 0.928 | 0.942 | 5015 | rs17076200 | chr6 | 114972372 | + | 0.908 | 0.917 | 0.905 |
| 1977 | rs11849613 | chr14 | 81422387 | + | 0.933 | 0.928 | 0.927 | 5016 | rs1357189 | chr6 | 115048616 | + | 0.933 | 0.917 | 0.905 |
| 1978 | rs11849585 | chr14 | 81422410 | + | 0.933 | 0.928 | 0.911 | 5017 | rs444666 | chr6 | 118716824 | + | 0.908 | 0.949 | 0.914 |
| 1979 | rs17116100 | chr14 | 81425328 | + | 0.933 | 0.928 | 0.923 | 5018 | rs176780200 | chr6 | 123102370 | + | 0.94 | 0.902 | 0.949 |
| 1980 | rs11845577 | chr14 | 81438087 | + | 0.933 | 0.927 | 0.923 | 5019 | rs2208782 | chr6 | 124536313 | + | 0.05 | 0.067 | 0.098 |
| 1981 | rs171161111 | chr14 | 81444000 | + | 0.933 | 0.928 | 0.909 | 5020 | rs2758826 | chr6 | 124537955 | + | 0.051 | 0.062 | 0.099 |
| 1982 | rs171161123 | chr14 | 81446044 | + | 0.933 | 0.928 | 0.911 | 5021 | rs175571911 | chr6 | 124599326 | + | 0.942 | 0.95 | 0.929 |
| 1983 | rs71150314 | chr14 | 81453832 | + | 0.933 | 0.928 | 0.919 | 5022 | rs11757838 | chr6 | 124612490 | + | 0.942 | 0.95 | 0.92 |
| 1984 | rs1953846 | chr14 | 815265791 | + | 0.092 | 0.096 | 0.062 | 5023 | rs17557323 | chr6 | 124615215 | + | 0.942 | 0.95 | 0.919 |
| 1985 | rs10483952 | chr14 | 821233235 | + | 0.917 | 0.911 | 0.937 | 5024 | rs11758916 | chr6 | 124626407 | + | 0.942 | 0.95 | 0.917 |
| 1986 | rs17118325 | chr14 | 82827846 | + | 0.908 | 0.939 | 0.92 | 5025 | rs121930003 | chr6 | 125288875 | + | 0.907 | 0.938 | 0.905 |
| 1987 | rs1394131 | chr14 | 82837275 | + | 0.907 | 0.938 | 0.929 | 5026 | rs2745359 | chr6 | 127423649 | + | 0.949 | 0.949 | 0.926 |
| 1988 | rs17119249 | chr14 | 83435930 | + | 0.95 | 0.933 | 0.911 | 5027 | rs9491842 | chr6 | 127979594 | + | 0.917 | 0.937 | 0.931 |
| 1989 | rs17259979 | chr14 | 87282701 | + | 0.946 | 0.918 | 0.941 | 5028 | rs6901350 | chr6 | 127993875 | + | 0.927 | 0.906 | 0.92 |
| 1990 | rs8003808 | chr14 | 87628098 | + | 0.95 | 0.922 | 0.923 | 5029 | rs12661121 | chr6 | 128096991 | + | 0.95 | 0.927 | 0.911 |
| 1991 | rs12892799 | chr14 | 89272165 | + | 0.911 | 0.922 | 0.911 | 5030 | rs12660845 | chr6 | 128123079 | + | 0.933 | 0.928 | 0.902 |
| 1992 | rs17126387 | chr14 | 89371067 | + | 0.932 | 0.938 | 0.946 | 5031 | rs17055025 | chr6 | 128131675 | + | 0.95 | 0.928 | 0.923 |
| 1993 | rs11850807 | chr14 | 89372234 | + | 0.925 | 0.938 | 0.938 | 5032 | rs17055029 | chr6 | 128158072 | + | 0.95 | 0.928 | 0.911 |
| 1994 | rs11850845 | chr14 | 89372406 | + | 0.925 | 0.939 | 0.938 | 5033 | rs6935078 | chr6 | 128163087 | + | 0.908 | 0.928 | 0.923 |

Fig. 9 Cont. 57

| | | | | | | | | | | |
|---|---|---|---|---|---|---|---|---|---|---|
| 1995 | rs4117 | chr14 | 92588851 | + | 0.942 | 0.943 | 0.943 | 5034 | rs17055044 chr6 | 128171942 | + | 0.95 | 0.928 | 0.911 |
| 1996 | rs118513915 | chr14 | 93287901 | + | 0.942 | 0.949 | 0.905 | 5035 | rs12660847 chr6 | 128180582 | + | 0.948 | 0.928 | 0.911 |
| 1997 | rs2014136 | chr14 | 94013388 | + | 0.083 | 0.056 | 0.085 | 5036 | rs9385498 chr6 | 1299899843 | + | 0.925 | 0.917 | 0.901 |
| 1998 | rs9788623 | chr14 | 94260159 | + | 0.95 | 0.928 | 0.923 | 5037 | rs119683422 chr6 | 1300051834 | + | 0.931 | 0.91 | 0.92 |
| 1999 | rs11844932 | chr14 | 94345771 | + | 0.95 | 0.944 | 0.945 | 5038 | rs170576288 chr6 | 1300057903 | + | 0.924 | 0.911 | 0.92 |
| 2000 | rs6650496 | chr14 | 94376696 | + | 0.925 | 0.95 | 0.936 | 5039 | rs170576511 chr6 | 1300062431 | + | 0.933 | 0.911 | 0.901 |
| 2001 | rs17092955 | chr14 | 95151251 | + | 0.932 | 0.917 | 0.918 | 5040 | rs125290677 chr6 | 1300064906 | + | 0.933 | 0.911 | 0.901 |
| 2002 | rs7144328 | chr14 | 95172784 | + | 0.917 | 0.922 | 0.917 | 5041 | rs111545833 chr6 | 1300820648 | + | 0.917 | 0.933 | 0.945 |
| 2003 | rs12878705 | chr14 | 95181641 | + | 0.917 | 0.922 | 0.938 | 5042 | rs117582288 chr6 | 1311173343 | + | 0.95 | 0.906 | 0.923 |
| 2004 | rs17093106 | chr14 | 95186036 | + | 0.914 | 0.927 | 0.928 | 5043 | rs121964633 chr6 | 1315877247 | + | 0.949 | 0.904 | 0.909 |
| 2005 | rs1951296 | chr14 | 95371839 | + | 0.925 | 0.904 | 0.936 | 5044 | rs99402345 chr6 | 1321859066 | + | 0.95 | 0.922 | 0.902 |
| 2006 | rs2145626 | chr14 | 95375070 | + | 0.925 | 0.906 | 0.95 | 5045 | rs77590588 chr6 | 1330354733 | + | 0.915 | 0.928 | 0.929 |
| 2007 | rs4900301 | chr14 | 95441793 | + | 0.94 | 0.917 | 0.918 | 5046 | rs6162188 chr6 | 1342689166 | + | 0.912 | 0.906 | 0.92 |
| 2008 | rs17094879 | chr14 | 96575712 | + | 0.942 | 0.95 | 0.917 | 5047 | rs2142727 chr6 | 1352365544 | + | 0.936 | 0.934 | 0.941 |
| 2009 | rs966596 | chr14 | 97262101 | + | 0.083 | 0.05 | 0.055 | 5048 | rs4074263 chr6 | 1364025400 | + | 0.933 | 0.928 | 0.95 |
| 2010 | rs1478060 | chr14 | 97502976 | + | 0.05 | 0.062 | 0.054 | 5049 | rs4475338 chr6 | 1364086688 | + | 0.95 | 0.928 | 0.95 |
| 2011 | rs8022740 | chr14 | 97825286 | + | 0.917 | 0.926 | 0.94 | 5050 | rs111548511 chr6 | 1364096988 | + | 0.933 | 0.933 | 0.95 |
| 2012 | rs17595285 | chr14 | 98076478 | + | 0.917 | 0.927 | 0.95 | 5051 | rs177108255 chr6 | 1372021999 | + | 0.942 | 0.944 | 0.902 |
| 2013 | rs8005197 | chr14 | 98093062 | + | 0.927 | 0.936 | 0.915 | 5052 | rs13342643 chr6 | 1372476655 | + | 0.942 | 0.95 | 0.902 |
| 2014 | rs1951103 | chr14 | 98094532 | + | 0.907 | 0.917 | 0.911 | 5053 | rs9494717 chr6 | 1376674344 | + | 0.925 | 0.939 | 0.911 |
| 2015 | rs2400357 | chr14 | 98101184 | + | 0.912 | 0.932 | 0.918 | 5054 | rs9402899 chr6 | 1378822666 | + | 0.93 | 0.934 | 0.945 |
| 2016 | rs995364 | chr14 | 98102548 | + | 0.912 | 0.92 | 0.918 | 5055 | rs4896366 chr6 | 1388464600 | + | 0.95 | 0.927 | 0.929 |
| 2017 | rs1951087 | chr14 | 98107173 | + | 0.938 | 0.94 | 0.917 | 5056 | rs170686555 chr6 | 1398015011 | + | 0.917 | 0.928 | 0.932 |
| 2018 | rs116212222 | chr14 | 98276385 | + | 0.904 | 0.938 | 0.917 | 5057 | rs69107811 chr6 | 1398069333 | + | 0.925 | 0.928 | 0.929 |
| 2019 | rs170977755 | chr14 | 98299858 | + | 0.918 | 0.924 | 0.907 | 5058 | rs519740 chr6 | 1430777533 | + | 0.078 | 0.096 | 0.095 |
| 2020 | rs11625568 | chr14 | 100300639 | + | 0.925 | 0.928 | 0.946 | 5059 | rs125301677 chr6 | 1430986455 | + | 0.925 | 0.904 | 0.927 |
| 2021 | rs12882162 | chr14 | 100780720 | + | 0.921 | 0.909 | 0.919 | 5060 | rs125268577 chr6 | 1430999240 | + | 0.925 | 0.906 | 0.928 |
| 2022 | rs1959801 | chr14 | 100839491 | + | 0.067 | 0.1 | 0.087 | 5061 | rs125272733 chr6 | 1430995488 | + | 0.932 | 0.929 | 0.929 |
| 2023 | rs7149787 | chr14 | 101280151 | + | 0.95 | 0.906 | 0.946 | 5062 | rs1219142111 chr6 | 1439331133 | + | 0.941 | 0.927 | 0.927 |
| 2024 | rs17616316 | chr14 | 102892515 | + | 0.95 | 0.922 | 0.931 | 5063 | rs1049923811 chr6 | 1452070555 | + | 0.925 | 0.932 | 0.95 |
| 2025 | rs12435534 | chr14 | 103723597 | + | 0.944 | 0.906 | 0.907 | 5064 | rs99399540 chr6 | 1456142088 | + | 0.917 | 0.95 | 0.905 |
| 2026 | rs12886208 | chr14 | 106087426 | + | 0.915 | 0.921 | 0.942 | 5065 | rs125246155 chr6 | 1458159611 | + | 0.942 | 0.95 | 0.946 |
| 2027 | rs123729277 | chr15 | 19153817 | + | 0.95 | 0.91 | 0.911 | 5066 | rs170765244 chr6 | 1473482933 | + | 0.942 | 0.917 | 0.905 |
| 2028 | rs2252448 | chr15 | 19361339 | + | 0.931 | 0.944 | 0.907 | 5067 | rs7758196 chr6 | 1504875299 | + | 0.933 | 0.95 | 0.902 |
| 2029 | rs12592988 | chr15 | 22654319 | + | 0.949 | 0.904 | 0.907 | 5068 | rs6907224 chr6 | 1505586299 | + | 0.939 | 0.921 | 0.904 |

Fig. 9 Cont. 58

| | | | | | | | | |
|---|---|---|---|---|---|---|---|---|
| 2030 rs4906958 chr15 | 23289487 + | 0.95 | 0.922 | 0.926 | 5069 rs170799961 chr6 | 150971311 + | 0.94 | 0.927 | 0.92 |
| 2031 rs2880257 chr15 | 23481276 + | 0.912 | 0.929 | 0.915 | 5070 rs11758926 chr6 | 150994200 + | 0.908 | 0.933 | 0.902 |
| 2032 rs3743438 chr15 | 23484187 + | 0.917 | 0.922 | 0.91 | 5071 rs9480512 chr6 | 151029471 + | 0.942 | 0.921 | 0.92 |
| 2033 rs1872381 chr15 | 23492983 + | 0.917 | 0.927 | 0.92 | 5072 rs3734411 chr6 | 151119312 + | 0.948 | 0.904 | 0.919 |
| 2034 rs4906747 chr15 | 23493398 + | 0.917 | 0.928 | 0.92 | 5073 rs4869726 chr6 | 151579467 + | 0.94 | 0.948 | 0.946 |
| 2035 rs4906748 chr15 | 23495573 + | 0.917 | 0.928 | 0.905 | 5074 rs17688135 chr6 | 151890733 + | 0.949 | 0.917 | 0.91 |
| 2036 rs12592145 chr15 | 23496768 + | 0.917 | 0.928 | 0.91 | 5075 rs6900089 chr6 | 151892817 + | 0.933 | 0.917 | 0.91 |
| 2037 rs12438521 chr15 | 27204391 + | 0.075 | 0.067 | 0.098 | 5076 rs17838427 chr6 | 151893732 + | 0.933 | 0.917 | 0.902 |
| 2038 rs2636068 chr15 | 27205623 + | 0.075 | 0.062 | 0.098 | 5077 rs6916386 chr6 | 151895466 + | 0.933 | 0.917 | 0.902 |
| 2039 rs8037595 chr15 | 27452407 + | 0.942 | 0.944 | 0.932 | 5078 rs2982709 chr6 | 152398437 + | 0.908 | 0.928 | 0.911 |
| 2040 rs8037927 chr15 | 27452611 + | 0.942 | 0.944 | 0.909 | 5079 rs2013767 chr6 | 152679371 + | 0.925 | 0.933 | 0.946 |
| 2041 rs16955423 chr15 | 27477700 + | 0.925 | 0.928 | 0.919 | 5080 rs12194965 chr6 | 152976430 + | 0.922 | 0.904 | 0.906 |
| 2042 rs12438585 chr15 | 27763567 + | 0.917 | 0.937 | 0.92 | 5081 rs7356981 chr6 | 153342703 + | 0.935 | 0.935 | 0.927 |
| 2043 rs12440088 chr15 | 27778631 + | 0.917 | 0.933 | 0.918 | 5082 rs270316 chr6 | 153843385 + | 0.058 | 0.094 | 0.077 |
| 2044 rs17683205 chr15 | 27788620 + | 0.921 | 0.904 | 0.914 | 5083 rs270315 chr6 | 153844118 + | 0.07 | 0.094 | 0.082 |
| 2045 rs9972620 chr15 | 27795687 + | 0.917 | 0.911 | 0.906 | 5084 rs12199858 chr6 | 154246020 + | 0.917 | 0.944 | 0.937 |
| 2046 rs7179270 chr15 | 27805919 + | 0.917 | 0.914 | 0.91 | 5085 rs2093506 chr6 | 154273708 + | 0.917 | 0.944 | 0.937 |
| 2047 rs11073221 chr15 | 27807398 + | 0.917 | 0.911 | 0.91 | 5086 rs10457898 chr6 | 154283311 + | 0.917 | 0.927 | 0.937 |
| 2048 rs10852002 chr15 | 27825956 + | 0.917 | 0.921 | 0.918 | 5087 rs7746011 chr6 | 155386873 + | 0.058 | 0.085 | 0.059 |
| 2049 rs2293186 chr15 | 27840976 + | 0.908 | 0.915 | 0.91 | 5088 rs6929726 chr6 | 155814859 + | 0.909 | 0.923 | 0.917 |
| 2050 rs9920621 chr15 | 27857473 + | 0.932 | 0.92 | 0.911 | 5089 rs9478664 chr6 | 155961398 + | 0.924 | 0.92 | 0.938 |
| 2051 rs9920553 chr15 | 27859248 + | 0.924 | 0.911 | 0.91 | 5090 rs9384500 chr6 | 157117239 + | 0.91 | 0.932 | 0.941 |
| 2052 rs11073279 chr15 | 27893050 + | 0.917 | 0.911 | 0.919 | 5091 rs4870490 chr6 | 157169517 + | 0.908 | 0.927 | 0.935 |
| 2053 rs10519792 chr15 | 31201568 + | 0.908 | 0.911 | 0.95 | 5092 rs10945657 chr6 | 160572919 + | 0.917 | 0.904 | 0.918 |
| 2054 rs717411 chr15 | 31202466 + | 0.917 | 0.911 | 0.95 | 5093 rs3016539 chr6 | 162156065 + | 0.067 | 0.067 | 0.086 |
| 2055 rs16965431 chr15 | 31213383 + | 0.917 | 0.906 | 0.946 | 5094 rs12663205 chr6 | 164074919 + | 0.904 | 0.936 | 0.941 |
| 2056 rs12915153 chr15 | 31378155 + | 0.95 | 0.906 | 0.909 | 5095 rs77556548 chr6 | 164148084 + | 0.908 | 0.944 | 0.936 |
| 2057 rs11632118 chr15 | 31709565 + | 0.949 | 0.944 | 0.95 | 5096 rs12213075 chr6 | 164307231 + | 0.933 | 0.95 | 0.938 |
| 2058 rs17237263 chr15 | 33102857 + | 0.908 | 0.921 | 0.923 | 5097 rs794127 chr6 | 164627251 + | 0.932 | 0.922 | 0.902 |
| 2059 rs3759844 chr15 | 33617716 + | 0.908 | 0.949 | 0.937 | 5098 rs66301342 chr6 | 165247908 + | 0.05 | 0.061 | 0.068 |
| 2060 rs10162703 chr15 | 33631960 + | 0.95 | 0.911 | 0.937 | 5099 rs13209326 chr6 | 165327240 + | 0.915 | 0.95 | 0.909 |
| 2061 rs1992570 chr15 | 33641095 + | 0.932 | 0.933 | 0.946 | 5100 rs1923603 chr6 | 165426023 + | 0.917 | 0.917 | 0.923 |
| 2062 rs16961348 chr15 | 33711635 + | 0.925 | 0.922 | 0.941 | 5101 rs2983496 chr6 | 165946781 + | 0.908 | 0.922 | 0.919 |
| 2063 rs319886 chr15 | 33741906 + | 0.95 | 0.933 | 0.91 | 5102 rs3008014 chr6 | 165948896 + | 0.917 | 0.922 | 0.919 |
| 2064 rs319884 chr15 | 33742660 + | 0.95 | 0.933 | 0.905 | 5103 rs6931699 chr6 | 167471241 + | 0.949 | 0.927 | 0.944 |

Fig. 9 Cont. 59

| | | | | | | | | | |
|---|---|---|---|---|---|---|---|---|---|
| 2065 | rs12904414 | chr15 | 35304707 | + | 0.941 | 0.931 | 0.905 | 5104 | rs3093005 | chr6 | 167471663 | + | 0.942 | 0.928 | 0.95 |
| 2066 | rs12439193 | chr15 | 35307959 | + | 0.942 | 0.933 | 0.905 | 5105 | rs6911291 | chr6 | 167473024 | + | 0.942 | 0.928 | 0.95 |
| 2067 | rs11639391 | chr15 | 37419063 | + | 0.917 | 0.944 | 0.938 | 5106 | rs3093003 | chr6 | 167473464 | + | 0.941 | 0.926 | 0.95 |
| 2068 | rs7182018 | chr15 | 37419561 | + | 0.917 | 0.928 | 0.919 | 5107 | rs7750651 | chr6 | 167474309 | + | 0.942 | 0.928 | 0.946 |
| 2069 | rs1080066 | chr15 | 37421514 | + | 0.917 | 0.928 | 0.919 | 5108 | rs3092999 | chr6 | 167474537 | + | 0.942 | 0.928 | 0.945 |
| 2070 | rs17694988 | chr15 | 37423519 | + | 0.917 | 0.928 | 0.923 | 5109 | rs3092997 | chr6 | 167474734 | + | 0.95 | 0.928 | 0.945 |
| 2071 | rs16966424 | chr15 | 42793225 | + | 0.95 | 0.939 | 0.946 | 5110 | rs1029330 | chr6 | 167844119 | + | 0.925 | 0.928 | 0.905 |
| 2072 | rs3759882 | chr15 | 42836075 | + | 0.925 | 0.949 | 0.95 | 5111 | rs737495 | chr6 | 167854453 | + | 0.925 | 0.922 | 0.919 |
| 2073 | rs3759883 | chr15 | 42836133 | + | 0.925 | 0.939 | 0.95 | 5112 | rs3823461 | chr6 | 168207604 | + | 0.086 | 0.092 | 0.089 |
| 2074 | rs3784577 | chr15 | 43221136 | + | 0.95 | 0.944 | 0.907 | 5113 | rs9295040 | chr6 | 168209041 | + | 0.05 | 0.091 | 0.095 |
| 2075 | rs16963400 | chr15 | 48260052 | + | 0.932 | 0.917 | 0.938 | 5114 | rs6455478 | chr6 | 168227320 | + | 0.076 | 0.094 | 0.082 |
| 2076 | rs7183451 | chr15 | 51823890 | + | 0.917 | 0.933 | 0.946 | 5115 | rs7770108 | chr6 | 168288324 | + | 0.1 | 0.094 | 0.1 |
| 2077 | rs12916554 | chr15 | 52394547 | + | 0.908 | 0.921 | 0.919 | 5116 | rs680120 | chr6 | 168845878 | + | 0.924 | 0.928 | 0.902 |
| 2078 | rs11634623 | chr15 | 53865892 | + | 0.93 | 0.902 | 0.923 | 5117 | rs599957 | chr6 | 168846717 | + | 0.925 | 0.928 | 0.91 |
| 2079 | rs7178122 | chr15 | 53874464 | + | 0.938 | 0.934 | 0.928 | 5118 | rs626044 | chr6 | 168848071 | + | 0.908 | 0.927 | 0.902 |
| 2080 | rs17238482 | chr15 | 53942234 | + | 0.949 | 0.917 | 0.911 | 5119 | rs627732 | chr6 | 168848430 | + | 0.922 | 0.925 | 0.91 |
| 2081 | rs17819282 | chr15 | 53984101 | + | 0.942 | 0.916 | 0.905 | 5120 | rs627782 | chr6 | 168848473 | + | 0.915 | 0.922 | 0.91 |
| 2082 | rs2909544 | chr15 | 55418254 | + | 0.094 | 0.071 | 0.059 | 5121 | rs641512 | chr6 | 168849240 | + | 0.915 | 0.921 | 0.91 |
| 2083 | rs12594992 | chr15 | 58819627 | + | 0.932 | 0.933 | 0.945 | 5122 | rs643731 | chr6 | 168849764 | + | 0.914 | 0.919 | 0.902 |
| 2084 | rs10519095 | chr15 | 59076075 | + | 0.925 | 0.916 | 0.911 | 5123 | rs644228 | chr6 | 168849909 | + | 0.925 | 0.927 | 0.902 |
| 2085 | rs2414723 | chr15 | 59673351 | + | 0.933 | 0.944 | 0.928 | 5124 | rs672362 | chr6 | 168850184 | + | 0.915 | 0.927 | 0.902 |
| 2086 | rs10519128 | chr15 | 59748312 | + | 0.917 | 0.949 | 0.946 | 5125 | rs645236 | chr6 | 168850721 | + | 0.931 | 0.926 | 0.902 |
| 2087 | rs11858355 | chr15 | 60181616 | + | 0.907 | 0.931 | 0.941 | 5126 | rs675013 | chr6 | 168850737 | + | 0.94 | 0.926 | 0.902 |
| 2088 | rs10519149 | chr15 | 60510189 | + | 0.908 | 0.921 | 0.92 | 5127 | rs646068 | chr6 | 168850855 | + | 0.925 | 0.927 | 0.91 |
| 2089 | rs1108679 | chr15 | 60917608 | + | 0.933 | 0.911 | 0.902 | 5128 | rs686357 | chr6 | 168850944 | + | 0.915 | 0.922 | 0.902 |
| 2090 | rs4776654 | chr15 | 63030404 | + | 0.907 | 0.925 | 0.905 | 5129 | rs647406 | chr6 | 168851147 | + | 0.935 | 0.923 | 0.944 |
| 2091 | rs754457 | chr15 | 64709476 | + | 0.932 | 0.944 | 0.918 | 5130 | rs688227 | chr6 | 168851406 | + | 0.915 | 0.927 | 0.902 |
| 2092 | rs17206172 | chr15 | 64882924 | + | 0.915 | 0.944 | 0.932 | 5131 | rs660039 | chr6 | 168851664 | + | 0.915 | 0.926 | 0.902 |
| 2093 | rs1381545 | chr15 | 65036330 | + | 0.908 | 0.916 | 0.938 | 5132 | rs593270 | chr6 | 168851955 | + | 0.915 | 0.928 | 0.902 |
| 2094 | rs2899721 | chr15 | 65036351 | + | 0.93 | 0.917 | 0.914 | 5133 | rs661438 | chr6 | 168852014 | + | 0.924 | 0.928 | 0.914 |
| 2095 | rs11855908 | chr15 | 65038748 | + | 0.922 | 0.917 | 0.914 | 5134 | rs593723 | chr6 | 168852057 | + | 0.918 | 0.928 | 0.944 |
| 2096 | rs12050749 | chr15 | 65824425 | + | 0.908 | 0.906 | 0.914 | 5135 | rs582613 | chr6 | 168852491 | + | 0.922 | 0.925 | 0.902 |
| 2097 | rs12050676 | chr15 | 65826667 | + | 0.922 | 0.906 | 0.909 | 5136 | rs582637 | chr6 | 168852507 | + | 0.915 | 0.932 | 0.909 |
| 2098 | rs12050605 | chr15 | 65826994 | + | 0.908 | 0.906 | 0.911 | 5137 | rs196456 | chr6 | 168858212 | + | 0.925 | 0.927 | 0.902 |
| 2099 | rs12592919 | chr15 | 65827918 | + | 0.907 | 0.904 | 0.914 | 5138 | rs196459 | chr6 | 168859344 | + | 0.925 | 0.927 | 0.902 |

Fig. 9 Cont. 60

| | | | | | | | | | | | | |
|---|---|---|---|---|---|---|---|---|---|---|---|---|
| 2100 | rs7177848 | chr15 | 65828353 | + | 0.924 | 0.906 | 0.909 | 5139 | rs9346601 | chr6 | 169137013 | + | 0.914 | 0.909 | 0.945 |
| 2101 | rs16951231 | chr15 | 65834069 | + | 0.925 | 0.904 | 0.914 | 5140 | rs125299525 | chr6 | 169467011 | + | 0.933 | 0.904 | 0.941 |
| 2102 | rs8043459 | chr15 | 65836015 | + | 0.067 | 0.09 | 0.08 | 5141 | rs13205583 | chr6 | 170595350 | + | 0.938 | 0.948 | 0.941 |
| 2103 | rs7183639 | chr15 | 65837831 | + | 0.051 | 0.08 | 0.081 | 5142 | rs12673588 | chr7 | 139491 | + | 0.939 | 0.915 | 0.936 |
| 2104 | rs71714429 | chr15 | 65842998 | + | 0.065 | 0.099 | 0.085 | 5143 | rs12670854 | chr7 | 1698392 | + | 0.942 | 0.949 | 0.91 |
| 2105 | rs3784708 | chr15 | 65843367 | + | 0.058 | 0.096 | 0.08 | 5144 | rs2644302 | chr7 | 2894098 | + | 0.1 | 0.056 | 0.05 |
| 2106 | rs12903497 | chr15 | 67581007 | + | 0.933 | 0.911 | 0.919 | 5145 | rs12531335 | chr7 | 3164965 | + | 0.934 | 0.926 | 0.906 |
| 2107 | rs12910471 | chr15 | 67591429 | + | 0.933 | 0.911 | 0.943 | 5146 | rs7798732 | chr7 | 3441649 | + | 0.904 | 0.924 | 0.945 |
| 2108 | rs7177748 | chr15 | 67623545 | + | 0.933 | 0.91 | 0.946 | 5147 | rs2568526 | chr7 | 3649668 | + | 0.089 | 0.087 | 0.062 |
| 2109 | rs10459644 | chr15 | 68299677 | + | 0.95 | 0.922 | 0.901 | 5148 | rs9655348 | chr7 | 3890828 | + | 0.913 | 0.946 | 0.946 |
| 2110 | rs12902263 | chr15 | 69429108 | + | 0.933 | 0.95 | 0.909 | 5149 | rs6957713 | chr7 | 4289919 | + | 0.931 | 0.915 | 0.91 |
| 2111 | rs12101445 | chr15 | 69438665 | + | 0.924 | 0.92 | 0.902 | 5150 | rs4415230 | chr7 | 5676953 | + | 0.95 | 0.906 | 0.901 |
| 2112 | rs7170166 | chr15 | 71503373 | + | 0.907 | 0.927 | 0.938 | 5151 | rs17136358 | chr7 | 6046188 | + | 0.95 | 0.933 | 0.946 |
| 2113 | rs11072242C | chr15 | 71507759 | + | 0.922 | 0.922 | 0.909 | 5152 | rs7791808 | chr7 | 7522238 | + | 0.083 | 0.072 | 0.059 |
| 2114 | rs11854138 | chr15 | 71651884 | + | 0.917 | 0.922 | 0.937 | 5153 | rs12702685 | chr7 | 8052922 | + | 0.917 | 0.916 | 0.92 |
| 2115 | rs11072453 | chr15 | 72036909 | + | 0.932 | 0.916 | 0.911 | 5154 | rs881451 | chr7 | 8183547 | + | 0.076 | 0.092 | 0.077 |
| 2116 | rs1742213C | chr15 | 73127510 | + | 0.917 | 0.938 | 0.929 | 5155 | rs11768939 | chr7 | 8798990 | + | 0.925 | 0.939 | 0.946 |
| 2117 | rs8026257 | chr15 | 76377510 | + | 0.908 | 0.943 | 0.946 | 5156 | rs12702783 | chr7 | 8816058 | + | 0.933 | 0.939 | 0.92 |
| 2118 | rs16970187 | chr15 | 76964515 | + | 0.933 | 0.911 | 0.946 | 5157 | rs17165288 | chr7 | 11882732 | + | 0.917 | 0.95 | 0.932 |
| 2119 | rs16970254 | chr15 | 76987577 | + | 0.933 | 0.911 | 0.95 | 5158 | rs10279548 | chr7 | 12676174 | + | 0.914 | 0.937 | 0.919 |
| 2120 | rs1541965 | chr15 | 76992181 | + | 0.933 | 0.906 | 0.95 | 5159 | rs17681117 | chr7 | 12825023 | + | 0.946 | 0.949 | 0.913 |
| 2121 | rs5849 | chr15 | 77001247 | + | 0.942 | 0.911 | 0.95 | 5160 | rs17166661 | chr7 | 13057658 | + | 0.95 | 0.917 | 0.929 |
| 2122 | rs12909993 | chr15 | 77334257 | + | 0.069 | 0.099 | 0.099 | 5161 | rs14432505 | chr7 | 13401072 | + | 0.95 | 0.944 | 0.91 |
| 2123 | rs4779043 | chr15 | 77335752 | + | 0.052 | 0.091 | 0.074 | 5162 | rs14432507 | chr7 | 13401227 | + | 0.95 | 0.943 | 0.911 |
| 2124 | rs8039712 | chr15 | 78264626 | + | 0.917 | 0.917 | 0.941 | 5163 | rs993311 | chr7 | 13402207 | + | 0.95 | 0.944 | 0.911 |
| 2125 | rs4384570 | chr15 | 78339535 | + | 0.95 | 0.95 | 0.905 | 5164 | rs6945308 | chr7 | 13402391 | + | 0.95 | 0.944 | 0.905 |
| 2126 | rs4778776 | chr15 | 78343047 | + | 0.95 | 0.95 | 0.909 | 5165 | rs10246018 | chr7 | 13474811 | + | 0.946 | 0.936 | 0.915 |
| 2127 | rs4497643 | chr15 | 78581085 | + | 0.921 | 0.944 | 0.909 | 5166 | rs17677972 | chr7 | 13860542 | + | 0.917 | 0.95 | 0.905 |
| 2128 | rs4778864 | chr15 | 78964792 | + | 0.95 | 0.939 | 0.91 | 5167 | rs17167612 | chr7 | 13883864 | + | 0.925 | 0.903 | 0.932 |
| 2129 | rs17248476 | chr15 | 78965513 | + | 0.917 | 0.944 | 0.938 | 5168 | rs7788182 | chr7 | 14909667 | + | 0.933 | 0.928 | 0.946 |
| 2130 | rs11163143C | chr15 | 79275425 | + | 0.933 | 0.933 | 0.901 | 5169 | rs6945425 | chr7 | 16471866 | + | 0.067 | 0.061 | 0.087 |
| 2131 | rs950070 | chr15 | 79305861 | + | 0.925 | 0.933 | 0.913 | 5170 | rs17138674 | chr7 | 18158780 | + | 0.949 | 0.939 | 0.941 |
| 2132 | rs7163199 | chr15 | 79432167 | + | 0.908 | 0.944 | 0.936 | 5171 | rs17138709 | chr7 | 18169273 | + | 0.95 | 0.944 | 0.941 |
| 2133 | rs12439684 | chr15 | 79622941 | + | 0.95 | 0.926 | 0.95 | 5172 | rs17138719 | chr7 | 18182594 | + | 0.95 | 0.939 | 0.946 |
| 2134 | rs7163891 | chr15 | 80022021 | + | 0.05 | 0.094 | 0.099 | 5173 | rs22190274 | chr7 | 18919351 | + | 0.076 | 0.094 | 0.099 |

Fig. 9 Cont. 61

| | | | | | | | | | |
|---|---|---|---|---|---|---|---|---|---|
| 2135 | rs7173672 | chr15 | 84871694 | + | 0.917 | 0.909 | 0.941 | 5174 rs17142627 chr7 | 20264291 | + | 0.917 | 0.917 | 0.95 |
| 2136 | rs2346712 | chr15 | 84967356 | + | 0.933 | 0.921 | 0.911 | 5175 rs17142674 chr7 | 20293783 | + | 0.95 | 0.944 | 0.946 |
| 2137 | rs11853216 | chr15 | 84992555 | + | 0.949 | 0.928 | 0.905 | 5176 rs12700265 chr7 | 21227509 | + | 0.912 | 0.913 | 0.918 |
| 2138 | rs16977909 | chr15 | 85013233 | + | 0.939 | 0.938 | 0.938 | 5177 rs16872823 chr7 | 21641124 | + | 0.905 | 0.944 | 0.931 |
| 2139 | rs7176712 | chr15 | 85121119 | + | 0.917 | 0.907 | 0.918 | 5178 rs2906680 chr7 | 21742631 | + | 0.058 | 0.089 | 0.059 |
| 2140 | rs4887170 | chr15 | 85526600 | + | 0.917 | 0.921 | 0.923 | 5179 rs2906682 chr7 | 21743690 | + | 0.058 | 0.089 | 0.054 |
| 2141 | rs2280214 | chr15 | 87243610 | + | 0.932 | 0.928 | 0.901 | 5180 rs17145316 chr7 | 21773596 | + | 0.948 | 0.931 | 0.937 |
| 2142 | rs12912909 | chr15 | 88706484 | + | 0.912 | 0.943 | 0.919 | 5181 rs961526 chr7 | 21791537 | + | 0.058 | 0.062 | 0.09 |
| 2143 | rs17176399 | chr15 | 88753331 | + | 0.925 | 0.933 | 0.911 | 5182 rs6958427 chr7 | 21919479 | + | 0.093 | 0.074 | 0.063 |
| 2144 | rs17151552 | chr15 | 89385408 | + | 0.907 | 0.938 | 0.928 | 5183 rs1636294 chr7 | 22006244 | + | 0.05 | 0.073 | 0.062 |
| 2145 | rs7495709 | chr15 | 89929548 | + | 0.092 | 0.079 | 0.08 | 5184 rs6944367 chr7 | 24110035 | + | 0.942 | 0.939 | 0.938 |
| 2146 | rs10520709 | chr15 | 90635589 | + | 0.933 | 0.948 | 0.928 | 5185 rs16484 chr7 | 24239656 | + | 0.942 | 0.917 | 0.932 |
| 2147 | rs4777718 | chr15 | 90839824 | + | 0.914 | 0.906 | 0.923 | 5186 rs2521635 chr7 | 24346160 | + | 0.067 | 0.089 | 0.081 |
| 2148 | rs17647421 | chr15 | 90917523 | + | 0.925 | 0.906 | 0.946 | 5187 rs2245662 chr7 | 24346712 | + | 0.08 | 0.083 | 0.082 |
| 2149 | rs17524213 | chr15 | 91022850 | + | 0.922 | 0.948 | 0.902 | 5188 rs2245657 chr7 | 24346910 | + | 0.076 | 0.089 | 0.081 |
| 2150 | rs10520711 | chr15 | 91023058 | + | 0.933 | 0.95 | 0.932 | 5189 rs7806309 chr7 | 27904204 | + | 0.907 | 0.944 | 0.936 |
| 2151 | rs17524193 | chr15 | 91023976 | + | 0.933 | 0.95 | 0.932 | 5190 rs7806217 chr7 | 27904302 | + | 0.93 | 0.943 | 0.937 |
| 2152 | rs16948292 | chr15 | 91959244 | + | 0.95 | 0.917 | 0.914 | 5191 rs10258887 chr7 | 27907103 | + | 0.907 | 0.939 | 0.92 |
| 2153 | rs17544094 | chr15 | 91959969 | + | 0.922 | 0.928 | 0.921 | 5192 rs6462098 chr7 | 28705943 | + | 0.078 | 0.084 | 0.08 |
| 2154 | rs8041485 | chr15 | 92318176 | + | 0.942 | 0.944 | 0.941 | 5193 rs9638855 chr7 | 28900414 | + | 0.932 | 0.903 | 0.927 |
| 2155 | rs7163608 | chr15 | 92345154 | + | 0.917 | 0.933 | 0.94 | 5194 rs317700 chr7 | 29003618 | + | 0.925 | 0.928 | 0.932 |
| 2156 | rs10520761 | chr15 | 93008795 | + | 0.917 | 0.916 | 0.932 | 5195 rs317693 chr7 | 29022088 | + | 0.942 | 0.928 | 0.912 |
| 2157 | rs16949686 | chr15 | 93310894 | + | 0.922 | 0.911 | 0.918 | 5196 rs2648661 chr7 | 29025906 | + | 0.942 | 0.938 | 0.911 |
| 2158 | rs167072 | chr15 | 93527328 | + | 0.902 | 0.937 | 0.909 | 5197 rs317764 chr7 | 29049514 | + | 0.942 | 0.917 | 0.914 |
| 2159 | rs290647 | chr15 | 93529908 | + | 0.948 | 0.939 | 0.911 | 5198 rs317701 chr7 | 29051235 | + | 0.942 | 0.917 | 0.914 |
| 2160 | rs11632614 | chr15 | 93593900 | + | 0.917 | 0.939 | 0.911 | 5199 rs317734 chr7 | 29058677 | + | 0.942 | 0.917 | 0.902 |
| 2161 | rs16975832 | chr15 | 94275984 | + | 0.933 | 0.927 | 0.946 | 5200 rs317735 chr7 | 29059221 | + | 0.942 | 0.916 | 0.902 |
| 2162 | rs16975836 | chr15 | 94277115 | + | 0.933 | 0.927 | 0.946 | 5201 rs317736 chr7 | 29060445 | + | 0.942 | 0.916 | 0.914 |
| 2163 | rs8034932 | chr15 | 94277209 | + | 0.933 | 0.927 | 0.946 | 5202 rs160859 chr7 | 29065705 | + | 0.95 | 0.915 | 0.923 |
| 2164 | rs6496188 | chr15 | 95155384 | + | 0.069 | 0.069 | 0.086 | 5203 rs2285850 chr7 | 29410225 | + | 0.933 | 0.906 | 0.909 |
| 2165 | rs7182555 | chr15 | 95177768 | + | 0.1 | 0.072 | 0.095 | 5204 rs7777560 chr7 | 29428441 | + | 0.085 | 0.076 | 0.081 |
| 2166 | rs1860620 | chr15 | 95300309 | + | 0.942 | 0.921 | 0.941 | 5205 rs10232672 chr7 | 29801955 | + | 0.908 | 0.901 | 0.932 |
| 2167 | rs8023715 | chr15 | 95408685 | + | 0.911 | 0.922 | 0.915 | 5206 rs11760473 chr7 | 31002142 | + | 0.925 | 0.921 | 0.907 |
| 2168 | rs12437527 | chr15 | 95424536 | + | 0.908 | 0.917 | 0.901 | 5207 rs1160169 chr7 | 31157868 | + | 0.917 | 0.928 | 0.917 |
| 2169 | rs7162920 | chr15 | 95767740 | + | 0.907 | 0.914 | 0.935 | 5208 rs17160143 chr7 | 31428570 | + | 0.941 | 0.906 | 0.919 |

Fig. 9 Cont. 62

| | | | | | | | | | | |
|---|---|---|---|---|---|---|---|---|---|---|
| 2170 | rs977835 | chr15 | 96518441 | + | 0.088 | 0.072 | 0.086 | 5209 | rs6462276 chr7 | 31430557 | + | 0.925 | 0.906 | 0.919 |
| 2171 | rs1058696 | chr15 | 97320050 | + | 0.925 | 0.938 | 0.945 | 5210 | rs17160545 chr7 | 31793942 | + | 0.925 | 0.928 | 0.932 |
| 2172 | rs7163488 | chr15 | 98262926 | + | 0.933 | 0.933 | 0.928 | 5211 | rs6943198 chr7 | 33158147 | + | 0.93 | 0.947 | 0.909 |
| 2173 | rs2587779 | chr15 | 98861924 | + | 0.1 | 0.078 | 0.054 | 5212 | rs17170104 chr7 | 33202571 | + | 0.948 | 0.921 | 0.902 |
| 2174 | rs7169514 | chr15 | 99106253 | + | 0.908 | 0.928 | 0.914 | 5213 | rs17170105 chr7 | 33202701 | + | 0.95 | 0.917 | 0.902 |
| 2175 | rs10162983 | chr15 | 99110525 | + | 0.942 | 0.928 | 0.917 | 5214 | rs7799346 chr7 | 33278545 | + | 0.95 | 0.926 | 0.903 |
| 2176 | rs4415993 | chr15 | 99115149 | + | 0.942 | 0.927 | 0.902 | 5215 | rs1029852 chr7 | 33375848 | + | 0.95 | 0.928 | 0.909 |
| 2177 | rs1163856C | chr15 | 99910471 | + | 0.1 | 0.084 | 0.1 | 5216 | rs17170217 chr7 | 33408395 | + | 0.933 | 0.932 | 0.901 |
| 2178 | rs804179 | chr16 | 4315530 | + | 0.067 | 0.073 | 0.082 | 5217 | rs1215476C chr7 | 33433370 | + | 0.907 | 0.928 | 0.901 |
| 2179 | rs1292520f | chr16 | 6614746 | + | 0.925 | 0.944 | 0.92 | 5218 | rs17170232 chr7 | 33438985 | + | 0.925 | 0.928 | 0.911 |
| 2180 | rs9927183 | chr16 | 6657744 | + | 0.908 | 0.928 | 0.932 | 5219 | rs7779777 chr7 | 33447262 | + | 0.93 | 0.937 | 0.918 |
| 2181 | rs12102441 | chr16 | 6678547 | + | 0.925 | 0.932 | 0.923 | 5220 | rs14585454 chr7 | 34667726 | + | 0.911 | 0.928 | 0.914 |
| 2182 | rs11860674 | chr16 | 6689406 | + | 0.93 | 0.95 | 0.936 | 5221 | rs2551790 chr7 | 35472880 | + | 0.908 | 0.928 | 0.949 |
| 2183 | rs9806855 | chr16 | 6689567 | + | 0.933 | 0.949 | 0.932 | 5222 | rs11762552 chr7 | 36177568 | + | 0.938 | 0.917 | 0.905 |
| 2184 | rs11864504 | chr16 | 6980831 | + | 0.925 | 0.911 | 0.946 | 5223 | rs11769392 chr7 | 36177635 | + | 0.921 | 0.916 | 0.905 |
| 2185 | rs1010884 | chr16 | 7250509 | + | 0.933 | 0.917 | 0.932 | 5224 | rs3847011 chr7 | 36583238 | + | 0.942 | 0.943 | 0.937 |
| 2186 | rs17739192 | chr16 | 7352744 | + | 0.907 | 0.944 | 0.936 | 5225 | rs2724007 chr7 | 37308131 | + | 0.05 | 0.094 | 0.054 |
| 2187 | rs17671833 | chr16 | 7367843 | + | 0.925 | 0.917 | 0.923 | 5226 | rs17235118 chr7 | 37868015 | + | 0.925 | 0.911 | 0.95 |
| 2188 | rs4519347 | chr16 | 7385061 | + | 0.93 | 0.937 | 0.927 | 5227 | rs1524056 chr7 | 38122192 | + | 0.075 | 0.096 | 0.081 |
| 2189 | rs4787011 | chr16 | 7389895 | + | 0.096 | 0.069 | 0.1 | 5228 | rs2052019 chr7 | 39472066 | + | 0.078 | 0.092 | 0.091 |
| 2190 | rs9788830 | chr16 | 7869762 | + | 0.932 | 0.911 | 0.92 | 5229 | rs11767548 chr7 | 40904137 | + | 0.948 | 0.924 | 0.901 |
| 2191 | rs12149787 | chr16 | 7952493 | + | 0.942 | 0.922 | 0.911 | 5230 | rs11767531 chr7 | 40904307 | + | 0.95 | 0.931 | 0.901 |
| 2192 | rs6501061 | chr16 | 8032172 | + | 0.093 | 0.091 | 0.073 | 5231 | rs9648489 chr7 | 40929731 | + | 0.917 | 0.95 | 0.95 |
| 2193 | rs9935792 | chr16 | 8033639 | + | 0.078 | 0.085 | 0.071 | 5232 | rs29888 chr7 | 40929820 | + | 0.908 | 0.928 | 0.914 |
| 2194 | rs3112665 | chr16 | 8042386 | + | 0.089 | 0.082 | 0.078 | 5233 | rs258077 chr7 | 40930193 | + | 0.907 | 0.92 | 0.914 |
| 2195 | rs3100048 | chr16 | 8052957 | + | 0.086 | 0.1 | 0.071 | 5234 | rs17172123 chr7 | 42851486 | + | 0.942 | 0.933 | 0.937 |
| 2196 | rs12600179 | chr16 | 8195543 | + | 0.941 | 0.906 | 0.946 | 5235 | rs17172124 chr7 | 42851538 | + | 0.942 | 0.933 | 0.941 |
| 2197 | rs17746463 | chr16 | 8202544 | + | 0.925 | 0.906 | 0.95 | 5236 | rs11768924 chr7 | 43744951 | + | 0.932 | 0.902 | 0.901 |
| 2198 | rs29577 | chr16 | 8318734 | + | 0.939 | 0.906 | 0.932 | 5237 | rs2528374 chr7 | 43943073 | + | 0.942 | 0.917 | 0.937 |
| 2199 | rs2437716 | chr16 | 8938605 | + | 0.1 | 0.072 | 0.055 | 5238 | rs2595647 chr7 | 43943159 | + | 0.942 | 0.917 | 0.937 |
| 2200 | rs12927015 | chr16 | 10119070 | + | 0.933 | 0.921 | 0.92 | 5239 | rs2595646 chr7 | 43943563 | + | 0.942 | 0.917 | 0.937 |
| 2201 | rs12932615 | chr16 | 10119747 | + | 0.933 | 0.922 | 0.92 | 5240 | rs735670 chr7 | 44199870 | + | 0.933 | 0.938 | 0.929 |
| 2202 | rs11862776 | chr16 | 10137637 | + | 0.948 | 0.938 | 0.932 | 5241 | rs12670584 chr7 | 44218543 | + | 0.933 | 0.933 | 0.929 |
| 2203 | rs7191935 | chr16 | 10145034 | + | 0.95 | 0.939 | 0.911 | 5242 | rs3801409 chr7 | 45181073 | + | 0.933 | 0.916 | 0.937 |
| 2204 | rs12446992 | chr16 | 10153870 | + | 0.942 | 0.949 | 0.929 | 5243 | rs4724371 chr7 | 45186701 | + | 0.942 | 0.927 | 0.938 |

Fig. 9  Cont. 63

| | | | | | | | | | |
|---|---|---|---|---|---|---|---|---|---|
| 2205 | rs7195491 | chr16 | 10158140 | + | 0.933 | 0.939 | 0.929 | 5244 | rs4724373 chr7 | 45189155 | + | 0.942 | 0.933 | 0.937 |
| 2206 | rs12928389 | chr16 | 10533623 | + | 0.949 | 0.928 | 0.901 | 5245 | rs11972406 chr7 | 46468384 | + | 0.908 | 0.95 | 0.938 |
| 2207 | rs7199627 | chr16 | 10568602 | + | 0.907 | 0.911 | 0.941 | 5246 | rs17659820 chr7 | 47827035 | + | 0.908 | 0.944 | 0.941 |
| 2208 | rs7202408 | chr16 | 10986116 | + | 0.915 | 0.927 | 0.902 | 5247 | rs17711066 chr7 | 47881264 | + | 0.908 | 0.922 | 0.923 |
| 2209 | rs16958021 | chr16 | 11077548 | + | 0.909 | 0.933 | 0.91 | 5248 | rs17662136 chr7 | 48427291 | + | 0.942 | 0.922 | 0.923 |
| 2210 | rs16958028 | chr16 | 11084169 | + | 0.947 | 0.92 | 0.929 | 5249 | rs2221656 chr7 | 50069950 | + | 0.074 | 0.074 | 0.077 |
| 2211 | rs1019553 | chr16 | 11303851 | + | 0.908 | 0.937 | 0.945 | 5250 | rs7778784 chr7 | 50105746 | + | 0.067 | 0.083 | 0.077 |
| 2212 | rs17606249 | chr16 | 11719229 | + | 0.941 | 0.914 | 0.901 | 5251 | rs7797772 chr7 | 50427702 | + | 0.942 | 0.933 | 0.914 |
| 2213 | rs204019 | chr16 | 13134742 | + | 0.941 | 0.92 | 0.938 | 5252 | rs11976368 chr7 | 50461701 | + | 0.939 | 0.943 | 0.91 |
| 2214 | rs11049277 | chr16 | 13628884 | + | 0.918 | 0.917 | 0.92 | 5253 | rs17133826 chr7 | 50465179 | + | 0.939 | 0.948 | 0.945 |
| 2215 | rs12920280 | chr16 | 15823942 | + | 0.908 | 0.922 | 0.902 | 5254 | rs11575321 chr7 | 50572601 | + | 0.95 | 0.928 | 0.938 |
| 2216 | rs12446522 | chr16 | 17687959 | + | 0.925 | 0.92 | 0.911 | 5255 | rs17152083 chr7 | 50707104 | + | 0.917 | 0.933 | 0.901 |
| 2217 | rs3751745 | chr16 | 18725463 | + | 0.908 | 0.938 | 0.919 | 5256 | rs7796817 chr7 | 52314832 | + | 0.908 | 0.95 | 0.946 |
| 2218 | rs3816919 | chr16 | 18754917 | + | 0.915 | 0.927 | 0.917 | 5257 | rs1442243 chr7 | 52615087 | + | 0.939 | 0.903 | 0.946 |
| 2219 | rs9635473 | chr16 | 18758880 | + | 0.908 | 0.927 | 0.919 | 5258 | rs17831541 chr7 | 52620893 | + | 0.933 | 0.933 | 0.932 |
| 2220 | rs7191057 | chr16 | 18760319 | + | 0.908 | 0.927 | 0.919 | 5259 | rs17769783 chr7 | 52622143 | + | 0.933 | 0.933 | 0.932 |
| 2221 | rs12931397 | chr16 | 18762565 | + | 0.908 | 0.927 | 0.92 | 5260 | rs17135293 chr7 | 52778519 | + | 0.925 | 0.938 | 0.937 |
| 2222 | rs12932088 | chr16 | 18762867 | + | 0.908 | 0.928 | 0.919 | 5261 | rs1919534 chr7 | 52778689 | + | 0.925 | 0.933 | 0.946 |
| 2223 | rs12926531 | chr16 | 18766931 | + | 0.908 | 0.928 | 0.919 | 5262 | rs11773685 chr7 | 52845778 | + | 0.95 | 0.95 | 0.902 |
| 2224 | rs2352983 | chr16 | 19150391 | + | 0.05 | 0.067 | 0.068 | 5263 | rs11766191 chr7 | 53321840 | + | 0.908 | 0.929 | 0.915 |
| 2225 | rs4578658 | chr16 | 20166271 | + | 0.933 | 0.944 | 0.928 | 5264 | rs11768111 chr7 | 53323837 | + | 0.905 | 0.933 | 0.923 |
| 2226 | rs13333101 | chr16 | 24500990 | + | 0.933 | 0.949 | 0.92 | 5265 | rs11766912 chr7 | 53343354 | + | 0.912 | 0.916 | 0.911 |
| 2227 | rs12210324 | chr16 | 26171765 | + | 0.95 | 0.911 | 0.929 | 5266 | rs13244415 chr7 | 53655251 | + | 0.917 | 0.933 | 0.941 |
| 2228 | rs2176166 | chr16 | 27028901 | + | 0.059 | 0.051 | 0.071 | 5267 | rs12718811 chr7 | 53660742 | + | 0.917 | 0.933 | 0.946 |
| 2229 | rs1805012 | chr16 | 27281465 | + | 0.915 | 0.939 | 0.905 | 5268 | rs633702 chr7 | 63428704 | + | 0.059 | 0.089 | 0.081 |
| 2230 | rs2370534 | chr16 | 29227104 | + | 0.924 | 0.94 | 0.923 | 5269 | rs581612 chr7 | 63444254 | + | 0.067 | 0.089 | 0.05 |
| 2231 | rs1510977 | chr16 | 47874838 | + | 0.933 | 0.938 | 0.946 | 5270 | rs10234472 chr7 | 63756097 | + | 0.05 | 0.1 | 0.063 |
| 2232 | rs16949558 | chr16 | 49854532 | + | 0.908 | 0.939 | 0.937 | 5271 | rs100859110 chr7 | 63765883 | + | 0.083 | 0.096 | 0.064 |
| 2233 | rs8061602 | chr16 | 49857128 | + | 0.908 | 0.939 | 0.909 | 5272 | rs1589895 chr7 | 63863934 | + | 0.065 | 0.054 | 0.059 |
| 2234 | rs4238763 | chr16 | 49876394 | + | 0.058 | 0.057 | 0.08 | 5273 | rs12674122 chr7 | 66977407 | + | 0.95 | 0.943 | 0.911 |
| 2235 | rs13335585 | chr16 | 50258323 | + | 0.942 | 0.906 | 0.941 | 5274 | rs12668927 chr7 | 66980221 | + | 0.942 | 0.933 | 0.919 |
| 2236 | rs16950315 | chr16 | 50328000 | + | 0.947 | 0.917 | 0.923 | 5275 | rs7807405 chr7 | 67303608 | + | 0.932 | 0.927 | 0.918 |
| 2237 | rs4296257 | chr16 | 50330627 | + | 0.95 | 0.917 | 0.923 | 5276 | rs1917406 chr7 | 67403307 | + | 0.925 | 0.933 | 0.901 |
| 2238 | rs4784353 | chr16 | 52656430 | + | 0.914 | 0.901 | 0.946 | 5277 | rs11766421 chr7 | 68181585 | + | 0.914 | 0.918 | 0.922 |
| 2239 | rs4146345 | chr16 | 52947131 | + | 0.057 | 0.054 | 0.077 | 5278 | rs12698810 chr7 | 68938904 | + | 0.95 | 0.949 | 0.919 |

Fig. 9 Cont. 64

| | | | | | | | | | |
|---|---|---|---|---|---|---|---|---|---|
| 2240 rs17281013 chr16 | 54877936 | + | 0.918 | 0.93 | 0.928 | 5279 rs12698811 chr7 | 68986063 | + | 0.95 | 0.95 | 0.919 |
| 2241 rs12445477 chr16 | 55147360 | + | 0.942 | 0.906 | 0.914 | 5280 rs13221186 chr7 | 69040312 | + | 0.95 | 0.949 | 0.92 |
| 2242 rs12443821 chr16 | 55443704 | + | 0.915 | 0.913 | 0.909 | 5281 rs13228686 chr7 | 69102456 | + | 0.95 | 0.949 | 0.911 |
| 2243 rs247608 chr16 | 55520969 | + | 0.902 | 0.915 | 0.92 | 5282 rs12698833 chr7 | 69104250 | + | 0.939 | 0.943 | 0.913 |
| 2244 rs17372800 chr16 | 55743262 | + | 0.933 | 0.95 | 0.905 | 5283 rs13227197 chr7 | 69162457 | + | 0.95 | 0.949 | 0.911 |
| 2245 rs17240911 chr16 | 56260394 | + | 0.917 | 0.939 | 0.914 | 5284 rs12698854 chr7 | 69231103 | + | 0.942 | 0.95 | 0.919 |
| 2246 rs16958708 chr16 | 56260853 | + | 0.917 | 0.938 | 0.914 | 5285 rs7788868 chr7 | 69236134 | + | 0.942 | 0.95 | 0.919 |
| 2247 rs366589 chr16 | 56462677 | + | 0.051 | 0.09 | 0.086 | 5286 rs12698878 chr7 | 69341624 | + | 0.942 | 0.948 | 0.93 |
| 2248 rs16959572 chr16 | 56537803 | + | 0.925 | 0.911 | 0.923 | 5287 rs12698891 chr7 | 69403441 | + | 0.925 | 0.95 | 0.914 |
| 2249 rs3743552 chr16 | 56587455 | + | 0.926 | 0.934 | 0.913 | 5288 rs7780636 chr7 | 70664399 | + | 0.925 | 0.949 | 0.914 |
| 2250 rs2241414 chr16 | 56871934 | + | 0.941 | 0.927 | 0.914 | 5289 rs6961201 chr7 | 70692586 | + | 0.942 | 0.95 | 0.901 |
| 2251 rs1052276 chr16 | 56872099 | + | 0.942 | 0.927 | 0.914 | 5290 rs2293757 chr7 | 73268091 | + | 0.922 | 0.938 | 0.919 |
| 2252 rs16960035 chr16 | 56873132 | + | 0.936 | 0.926 | 0.914 | 5291 rs3135695 chr7 | 73288501 | + | 0.932 | 0.938 | 0.919 |
| 2253 rs3743580 chr16 | 56874016 | + | 0.941 | 0.927 | 0.935 | 5292 rs3135676 chr7 | 73293577 | + | 0.933 | 0.938 | 0.919 |
| 2254 rs1820237 chr16 | 56876699 | + | 0.942 | 0.928 | 0.914 | 5293 rs794349 chr7 | 75043058 | + | 0.1 | 0.06 | 0.086 |
| 2255 rs1820238 chr16 | 56876726 | + | 0.949 | 0.928 | 0.944 | 5294 rs237240 chr7 | 75048595 | + | 0.917 | 0.927 | 0.904 |
| 2256 rs3743707 chr16 | 58343427 | + | 0.92 | 0.922 | 0.941 | 5295 rs237238 chr7 | 75049350 | + | 0.925 | 0.927 | 0.914 |
| 2257 rs3743706 chr16 | 58343521 | + | 0.95 | 0.922 | 0.941 | 5296 rs12668335 chr7 | 78074126 | + | 0.925 | 0.933 | 0.927 |
| 2258 rs1183259 chr16 | 58972888 | + | 0.925 | 0.932 | 0.901 | 5297 rs10281272 chr7 | 78431484 | + | 0.942 | 0.915 | 0.918 |
| 2259 rs105000464 chr16 | 60893955 | + | 0.942 | 0.939 | 0.905 | 5298 rs6979533 chr7 | 79122545 | + | 0.949 | 0.933 | 0.95 |
| 2260 rs72066260 chr16 | 63768909 | + | 0.1 | 0.072 | 0.09 | 5299 rs17832522 chr7 | 79204567 | + | 0.925 | 0.933 | 0.919 |
| 2261 rs2042366 chr16 | 63776455 | + | 0.1 | 0.056 | 0.095 | 5300 rs12666914 chr7 | 79949171 | + | 0.932 | 0.91 | 0.929 |
| 2262 rs1186013C chr16 | 63779134 | + | 0.093 | 0.056 | 0.098 | 5301 rs10486940 chr7 | 81439695 | + | 0.925 | 0.916 | 0.923 |
| 2263 rs12923374 chr16 | 63779463 | + | 0.096 | 0.054 | 0.093 | 5302 rs16885325 chr7 | 81439955 | + | 0.925 | 0.917 | 0.938 |
| 2264 rs80599958 chr16 | 63780673 | + | 0.1 | 0.056 | 0.095 | 5303 rs16887158 chr7 | 81440439 | + | 0.925 | 0.917 | 0.938 |
| 2265 rs12600178 chr16 | 63781307 | + | 0.1 | 0.056 | 0.098 | 5304 rs17715570 chr7 | 81440778 | + | 0.925 | 0.917 | 0.938 |
| 2266 rs2113179 chr16 | 63784806 | + | 0.082 | 0.064 | 0.093 | 5305 rs2159567 chr7 | 81441389 | + | 0.925 | 0.916 | 0.938 |
| 2267 rs1125739 chr16 | 64534169 | + | 0.95 | 0.938 | 0.926 | 5306 rs10273056 chr7 | 81620715 | + | 0.095 | 0.089 | 0.055 |
| 2268 rs235139 chr16 | 64799973 | + | 0.067 | 0.084 | 0.098 | 5307 rs17263943 chr7 | 81807882 | + | 0.933 | 0.917 | 0.92 |
| 2269 rs9922928 chr16 | 67531008 | + | 0.915 | 0.949 | 0.906 | 5308 rs2189031 chr7 | 82183460 | + | 0.95 | 0.949 | 0.938 |
| 2270 rs11075766 chr16 | 69120772 | + | 0.95 | 0.939 | 0.928 | 5309 rs10261138 chr7 | 82714011 | + | 0.908 | 0.922 | 0.905 |
| 2271 rs3785425 chr16 | 69285978 | + | 0.904 | 0.915 | 0.931 | 5310 rs16887700 chr7 | 83829495 | + | 0.945 | 0.911 | 0.927 |
| 2272 rs4448948 chr16 | 71126737 | + | 0.921 | 0.934 | 0.938 | 5311 rs2462063 chr7 | 84929368 | + | 0.939 | 0.908 | 0.934 |
| 2273 rs17288954 chr16 | 71296866 | + | 0.917 | 0.95 | 0.923 | 5312 rs6965910 chr7 | 85615689 | + | 0.904 | 0.931 | 0.945 |
| 2274 rs7189261 chr16 | 72015423 | + | 0.1 | 0.061 | 0.081 | 5313 rs3897749 chr7 | 85972133 | + | 0.932 | 0.944 | 0.92 |

Fig. 9 Cont. 65

| | | | | | | | | | |
|---|---|---|---|---|---|---|---|---|---|
| 2275 | rs7191483 | chr16 | 72804408 | + | 0.079 | 0.051 | 0.098 | 5314 | rs17342208 chr7 | 85973643 | + | 0.938 | 0.944 | 0.918 |
| 2276 | rs7196131 | chr16 | 73416119 | + | 0.925 | 0.933 | 0.92 | 5315 | rs10254168 chr7 | 85976420 | + | 0.932 | 0.944 | 0.923 |
| 2277 | rs4888320 | chr16 | 73549365 | + | 0.907 | 0.944 | 0.941 | 5316 | rs12672429 chr7 | 87730992 | + | 0.95 | 0.933 | 0.918 |
| 2278 | rs11648478 | chr16 | 74211532 | + | 0.933 | 0.939 | 0.91 | 5317 | rs11767123 chr7 | 87952839 | + | 0.931 | 0.949 | 0.936 |
| 2279 | rs9921233 | chr16 | 74212249 | + | 0.942 | 0.911 | 0.95 | 5318 | rs16868110 chr7 | 90585193 | + | 0.925 | 0.944 | 0.941 |
| 2280 | rs12599014 | chr16 | 75972886 | + | 0.086 | 0.09 | 0.074 | 5319 | rs11970859 chr7 | 90678289 | + | 0.933 | 0.925 | 0.91 |
| 2281 | rs277506 | chr16 | 76101941 | + | 0.942 | 0.95 | 0.918 | 5320 | rs2052258 chr7 | 91007017 | + | 0.925 | 0.926 | 0.911 |
| 2282 | rs7192903 | chr16 | 76122403 | + | 0.95 | 0.95 | 0.923 | 5321 | rs6964811 chr7 | 91953983 | + | 0.925 | 0.938 | 0.938 |
| 2283 | rs7193432 | chr16 | 76122637 | + | 0.95 | 0.95 | 0.929 | 5322 | rs13236112 chr7 | 93045809 | + | 0.942 | 0.906 | 0.92 |
| 2284 | rs13336488 | chr16 | 76197733 | + | 0.917 | 0.909 | 0.95 | 5323 | rs12668387 chr7 | 93046331 | + | 0.941 | 0.904 | 0.92 |
| 2285 | rs17624394 | chr16 | 76300468 | + | 0.917 | 0.922 | 0.928 | 5324 | rs17735265 chr7 | 93047142 | + | 0.942 | 0.906 | 0.928 |
| 2286 | rs4519341 | chr16 | 76300498 | + | 0.939 | 0.948 | 0.938 | 5325 | rs12669252 chr7 | 93072362 | + | 0.942 | 0.91 | 0.911 |
| 2287 | rs116425543 | chr16 | 76594368 | + | 0.917 | 0.944 | 0.905 | 5326 | rs17736498 chr7 | 93077753 | + | 0.942 | 0.906 | 0.911 |
| 2288 | rs9939233 | chr16 | 77386994 | + | 0.917 | 0.91 | 0.91 | 5327 | rs13247918 chr7 | 93079186 | + | 0.941 | 0.909 | 0.923 |
| 2289 | rs11643738 | chr16 | 77704066 | + | 0.911 | 0.932 | 0.917 | 5328 | rs957728 chr7 | 93090336 | + | 0.94 | 0.904 | 0.923 |
| 2290 | rs17723632 | chr16 | 77809010 | + | 0.917 | 0.938 | 0.941 | 5329 | rs13227315 chr7 | 93093597 | + | 0.942 | 0.909 | 0.911 |
| 2291 | rs12930954 | chr16 | 78053259 | + | 0.933 | 0.933 | 0.932 | 5330 | rs17799060 chr7 | 93094619 | + | 0.941 | 0.909 | 0.923 |
| 2292 | rs422965 | chr16 | 78208794 | + | 0.942 | 0.933 | 0.919 | 5331 | rs17737212 chr7 | 93100110 | + | 0.942 | 0.906 | 0.911 |
| 2293 | rs7342775 | chr16 | 78285281 | + | 0.1 | 0.062 | 0.05 | 5332 | rs17799235 chr7 | 93100269 | + | 0.942 | 0.906 | 0.927 |
| 2294 | rs8050088 | chr16 | 78530943 | + | 0.915 | 0.922 | 0.919 | 5333 | rs10263559 chr7 | 94044651 | + | 0.925 | 0.922 | 0.908 |
| 2295 | rs16951706 | chr16 | 78531396 | + | 0.915 | 0.93 | 0.914 | 5334 | rs4729206 chr7 | 95258613 | + | 0.932 | 0.917 | 0.928 |
| 2296 | rs16951782 | chr16 | 78551094 | + | 0.942 | 0.91 | 0.914 | 5335 | rs2045981 chr7 | 95275082 | + | 0.95 | 0.917 | 0.911 |
| 2297 | rs4474699 | chr16 | 78566806 | + | 0.942 | 0.939 | 0.919 | 5336 | rs17167184 chr7 | 95279387 | + | 0.95 | 0.917 | 0.919 |
| 2298 | rs16952436 | chr16 | 78709391 | + | 0.908 | 0.949 | 0.926 | 5337 | rs3779484 chr7 | 95314607 | + | 0.95 | 0.906 | 0.911 |
| 2299 | rs10514482 | chr16 | 78709428 | + | 0.908 | 0.944 | 0.937 | 5338 | rs21171555 chr7 | 95325994 | + | 0.942 | 0.904 | 0.914 |
| 2300 | rs4889139 | chr16 | 78941525 | + | 0.907 | 0.916 | 0.937 | 5339 | rs12538593 chr7 | 95374609 | + | 0.95 | 0.904 | 0.923 |
| 2301 | rs13335540 | chr16 | 78948409 | + | 0.912 | 0.927 | 0.914 | 5340 | rs1848856 chr7 | 97239960 | + | 0.942 | 0.902 | 0.936 |
| 2302 | rs17730942 | chr16 | 79493892 | + | 0.933 | 0.91 | 0.917 | 5341 | rs7808642 chr7 | 97288397 | + | 0.925 | 0.906 | 0.938 |
| 2303 | rs9926366 | chr16 | 79645030 | + | 0.942 | 0.939 | 0.91 | 5342 | rs903453 chr7 | 97930304 | + | 0.085 | 0.051 | 0.059 |
| 2304 | rs8057244 | chr16 | 80019455 | + | 0.933 | 0.902 | 0.92 | 5343 | rs12536662 chr7 | 98043327 | + | 0.908 | 0.928 | 0.901 |
| 2305 | rs9922146 | chr16 | 81002557 | + | 0.085 | 0.084 | 0.055 | 5344 | rs6948942 chr7 | 98059798 | + | 0.94 | 0.933 | 0.927 |
| 2306 | rs3909534 | chr16 | 81005188 | + | 0.059 | 0.08 | 0.054 | 5345 | rs17161599 chr7 | 98613389 | + | 0.941 | 0.91 | 0.911 |
| 2307 | rs105114552 | chr16 | 81262612 | + | 0.942 | 0.95 | 0.948 | 5346 | rs13235702 chr7 | 98623262 | + | 0.942 | 0.933 | 0.918 |
| 2308 | rs9936363 | chr16 | 81264849 | + | 0.941 | 0.944 | 0.946 | 5347 | rs7787830 chr7 | 98634956 | + | 0.917 | 0.911 | 0.941 |
| 2309 | rs4782778 | chr16 | 81960293 | + | 0.06 | 0.099 | 0.052 | 5348 | rs13247877 chr7 | 98636702 | + | 0.92 | 0.916 | 0.938 |

Fig. 9 Cont. 66

| | | | | | | | | | | |
|---|---|---|---|---|---|---|---|---|---|---|
| 2310 | rs7196123 | chr16 | 82212035 | + | 0.942 | 0.943 | 0.911 | 5349 | rs13224433 | chr7 | 98637708 | + | 0.933 | 0.911 | 0.938 |
| 2311 | rs7200398 | chr16 | 82217721 | + | 0.925 | 0.922 | 0.911 | 5350 | rs12705035 | chr7 | 98638052 | + | 0.914 | 0.91 | 0.938 |
| 2312 | rs7200503 | chr16 | 82217946 | + | 0.932 | 0.916 | 0.911 | 5351 | rs12705036 | chr7 | 98638081 | + | 0.917 | 0.911 | 0.946 |
| 2313 | rs11862594 | chr16 | 82219365 | + | 0.069 | 0.064 | 0.067 | 5352 | rs13233950 | chr7 | 98641430 | + | 0.933 | 0.911 | 0.938 |
| 2314 | rs722940 | chr16 | 82221837 | + | 0.95 | 0.922 | 0.902 | 5353 | rs13239596 | chr7 | 98641472 | + | 0.933 | 0.911 | 0.946 |
| 2315 | rs17766794 | chr16 | 82222217 | + | 0.917 | 0.926 | 0.902 | 5354 | rs6960542 | chr7 | 99421155 | + | 0.085 | 0.05 | 0.072 |
| 2316 | rs2136665 | chr16 | 82679707 | + | 0.941 | 0.906 | 0.914 | 5355 | rs191137 | chr7 | 100224836 | + | 0.067 | 0.056 | 0.059 |
| 2317 | rs2435177 | chr16 | 83018941 | + | 0.086 | 0.085 | 0.098 | 5356 | rs757718 | chr7 | 100579530 | + | 0.075 | 0.067 | 0.082 |
| 2318 | rs12931468 | chr16 | 83052802 | + | 0.925 | 0.933 | 0.95 | 5357 | rs7803909 | chr7 | 100929843 | + | 0.941 | 0.933 | 0.92 |
| 2319 | rs7191339 | chr16 | 83102109 | + | 0.922 | 0.95 | 0.941 | 5358 | rs11772334 | chr7 | 100936205 | + | 0.942 | 0.938 | 0.901 |
| 2320 | rs4783107 | chr16 | 83553948 | + | 0.096 | 0.06 | 0.068 | 5359 | rs877702 | chr7 | 100939644 | + | 0.93 | 0.947 | 0.902 |
| 2321 | rs16975132 | chr16 | 83618511 | + | 0.924 | 0.922 | 0.944 | 5360 | rs10487166 | chr7 | 103162502 | + | 0.933 | 0.916 | 0.904 |
| 2322 | rs3803638 | chr16 | 83639089 | + | 0.95 | 0.939 | 0.946 | 5361 | rs7798871 | chr7 | 104921397 | + | 0.933 | 0.931 | 0.908 |
| 2323 | rs9888865 | chr16 | 83929425 | + | 0.932 | 0.943 | 0.914 | 5362 | rs13223425 | chr7 | 105115222 | + | 0.934 | 0.94 | 0.934 |
| 2324 | rs4843881 | chr16 | 84571645 | + | 0.946 | 0.928 | 0.923 | 5363 | rs13223649 | chr7 | 105115428 | + | 0.917 | 0.917 | 0.911 |
| 2325 | rs2696845 | chr16 | 84929010 | + | 0.067 | 0.062 | 0.063 | 5364 | rs12705321 | chr7 | 105122524 | + | 0.927 | 0.909 | 0.907 |
| 2326 | rs2581304 | chr16 | 84931119 | + | 0.059 | 0.07 | 0.082 | 5365 | rs2075114 | chr7 | 105124158 | + | 0.925 | 0.921 | 0.928 |
| 2327 | rs16941798 | chr16 | 85237877 | + | 0.933 | 0.928 | 0.937 | 5366 | rs16872316 | chr7 | 106375132 | + | 0.942 | 0.922 | 0.909 |
| 2328 | rs7186606 | chr16 | 85486830 | + | 0.94 | 0.922 | 0.905 | 5367 | rs121154324 | chr7 | 106508168 | + | 0.95 | 0.933 | 0.919 |
| 2329 | rs2306424 | chr16 | 87110740 | + | 0.939 | 0.914 | 0.936 | 5368 | rs3752645 | chr7 | 106569919 | + | 0.942 | 0.933 | 0.919 |
| 2330 | rs9931810 | chr16 | 87220820 | + | 0.92 | 0.901 | 0.926 | 5369 | rs17154444 | chr7 | 107223104 | + | 0.908 | 0.944 | 0.937 |
| 2331 | rs3736112 | chr16 | 87249513 | + | 0.95 | 0.938 | 0.917 | 5370 | rs3752639 | chr7 | 107913834 | + | 0.915 | 0.918 | 0.909 |
| 2332 | rs1040101C | chr17 | 1100906 | + | 0.908 | 0.927 | 0.938 | 5371 | rs16872576 | chr7 | 107926521 | + | 0.905 | 0.911 | 0.915 |
| 2333 | rs2302458 | chr17 | 1317292 | + | 0.924 | 0.932 | 0.927 | 5372 | rs1949853 | chr7 | 108258784 | + | 0.933 | 0.944 | 0.95 |
| 2334 | rs7502466 | chr17 | 1319720 | + | 0.95 | 0.909 | 0.914 | 5373 | rs7457714 | chr7 | 108415207 | + | 0.915 | 0.903 | 0.937 |
| 2335 | rs11553568 | chr17 | 2615031 | + | 0.912 | 0.93 | 0.932 | 5374 | rs10276365 | chr7 | 111763782 | + | 0.942 | 0.947 | 0.92 |
| 2336 | rs11657669 | chr17 | 2696100 | + | 0.934 | 0.938 | 0.913 | 5375 | rs6956741 | chr7 | 111881979 | + | 0.942 | 0.906 | 0.95 |
| 2337 | rs1695267C | chr17 | 2984756 | + | 0.908 | 0.939 | 0.92 | 5376 | rs10487291 | chr7 | 111890873 | + | 0.95 | 0.906 | 0.946 |
| 2338 | rs16952712 | chr17 | 3004540 | + | 0.908 | 0.939 | 0.932 | 5377 | rs4730550 | chr7 | 111896959 | + | 0.941 | 0.948 | 0.901 |
| 2339 | rs17764053 | chr17 | 4029969 | + | 0.939 | 0.917 | 0.909 | 5378 | rs11773335 | chr7 | 111906938 | + | 0.942 | 0.906 | 0.946 |
| 2340 | rs11078586 | chr17 | 5636166 | + | 0.067 | 0.072 | 0.062 | 5379 | rs6961386 | chr7 | 114441275 | + | 0.933 | 0.944 | 0.937 |
| 2341 | rs218687 | chr17 | 6529571 | + | 0.925 | 0.927 | 0.919 | 5380 | rs11766431 | chr7 | 114448456 | + | 0.941 | 0.944 | 0.946 |
| 2342 | rs13894 | chr17 | 7470627 | + | 0.942 | 0.941 | 0.917 | 5381 | rs12706005 | chr7 | 114459417 | + | 0.933 | 0.944 | 0.937 |
| 2343 | rs8079544 | chr17 | 7520777 | + | 0.905 | 0.916 | 0.946 | 5382 | rs655186 | chr7 | 114502721 | + | 0.95 | 0.949 | 0.946 |
| 2344 | rs17809614 | chr17 | 9522080 | + | 0.917 | 0.911 | 0.928 | 5383 | rs12539654 | chr7 | 116117219 | + | 0.942 | 0.928 | 0.929 |

Fig. 9 Cont. 67

| | | | | | | | | | | | |
|---|---|---|---|---|---|---|---|---|---|---|---|
| 2345 | rs7221426 | chr17 | 9611444 | + | 0.933 | 0.906 | 0.905 | 5384 | rs17138943 | chr7 | 116129516 | + | 0.942 | 0.928 | 0.95 |
| 2346 | rs2280490 | chr17 | 9616859 | + | 0.94 | 0.903 | 0.914 | 5385 | rs17139184 | chr7 | 116366112 | + | 0.949 | 0.917 | 0.909 |
| 2347 | rs8075056 | chr17 | 9740165 | + | 0.925 | 0.95 | 0.928 | 5386 | rs2429008 | chr7 | 116518624 | + | 0.95 | 0.911 | 0.945 |
| 2348 | rs916582 | chr17 | 9949591 | + | 0.05 | 0.078 | 0.062 | 5387 | rs10269727 | chr7 | 122175491 | + | 0.925 | 0.949 | 0.905 |
| 2349 | rs9893585 | chr17 | 10301980 | + | 0.932 | 0.944 | 0.95 | 5388 | rs2067504 | chr7 | 124762669 | + | 0.905 | 0.913 | 0.925 |
| 2350 | rs12944031 | chr17 | 10337719 | + | 0.932 | 0.944 | 0.95 | 5389 | rs10500107 | chr7 | 124779468 | + | 0.917 | 0.904 | 0.923 |
| 2351 | rs12947406 | chr17 | 10368291 | + | 0.942 | 0.944 | 0.95 | 5390 | rs1526411 | chr7 | 124851594 | + | 0.933 | 0.916 | 0.932 |
| 2352 | rs3744566 | chr17 | 10379416 | + | 0.915 | 0.943 | 0.95 | 5391 | rs17132917 | chr7 | 124862632 | + | 0.933 | 0.92 | 0.932 |
| 2353 | rs3744568 | chr17 | 10380495 | + | 0.95 | 0.944 | 0.95 | 5392 | rs10487430 | chr7 | 125445706 | + | 0.925 | 0.933 | 0.946 |
| 2354 | rs12953213 | chr17 | 10381105 | + | 0.942 | 0.943 | 0.95 | 5393 | rs6972001 | chr7 | 125684544 | + | 0.95 | 0.95 | 0.95 |
| 2355 | rs17561509 | chr17 | 12967860 | + | 0.942 | 0.921 | 0.919 | 5394 | rs17713208 | chr7 | 126867052 | + | 0.908 | 0.944 | 0.928 |
| 2356 | rs16948066 | chr17 | 13388867 | + | 0.942 | 0.939 | 0.946 | 5395 | rs11977915 | chr7 | 127070406 | + | 0.94 | 0.908 | 0.905 |
| 2357 | rs16948215 | chr17 | 13491726 | + | 0.95 | 0.906 | 0.92 | 5396 | rs4731430 | chr7 | 127693219 | + | 0.076 | 0.052 | 0.059 |
| 2358 | rs8074146 | chr17 | 13645883 | + | 0.905 | 0.925 | 0.911 | 5397 | rs6957529 | chr7 | 128392696 | + | 0.942 | 0.927 | 0.92 |
| 2359 | rs4792420 | chr17 | 13784044 | + | 0.925 | 0.928 | 0.909 | 5398 | rs2293492 | chr7 | 128402302 | + | 0.942 | 0.925 | 0.923 |
| 2360 | rs9901316 | chr17 | 14041963 | + | 0.933 | 0.933 | 0.928 | 5399 | rs2402972 | chr7 | 129169189 | + | 0.085 | 0.05 | 0.086 |
| 2361 | rs17680211 | chr17 | 14112411 | + | 0.908 | 0.933 | 0.94 | 5400 | rs121126661 | chr7 | 130485114 | + | 0.95 | 0.933 | 0.936 |
| 2362 | rs16949533 | chr17 | 14283144 | + | 0.908 | 0.911 | 0.937 | 5401 | rs12112721 | chr7 | 130486087 | + | 0.95 | 0.933 | 0.937 |
| 2363 | rs8066195 | chr17 | 14853631 | + | 0.925 | 0.928 | 0.92 | 5402 | rs13230718 | chr7 | 134653917 | + | 0.942 | 0.917 | 0.905 |
| 2364 | rs10521297 | chr17 | 14999716 | + | 0.933 | 0.911 | 0.946 | 5403 | rs6951371 | chr7 | 134655846 | + | 0.942 | 0.917 | 0.92 |
| 2365 | rs7207127 | chr17 | 17310882 | + | 0.913 | 0.935 | 0.95 | 5404 | rs12707224 | chr7 | 134660025 | + | 0.942 | 0.917 | 0.905 |
| 2366 | rs1992649 | chr17 | 18720500 | + | 0.95 | 0.938 | 0.901 | 5405 | rs4075518 | chr7 | 134669402 | + | 0.95 | 0.916 | 0.905 |
| 2367 | rs11656953 | chr17 | 18769428 | + | 0.925 | 0.933 | 0.901 | 5406 | rs10261625 | chr7 | 134824084 | + | 0.942 | 0.939 | 0.902 |
| 2368 | rs2891982 | chr17 | 18773787 | + | 0.925 | 0.933 | 0.901 | 5407 | rs17481669 | chr7 | 134843569 | + | 0.942 | 0.939 | 0.902 |
| 2369 | rs886284 | chr17 | 18837022 | + | 0.95 | 0.916 | 0.927 | 5408 | rs9691881 | chr7 | 135110330 | + | 0.925 | 0.944 | 0.909 |
| 2370 | rs10459970 | chr17 | 19877933 | + | 0.917 | 0.906 | 0.91 | 5409 | rs7779661 | chr7 | 135138732 | + | 0.907 | 0.906 | 0.946 |
| 2371 | rs16960660 | chr17 | 19906179 | + | 0.907 | 0.912 | 0.905 | 5410 | rs10500130 | chr7 | 138466453 | + | 0.917 | 0.921 | 0.905 |
| 2372 | rs4965969 | chr17 | 24410874 | + | 0.083 | 0.089 | 0.089 | 5411 | rs41724 | chr7 | 139909373 | + | 0.062 | 0.087 | 0.081 |
| 2373 | rs223136 | chr17 | 26956485 | + | 0.092 | 0.073 | 0.059 | 5412 | rs38715 | chr7 | 140338032 | + | 0.942 | 0.917 | 0.911 |
| 2374 | rs4795708 | chr17 | 27925442 | + | 0.902 | 0.91 | 0.914 | 5413 | rs38722 | chr7 | 140341899 | + | 0.949 | 0.915 | 0.911 |
| 2375 | rs12602361 | chr17 | 28386977 | + | 0.907 | 0.937 | 0.92 | 5414 | rs38723 | chr7 | 140342281 | + | 0.95 | 0.916 | 0.932 |
| 2376 | rs11080214 | chr17 | 28733398 | + | 0.933 | 0.944 | 0.911 | 5415 | rs2177451 | chr7 | 144821946 | + | 0.941 | 0.932 | 0.909 |
| 2377 | rs12150421 | chr17 | 28733736 | + | 0.915 | 0.944 | 0.911 | 5416 | rs13233813 | chr7 | 145291063 | + | 0.933 | 0.944 | 0.905 |
| 2378 | rs11867162 | chr17 | 28733852 | + | 0.917 | 0.944 | 0.91 | 5417 | rs17169912 | chr7 | 145330527 | + | 0.925 | 0.944 | 0.909 |
| 2379 | rs16968847 | chr17 | 29093572 | + | 0.93 | 0.914 | 0.932 | 5418 | rs12703750 | chr7 | 145350690 | + | 0.941 | 0.927 | 0.937 |

Fig. 9 Cont. 68

| | | | | | | | | | | |
|---|---|---|---|---|---|---|---|---|---|---|
| 2380 | rs11657183 | chr17 | 30792496 | + | 0.922 | 0.92 | 0.917 | 5419 | rs17133773 | chr7 | 145359816 | + | 0.933 | 0.928 | 0.927 |
| 2381 | rs9903158 | chr17 | 31336450 | + | 0.933 | 0.917 | 0.918 | 5420 | rs104880072 | chr7 | 148049999 | + | 0.942 | 0.926 | 0.91 |
| 2382 | rs9992586 | chr17 | 31338028 | + | 0.941 | 0.932 | 0.919 | 5421 | rs12671822 | chr7 | 150052533 | + | 0.933 | 0.939 | 0.923 |
| 2383 | rs9901582 | chr17 | 32092395 | + | 0.075 | 0.061 | 0.054 | 5422 | rs6967921 | chr7 | 151935250 | + | 0.938 | 0.944 | 0.909 |
| 2384 | rs3826330 | chr17 | 35403762 | + | 0.051 | 0.1 | 0.083 | 5423 | rs4725462 | chr7 | 151959997 | + | 0.092 | 0.09 | 0.062 |
| 2385 | rs17729634 | chr17 | 36754792 | + | 0.942 | 0.939 | 0.905 | 5424 | rs7795690 | chr7 | 151964520 | + | 0.069 | 0.06 | 0.05 |
| 2386 | rs3829602 | chr17 | 36792719 | + | 0.95 | 0.944 | 0.905 | 5425 | rs757052 | chr7 | 151964915 | + | 0.083 | 0.096 | 0.054 |
| 2387 | rs17494081 | chr17 | 36842609 | + | 0.915 | 0.939 | 0.905 | 5426 | rs757051 | chr7 | 151964960 | + | 0.076 | 0.097 | 0.064 |
| 2388 | rs7224769 | chr17 | 36844101 | + | 0.95 | 0.944 | 0.911 | 5427 | rs886240 | chr7 | 151965995 | + | 0.083 | 0.096 | 0.062 |
| 2389 | rs2857258 | chr17 | 36872604 | + | 0.908 | 0.939 | 0.906 | 5428 | rs757050 | chr7 | 151967861 | + | 0.083 | 0.094 | 0.054 |
| 2390 | rs4796704 | chr17 | 36909190 | + | 0.05 | 0.057 | 0.089 | 5429 | rs6964582 | chr7 | 151982395 | + | 0.075 | 0.096 | 0.055 |
| 2391 | rs8079825 | chr17 | 40115762 | + | 0.935 | 0.923 | 0.925 | 5430 | rs7779540 | chr7 | 153253595 | + | 0.921 | 0.933 | 0.944 |
| 2392 | rs16970944 | chr17 | 40155291 | + | 0.915 | 0.92 | 0.901 | 5431 | rs6464375 | chr7 | 153256776 | + | 0.907 | 0.932 | 0.937 |
| 2393 | rs9675174 | chr17 | 40352191 | + | 0.94 | 0.948 | 0.946 | 5432 | rs2533578 | chr7 | 153324735 | + | 0.06 | 0.096 | 0.09 |
| 2394 | rs9906359 | chr17 | 40668583 | + | 0.942 | 0.928 | 0.905 | 5433 | rs11772266 | chr7 | 153593662 | + | 0.908 | 0.95 | 0.937 |
| 2395 | rs2018861 | chr17 | 41066131 | + | 0.94 | 0.934 | 0.95 | 5434 | rs12703359 | chr7 | 153831477 | + | 0.908 | 0.933 | 0.909 |
| 2396 | rs4629011 | chr17 | 44188297 | + | 0.059 | 0.056 | 0.05 | 5435 | rs11766087 | chr7 | 153833901 | + | 0.923 | 0.935 | 0.927 |
| 2397 | rs11650852 | chr17 | 47448451 | + | 0.917 | 0.944 | 0.901 | 5436 | rs11772385 | chr7 | 153846970 | + | 0.933 | 0.933 | 0.919 |
| 2398 | rs2907784 | chr17 | 47491588 | + | 0.908 | 0.944 | 0.923 | 5437 | rs3808331 | chr7 | 154947535 | + | 0.939 | 0.938 | 0.923 |
| 2399 | rs2907786 | chr17 | 47492207 | + | 0.915 | 0.949 | 0.926 | 5438 | rs6968788 | chr7 | 155010586 | + | 0.917 | 0.917 | 0.938 |
| 2400 | rs7211116 | chr17 | 48144924 | + | 0.917 | 0.925 | 0.906 | 5439 | rs288758 | chr7 | 155319096 | + | 0.908 | 0.944 | 0.941 |
| 2401 | rs16952227 | chr17 | 48244834 | + | 0.925 | 0.906 | 0.929 | 5440 | rs12670182 | chr7 | 157008926 | + | 0.941 | 0.947 | 0.947 |
| 2402 | rs2320096 | chr17 | 48253466 | + | 0.941 | 0.904 | 0.927 | 5441 | rs896774 | chr7 | 157844492 | + | 0.094 | 0.071 | 0.082 |
| 2403 | rs8081542 | chr17 | 48272778 | + | 0.941 | 0.902 | 0.929 | 5442 | rs1563067 | chr7 | 157872283 | + | 0.085 | 0.064 | 0.086 |
| 2404 | rs4258667 | chr17 | 48275458 | + | 0.941 | 0.904 | 0.927 | 5443 | rs9638135 | chr7 | 158229647 | + | 0.051 | 0.056 | 0.098 |
| 2405 | rs16954329 | chr17 | 49668382 | + | 0.95 | 0.939 | 0.946 | 5444 | rs859768 | chr7 | 158235666 | + | 0.067 | 0.062 | 0.098 |
| 2406 | rs2063166 | chr17 | 49671823 | + | 0.917 | 0.939 | 0.946 | 5445 | rs842434 | chr7 | 158236385 | + | 0.059 | 0.056 | 0.098 |
| 2407 | rs4239186 | chr17 | 49932218 | + | 0.059 | 0.091 | 0.086 | 5446 | rs1189191 | chr7 | 158237795 | + | 0.067 | 0.056 | 0.077 |
| 2408 | rs1896878 | chr17 | 49936397 | + | 0.051 | 0.06 | 0.062 | 5447 | rs842433 | chr7 | 158243493 | + | 0.05 | 0.056 | 0.098 |
| 2409 | rs12150099 | chr17 | 49939613 | + | 0.05 | 0.1 | 0.099 | 5448 | rs842436 | chr7 | 158247376 | + | 0.067 | 0.051 | 0.077 |
| 2410 | rs2934885 | chr17 | 50276086 | + | 0.059 | 0.056 | 0.091 | 5449 | rs1189202 | chr7 | 158254555 | + | 0.052 | 0.061 | 0.077 |
| 2411 | rs2934894 | chr17 | 50295580 | + | 0.052 | 0.058 | 0.099 | 5450 | rs1070828 | chr7 | 158261814 | + | 0.052 | 0.056 | 0.098 |
| 2412 | rs2934914 | chr17 | 50304454 | + | 0.05 | 0.061 | 0.073 | 5451 | rs1189214 | chr7 | 158267687 | + | 0.058 | 0.056 | 0.089 |
| 2413 | rs4479313 | chr17 | 50923917 | + | 0.908 | 0.906 | 0.927 | 5452 | rs2788491 | chr7 | 158318001 | + | 0.067 | 0.061 | 0.087 |
| 2414 | rs17758615 | chr17 | 51292323 | + | 0.942 | 0.906 | 0.901 | 5453 | rs842686 | chr7 | 158329990 | + | 0.95 | 0.938 | 0.923 |

Fig. 9 Cont. 69

| | | | | | | | | | | | |
|---|---|---|---|---|---|---|---|---|---|---|---|
| 2415 | rs10515117 | chr17 | 51403088 | + | 0.925 | 0.949 | 0.946 | 5454 | rs7790987 | chr7 | 158558805 | + | 0.941 | 0.943 | 0.941 |
| 2416 | rs8160353 | chr17 | 51414078 | + | 0.917 | 0.949 | 0.946 | 5455 | rs17738513 | chr8 | 436359 | + | 0.908 | 0.928 | 0.91 |
| 2417 | rs7224448 | chr17 | 51515464 | + | 0.95 | 0.917 | 0.941 | 5456 | rs1669648 | chr8 | 518709 | + | 0.051 | 0.074 | 0.075 |
| 2418 | rs12947724 | chr17 | 52706265 | + | 0.942 | 0.917 | 0.938 | 5457 | rs1669715 | chr8 | 583641 | + | 0.083 | 0.084 | 0.086 |
| 2419 | rs3785494 | chr17 | 53644950 | + | 0.904 | 0.942 | 0.946 | 5458 | rs7834337 | chr8 | 645828 | + | 0.078 | 0.083 | 0.091 |
| 2420 | rs2687065 | chr17 | 54610592 | + | 0.938 | 0.921 | 0.91 | 5459 | rs11137117 | chr8 | 920235 | + | 0.949 | 0.938 | 0.932 |
| 2421 | rs12949992 | chr17 | 54810402 | + | 0.905 | 0.943 | 0.919 | 5460 | rs2280894 | chr8 | 2044422 | + | 0.922 | 0.924 | 0.926 |
| 2422 | rs4968361 | chr17 | 54857610 | + | 0.942 | 0.938 | 0.904 | 5461 | rs10103522 | chr8 | 2491998 | + | 0.943 | 0.93 | 0.945 |
| 2423 | rs4968363 | chr17 | 54865855 | + | 0.925 | 0.95 | 0.919 | 5462 | rs17078479 | chr8 | 2656466 | + | 0.931 | 0.938 | 0.911 |
| 2424 | rs7218485 | chr17 | 56915245 | + | 0.939 | 0.937 | 0.932 | 5463 | rs11984719 | chr8 | 2853293 | + | 0.933 | 0.933 | 0.919 |
| 2425 | rs16945325 | chr17 | 56922573 | + | 0.915 | 0.906 | 0.932 | 5464 | rs7845140 | chr8 | 2864416 | + | 0.932 | 0.933 | 0.929 |
| 2426 | rs11651658 | chr17 | 61629102 | + | 0.925 | 0.939 | 0.932 | 5465 | rs1011588 | chr8 | 2865700 | + | 0.95 | 0.933 | 0.919 |
| 2427 | rs7211380 | chr17 | 61637230 | + | 0.925 | 0.939 | 0.929 | 5466 | rs7016896 | chr8 | 3037257 | + | 0.095 | 0.072 | 0.062 |
| 2428 | rs8178853 | chr17 | 61645520 | + | 0.908 | 0.944 | 0.929 | 5467 | rs6558727 | chr8 | 3037429 | + | 0.092 | 0.078 | 0.05 |
| 2429 | rs8178851 | chr17 | 61645701 | + | 0.908 | 0.944 | 0.929 | 5468 | rs983778 | chr8 | 3038575 | + | 0.085 | 0.083 | 0.05 |
| 2430 | rs8178847 | chr17 | 61647277 | + | 0.924 | 0.944 | 0.941 | 5469 | rs2161752 | chr8 | 3188284 | + | 0.906 | 0.914 | 0.915 |
| 2431 | rs8178841 | chr17 | 61649659 | + | 0.932 | 0.944 | 0.941 | 5470 | rs13259787 | chr8 | 3719050 | + | 0.922 | 0.929 | 0.928 |
| 2432 | rs8178838 | chr17 | 61650003 | + | 0.908 | 0.944 | 0.941 | 5471 | rs2740853 | chr8 | 3801468 | + | 0.939 | 0.937 | 0.943 |
| 2433 | rs8178822 | chr17 | 61655991 | + | 0.925 | 0.944 | 0.941 | 5472 | rs2740830 | chr8 | 3806284 | + | 0.948 | 0.933 | 0.911 |
| 2434 | rs9895850 | chr17 | 61965475 | + | 0.907 | 0.911 | 0.937 | 5473 | rs2140340 | chr8 | 3806986 | + | 0.932 | 0.938 | 0.905 |
| 2435 | rs11659139 | chr17 | 62089497 | + | 0.921 | 0.945 | 0.906 | 5474 | rs17404267 | chr8 | 3941652 | + | 0.95 | 0.933 | 0.92 |
| 2436 | rs16960016 | chr17 | 62115463 | + | 0.95 | 0.944 | 0.945 | 5475 | rs17404336 | chr8 | 3943641 | + | 0.947 | 0.933 | 0.905 |
| 2437 | rs16960039 | chr17 | 62118715 | + | 0.95 | 0.944 | 0.929 | 5476 | rs17332525 | chr8 | 3946587 | + | 0.95 | 0.928 | 0.901 |
| 2438 | rs16960047 | chr17 | 62119429 | + | 0.95 | 0.944 | 0.929 | 5477 | rs17332566 | chr8 | 3947136 | + | 0.933 | 0.906 | 0.91 |
| 2439 | rs16960050 | chr17 | 62121315 | + | 0.95 | 0.944 | 0.937 | 5478 | rs17404503 | chr8 | 3948987 | + | 0.942 | 0.911 | 0.907 |
| 2440 | rs16960053 | chr17 | 62121494 | + | 0.95 | 0.944 | 0.929 | 5479 | rs11780970 | chr8 | 3949273 | + | 0.949 | 0.933 | 0.923 |
| 2441 | rs16960068 | chr17 | 62122530 | + | 0.95 | 0.944 | 0.929 | 5480 | rs17069552 | chr8 | 4064598 | + | 0.908 | 0.906 | 0.941 |
| 2442 | rs16960077 | chr17 | 62132371 | + | 0.95 | 0.944 | 0.937 | 5481 | rs10503242 | chr8 | 4066813 | + | 0.917 | 0.906 | 0.945 |
| 2443 | rs10491200 | chr17 | 62134339 | + | 0.948 | 0.943 | 0.937 | 5482 | rs10098573 | chr8 | 4221610 | + | 0.938 | 0.931 | 0.929 |
| 2444 | rs16960087 | chr17 | 62137164 | + | 0.95 | 0.944 | 0.936 | 5483 | rs2724952 | chr8 | 4441992 | + | 0.058 | 0.05 | 0.089 |
| 2445 | rs7223624 | chr17 | 62969709 | + | 0.915 | 0.929 | 0.949 | 5484 | rs1370757 | chr8 | 4738480 | + | 0.092 | 0.051 | 0.1 |
| 2446 | rs12601012 | chr17 | 64661152 | + | 0.949 | 0.914 | 0.945 | 5485 | rs12675855 | chr8 | 4797340 | + | 0.95 | 0.906 | 0.95 |
| 2447 | rs15973722 | chr17 | 64698761 | + | 0.933 | 0.903 | 0.944 | 5486 | rs7004989 | chr8 | 5435755 | + | 0.941 | 0.92 | 0.943 |
| 2448 | rs1476749 | chr17 | 64754528 | + | 0.925 | 0.95 | 0.914 | 5487 | rs6559038 | chr8 | 5519532 | + | 0.908 | 0.911 | 0.946 |
| 2449 | rs2366489 | chr17 | 65645359 | + | 0.942 | 0.944 | 0.923 | 5488 | rs12386933 | chr8 | 5923665 | + | 0.915 | 0.904 | 0.911 |

Fig. 9  Cont. 70

| | | | | | | | | | | | |
|---|---|---|---|---|---|---|---|---|---|---|---|
| 2450 | rs17702078 | chr17 | 65646213 | + | 0.942 | 0.944 | 0.911 | 5489 | rs7819050 | chr8 | 6102088 | + | 0.907 | 0.949 | 0.946 |
| 2451 | rs7217293 | chr17 | 65646889 | + | 0.924 | 0.944 | 0.911 | 5490 | rs12543837 | chr8 | 6401356 | + | 0.933 | 0.906 | 0.914 |
| 2452 | rs7217947 | chr17 | 65647291 | + | 0.917 | 0.944 | 0.923 | 5491 | rs11199674 | chr8 | 6406238 | + | 0.917 | 0.906 | 0.911 |
| 2453 | rs4405595 | chr17 | 65647335 | + | 0.922 | 0.944 | 0.909 | 5492 | rs3739392 | chr8 | 6407982 | + | 0.95 | 0.906 | 0.905 |
| 2454 | rs9916550 | chr17 | 65648782 | + | 0.917 | 0.944 | 0.911 | 5493 | rs1974947 | chr8 | 6627765 | + | 0.904 | 0.935 | 0.919 |
| 2455 | rs9896573 | chr17 | 65650639 | + | 0.915 | 0.944 | 0.923 | 5494 | rs2976971 | chr8 | 8265703 | + | 0.938 | 0.933 | 0.941 |
| 2456 | rs1817630 | chr17 | 66050707 | + | 0.942 | 0.91 | 0.932 | 5495 | rs2976955 | chr8 | 8280470 | + | 0.939 | 0.948 | 0.905 |
| 2457 | rs10512540 | chr17 | 66052347 | + | 0.942 | 0.911 | 0.941 | 5496 | rs17155132 | chr8 | 8935292 | + | 0.908 | 0.922 | 0.946 |
| 2458 | rs17779190 | chr17 | 66099600 | + | 0.925 | 0.917 | 0.929 | 5497 | rs330003 | chr8 | 9154966 | + | 0.933 | 0.939 | 0.923 |
| 2459 | rs2109053 | chr17 | 66146954 | + | 0.925 | 0.916 | 0.946 | 5498 | rs329992 | chr8 | 9161350 | + | 0.092 | 0.056 | 0.077 |
| 2460 | rs16976201 | chr17 | 66239743 | + | 0.918 | 0.944 | 0.906 | 5499 | rs17149826 | chr8 | 9235032 | + | 0.922 | 0.921 | 0.936 |
| 2461 | rs9897758 | chr17 | 67053316 | + | 0.915 | 0.918 | 0.937 | 5500 | rs17149836 | chr8 | 9237672 | + | 0.942 | 0.922 | 0.945 |
| 2462 | rs10852735 | chr17 | 67421373 | + | 0.083 | 0.05 | 0.054 | 5501 | rs10106967 | chr8 | 9238853 | + | 0.947 | 0.916 | 0.92 |
| 2463 | rs477963 | chr17 | 70153035 | + | 0.95 | 0.928 | 0.941 | 5502 | rs9329192 | chr8 | 9254057 | + | 0.925 | 0.918 | 0.934 |
| 2464 | rs9909030 | chr17 | 73230147 | + | 0.933 | 0.944 | 0.937 | 5503 | rs1381350 | chr8 | 9254605 | + | 0.917 | 0.922 | 0.928 |
| 2465 | rs8078066 | chr17 | 73406409 | + | 0.917 | 0.906 | 0.911 | 5504 | rs10095404 | chr8 | 9271192 | + | 0.948 | 0.902 | 0.935 |
| 2466 | rs748708 | chr17 | 73654390 | + | 0.926 | 0.908 | 0.94 | 5505 | rs17661793 | chr8 | 9274850 | + | 0.917 | 0.939 | 0.929 |
| 2467 | rs8072887 | chr17 | 73682872 | + | 0.925 | 0.938 | 0.95 | 5506 | rs7013369 | chr8 | 9442073 | + | 0.942 | 0.917 | 0.946 |
| 2468 | rs9896036 | chr17 | 73788369 | + | 0.932 | 0.916 | 0.901 | 5507 | rs7018268 | chr8 | 9487859 | + | 0.915 | 0.91 | 0.927 |
| 2469 | rs7222391 | chr17 | 73838232 | + | 0.925 | 0.922 | 0.928 | 5508 | rs10105767 | chr8 | 9491737 | + | 0.931 | 0.924 | 0.927 |
| 2470 | rs11870893 | chr17 | 74728695 | + | 0.924 | 0.932 | 0.923 | 5509 | rs4383973 | chr8 | 9516537 | + | 0.942 | 0.91 | 0.94 |
| 2471 | rs8070406 | chr17 | 74896738 | + | 0.908 | 0.95 | 0.95 | 5510 | rs11249944 | chr8 | 9647140 | + | 0.914 | 0.949 | 0.929 |
| 2472 | rs3185057 | chr17 | 75978442 | + | 0.925 | 0.944 | 0.901 | 5511 | rs2220149 | chr8 | 10006136 | + | 0.092 | 0.061 | 0.055 |
| 2473 | rs9901366 | chr17 | 76275918 | + | 0.917 | 0.916 | 0.91 | 5512 | rs3976518 | chr8 | 12285820 | + | 0.942 | 0.939 | 0.929 |
| 2474 | rs12150860 | chr18 | 1449762 | + | 0.929 | 0.917 | 0.923 | 5513 | rs7460390 | chr8 | 12744293 | + | 0.092 | 0.051 | 0.054 |
| 2475 | rs12966793 | chr18 | 1450455 | + | 0.95 | 0.922 | 0.914 | 5514 | rs17127548 | chr8 | 13142719 | + | 0.917 | 0.939 | 0.95 |
| 2476 | rs11661932 | chr18 | 2991286 | + | 0.908 | 0.927 | 0.928 | 5515 | rs1671361 | chr8 | 13236082 | + | 0.059 | 0.067 | 0.066 |
| 2477 | rs16944391 | chr18 | 3072913 | + | 0.908 | 0.939 | 0.923 | 5516 | rs11785331 | chr8 | 13479292 | + | 0.917 | 0.949 | 0.941 |
| 2478 | rs9635813 | chr18 | 3885467 | + | 0.942 | 0.904 | 0.902 | 5517 | rs13255876 | chr8 | 13479318 | + | 0.907 | 0.911 | 0.947 |
| 2479 | rs17381081 | chr18 | 5292477 | + | 0.925 | 0.95 | 0.91 | 5518 | rs12548310 | chr8 | 14142318 | + | 0.948 | 0.942 | 0.931 |
| 2480 | rs11664536 | chr18 | 5568982 | + | 0.931 | 0.908 | 0.935 | 5519 | rs12549721 | chr8 | 14165011 | + | 0.933 | 0.928 | 0.902 |
| 2481 | rs12954290 | chr18 | 6506024 | + | 0.927 | 0.903 | 0.902 | 5520 | rs1896211 | chr8 | 14167116 | + | 0.083 | 0.079 | 0.055 |
| 2482 | rs13381425 | chr18 | 6991159 | + | 0.915 | 0.944 | 0.941 | 5521 | rs12549343 | chr8 | 14211893 | + | 0.083 | 0.078 | 0.062 |
| 2483 | rs10164234 | chr18 | 6994307 | + | 0.925 | 0.944 | 0.929 | 5522 | rs6994152 | chr8 | 14216544 | + | 0.085 | 0.067 | 0.08 |
| 2484 | rs8097374 | chr18 | 7262833 | + | 0.95 | 0.917 | 0.929 | 5523 | rs2059670 | chr8 | 14220381 | + | 0.083 | 0.073 | 0.072 |

Fig. 9 Cont. 71

| | | | | | | | | | |
|---|---|---|---|---|---|---|---|---|---|
| 2485 | rs8088882 | chr18 | 7920046 | + | 0.941 | 0.933 | 0.929 | 5524 | rs2202987 chr8 | 14520808 | + | 0.092 | 0.051 | 0.05 |
| 2486 | rs17566876 | chr18 | 7946629 | + | 0.925 | 0.911 | 0.914 | 5525 | rs6995984 chr8 | 14711654 | + | 0.917 | 0.916 | 0.901 |
| 2487 | rs8084791 | chr18 | 8002208 | + | 0.95 | 0.904 | 0.923 | 5526 | rs1457219 chr8 | 15050696 | + | 0.942 | 0.939 | 0.937 |
| 2488 | rs6506543 | chr18 | 8002953 | + | 0.933 | 0.941 | 0.918 | 5527 | rs10503538 chr8 | 15060320 | + | 0.908 | 0.938 | 0.911 |
| 2489 | rs13381562 | chr18 | 8009465 | + | 0.907 | 0.939 | 0.902 | 5528 | rs10503539 chr8 | 15060543 | + | 0.908 | 0.944 | 0.911 |
| 2490 | rs7229479 | chr18 | 8010992 | + | 0.908 | 0.906 | 0.923 | 5529 | rs17575734 chr8 | 15090196 | + | 0.925 | 0.939 | 0.95 |
| 2491 | rs16952768 | chr18 | 8022770 | + | 0.942 | 0.911 | 0.923 | 5530 | rs507053 chr8 | 15092491 | + | 0.058 | 0.083 | 0.099 |
| 2492 | rs8095101 | chr18 | 8097220 | + | 0.917 | 0.928 | 0.932 | 5531 | rs1455065 chr8 | 15720104 | + | 0.083 | 0.078 | 0.062 |
| 2493 | rs4456614 | chr18 | 8101888 | + | 0.95 | 0.939 | 0.911 | 5532 | rs2720626 chr8 | 15730363 | + | 0.076 | 0.067 | 0.064 |
| 2494 | rs16952894 | chr18 | 8106369 | + | 0.909 | 0.937 | 0.911 | 5533 | rs1840420 chr8 | 15736074 | + | 0.083 | 0.067 | 0.062 |
| 2495 | rs16953305 | chr18 | 8328100 | + | 0.908 | 0.906 | 0.923 | 5534 | rs1840421 chr8 | 15736327 | + | 0.092 | 0.073 | 0.062 |
| 2496 | rs16953742 | chr18 | 8545808 | + | 0.936 | 0.907 | 0.949 | 5535 | rs2736011 chr8 | 15746755 | + | 0.051 | 0.067 | 0.062 |
| 2497 | rs12455669 | chr18 | 8553113 | + | 0.917 | 0.928 | 0.95 | 5536 | rs2604316 chr8 | 15746804 | + | 0.051 | 0.067 | 0.05 |
| 2498 | rs16953821 | chr18 | 8571394 | + | 0.95 | 0.928 | 0.95 | 5537 | rs823596 chr8 | 16864991 | + | 0.94 | 0.938 | 0.926 |
| 2499 | rs7238137 | chr18 | 9583169 | + | 0.902 | 0.95 | 0.913 | 5538 | rs6993403 chr8 | 17076986 | + | 0.925 | 0.939 | 0.941 |
| 2500 | rs29186 | chr18 | 9960076 | + | 0.917 | 0.944 | 0.91 | 5539 | rs17632001 chr8 | 17347762 | + | 0.933 | 0.933 | 0.941 |
| 2501 | rs9303733 | chr18 | 11469940 | + | 0.95 | 0.922 | 0.935 | 5540 | rs17632013 chr8 | 17348088 | + | 0.95 | 0.933 | 0.941 |
| 2502 | rs11874945 | chr18 | 12744775 | + | 0.946 | 0.907 | 0.925 | 5541 | rs1768852 chr8 | 17366082 | + | 0.95 | 0.938 | 0.946 |
| 2503 | rs1785114 | chr18 | 13473153 | + | 0.098 | 0.093 | 0.083 | 5542 | rs2739670 chr8 | 18007986 | + | 0.942 | 0.926 | 0.941 |
| 2504 | rs3887193 | chr18 | 13584999 | + | 0.931 | 0.949 | 0.902 | 5543 | rs13270961 chr8 | 18183443 | + | 0.933 | 0.904 | 0.905 |
| 2505 | rs7230259 | chr18 | 15308075 | + | 0.942 | 0.916 | 0.92 | 5544 | rs17126664 chr8 | 18393182 | + | 0.95 | 0.906 | 0.909 |
| 2506 | rs17604918 | chr18 | 22332158 | + | 0.915 | 0.922 | 0.923 | 5545 | rs13251176 chr8 | 18587864 | + | 0.05 | 0.094 | 0.089 |
| 2507 | rs8095881 | chr18 | 22449713 | + | 0.917 | 0.911 | 0.932 | 5546 | rs7815682 chr8 | 18623918 | + | 0.1 | 0.079 | 0.054 |
| 2508 | rs4800769 | chr18 | 22652174 | + | 0.917 | 0.944 | 0.911 | 5547 | rs7828727 chr8 | 18638968 | + | 0.058 | 0.084 | 0.062 |
| 2509 | rs17612687 | chr18 | 22654056 | + | 0.946 | 0.939 | 0.905 | 5548 | rs1565140 chr8 | 18645909 | + | 0.059 | 0.067 | 0.062 |
| 2510 | rs7239540 | chr18 | 23540465 | + | 0.912 | 0.916 | 0.932 | 5549 | rs7836936 chr8 | 18779885 | + | 0.925 | 0.917 | 0.901 |
| 2511 | rs12606601 | chr18 | 23541951 | + | 0.915 | 0.916 | 0.932 | 5550 | rs890520 chr8 | 18819716 | + | 0.91 | 0.94 | 0.913 |
| 2512 | rs16944011 | chr18 | 23546361 | + | 0.908 | 0.917 | 0.932 | 5551 | rs1157546 chr8 | 18821286 | + | 0.925 | 0.944 | 0.946 |
| 2513 | rs17468095 | chr18 | 23809444 | + | 0.95 | 0.91 | 0.929 | 5552 | rs4921684 chr8 | 19869408 | + | 0.95 | 0.911 | 0.902 |
| 2514 | rs17445742 | chr18 | 23811303 | + | 0.95 | 0.91 | 0.929 | 5553 | rs4922154 chr8 | 20189397 | + | 0.95 | 0.911 | 0.901 |
| 2515 | rs6508523 | chr18 | 23825464 | + | 0.925 | 0.921 | 0.941 | 5554 | rs4922160 chr8 | 20252063 | + | 0.917 | 0.904 | 0.92 |
| 2516 | rs505314 | chr18 | 23862095 | + | 0.942 | 0.921 | 0.946 | 5555 | rs17092919 chr8 | 20566160 | + | 0.949 | 0.931 | 0.92 |
| 2517 | rs7233570 | chr18 | 25417643 | + | 0.067 | 0.056 | 0.081 | 5556 | rs10503688 chr8 | 20635206 | + | 0.917 | 0.944 | 0.946 |
| 2518 | rs7234172 | chr18 | 25421520 | + | 0.068 | 0.061 | 0.081 | 5557 | rs894214 chr8 | 20773384 | + | 0.917 | 0.922 | 0.902 |
| 2519 | rs12458642 | chr18 | 26087203 | + | 0.911 | 0.944 | 0.919 | 5558 | rs1020221 chr8 | 20777539 | + | 0.917 | 0.928 | 0.911 |

Fig. 9 Cont. 72

| | | | | | | | | | | |
|---|---|---|---|---|---|---|---|---|---|---|
| 2520 | rs16947785 | chr18 | 26112543 | + | 0.941 | 0.95 | 0.919 | 5559 rs17578499 chr8 | 21091664 | + | 0.917 | 0.944 | 0.936 |
| 2521 | rs16947786 | chr18 | 26112579 | + | 0.933 | 0.949 | 0.919 | 5560 rs1381005 chr8 | 21104461 | + | 0.917 | 0.911 | 0.946 |
| 2522 | rs16962783 | chr18 | 28025972 | + | 0.908 | 0.928 | 0.923 | 5561 rs1709387C chr8 | 21242912 | + | 0.933 | 0.944 | 0.905 |
| 2523 | rs16962786 | chr18 | 28027169 | + | 0.949 | 0.928 | 0.923 | 5562 rs12114901 chr8 | 21247722 | + | 0.925 | 0.944 | 0.905 |
| 2524 | rs11662069 | chr18 | 28083340 | + | 0.925 | 0.916 | 0.945 | 5563 rs1051647 chr8 | 22335343 | + | 0.941 | 0.911 | 0.923 |
| 2525 | rs10502591 | chr18 | 28201915 | + | 0.95 | 0.949 | 0.928 | 5564 rs8594 chr8 | 22335761 | + | 0.942 | 0.911 | 0.915 |
| 2526 | rs8084485 | chr18 | 29365588 | + | 0.925 | 0.927 | 0.938 | 5565 rs7837713 chr8 | 22375143 | + | 0.908 | 0.91 | 0.932 |
| 2527 | rs8098239 | chr18 | 29507636 | + | 0.95 | 0.917 | 0.929 | 5566 rs17089312 chr8 | 23421829 | + | 0.941 | 0.944 | 0.914 |
| 2528 | rs714042 | chr18 | 29535155 | + | 0.941 | 0.938 | 0.919 | 5567 rs1866348 chr8 | 23665123 | + | 0.917 | 0.91 | 0.902 |
| 2529 | rs1032454 | chr18 | 29664346 | + | 0.925 | 0.949 | 0.923 | 5568 rs6988827 chr8 | 23708854 | + | 0.942 | 0.944 | 0.937 |
| 2530 | rs1696696C | chr18 | 31484044 | + | 0.941 | 0.922 | 0.941 | 5569 rs2709621 chr8 | 25221647 | + | 0.051 | 0.083 | 0.068 |
| 2531 | rs3810055 | chr18 | 31486875 | + | 0.933 | 0.927 | 0.941 | 5570 rs1425716 chr8 | 25719021 | + | 0.067 | 0.056 | 0.072 |
| 2532 | rs10502651 | chr18 | 31498026 | + | 0.933 | 0.927 | 0.941 | 5571 rs1050378 chr8 | 26475977 | + | 0.95 | 0.939 | 0.905 |
| 2533 | rs16966986 | chr18 | 31501881 | + | 0.933 | 0.927 | 0.938 | 5572 rs7826422 chr8 | 26658565 | + | 0.925 | 0.928 | 0.95 |
| 2534 | rs3744988 | chr18 | 31510479 | + | 0.933 | 0.927 | 0.932 | 5573 rs1050379S chr8 | 26661541 | + | 0.917 | 0.928 | 0.95 |
| 2535 | rs16966998 | chr18 | 31513635 | + | 0.933 | 0.922 | 0.941 | 5574 rs6986328 chr8 | 26664697 | + | 0.925 | 0.928 | 0.95 |
| 2536 | rs16967025 | chr18 | 31534140 | + | 0.933 | 0.922 | 0.941 | 5575 rs6986973 chr8 | 26665032 | + | 0.925 | 0.927 | 0.95 |
| 2537 | rs1791482 | chr18 | 33268969 | + | 0.922 | 0.911 | 0.904 | 5576 rs1442341 chr8 | 26666344 | + | 0.1 | 0.084 | 0.073 |
| 2538 | rs11661422 | chr18 | 33464299 | + | 0.933 | 0.906 | 0.91 | 5577 rs4297048 chr8 | 26947197 | + | 0.059 | 0.074 | 0.085 |
| 2539 | rs12709704 | chr18 | 36177256 | + | 0.907 | 0.916 | 0.902 | 5578 rs7827420 chr8 | 27637275 | + | 0.911 | 0.928 | 0.906 |
| 2540 | rs9954277 | chr18 | 38502155 | + | 0.95 | 0.922 | 0.929 | 5579 rs17058979 chr8 | 28251850 | + | 0.908 | 0.95 | 0.92 |
| 2541 | rs9965590 | chr18 | 38523362 | + | 0.949 | 0.922 | 0.927 | 5580 rs12679764 chr8 | 30430525 | + | 0.95 | 0.928 | 0.95 |
| 2542 | rs9947484 | chr18 | 38535772 | + | 0.933 | 0.922 | 0.929 | 5581 rs4733256 chr8 | 31416456 | + | 0.925 | 0.933 | 0.946 |
| 2543 | rs17644209 | chr18 | 38950409 | + | 0.949 | 0.921 | 0.946 | 5582 rs3963530 chr8 | 31433956 | + | 0.933 | 0.939 | 0.95 |
| 2544 | rs8088988 | chr18 | 38958572 | + | 0.942 | 0.911 | 0.945 | 5583 rs4733257 chr8 | 31434063 | + | 0.949 | 0.939 | 0.95 |
| 2545 | rs17700203 | chr18 | 40336043 | + | 0.95 | 0.922 | 0.902 | 5584 rs1327620C chr8 | 31955371 | + | 0.933 | 0.927 | 0.92 |
| 2546 | rs16978325 | chr18 | 41117753 | + | 0.924 | 0.933 | 0.923 | 5585 rs16879361 chr8 | 32403343 | + | 0.925 | 0.906 | 0.911 |
| 2547 | rs11663672 | chr18 | 42387386 | + | 0.917 | 0.933 | 0.902 | 5586 rs1439160 chr8 | 35549466 | + | 0.933 | 0.95 | 0.919 |
| 2548 | rs9963019 | chr18 | 42456951 | + | 0.915 | 0.94 | 0.932 | 5587 rs2978568 chr8 | 35570418 | + | 0.933 | 0.95 | 0.918 |
| 2549 | rs12970992 | chr18 | 42458377 | + | 0.917 | 0.904 | 0.913 | 5588 rs1821746 chr8 | 35647821 | + | 0.075 | 0.061 | 0.098 |
| 2550 | rs7359758 | chr18 | 43296514 | + | 0.907 | 0.938 | 0.914 | 5589 rs4733946 chr8 | 38438506 | + | 0.933 | 0.904 | 0.932 |
| 2551 | rs4939841 | chr18 | 43301668 | + | 0.908 | 0.921 | 0.909 | 5590 rs7460786 chr8 | 39683308 | + | 0.096 | 0.083 | 0.09 |
| 2552 | rs1105471 | chr18 | 43340500 | + | 0.942 | 0.933 | 0.918 | 5591 rs6983223 chr8 | 40020530 | + | 0.917 | 0.95 | 0.905 |
| 2553 | rs13381464 | chr18 | 43887966 | + | 0.942 | 0.931 | 0.915 | 5592 rs10096859 chr8 | 41058650 | + | 0.908 | 0.944 | 0.935 |
| 2554 | rs11664663 | chr18 | 44397104 | + | 0.942 | 0.938 | 0.928 | 5593 rs2304877 chr8 | 41685595 | + | 0.95 | 0.933 | 0.931 |

Fig. 9 Cont. 73

| | | | | | | | | | | | |
|---|---|---|---|---|---|---|---|---|---|---|---|
| 2555 | rs3816755 | chr18 | 44444719 | + | 0.925 | 0.949 | 0.923 | 5594 | rs16890776 | chr8 | 41690959 | + | 0.94 | 0.931 | 0.926 |
| 2556 | rs17663355 | chr18 | 46598496 | + | 0.908 | 0.928 | 0.917 | 5595 | rs2726718 | chr8 | 50259828 | + | 0.95 | 0.949 | 0.92 |
| 2557 | rs17665901 | chr18 | 47344665 | + | 0.942 | 0.944 | 0.911 | 5596 | rs7832761 | chr8 | 50296038 | + | 0.05 | 0.051 | 0.059 |
| 2558 | rs10502923 | chr18 | 47425809 | + | 0.917 | 0.933 | 0.92 | 5597 | rs1585895 | chr8 | 50303287 | + | 0.05 | 0.051 | 0.062 |
| 2559 | rs7231613 | chr18 | 47548000 | + | 0.933 | 0.95 | 0.929 | 5598 | rs9792367 | chr8 | 50306437 | + | 0.05 | 0.05 | 0.062 |
| 2560 | rs975903 | chr18 | 47560113 | + | 0.95 | 0.95 | 0.905 | 5599 | rs1480389 | chr8 | 50309437 | + | 0.05 | 0.05 | 0.062 |
| 2561 | rs17667456 | chr18 | 47569080 | + | 0.95 | 0.95 | 0.945 | 5600 | rs1480388 | chr8 | 50309690 | + | 0.05 | 0.05 | 0.062 |
| 2562 | rs17667578 | chr18 | 47593601 | + | 0.942 | 0.95 | 0.946 | 5601 | rs1021034 | chr8 | 50351265 | + | 0.05 | 0.051 | 0.062 |
| 2563 | rs11872593 | chr18 | 47704303 | + | 0.914 | 0.931 | 0.929 | 5602 | rs2385334 | chr8 | 50363233 | + | 0.05 | 0.05 | 0.054 |
| 2564 | rs11082940 | chr18 | 48479312 | + | 0.95 | 0.902 | 0.929 | 5603 | rs16906822 | chr8 | 50398083 | + | 0.905 | 0.906 | 0.91 |
| 2565 | rs9947544 | chr18 | 48588199 | + | 0.933 | 0.933 | 0.92 | 5604 | rs10504079 | chr8 | 50423988 | + | 0.95 | 0.941 | 0.911 |
| 2566 | rs8098877 | chr18 | 48624309 | + | 0.917 | 0.906 | 0.946 | 5605 | rs7831715 | chr8 | 50705957 | + | 0.092 | 0.1 | 0.089 |
| 2567 | rs11664765 | chr18 | 49331155 | + | 0.902 | 0.919 | 0.94 | 5606 | rs13281357 | chr8 | 50733106 | + | 0.093 | 0.1 | 0.089 |
| 2568 | rs7236483 | chr18 | 49367477 | + | 0.924 | 0.92 | 0.923 | 5607 | rs13260820 | chr8 | 52673159 | + | 0.933 | 0.944 | 0.902 |
| 2569 | rs7241967 | chr18 | 49368373 | + | 0.921 | 0.933 | 0.922 | 5608 | rs12541286 | chr8 | 53112110 | + | 0.933 | 0.944 | 0.928 |
| 2570 | rs4940406 | chr18 | 53262482 | + | 0.907 | 0.904 | 0.941 | 5609 | rs16918941 | chr8 | 54323255 | + | 0.941 | 0.939 | 0.919 |
| 2571 | rs17834703 | chr18 | 54796217 | + | 0.925 | 0.944 | 0.95 | 5610 | rs12680620 | chr8 | 54344420 | + | 0.933 | 0.939 | 0.946 |
| 2572 | rs17761686 | chr18 | 54798615 | + | 0.941 | 0.944 | 0.95 | 5611 | rs12680643 | chr8 | 54344509 | + | 0.933 | 0.939 | 0.936 |
| 2573 | rs2564463 | chr18 | 55386378 | + | 0.925 | 0.904 | 0.909 | 5612 | rs6473976 | chr8 | 56290159 | + | 0.06 | 0.1 | 0.05 |
| 2574 | rs3097388 | chr18 | 55388197 | + | 0.933 | 0.904 | 0.911 | 5613 | rs4737945 | chr8 | 56291117 | + | 0.067 | 0.1 | 0.05 |
| 2575 | rs3133205 | chr18 | 55388314 | + | 0.933 | 0.906 | 0.911 | 5614 | rs10504187 | chr8 | 56387673 | + | 0.95 | 0.916 | 0.941 |
| 2576 | rs2115675 | chr18 | 55389505 | + | 0.933 | 0.904 | 0.911 | 5615 | rs16921965 | chr8 | 56601712 | + | 0.933 | 0.95 | 0.901 |
| 2577 | rs1429589 | chr18 | 55403516 | + | 0.942 | 0.909 | 0.91 | 5616 | rs16922265 | chr8 | 56884151 | + | 0.912 | 0.938 | 0.936 |
| 2578 | rs2851843 | chr18 | 55414028 | + | 0.942 | 0.906 | 0.91 | 5617 | rs17187027 | chr8 | 57998043 | + | 0.933 | 0.922 | 0.911 |
| 2579 | rs12458374 | chr18 | 55800452 | + | 0.932 | 0.942 | 0.92 | 5618 | rs2873603 | chr8 | 58009628 | + | 0.05 | 0.067 | 0.08 |
| 2580 | rs11662056 | chr18 | 56214698 | + | 0.914 | 0.948 | 0.943 | 5619 | rs8718 | chr8 | 58033401 | + | 0.1 | 0.084 | 0.095 |
| 2581 | rs17066890 | chr18 | 56219815 | + | 0.917 | 0.944 | 0.946 | 5620 | rs16922718 | chr8 | 58952563 | + | 0.95 | 0.938 | 0.911 |
| 2582 | rs10503036 | chr18 | 56224637 | + | 0.917 | 0.944 | 0.95 | 5621 | rs7839850 | chr8 | 59250136 | + | 0.942 | 0.949 | 0.929 |
| 2583 | rs17066900 | chr18 | 56232822 | + | 0.917 | 0.944 | 0.938 | 5622 | rs7016329 | chr8 | 59258542 | + | 0.922 | 0.941 | 0.919 |
| 2584 | rs17068185 | chr18 | 57154276 | + | 0.917 | 0.922 | 0.932 | 5623 | rs13256758 | chr8 | 62536633 | + | 0.948 | 0.93 | 0.902 |
| 2585 | rs7242062 | chr18 | 57213326 | + | 0.058 | 0.09 | 0.086 | 5624 | rs13248406 | chr8 | 62836855 | + | 0.915 | 0.911 | 0.936 |
| 2586 | rs12386106 | chr18 | 57673130 | + | 0.939 | 0.939 | 0.923 | 5625 | rs10101797 | chr8 | 63011506 | + | 0.912 | 0.917 | 0.941 |
| 2587 | rs9949450 | chr18 | 58033664 | + | 0.907 | 0.948 | 0.95 | 5626 | rs1879489 | chr8 | 63406896 | + | 0.942 | 0.915 | 0.929 |
| 2588 | rs7231324 | chr18 | 63581819 | + | 0.933 | 0.927 | 0.919 | 5627 | rs12550126 | chr8 | 63418393 | + | 0.932 | 0.926 | 0.938 |
| 2589 | rs7234944 | chr18 | 63585673 | + | 0.932 | 0.922 | 0.938 | 5628 | rs17264264 | chr8 | 63828719 | + | 0.908 | 0.911 | 0.916 |

Fig. 9 Cont. 74

| | | | | | | | | |
|---|---|---|---|---|---|---|---|---|
| 2590 | rs11876276 | chr18 | 63870704 | + | 0.912 | 0.928 | 0.946 | 5629 rs17264551 chr8 | 63836931 | + | 0.925 | 0.911 | 0.917 |
| 2591 | rs1477992 | chr18 | 64483488 | + | 0.917 | 0.911 | 0.929 | 5630 rs2883014 chr8 | 63869108 | + | 0.925 | 0.916 | 0.91 |
| 2592 | rs7231899 | chr18 | 64493958 | + | 0.95 | 0.921 | 0.929 | 5631 rs4416814 chr8 | 63882398 | + | 0.925 | 0.91 | 0.909 |
| 2593 | rs17080662 | chr18 | 65051787 | + | 0.949 | 0.933 | 0.932 | 5632 rs4256588 chr8 | 63893176 | + | 0.932 | 0.911 | 0.91 |
| 2594 | rs17777278 | chr18 | 65455709 | + | 0.917 | 0.939 | 0.923 | 5633 rs2289418 chr8 | 65457385 | + | 0.925 | 0.921 | 0.929 |
| 2595 | rs1124973 | chr18 | 65456774 | + | 0.925 | 0.938 | 0.92 | 5634 rs10504378 chr8 | 65556040 | + | 0.933 | 0.917 | 0.901 |
| 2596 | rs17777598 | chr18 | 65457702 | + | 0.925 | 0.939 | 0.92 | 5635 rs2255882 chr8 | 69467502 | + | 0.917 | 0.904 | 0.911 |
| 2597 | rs8090514 | chr18 | 65460685 | + | 0.925 | 0.944 | 0.932 | 5636 rs2587563 chr8 | 73154551 | + | 0.062 | 0.061 | 0.098 |
| 2598 | rs7241487 | chr18 | 65530205 | + | 0.915 | 0.92 | 0.912 | 5637 rs125417712 chr8 | 74408885 | + | 0.942 | 0.922 | 0.945 |
| 2599 | rs17202425 | chr18 | 65559515 | + | 0.907 | 0.906 | 0.911 | 5638 rs2004484 chr8 | 74429674 | + | 0.05 | 0.067 | 0.059 |
| 2600 | rs12960252 | chr18 | 65560694 | + | 0.932 | 0.92 | 0.936 | 5639 rs2570157 chr8 | 75979052 | + | 0.917 | 0.95 | 0.945 |
| 2601 | rs17062094 | chr18 | 65602502 | + | 0.924 | 0.917 | 0.932 | 5640 rs10504595 chr8 | 76738610 | + | 0.925 | 0.909 | 0.937 |
| 2602 | rs17081746 | chr18 | 65588316 | + | 0.95 | 0.944 | 0.92 | 5641 rs16939614 chr8 | 79201062 | + | 0.908 | 0.944 | 0.938 |
| 2603 | rs9947886 | chr18 | 66029050 | + | 0.93 | 0.917 | 0.92 | 5642 rs12677810 chr8 | 79202085 | + | 0.908 | 0.944 | 0.938 |
| 2604 | rs9807770 | chr18 | 66032572 | + | 0.917 | 0.921 | 0.932 | 5643 rs12680674 chr8 | 79207022 | + | 0.917 | 0.944 | 0.938 |
| 2605 | rs7505525 | chr18 | 66187616 | + | 0.933 | 0.922 | 0.901 | 5644 rs6989014 chr8 | 79213652 | + | 0.908 | 0.944 | 0.935 |
| 2606 | rs17082817 | chr18 | 66372213 | + | 0.917 | 0.944 | 0.946 | 5645 rs10957886 chr8 | 79246303 | + | 0.908 | 0.938 | 0.938 |
| 2607 | rs2698139 | chr18 | 66869867 | + | 0.95 | 0.914 | 0.941 | 5646 rs13259144 chr8 | 79248958 | + | 0.908 | 0.95 | 0.945 |
| 2608 | rs4410184 | chr18 | 67454663 | + | 0.949 | 0.936 | 0.905 | 5647 rs13266282 chr8 | 79249068 | + | 0.915 | 0.95 | 0.935 |
| 2609 | rs8091327 | chr18 | 67931021 | + | 0.908 | 0.95 | 0.946 | 5648 rs17484533 chr8 | 79252896 | + | 0.908 | 0.939 | 0.941 |
| 2610 | rs1943853 | chr18 | 69450055 | + | 0.917 | 0.928 | 0.936 | 5649 rs12681731 chr8 | 79254996 | + | 0.908 | 0.95 | 0.936 |
| 2611 | rs1943880 | chr18 | 69468747 | + | 0.95 | 0.938 | 0.929 | 5650 rs17484707 chr8 | 79268670 | + | 0.907 | 0.95 | 0.941 |
| 2612 | rs21115978 | chr18 | 69622071 | + | 0.933 | 0.938 | 0.914 | 5651 rs11780821 chr8 | 79270073 | + | 0.908 | 0.949 | 0.941 |
| 2613 | rs12607880 | chr18 | 69642937 | + | 0.907 | 0.911 | 0.92 | 5652 rs1835478 chr8 | 79299520 | + | 0.908 | 0.948 | 0.938 |
| 2614 | rs12457492 | chr18 | 70187123 | + | 0.93 | 0.948 | 0.901 | 5653 rs17407066 chr8 | 79307349 | + | 0.908 | 0.95 | 0.923 |
| 2615 | rs17089131 | chr18 | 70187547 | + | 0.917 | 0.939 | 0.95 | 5654 rs13275966 chr8 | 79595987 | + | 0.942 | 0.944 | 0.919 |
| 2616 | rs12969489 | chr18 | 71137348 | + | 0.908 | 0.944 | 0.946 | 5655 rs17501994 chr8 | 79617132 | + | 0.942 | 0.944 | 0.92 |
| 2617 | rs1866734 | chr18 | 71151838 | + | 0.933 | 0.922 | 0.901 | 5656 rs17519149 chr8 | 80185007 | + | 0.95 | 0.911 | 0.902 |
| 2618 | rs4635418 | chr18 | 72553731 | + | 0.925 | 0.939 | 0.923 | 5657 rs2222361 chr8 | 80207981 | + | 0.95 | 0.91 | 0.901 |
| 2619 | rs116595977 | chr18 | 73121486 | + | 0.95 | 0.927 | 0.923 | 5658 rs10504695 chr8 | 80208220 | + | 0.95 | 0.908 | 0.902 |
| 2620 | rs9954180 | chr18 | 73278738 | + | 0.092 | 0.056 | 0.081 | 5659 rs16907106 chr8 | 80789804 | + | 0.933 | 0.916 | 0.937 |
| 2621 | rs165126 | chr18 | 73487820 | + | 0.05 | 0.061 | 0.051 | 5660 rs11997228 chr8 | 81992356 | + | 0.902 | 0.948 | 0.919 |
| 2622 | rs673429 | chr18 | 74844401 | + | 0.908 | 0.949 | 0.932 | 5661 rs11994481 chr8 | 82732439 | + | 0.908 | 0.928 | 0.925 |
| 2623 | rs497785 | chr18 | 74848400 | + | 0.915 | 0.947 | 0.932 | 5662 rs10096714 chr8 | 82735946 | + | 0.907 | 0.928 | 0.926 |
| 2624 | rs2286364 | chr19 | 2024354 | + | 0.915 | 0.917 | 0.936 | 5663 rs2300491 chr8 | 82751493 | + | 0.908 | 0.938 | 0.918 |

Fig. 9 Cont. 75

| | | | | | | | | |
|---|---|---|---|---|---|---|---|---|
| 2625 rs3795024 chr19 | 2426411 | + | 0.922 | 0.945 | 0.947 | 5664 rs3815882 chr8 | 82756733 | + | 0.908 | 0.927 | 0.911 |
| 2626 rs3729535 chr19 | 2426685 | + | 0.917 | 0.933 | 0.919 | 5665 rs7814202 chr8 | 83225432 | + | 0.946 | 0.903 | 0.935 |
| 2627 rs10411547 chr19 | 2568422 | + | 0.924 | 0.928 | 0.919 | 5666 rs717498 chr8 | 83493162 | + | 0.925 | 0.921 | 0.941 |
| 2628 rs8111211 chr19 | 3356426 | + | 0.067 | 0.052 | 0.063 | 5667 rs16910767 chr8 | 83778864 | + | 0.95 | 0.906 | 0.938 |
| 2629 rs758504 chr19 | 3363035 | + | 0.083 | 0.05 | 0.072 | 5668 rs10100698 chr8 | 87425845 | + | 0.942 | 0.926 | 0.913 |
| 2630 rs11880534 chr19 | 5514342 | + | 0.905 | 0.93 | 0.913 | 5669 rs13278533 chr8 | 87733020 | + | 0.942 | 0.939 | 0.929 |
| 2631 rs6603110 chr19 | 7334146 | + | 0.1 | 0.056 | 0.089 | 5670 rs7005386 chr8 | 89495289 | + | 0.932 | 0.939 | 0.944 |
| 2632 rs8110612 chr19 | 8155396 | + | 0.938 | 0.922 | 0.918 | 5671 rs16883803 chr8 | 89582902 | + | 0.925 | 0.928 | 0.945 |
| 2633 rs1730452C chr19 | 9114405 | + | 0.908 | 0.95 | 0.92 | 5672 rs7832582 chr8 | 89790109 | + | 0.942 | 0.927 | 0.95 |
| 2634 rs12608531 chr19 | 9116204 | + | 0.908 | 0.95 | 0.92 | 5673 rs10504868 chr8 | 89993930 | + | 0.908 | 0.933 | 0.901 |
| 2635 rs17304527 chr19 | 9120416 | + | 0.908 | 0.95 | 0.937 | 5674 rs7832907 chr8 | 90014565 | + | 0.908 | 0.949 | 0.902 |
| 2636 rs11672096 chr19 | 10760112 | + | 0.942 | 0.949 | 0.929 | 5675 rs7812413 chr8 | 90037539 | + | 0.925 | 0.944 | 0.902 |
| 2637 rs11666111 chr19 | 10761633 | + | 0.933 | 0.949 | 0.928 | 5676 rs10109745 chr8 | 90045890 | + | 0.925 | 0.933 | 0.902 |
| 2638 rs11672991 chr19 | 10768425 | + | 0.941 | 0.949 | 0.929 | 5677 rs1028333C chr8 | 90059964 | + | 0.925 | 0.944 | 0.902 |
| 2639 rs7259310 chr19 | 15507051 | + | 0.917 | 0.95 | 0.946 | 5678 rs11998195 chr8 | 92739255 | + | 0.925 | 0.933 | 0.95 |
| 2640 rs2733760 chr19 | 15631752 | + | 0.907 | 0.921 | 0.95 | 5679 rs11988655 chr8 | 94418334 | + | 0.942 | 0.904 | 0.94 |
| 2641 rs12462232 chr19 | 16500369 | + | 0.908 | 0.933 | 0.911 | 5680 rs11998093 chr8 | 95346711 | + | 0.931 | 0.941 | 0.912 |
| 2642 rs1745451C chr19 | 17025173 | + | 0.932 | 0.944 | 0.926 | 5681 rs4548145 chr8 | 95863938 | + | 0.067 | 0.05 | 0.091 |
| 2643 rs998488 chr19 | 17050468 | + | 0.924 | 0.928 | 0.902 | 5682 rs6988791 chr8 | 95866333 | + | 0.058 | 0.05 | 0.098 |
| 2644 rs17281945 chr19 | 17057025 | + | 0.924 | 0.933 | 0.902 | 5683 rs1177532C chr8 | 96376135 | + | 0.95 | 0.904 | 0.946 |
| 2645 rs8109263 chr19 | 20589484 | + | 0.933 | 0.926 | 0.923 | 5684 rs3134189 chr8 | 96669173 | + | 0.904 | 0.909 | 0.934 |
| 2646 rs8106117 chr19 | 20620362 | + | 0.905 | 0.948 | 0.926 | 5685 rs16894295 chr8 | 97172072 | + | 0.925 | 0.95 | 0.946 |
| 2647 rs8100739 chr19 | 20726277 | + | 0.948 | 0.94 | 0.93 | 5686 rs17781834 chr8 | 97436654 | + | 0.917 | 0.916 | 0.929 |
| 2648 rs1246295C chr19 | 33156634 | + | 0.933 | 0.944 | 0.911 | 5687 rs17782868 chr8 | 97478788 | + | 0.932 | 0.933 | 0.92 |
| 2649 rs17621005 chr19 | 33157750 | + | 0.933 | 0.944 | 0.901 | 5688 rs17710204 chr8 | 97483773 | + | 0.932 | 0.934 | 0.917 |
| 2650 rs1246189S chr19 | 33158323 | + | 0.933 | 0.944 | 0.902 | 5689 rs17782992 chr8 | 97486910 | + | 0.933 | 0.933 | 0.936 |
| 2651 rs1297977C chr19 | 33480219 | + | 0.918 | 0.91 | 0.911 | 5690 rs17710274 chr8 | 97488659 | + | 0.932 | 0.933 | 0.937 |
| 2652 rs11083952 chr19 | 34587686 | + | 0.917 | 0.949 | 0.941 | 5691 rs17783045 chr8 | 97488711 | + | 0.933 | 0.933 | 0.937 |
| 2653 rs11665821 chr19 | 35386827 | + | 0.94 | 0.909 | 0.92 | 5692 rs17710314 chr8 | 97489083 | + | 0.933 | 0.933 | 0.92 |
| 2654 rs11882104 chr19 | 359083822 | + | 0.908 | 0.906 | 0.928 | 5693 rs1711035C chr8 | 97489781 | + | 0.933 | 0.933 | 0.937 |
| 2655 rs10403107 chr19 | 36579452 | + | 0.941 | 0.944 | 0.902 | 5694 rs17710398 chr8 | 97493635 | + | 0.933 | 0.933 | 0.92 |
| 2656 rs2194200 chr19 | 36741604 | + | 0.067 | 0.09 | 0.099 | 5695 rs17783201 chr8 | 97494674 | + | 0.933 | 0.933 | 0.936 |
| 2657 rs1696648Z chr19 | 37056994 | + | 0.942 | 0.904 | 0.901 | 5696 rs17783633 chr8 | 97528176 | + | 0.95 | 0.95 | 0.941 |
| 2658 rs17304611 chr19 | 38065380 | + | 0.917 | 0.939 | 0.95 | 5697 rs17710908 chr8 | 97529834 | + | 0.95 | 0.95 | 0.929 |
| 2659 rs10409494 chr19 | 38069376 | + | 0.925 | 0.938 | 0.95 | 5698 rs479892 chr8 | 98595942 | + | 0.932 | 0.906 | 0.911 |

Fig. 9 Cont. 76

| | | | | | | | | | |
|---|---|---|---|---|---|---|---|---|---|
| 2660 | rs2404981 | chr19 | 38108031 | + | 0.908 | 0.939 | 0.95 | 5699 | rs1478951 | chr8 | 98623731 | + | 0.94 | 0.91 | 0.918 |
| 2661 | rs3813150 | chr19 | 38108884 | + | 0.933 | 0.938 | 0.92 | 5700 | rs2512459 | chr8 | 98624149 | + | 0.933 | 0.906 | 0.911 |
| 2662 | rs124596662 | chr19 | 38629162 | + | 0.925 | 0.927 | 0.919 | 5701 | rs1564283 | chr8 | 98629107 | + | 0.933 | 0.906 | 0.941 |
| 2663 | rs4805889 | chr19 | 38646428 | + | 0.925 | 0.914 | 0.914 | 5702 | rs2448182 | chr8 | 98640397 | + | 0.933 | 0.906 | 0.941 |
| 2664 | rs3786911 | chr19 | 38660555 | + | 0.925 | 0.927 | 0.919 | 5703 | rs6987225 | chr8 | 99044848 | + | 0.925 | 0.917 | 0.938 |
| 2665 | rs4805895 | chr19 | 38670264 | + | 0.925 | 0.928 | 0.946 | 5704 | rs4735588 | chr8 | 100039152 | + | 0.95 | 0.944 | 0.938 |
| 2666 | rs9676549 | chr19 | 39212357 | + | 0.933 | 0.95 | 0.901 | 5705 | rs11995381 | chr8 | 100135466 | + | 0.925 | 0.944 | 0.938 |
| 2667 | rs17342179 | chr19 | 47362473 | + | 0.914 | 0.944 | 0.918 | 5706 | rs4501558 | chr8 | 100196370 | + | 0.917 | 0.944 | 0.936 |
| 2668 | rs2158455 | chr19 | 48159734 | + | 0.94 | 0.929 | 0.94 | 5707 | rs4735611 | chr8 | 100413689 | + | 0.917 | 0.944 | 0.945 |
| 2669 | rs3746096 | chr19 | 48277714 | + | 0.932 | 0.933 | 0.901 | 5708 | rs105049888 | chr8 | 100456378 | + | 0.917 | 0.944 | 0.938 |
| 2670 | rs4803750 | chr19 | 49939467 | + | 0.942 | 0.922 | 0.91 | 5709 | rs11989337 | chr8 | 100465360 | + | 0.917 | 0.944 | 0.938 |
| 2671 | rs3859419 | chr19 | 50184973 | + | 0.05 | 0.062 | 0.089 | 5710 | rs16897325 | chr8 | 100469467 | + | 0.917 | 0.944 | 0.95 |
| 2672 | rs2060251 | chr19 | 50200864 | + | 0.059 | 0.057 | 0.089 | 5711 | rs16897326 | chr8 | 100469958 | + | 0.938 | 0.943 | 0.95 |
| 2673 | rs7256865 | chr19 | 50710247 | + | 0.933 | 0.917 | 0.902 | 5712 | rs11989163 | chr8 | 100491723 | + | 0.917 | 0.944 | 0.929 |
| 2674 | rs2694559 | chr19 | 52567261 | + | 0.083 | 0.067 | 0.062 | 5713 | rs1050499C | chr8 | 100580157 | + | 0.917 | 0.943 | 0.938 |
| 2675 | rs11879047 | chr19 | 53226824 | + | 0.908 | 0.906 | 0.929 | 5714 | rs7003410 | chr8 | 102782472 | + | 0.076 | 0.097 | 0.055 |
| 2676 | rs875765 | chr19 | 53233536 | + | 0.917 | 0.906 | 0.933 | 5715 | rs1269707 | chr8 | 103113852 | + | 0.075 | 0.067 | 0.1 |
| 2677 | rs891015 | chr19 | 53234226 | + | 0.932 | 0.938 | 0.946 | 5716 | rs13260228 | chr8 | 103769064 | + | 0.94 | 0.924 | 0.946 |
| 2678 | rs115646716 | chr19 | 53243682 | + | 0.915 | 0.927 | 0.95 | 5717 | rs1687024C | chr8 | 104269181 | + | 0.907 | 0.949 | 0.944 |
| 2679 | rs2287755 | chr19 | 54188363 | + | 0.917 | 0.933 | 0.945 | 5718 | rs3779786 | chr8 | 106862294 | + | 0.924 | 0.904 | 0.946 |
| 2680 | rs3764622 | chr19 | 54198202 | + | 0.917 | 0.944 | 0.919 | 5719 | rs16873678 | chr8 | 106865716 | + | 0.926 | 0.919 | 0.945 |
| 2681 | rs2304203 | chr19 | 54940507 | + | 0.933 | 0.906 | 0.946 | 5720 | rs16874761 | chr8 | 107576391 | + | 0.917 | 0.949 | 0.938 |
| 2682 | rs6509685 | chr19 | 57992266 | + | 0.092 | 0.094 | 0.054 | 5721 | rs16874762 | chr8 | 107576706 | + | 0.917 | 0.95 | 0.938 |
| 2683 | rs9917029 | chr19 | 57992796 | + | 0.092 | 0.096 | 0.072 | 5722 | rs16874781 | chr8 | 107582430 | + | 0.932 | 0.95 | 0.936 |
| 2684 | rs10408156 | chr19 | 57994434 | + | 0.1 | 0.083 | 0.064 | 5723 | rs1725724C | chr8 | 107626083 | + | 0.917 | 0.944 | 0.913 |
| 2685 | rs81107444 | chr19 | 57995339 | + | 0.1 | 0.084 | 0.054 | 5724 | rs7010155 | chr8 | 107626396 | + | 0.917 | 0.949 | 0.946 |
| 2686 | rs1019497 | chr19 | 58002621 | + | 0.095 | 0.094 | 0.065 | 5725 | rs3018911 | chr8 | 107900097 | + | 0.939 | 0.913 | 0.929 |
| 2687 | rs124629254 | chr19 | 58036238 | + | 0.939 | 0.937 | 0.909 | 5726 | rs3018913 | chr8 | 107901079 | + | 0.922 | 0.903 | 0.929 |
| 2688 | rs16984267 | chr19 | 58164369 | + | 0.905 | 0.918 | 0.934 | 5727 | rs2981220 | chr8 | 107902953 | + | 0.931 | 0.933 | 0.941 |
| 2689 | rs11672776 | chr19 | 58735200 | + | 0.93 | 0.911 | 0.909 | 5728 | rs2981218 | chr8 | 107904720 | + | 0.925 | 0.939 | 0.941 |
| 2690 | rs1645784 | chr19 | 59518852 | + | 0.942 | 0.917 | 0.914 | 5729 | rs2981213 | chr8 | 107908068 | + | 0.924 | 0.939 | 0.941 |
| 2691 | rs1865956 | chr19 | 61116501 | + | 0.915 | 0.944 | 0.928 | 5730 | rs1529747 | chr8 | 108517191 | + | 0.931 | 0.927 | 0.946 |
| 2692 | rs124596668 | chr19 | 63575709 | + | 0.092 | 0.079 | 0.063 | 5731 | rs16876325 | chr8 | 108541389 | + | 0.933 | 0.922 | 0.95 |
| 2693 | rs7557993 | chr2 | 1090357 | + | 0.95 | 0.933 | 0.908 | 5732 | rs1433169 | chr8 | 108553474 | + | 0.925 | 0.927 | 0.95 |
| 2694 | rs9653594 | chr2 | 1783152 | + | 0.95 | 0.92 | 0.937 | 5733 | rs1433171 | chr8 | 108561416 | + | 0.925 | 0.922 | 0.95 |

Fig. 9 Cont. 77

| | | | | | | | | | | | |
|---|---|---|---|---|---|---|---|---|---|---|---|
| 2695 | rs10201019 | chr2 | 1784901 | + | 0.942 | 0.918 | 0.945 | 5734 | rs7820162 | chr8 | 108729788 | + | 0.933 | 0.915 | 0.905 |
| 2696 | rs4077010 | chr2 | 1786518 | + | 0.95 | 0.915 | 0.937 | 5735 | rs13253636 | chr8 | 110760643 | + | 0.95 | 0.907 | 0.911 |
| 2697 | rs13422055 | chr2 | 1788229 | + | 0.95 | 0.921 | 0.937 | 5736 | rs17380139 | chr8 | 110780361 | + | 0.95 | 0.906 | 0.929 |
| 2698 | rs12105894 | chr2 | 2191652 | + | 0.925 | 0.922 | 0.902 | 5737 | rs10093999 | chr8 | 110781327 | + | 0.95 | 0.906 | 0.929 |
| 2699 | rs17039421 | chr2 | 2215477 | + | 0.95 | 0.917 | 0.95 | 5738 | rs10098812 | chr8 | 110782954 | + | 0.95 | 0.906 | 0.929 |
| 2700 | rs7584537 | chr2 | 2262076 | + | 0.925 | 0.904 | 0.946 | 5739 | rs10102228 | chr8 | 110783497 | + | 0.95 | 0.906 | 0.923 |
| 2701 | rs6719244 | chr2 | 2632972 | + | 0.092 | 0.083 | 0.089 | 5740 | rs10088881 | chr8 | 110783544 | + | 0.95 | 0.906 | 0.929 |
| 2702 | rs11892605 | chr2 | 2634542 | + | 0.093 | 0.083 | 0.094 | 5741 | rs16880299 | chr8 | 111117054 | + | 0.915 | 0.922 | 0.946 |
| 2703 | rs4853886 | chr2 | 2634694 | + | 0.092 | 0.083 | 0.091 | 5742 | rs16880318 | chr8 | 111134023 | + | 0.917 | 0.921 | 0.932 |
| 2704 | rs1349458 | chr2 | 2640376 | + | 0.058 | 0.079 | 0.089 | 5743 | rs16880360 | chr8 | 113520838 | + | 0.942 | 0.916 | 0.946 |
| 2705 | rs1190201C | chr2 | 3305424 | + | 0.925 | 0.938 | 0.901 | 5744 | rs11984768 | chr8 | 115564461 | + | 0.908 | 0.933 | 0.911 |
| 2706 | rs11885867 | chr2 | 3318083 | + | 0.933 | 0.933 | 0.901 | 5745 | rs11994209 | chr8 | 115614269 | + | 0.908 | 0.944 | 0.911 |
| 2707 | rs12612251 | chr2 | 3337302 | + | 0.943 | 0.949 | 0.905 | 5746 | rs1390806 | chr8 | 115704458 | + | 0.933 | 0.934 | 0.926 |
| 2708 | rs897067 | chr2 | 3869667 | + | 0.092 | 0.056 | 0.099 | 5747 | rs931614 | chr8 | 115723174 | + | 0.933 | 0.939 | 0.92 |
| 2709 | rs1902021 | chr2 | 3874273 | + | 0.092 | 0.067 | 0.1 | 5748 | rs931613 | chr8 | 115723447 | + | 0.945 | 0.939 | 0.92 |
| 2710 | rs766904 | chr2 | 3899201 | + | 0.933 | 0.916 | 0.932 | 5749 | rs9792319 | chr8 | 115729309 | + | 0.933 | 0.939 | 0.92 |
| 2711 | rs1746325C | chr2 | 3902224 | + | 0.925 | 0.917 | 0.932 | 5750 | rs988497 | chr8 | 115729747 | + | 0.907 | 0.949 | 0.92 |
| 2712 | rs1049550C | chr2 | 4530564 | + | 0.942 | 0.949 | 0.938 | 5751 | rs1793747 | chr8 | 118444213 | + | 0.924 | 0.949 | 0.92 |
| 2713 | rs12991814 | chr2 | 6330854 | + | 0.907 | 0.944 | 0.937 | 5752 | rs16889698 | chr8 | 118464949 | + | 0.917 | 0.95 | 0.932 |
| 2714 | rs1870131 | chr2 | 6612612 | + | 0.942 | 0.921 | 0.91 | 5753 | rs1955080 | chr8 | 118469730 | + | 0.917 | 0.95 | 0.92 |
| 2715 | rs10495542 | chr2 | 6758355 | + | 0.938 | 0.946 | 0.902 | 5754 | rs16889708 | chr8 | 118471533 | + | 0.917 | 0.95 | 0.932 |
| 2716 | rs13426351 | chr2 | 8066216 | + | 0.942 | 0.933 | 0.946 | 5755 | rs6993408 | chr8 | 118479144 | + | 0.925 | 0.944 | 0.932 |
| 2717 | rs1913680 | chr2 | 9870195 | + | 0.05 | 0.057 | 0.087 | 5756 | rs17667932 | chr8 | 118605622 | + | 0.932 | 0.944 | 0.932 |
| 2718 | rs17454513 | chr2 | 9906627 | + | 0.942 | 0.907 | 0.902 | 5757 | rs1766799C | chr8 | 118618557 | + | 0.925 | 0.944 | 0.932 |
| 2719 | rs1468780 | chr2 | 10298885 | + | 0.933 | 0.911 | 0.905 | 5758 | rs7841489 | chr8 | 118626310 | + | 0.932 | 0.91 | 0.937 |
| 2720 | rs1020605 | chr2 | 12314886 | + | 0.083 | 0.068 | 0.086 | 5759 | rs4876856 | chr8 | 119827608 | + | 0.933 | 0.933 | 0.945 |
| 2721 | rs6432280 | chr2 | 12397850 | + | 0.058 | 0.062 | 0.071 | 5760 | rs11988997 | chr8 | 119827722 | + | 0.933 | 0.911 | 0.937 |
| 2722 | rs6432282 | chr2 | 12398070 | + | 0.058 | 0.061 | 0.071 | 5761 | rs7842611 | chr8 | 119835375 | + | 0.933 | 0.911 | 0.937 |
| 2723 | rs16859219 | chr2 | 12711781 | + | 0.925 | 0.903 | 0.946 | 5762 | rs7821616 | chr8 | 119836055 | + | 0.942 | 0.911 | 0.937 |
| 2724 | rs13406567 | chr2 | 13110996 | + | 0.942 | 0.917 | 0.927 | 5763 | rs2432970 | chr8 | 119844268 | + | 0.075 | 0.068 | 0.059 |
| 2725 | rs12618412 | chr2 | 13141864 | + | 0.949 | 0.917 | 0.927 | 5764 | rs1960814 | chr8 | 120362977 | + | 0.075 | 0.067 | 0.059 |
| 2726 | rs1020532̈7 | chr2 | 13142472 | + | 0.946 | 0.916 | 0.926 | 5765 | rs16892827 | chr8 | 120380795 | + | 0.95 | 0.906 | 0.914 |
| 2727 | rs13417983 | chr2 | 13145248 | + | 0.949 | 0.917 | 0.927 | 5766 | rs4870736 | chr8 | 120670146 | + | 0.07 | 0.094 | 0.077 |
| 2728 | rs7592173 | chr2 | 13147872 | + | 0.929 | 0.917 | 0.927 | 5767 | rs7017303 | chr8 | 121685526 | + | 0.051 | 0.062 | 0.089 |
| 2729 | rs7583313 | chr2 | 13148180 | + | 0.942 | 0.916 | 0.929 | 5768 | rs17297352 | chr8 | 125428453 | + | 0.949 | 0.937 | 0.927 |

Fig. 9 Cont. 78

| | | | | | | | | | | | |
|---|---|---|---|---|---|---|---|---|---|---|---|
| 2730 | rs10084422 | chr2 | 13150788 | + | 0.942 | 0.917 | 0.927 | 5769 | rs17369758 | chr8 | 125437483 | + | 0.905 | 0.938 | 0.932 |
| 2731 | rs7561656 | chr2 | 13151928 | + | 0.942 | 0.917 | 0.927 | 5770 | rs3936120 | chr8 | 125519498 | + | 0.902 | 0.904 | 0.95 |
| 2732 | rs12622285 | chr2 | 13152208 | + | 0.942 | 0.917 | 0.927 | 5771 | rs7822730 | chr8 | 126495568 | + | 0.933 | 0.938 | 0.941 |
| 2733 | rs7355592 | chr2 | 14209050 | + | 0.925 | 0.95 | 0.914 | 5772 | rs10505503 | chr8 | 127574521 | + | 0.942 | 0.939 | 0.95 |
| 2734 | rs13408357 | chr2 | 14328405 | + | 0.933 | 0.909 | 0.923 | 5773 | rs2385669 | chr8 | 127576694 | + | 0.075 | 0.09 | 0.099 |
| 2735 | rs2342001 | chr2 | 16722397 | + | 0.949 | 0.95 | 0.945 | 5774 | rs13266597C | chr8 | 127588132 | + | 0.075 | 0.083 | 0.089 |
| 2736 | rs7582699 | chr2 | 18152630 | + | 0.905 | 0.95 | 0.932 | 5775 | rs7015430 | chr8 | 127995614 | + | 0.95 | 0.939 | 0.946 |
| 2737 | rs11684345 | chr2 | 18179639 | + | 0.95 | 0.911 | 0.941 | 5776 | rs4870999 | chr8 | 128010407 | + | 0.95 | 0.939 | 0.902 |
| 2738 | rs12475465 | chr2 | 18191492 | + | 0.949 | 0.921 | 0.927 | 5777 | rs4871000 | chr8 | 128010458 | + | 0.95 | 0.939 | 0.91 |
| 2739 | rs16985174 | chr2 | 18561121 | + | 0.925 | 0.939 | 0.929 | 5778 | rs17828621 | chr8 | 128020524 | + | 0.95 | 0.938 | 0.902 |
| 2740 | rs10495688 | chr2 | 18580752 | + | 0.917 | 0.911 | 0.928 | 5779 | rs7814837 | chr8 | 128591384 | + | 0.096 | 0.095 | 0.077 |
| 2741 | rs12620117 | chr2 | 18586706 | + | 0.917 | 0.911 | 0.931 | 5780 | rs16904101 | chr8 | 130593820 | + | 0.942 | 0.911 | 0.934 |
| 2742 | rs12624286 | chr2 | 18624286 | + | 0.944 | 0.904 | 0.927 | 5781 | rs16904222C | chr8 | 131304370 | + | 0.95 | 0.938 | 0.91 |
| 2743 | rs12185564 | chr2 | 18694461 | + | 0.95 | 0.904 | 0.914 | 5782 | rs12676014 | chr8 | 131314273 | + | 0.95 | 0.939 | 0.914 |
| 2744 | rs17756076 | chr2 | 19092429 | + | 0.942 | 0.944 | 0.919 | 5783 | rs6986746 | chr8 | 131366033 | + | 0.95 | 0.939 | 0.938 |
| 2745 | rs17756619C | chr2 | 19093363 | + | 0.941 | 0.944 | 0.923 | 5784 | rs4581035 | chr8 | 132169605 | + | 0.95 | 0.921 | 0.92 |
| 2746 | rs17770548C | chr2 | 19098788 | + | 0.95 | 0.944 | 0.919 | 5785 | rs17615261 | chr8 | 132169926 | + | 0.941 | 0.926 | 0.923 |
| 2747 | rs4666378 | chr2 | 19108525 | + | 0.942 | 0.928 | 0.938 | 5786 | rs277009 | chr8 | 132707785 | + | 0.941 | 0.914 | 0.946 |
| 2748 | rs17756626 | chr2 | 19109063 | + | 0.942 | 0.928 | 0.938 | 5787 | rs6470988 | chr8 | 132729029 | + | 0.06 | 0.085 | 0.054 |
| 2749 | rs4832643 | chr2 | 19113452 | + | 0.942 | 0.939 | 0.938 | 5788 | rs4464950 | chr8 | 132749109 | + | 0.078 | 0.053 | 0.077 |
| 2750 | rs2881432 | chr2 | 19115198 | + | 0.948 | 0.949 | 0.945 | 5789 | rs16904502 | chr8 | 132766082 | + | 0.915 | 0.911 | 0.92 |
| 2751 | rs4666303 | chr2 | 19119482 | + | 0.932 | 0.936 | 0.935 | 5790 | rs1420500 | chr8 | 132770745 | + | 0.907 | 0.91 | 0.92 |
| 2752 | rs17756846 | chr2 | 19120777 | + | 0.949 | 0.939 | 0.909 | 5791 | rs1870233 | chr8 | 133362517 | + | 0.908 | 0.922 | 0.946 |
| 2753 | rs4666381 | chr2 | 19120927 | + | 0.942 | 0.938 | 0.929 | 5792 | rs12682536 | chr8 | 133436036 | + | 0.938 | 0.919 | 0.941 |
| 2754 | rs4666291 | chr2 | 21978872 | + | 0.917 | 0.938 | 0.905 | 5793 | rs2721908 | chr8 | 133533919 | + | 0.067 | 0.05 | 0.059 |
| 2755 | rs2723131 | chr2 | 23439259 | + | 0.925 | 0.927 | 0.911 | 5794 | rs2673563 | chr8 | 133553443 | + | 0.1 | 0.061 | 0.072 |
| 2756 | rs2723132 | chr2 | 23440721 | + | 0.918 | 0.927 | 0.918 | 5795 | rs2597365 | chr8 | 133555695 | + | 0.1 | 0.062 | 0.064 |
| 2757 | rs2577707 | chr2 | 23442296 | + | 0.925 | 0.928 | 0.911 | 5796 | rs2673571 | chr8 | 133575983 | + | 0.058 | 0.083 | 0.09 |
| 2758 | rs2577700 | chr2 | 23446959 | + | 0.925 | 0.927 | 0.91 | 5797 | rs16905011 | chr8 | 134973469 | + | 0.921 | 0.911 | 0.927 |
| 2759 | rs2577699 | chr2 | 23448543 | + | 0.905 | 0.929 | 0.912 | 5798 | rs7460111 | chr8 | 135555436 | + | 0.95 | 0.938 | 0.901 |
| 2760 | rs2723119 | chr2 | 23457414 | + | 0.922 | 0.915 | 0.907 | 5799 | rs11783215 | chr8 | 136839022 | + | 0.922 | 0.91 | 0.904 |
| 2761 | rs2702122 | chr2 | 24415041 | + | 0.942 | 0.91 | 0.929 | 5800 | rs13260793 | chr8 | 137355905 | + | 0.949 | 0.905 | 0.909 |
| 2762 | rs17789849 | chr2 | 24424993 | + | 0.933 | 0.911 | 0.929 | 5801 | rs7830617 | chr8 | 137926783 | + | 0.098 | 0.057 | 0.054 |
| 2763 | rs17759655 | chr2 | 28240704 | + | 0.942 | 0.95 | 0.928 | 5802 | rs11166668 | chr8 | 137932376 | + | 0.092 | 0.061 | 0.054 |
| 2764 | rs13395604 | chr2 | 28539632 | + | 0.942 | 0.949 | 0.937 | 5803 | rs1548152 | chr8 | 137974380 | + | 0.075 | 0.062 | 0.054 |

Fig. 9  Cont. 79

| | | | | | | | | | | |
|---|---|---|---|---|---|---|---|---|---|---|
| 2765 | rs7423095 chr2 | 29015267 | + | 0.095 | 0.09 | 0.071 | 5804 | rs4465005 chr8 | 138087747 | + | 0.95 | 0.925 | 0.944 |
| 2766 | rs12475073 chr2 | 29028221 | + | 0.095 | 0.099 | 0.073 | 5805 | rs4451334 chr8 | 138344030 | + | 0.05 | 0.084 | 0.09 |
| 2767 | rs12622784 chr2 | 29100962 | + | 0.908 | 0.911 | 0.95 | 5806 | rs990712 chr8 | 138625306 | + | 0.917 | 0.927 | 0.946 |
| 2768 | rs12473556 chr2 | 29116699 | + | 0.94 | 0.916 | 0.934 | 5807 | rs7003232 chr8 | 139000784 | + | 0.917 | 0.943 | 0.914 |
| 2769 | rs6734543 chr2 | 29127087 | + | 0.929 | 0.906 | 0.914 | 5808 | rs4454319 chr8 | 139781174 | + | 0.092 | 0.056 | 0.086 |
| 2770 | rs7580471 chr2 | 30461532 | + | 0.931 | 0.915 | 0.935 | 5809 | rs7843846 chr8 | 140828138 | + | 0.933 | 0.904 | 0.923 |
| 2771 | rs2609929 chr2 | 30673778 | + | 0.95 | 0.911 | 0.928 | 5810 | rs4736006 chr8 | 140885321 | + | 0.932 | 0.903 | 0.938 |
| 2772 | rs2042490 chr2 | 30957292 | + | 0.915 | 0.928 | 0.919 | 5811 | rs730069 chr8 | 140922297 | + | 0.94 | 0.938 | 0.909 |
| 2773 | rs6705710 chr2 | 31152939 | + | 0.924 | 0.932 | 0.931 | 5812 | rs6996361 chr8 | 142173158 | + | 0.908 | 0.928 | 0.937 |
| 2774 | rs13404171 chr2 | 31161523 | + | 0.933 | 0.925 | 0.932 | 5813 | rs10975748 chr9 | 667509 | + | 0.933 | 0.933 | 0.902 |
| 2775 | rs4670651 chr2 | 37132761 | + | 0.942 | 0.921 | 0.929 | 5814 | rs10961783 chr9 | 1489116 | + | 0.917 | 0.939 | 0.911 |
| 2776 | rs12328034 chr2 | 38643186 | + | 0.95 | 0.928 | 0.941 | 5815 | rs13301871 chr9 | 2302156 | + | 0.945 | 0.924 | 0.902 |
| 2777 | rs6760524 chr2 | 38722333 | + | 0.908 | 0.927 | 0.938 | 5816 | rs10970270 chr9 | 3128925 | + | 0.939 | 0.907 | 0.926 |
| 2778 | rs17023025 chr2 | 38731140 | + | 0.904 | 0.932 | 0.941 | 5817 | rs6476327 chr9 | 3205842 | + | 0.908 | 0.933 | 0.941 |
| 2779 | rs17023542 chr2 | 39360027 | + | 0.95 | 0.939 | 0.941 | 5818 | rs10971441 chr9 | 3317362 | + | 0.95 | 0.917 | 0.902 |
| 2780 | rs17023611 chr2 | 39374067 | + | 0.917 | 0.939 | 0.946 | 5819 | rs972519 chr9 | 4482098 | + | 0.052 | 0.079 | 0.098 |
| 2781 | rs17531732 chr2 | 39552674 | + | 0.917 | 0.95 | 0.908 | 5820 | rs3780394 chr9 | 5454376 | + | 0.932 | 0.949 | 0.91 |
| 2782 | rs4670285 chr2 | 39611678 | + | 0.942 | 0.904 | 0.91 | 5821 | rs4587383 chr9 | 7025311 | + | 0.917 | 0.909 | 0.946 |
| 2783 | rs17023923 chr2 | 39614871 | + | 0.941 | 0.91 | 0.918 | 5822 | rs16925278 chr9 | 7057495 | + | 0.942 | 0.944 | 0.95 |
| 2784 | rs17476641 chr2 | 40641290 | + | 0.942 | 0.95 | 0.929 | 5823 | rs3802398 chr9 | 7468148 | + | 0.905 | 0.914 | 0.91 |
| 2785 | rs17028189 chr2 | 41715718 | + | 0.917 | 0.911 | 0.95 | 5824 | rs1159842 chr9 | 8105013 | + | 0.083 | 0.1 | 0.098 |
| 2786 | rs17028207 chr2 | 41721349 | + | 0.917 | 0.911 | 0.945 | 5825 | rs7030827 chr9 | 8113227 | + | 0.075 | 0.05 | 0.1 |
| 2787 | rs10490655 chr2 | 41722593 | + | 0.942 | 0.922 | 0.945 | 5826 | rs17550688 chr9 | 8231736 | + | 0.933 | 0.95 | 0.909 |
| 2788 | rs17028226 chr2 | 41724771 | + | 0.942 | 0.911 | 0.945 | 5827 | rs10976939 chr9 | 8300575 | + | 0.926 | 0.95 | 0.92 |
| 2789 | rs10490653 chr2 | 41725955 | + | 0.942 | 0.911 | 0.936 | 5828 | rs10815825 chr9 | 8334187 | + | 0.95 | 0.944 | 0.902 |
| 2790 | rs10490651 chr2 | 41734296 | + | 0.948 | 0.931 | 0.938 | 5829 | rs10976995 chr9 | 8356231 | + | 0.95 | 0.944 | 0.911 |
| 2791 | rs17660215 chr2 | 41754400 | + | 0.942 | 0.928 | 0.946 | 5830 | rs10115782 chr9 | 8356629 | + | 0.921 | 0.944 | 0.927 |
| 2792 | rs17660315 chr2 | 41758995 | + | 0.941 | 0.942 | 0.925 | 5831 | rs7872008 chr9 | 8457002 | + | 0.933 | 0.933 | 0.936 |
| 2793 | rs17028344 chr2 | 41759182 | + | 0.933 | 0.928 | 0.941 | 5832 | rs13301764 chr9 | 8457855 | + | 0.942 | 0.933 | 0.932 |
| 2794 | rs17608482 chr2 | 41759272 | + | 0.949 | 0.926 | 0.941 | 5833 | rs13359120 chr9 | 8460974 | + | 0.925 | 0.933 | 0.928 |
| 2795 | rs970454 chr2 | 41759938 | + | 0.933 | 0.927 | 0.929 | 5834 | rs11791244 chr9 | 9274569 | + | 0.907 | 0.928 | 0.927 |
| 2796 | rs17660548 chr2 | 41760071 | + | 0.942 | 0.928 | 0.939 | 5835 | rs11795233 chr9 | 9282430 | + | 0.907 | 0.933 | 0.901 |
| 2797 | rs17028353 chr2 | 41761172 | + | 0.93 | 0.916 | 0.941 | 5836 | rs932997 chr9 | 9292828 | + | 0.949 | 0.944 | 0.927 |
| 2798 | rs10490647 chr2 | 41768344 | + | 0.933 | 0.931 | 0.929 | 5837 | rs17767692 chr9 | 9423671 | + | 0.933 | 0.933 | 0.938 |
| 2799 | rs10490646 chr2 | 41768751 | + | 0.933 | 0.915 | 0.941 | 5838 | rs17232558 chr9 | 9779202 | + | 0.95 | 0.906 | 0.91 |

Fig. 9 Cont. 80

| | | | | | | | | | | | |
|---|---|---|---|---|---|---|---|---|---|---|---|
| 2800 | rs6747971 | chr2 | 41768886 | + | 0.933 | 0.916 | 0.929 | 5839 | rs13299491 | chr9 | 10136048 | + | 0.925 | 0.908 | 0.936 |
| 2801 | rs4638842 | chr2 | 41776852 | + | 0.933 | 0.917 | 0.941 | 5840 | rs13298702 | chr9 | 10136386 | + | 0.925 | 0.911 | 0.936 |
| 2802 | rs17028391 | chr2 | 41780176 | + | 0.942 | 0.916 | 0.941 | 5841 | rs12238349 | chr9 | 10299001 | + | 0.95 | 0.932 | 0.929 |
| 2803 | rs17028394 | chr2 | 41780323 | + | 0.942 | 0.915 | 0.927 | 5842 | rs1407917 | chr9 | 10380142 | + | 0.07 | 0.098 | 0.1 |
| 2804 | rs1560261 | chr2 | 41787071 | + | 0.942 | 0.916 | 0.929 | 5843 | rs7023802 | chr9 | 10748044 | + | 0.05 | 0.078 | 0.081 |
| 2805 | rs3929081 | chr2 | 41787207 | + | 0.942 | 0.917 | 0.941 | 5844 | rs13293708 | chr9 | 10934766 | + | 0.942 | 0.917 | 0.929 |
| 2806 | rs17028437 | chr2 | 41787244 | + | 0.94 | 0.917 | 0.941 | 5845 | rs13301898 | chr9 | 12740271 | + | 0.942 | 0.944 | 0.902 |
| 2807 | rs17028441 | chr2 | 41787540 | + | 0.941 | 0.921 | 0.927 | 5846 | rs3802478 | chr9 | 12807065 | + | 0.942 | 0.916 | 0.946 |
| 2808 | rs17028474 | chr2 | 41794234 | + | 0.942 | 0.916 | 0.927 | 5847 | rs1692963C | chr9 | 12812678 | + | 0.95 | 0.932 | 0.936 |
| 2809 | rs17028502 | chr2 | 41795779 | + | 0.942 | 0.916 | 0.927 | 5848 | rs11791646 | chr9 | 12892068 | + | 0.902 | 0.914 | 0.913 |
| 2810 | rs17028515 | chr2 | 41798357 | + | 0.942 | 0.916 | 0.935 | 5849 | rs12380864 | chr9 | 13786248 | + | 0.92 | 0.94 | 0.933 |
| 2811 | rs7580548 | chr2 | 41805384 | + | 0.942 | 0.911 | 0.937 | 5850 | rs10961575 | chr9 | 14551506 | + | 0.948 | 0.939 | 0.918 |
| 2812 | rs13426621 | chr2 | 41962975 | + | 0.942 | 0.92 | 0.95 | 5851 | rs7867360 | chr9 | 14556116 | + | 0.917 | 0.933 | 0.923 |
| 2813 | rs2888818 | chr2 | 42007317 | + | 0.908 | 0.949 | 0.911 | 5852 | rs10448192 | chr9 | 14644281 | + | 0.083 | 0.074 | 0.082 |
| 2814 | rs17731172 | chr2 | 42012369 | + | 0.942 | 0.95 | 0.914 | 5853 | rs7867569 | chr9 | 14653394 | + | 0.093 | 0.096 | 0.095 |
| 2815 | rs17773337 | chr2 | 42013266 | + | 0.925 | 0.95 | 0.911 | 5854 | rs17292106 | chr9 | 14782121 | + | 0.942 | 0.917 | 0.905 |
| 2816 | rs2276699 | chr2 | 42014143 | + | 0.925 | 0.95 | 0.918 | 5855 | rs1780159 | chr9 | 15147977 | + | 0.907 | 0.91 | 0.923 |
| 2817 | rs7584974 | chr2 | 42015779 | + | 0.933 | 0.95 | 0.914 | 5856 | rs10733356 | chr9 | 18744211 | + | 0.083 | 0.067 | 0.054 |
| 2818 | rs17773439 | chr2 | 42016839 | + | 0.933 | 0.95 | 0.914 | 5857 | rs1599698 | chr9 | 22946519 | + | 0.1 | 0.09 | 0.068 |
| 2819 | rs7590928 | chr2 | 42019452 | + | 0.933 | 0.95 | 0.911 | 5858 | rs9697131 | chr9 | 23685277 | + | 0.941 | 0.949 | 0.91 |
| 2820 | rs17336182 | chr2 | 43834135 | + | 0.933 | 0.906 | 0.928 | 5859 | rs2383452 | chr9 | 24418103 | + | 0.908 | 0.944 | 0.937 |
| 2821 | rs3792026 | chr2 | 43858354 | + | 0.907 | 0.911 | 0.945 | 5860 | rs4348588 | chr9 | 24441958 | + | 0.925 | 0.95 | 0.938 |
| 2822 | rs3792013 | chr2 | 43881452 | + | 0.908 | 0.916 | 0.932 | 5861 | rs17782547 | chr9 | 25019042 | + | 0.922 | 0.938 | 0.937 |
| 2823 | rs7580868 | chr2 | 43966807 | + | 0.912 | 0.948 | 0.927 | 5862 | rs11790568 | chr9 | 26580984 | + | 0.933 | 0.95 | 0.909 |
| 2824 | rs17499606 | chr2 | 44625285 | + | 0.933 | 0.906 | 0.923 | 5863 | rs10812540 | chr9 | 27218564 | + | 0.933 | 0.917 | 0.901 |
| 2825 | rs7586888 | chr2 | 45289456 | + | 0.075 | 0.08 | 0.081 | 5864 | rs10812541 | chr9 | 27218679 | + | 0.933 | 0.917 | 0.911 |
| 2826 | rs6744444 | chr2 | 45290638 | + | 0.07 | 0.095 | 0.087 | 5865 | rs2477522 | chr9 | 27500492 | + | 0.067 | 0.083 | 0.062 |
| 2827 | rs1357435 | chr2 | 45833637 | + | 0.942 | 0.95 | 0.936 | 5866 | rs10968305 | chr9 | 28043277 | + | 0.917 | 0.95 | 0.938 |
| 2828 | rs7596891 | chr2 | 45899087 | + | 0.909 | 0.909 | 0.923 | 5867 | rs16913449 | chr9 | 28631544 | + | 0.942 | 0.933 | 0.929 |
| 2829 | rs4146906 | chr2 | 46357725 | + | 0.933 | 0.928 | 0.946 | 5868 | rs16913525 | chr9 | 28677561 | + | 0.908 | 0.904 | 0.932 |
| 2830 | rs1867788 | chr2 | 46362869 | + | 0.933 | 0.933 | 0.946 | 5869 | rs7860488 | chr9 | 28681603 | + | 0.942 | 0.931 | 0.904 |
| 2831 | rs6731970 | chr2 | 46805307 | + | 0.948 | 0.935 | 0.906 | 5870 | rs1583668 | chr9 | 28695578 | + | 0.942 | 0.933 | 0.905 |
| 2832 | rs7579295 | chr2 | 48974762 | + | 0.908 | 0.933 | 0.932 | 5871 | rs1583667 | chr9 | 28695864 | + | 0.926 | 0.935 | 0.91 |
| 2833 | rs1703811C | chr2 | 49121667 | + | 0.924 | 0.931 | 0.926 | 5872 | rs10491623 | chr9 | 28765609 | + | 0.942 | 0.95 | 0.914 |
| 2834 | rs10192212 | chr2 | 49411091 | + | 0.915 | 0.931 | 0.928 | 5873 | rs1434302 | chr9 | 28965706 | + | 0.092 | 0.056 | 0.069 |

Fig. 9 Cont. 81

| | | | | | | | | | | | |
|---|---|---|---|---|---|---|---|---|---|---|---|
| 2835 | rs969720 | chr2 | 50728288 | + | 0.933 | 0.938 | 0.938 | 5874 | rs10969066 | chr9 | 29279054 | + | 0.942 | 0.944 | 0.935 |
| 2836 | rs6750228 | chr2 | 51165628 | + | 0.924 | 0.929 | 0.95 | 5875 | rs9298912 | chr9 | 29975893 | + | 0.917 | 0.95 | 0.941 |
| 2837 | rs10048635 | chr2 | 51210795 | + | 0.911 | 0.932 | 0.902 | 5876 | rs2813931 | chr9 | 30009601 | + | 0.908 | 0.95 | 0.941 |
| 2838 | rs11125339 | chr2 | 51283384 | + | 0.942 | 0.933 | 0.95 | 5877 | rs1419375 | chr9 | 30184560 | + | 0.075 | 0.085 | 0.077 |
| 2839 | rs2160650 | chr2 | 51292261 | + | 0.933 | 0.928 | 0.92 | 5878 | rs2800336 | chr9 | 30192068 | + | 0.075 | 0.089 | 0.077 |
| 2840 | rs2111374 | chr2 | 51308643 | + | 0.933 | 0.932 | 0.925 | 5879 | rs16918981 | chr9 | 33058152 | + | 0.95 | 0.909 | 0.946 |
| 2841 | rs11689416 | chr2 | 52174529 | + | 0.942 | 0.95 | 0.945 | 5880 | rs1065765 | chr9 | 33125238 | + | 0.941 | 0.933 | 0.946 |
| 2842 | rs1918086 | chr2 | 52553973 | + | 0.925 | 0.949 | 0.914 | 5881 | rs7866990 | chr9 | 33291098 | + | 0.947 | 0.912 | 0.914 |
| 2843 | rs17042980 | chr2 | 52557317 | + | 0.949 | 0.911 | 0.913 | 5882 | rs11574915 | chr9 | 34700084 | + | 0.95 | 0.949 | 0.907 |
| 2844 | rs12473629 | chr2 | 52562101 | + | 0.932 | 0.906 | 0.936 | 5883 | rs10973115 | chr9 | 36869510 | + | 0.941 | 0.941 | 0.945 |
| 2845 | rs17043033 | chr2 | 52576480 | + | 0.925 | 0.904 | 0.929 | 5884 | rs4295756 | chr9 | 36871353 | + | 0.079 | 0.069 | 0.1 |
| 2846 | rs1446447 | chr2 | 53110539 | + | 0.942 | 0.944 | 0.929 | 5885 | rs17482790 | chr9 | 36871493 | + | 0.939 | 0.932 | 0.917 |
| 2847 | rs4672234 | chr2 | 53237521 | + | 0.074 | 0.066 | 0.05 | 5886 | rs12553613 | chr9 | 36871623 | + | 0.942 | 0.932 | 0.915 |
| 2848 | rs12386201 | chr2 | 53237841 | + | 0.915 | 0.941 | 0.925 | 5887 | rs2277143 | chr9 | 36872141 | + | 0.949 | 0.927 | 0.905 |
| 2849 | rs17044148 | chr2 | 53238096 | + | 0.95 | 0.939 | 0.917 | 5888 | rs3780142 | chr9 | 36875598 | + | 0.086 | 0.084 | 0.054 |
| 2850 | rs10181311 | chr2 | 53242764 | + | 0.908 | 0.938 | 0.91 | 5889 | rs3780144 | chr9 | 36877241 | + | 0.925 | 0.933 | 0.919 |
| 2851 | rs13428097 | chr2 | 53248596 | + | 0.914 | 0.921 | 0.927 | 5890 | rs11999001 | chr9 | 36878752 | + | 0.931 | 0.938 | 0.909 |
| 2852 | rs13416224 | chr2 | 53248642 | + | 0.908 | 0.921 | 0.907 | 5891 | rs11999298 | chr9 | 36884151 | + | 0.917 | 0.933 | 0.937 |
| 2853 | rs1424974 | chr2 | 53260611 | + | 0.058 | 0.089 | 0.095 | 5892 | rs10814467 | chr9 | 36885099 | + | 0.931 | 0.938 | 0.935 |
| 2854 | rs7562698 | chr2 | 53284644 | + | 0.058 | 0.094 | 0.091 | 5893 | rs10814468 | chr9 | 36885144 | + | 0.908 | 0.928 | 0.937 |
| 2855 | rs1364663 | chr2 | 53313339 | + | 0.095 | 0.096 | 0.093 | 5894 | rs10973121 | chr9 | 36885654 | + | 0.925 | 0.938 | 0.937 |
| 2856 | rs3770401 | chr2 | 53793421 | + | 0.918 | 0.904 | 0.932 | 5895 | rs12551935 | chr9 | 36886392 | + | 0.94 | 0.949 | 0.937 |
| 2857 | rs12618587 | chr2 | 53904073 | + | 0.939 | 0.92 | 0.927 | 5896 | rs17536913 | chr9 | 38734094 | + | 0.948 | 0.95 | 0.902 |
| 2858 | rs17268437 | chr2 | 54432548 | + | 0.929 | 0.921 | 0.924 | 5897 | rs10780955 | chr9 | 70269635 | + | 0.933 | 0.927 | 0.946 |
| 2859 | rs4488702 | chr2 | 54452776 | + | 0.917 | 0.943 | 0.923 | 5898 | rs11142616 | chr9 | 70287603 | + | 0.917 | 0.921 | 0.946 |
| 2860 | rs6740018 | chr2 | 54758324 | + | 0.917 | 0.939 | 0.932 | 5899 | rs10868922 | chr9 | 70289960 | + | 0.933 | 0.91 | 0.946 |
| 2861 | rs12475185 | chr2 | 55012547 | + | 0.942 | 0.906 | 0.917 | 5900 | rs1412990 | chr9 | 70506274 | + | 0.908 | 0.938 | 0.909 |
| 2862 | rs4672011 | chr2 | 55152172 | + | 0.915 | 0.911 | 0.946 | 5901 | rs7020639 | chr9 | 71097689 | + | 0.942 | 0.904 | 0.914 |
| 2863 | rs10496040 | chr2 | 55161150 | + | 0.908 | 0.916 | 0.95 | 5902 | rs7034960 | chr9 | 71097881 | + | 0.939 | 0.903 | 0.914 |
| 2864 | rs17046658 | chr2 | 55163470 | + | 0.908 | 0.91 | 0.946 | 5903 | rs1330332 | chr9 | 71503007 | + | 0.05 | 0.1 | 0.081 |
| 2865 | rs2920863 | chr2 | 55168643 | + | 0.067 | 0.094 | 0.08 | 5904 | rs2150045 | chr9 | 71562649 | + | 0.05 | 0.097 | 0.054 |
| 2866 | rs7584448 | chr2 | 57158467 | + | 0.942 | 0.933 | 0.902 | 5905 | rs7863087 | chr9 | 71619570 | + | 0.95 | 0.92 | 0.923 |
| 2867 | rs10518825 | chr2 | 57762725 | + | 0.95 | 0.944 | 0.92 | 5906 | rs17054874 | chr9 | 72317759 | + | 0.908 | 0.911 | 0.941 |
| 2868 | rs10180540 | chr2 | 57803608 | + | 0.933 | 0.944 | 0.928 | 5907 | rs17055833 | chr9 | 72601982 | + | 0.941 | 0.927 | 0.91 |
| 2869 | rs13424099 | chr2 | 58175556 | + | 0.941 | 0.95 | 0.908 | 5908 | rs17055851 | chr9 | 72606093 | + | 0.941 | 0.928 | 0.91 |

Fig. 9 Cont. 82

| | | | | | | | | | | | | |
|---|---|---|---|---|---|---|---|---|---|---|---|---|
| 2870 | rs13384786 | chr2 | 58179884 | + | 0.942 | 0.927 | 0.901 | 5909 | rs17056169 | chr9 | 72806374 | + | 0.95 | 0.939 | 0.941 |
| 2871 | rs17049416 | chr2 | 58294505 | + | 0.925 | 0.95 | 0.929 | 5910 | rs1411164 | chr9 | 72844892 | + | 0.933 | 0.939 | 0.91 |
| 2872 | rs17049417 | chr2 | 58295046 | + | 0.925 | 0.95 | 0.923 | 5911 | rs12349882 | chr9 | 72952308 | + | 0.908 | 0.917 | 0.923 |
| 2873 | rs17049423 | chr2 | 58315407 | + | 0.941 | 0.949 | 0.914 | 5912 | rs11142758 | chr9 | 73062590 | + | 0.917 | 0.917 | 0.941 |
| 2874 | rs17398871 | chr2 | 58335093 | + | 0.925 | 0.939 | 0.929 | 5913 | rs11143345C | chr9 | 74859763 | + | 0.927 | 0.938 | 0.923 |
| 2875 | rs965683 | chr2 | 59275662 | + | 0.925 | 0.916 | 0.905 | 5914 | rs17058589 | chr9 | 74983264 | + | 0.95 | 0.938 | 0.902 |
| 2876 | rs4672511 | chr2 | 62497014 | + | 0.067 | 0.067 | 0.099 | 5915 | rs4745273 | chr9 | 75765561 | + | 0.1 | 0.067 | 0.05 |
| 2877 | rs3770714 | chr2 | 64721836 | + | 0.083 | 0.056 | 0.08 | 5916 | rs2029574 | chr9 | 75766064 | + | 0.1 | 0.067 | 0.05 |
| 2878 | rs2422277 | chr2 | 64731343 | + | 0.083 | 0.056 | 0.089 | 5917 | rs1602497 | chr9 | 75771422 | + | 0.1 | 0.067 | 0.05 |
| 2879 | rs1861402 | chr2 | 64733367 | + | 0.083 | 0.056 | 0.095 | 5918 | rs2933024 | chr9 | 75793688 | + | 0.1 | 0.067 | 0.05 |
| 2880 | rs1981730 | chr2 | 64738300 | + | 0.083 | 0.051 | 0.09 | 5919 | rs2933021 | chr9 | 75801547 | + | 0.092 | 0.067 | 0.05 |
| 2881 | rs2048262 | chr2 | 64955083 | + | 0.1 | 0.062 | 0.068 | 5920 | rs1586781 | chr9 | 75822504 | + | 0.085 | 0.072 | 0.05 |
| 2882 | rs17030693 | chr2 | 65802402 | + | 0.924 | 0.906 | 0.937 | 5921 | rs17060793 | chr9 | 76884339 | + | 0.95 | 0.928 | 0.929 |
| 2883 | rs4142761 | chr2 | 67123480 | + | 0.92 | 0.905 | 0.902 | 5922 | rs17060796 | chr9 | 76885964 | + | 0.95 | 0.928 | 0.937 |
| 2884 | rs730424 | chr2 | 67845579 | + | 0.942 | 0.921 | 0.928 | 5923 | rs2273764 | chr9 | 76887046 | + | 0.95 | 0.933 | 0.937 |
| 2885 | rs11126152 | chr2 | 67853420 | + | 0.95 | 0.917 | 0.936 | 5924 | rs2273765 | chr9 | 76887346 | + | 0.95 | 0.928 | 0.929 |
| 2886 | rs17034389 | chr2 | 67872426 | + | 0.907 | 0.911 | 0.946 | 5925 | rs12000133 | chr9 | 77334652 | + | 0.95 | 0.928 | 0.91 |
| 2887 | rs17034439C | chr2 | 67872846 | + | 0.907 | 0.911 | 0.946 | 5926 | rs11144588 | chr9 | 775203370 | + | 0.925 | 0.95 | 0.91 |
| 2888 | rs3762614 | chr2 | 68954557 | + | 0.933 | 0.904 | 0.946 | 5927 | rs11144589 | chr9 | 775204428 | + | 0.933 | 0.95 | 0.937 |
| 2889 | rs4366940 | chr2 | 69120638 | + | 0.908 | 0.927 | 0.937 | 5928 | rs3739517 | chr9 | 78306575 | + | 0.925 | 0.949 | 0.95 |
| 2890 | rs12465994 | chr2 | 69123765 | + | 0.908 | 0.928 | 0.936 | 5929 | rs7029812 | chr9 | 78497100 | + | 0.95 | 0.933 | 0.932 |
| 2891 | rs7579629 | chr2 | 69136036 | + | 0.913 | 0.926 | 0.937 | 5930 | rs12237165 | chr9 | 78589875 | + | 0.924 | 0.938 | 0.902 |
| 2892 | rs12473368 | chr2 | 69145728 | + | 0.907 | 0.928 | 0.935 | 5931 | rs17723908 | chr9 | 79017784 | + | 0.925 | 0.904 | 0.902 |
| 2893 | rs3915036 | chr2 | 70563914 | + | 0.942 | 0.928 | 0.92 | 5932 | rs17339571 | chr9 | 79143397 | + | 0.925 | 0.904 | 0.902 |
| 2894 | rs11126273 | chr2 | 70569332 | + | 0.942 | 0.927 | 0.937 | 5933 | rs10491845 | chr9 | 79155830 | + | 0.925 | 0.902 | 0.919 |
| 2895 | rs1459264 | chr2 | 71973085 | + | 0.95 | 0.921 | 0.92 | 5934 | rs12377293 | chr9 | 79359474 | + | 0.908 | 0.906 | 0.935 |
| 2896 | rs7589605 | chr2 | 75644173 | + | 0.092 | 0.072 | 0.073 | 5935 | rs11137654 | chr9 | 80210910 | + | 0.949 | 0.949 | 0.923 |
| 2897 | rs725774 | chr2 | 75648281 | + | 0.092 | 0.057 | 0.071 | 5936 | rs17198915 | chr9 | 81087185 | + | 0.95 | 0.927 | 0.923 |
| 2898 | rs7595746 | chr2 | 75650948 | + | 0.1 | 0.051 | 0.081 | 5937 | rs17791483 | chr9 | 81088800 | + | 0.95 | 0.928 | 0.927 |
| 2899 | rs2110487 | chr2 | 75664263 | + | 0.1 | 0.056 | 0.081 | 5938 | rs17791513 | chr9 | 81095410 | + | 0.95 | 0.948 | 0.929 |
| 2900 | rs7596733 | chr2 | 75666854 | + | 0.1 | 0.056 | 0.073 | 5939 | rs13290396 | chr9 | 81104798 | + | 0.922 | 0.938 | 0.929 |
| 2901 | rs12466443 | chr2 | 76471563 | + | 0.931 | 0.909 | 0.938 | 5940 | rs13292262 | chr9 | 81105203 | + | 0.908 | 0.933 | 0.928 |
| 2902 | rs7355718 | chr2 | 77063258 | + | 0.925 | 0.928 | 0.937 | 5941 | rs11999051 | chr9 | 81105694 | + | 0.933 | 0.933 | 0.929 |
| 2903 | rs2067968 | chr2 | 77154246 | + | 0.942 | 0.933 | 0.945 | 5942 | rs1328412 | chr9 | 81106947 | + | 0.941 | 0.933 | 0.928 |
| 2904 | rs7592577 | chr2 | 77679882 | + | 0.925 | 0.949 | 0.94 | 5943 | rs13292514 | chr9 | 81113823 | + | 0.94 | 0.933 | 0.92 |

Fig. 9 Cont. 83

| | | | | | | | | | |
|---|---|---|---|---|---|---|---|---|---|
| 2905 | rs17645837 | chr2 | 78825242 | + | 0.917 | 0.949 | 0.911 | 5944 | rs105120B5 chr9 | 81114533 | + | 0.942 | 0.933 | 0.923 |
| 2906 | rs6735871 | chr2 | 78852103 | + | 0.917 | 0.949 | 0.911 | 5945 | rs17801845 chr9 | 81769509 | + | 0.95 | 0.95 | 0.91 |
| 2907 | rs7602830 | chr2 | 78853059 | + | 0.918 | 0.94 | 0.913 | 5946 | rs17256298 chr9 | 82294178 | + | 0.95 | 0.917 | 0.923 |
| 2908 | rs6744763 | chr2 | 79078334 | + | 0.925 | 0.906 | 0.932 | 5947 | rs13287175 chr9 | 84638308 | + | 0.912 | 0.948 | 0.935 |
| 2909 | rs17702221 | chr2 | 79147207 | + | 0.942 | 0.922 | 0.95 | 5948 | rs11139822 chr9 | 84641133 | + | 0.907 | 0.948 | 0.935 |
| 2910 | rs3819315 | chr2 | 79218109 | + | 0.95 | 0.906 | 0.919 | 5949 | rs7029717 chr9 | 84749764 | + | 0.95 | 0.921 | 0.91 |
| 2911 | rs1963424 | chr2 | 79218736 | + | 0.95 | 0.91 | 0.929 | 5950 | rs17087204 chr9 | 86220709 | + | 0.915 | 0.949 | 0.938 |
| 2912 | rs17785176 | chr2 | 79784450 | + | 0.949 | 0.95 | 0.92 | 5951 | rs1409707 chr9 | 86225563 | + | 0.908 | 0.949 | 0.946 |
| 2913 | rs17261209 | chr2 | 80074457 | + | 0.942 | 0.917 | 0.901 | 5952 | rs1831040 chr9 | 86222819 | + | 0.905 | 0.949 | 0.938 |
| 2914 | rs17261454 | chr2 | 80196630 | + | 0.925 | 0.938 | 0.926 | 5953 | rs17087213 chr9 | 86224408 | + | 0.908 | 0.95 | 0.946 |
| 2915 | rs11688262 | chr2 | 80416125 | + | 0.942 | 0.944 | 0.918 | 5954 | rs13294268 chr9 | 86226151 | + | 0.941 | 0.95 | 0.945 |
| 2916 | rs11688356 | chr2 | 80416300 | + | 0.942 | 0.944 | 0.918 | 5955 | rs13283953 chr9 | 86227944 | + | 0.917 | 0.95 | 0.938 |
| 2917 | rs11677246 | chr2 | 80416378 | + | 0.942 | 0.944 | 0.918 | 5956 | rs11791891 chr9 | 86702232 | + | 0.924 | 0.95 | 0.932 |
| 2918 | rs4432477 | chr2 | 80416478 | + | 0.942 | 0.944 | 0.928 | 5957 | rs17087839 chr9 | 86709785 | + | 0.908 | 0.95 | 0.902 |
| 2919 | rs1562775 | chr2 | 80416641 | + | 0.942 | 0.933 | 0.927 | 5958 | rs17087846 chr9 | 86713056 | + | 0.908 | 0.95 | 0.902 |
| 2920 | rs182571 | chr2 | 80431534 | + | 0.917 | 0.944 | 0.92 | 5959 | rs2165893 chr9 | 86721244 | + | 0.908 | 0.949 | 0.932 |
| 2921 | rs17261545 | chr2 | 80471047 | + | 0.925 | 0.944 | 0.936 | 5960 | rs11788800 chr9 | 86752739 | + | 0.908 | 0.928 | 0.946 |
| 2922 | rs11688319 | chr2 | 81534792 | + | 0.908 | 0.944 | 0.95 | 5961 | rs2289657 chr9 | 86753280 | + | 0.925 | 0.927 | 0.946 |
| 2923 | rs12623844 | chr2 | 81599403 | + | 0.95 | 0.928 | 0.901 | 5962 | rs7026337 chr9 | 86757834 | + | 0.925 | 0.926 | 0.913 |
| 2924 | rs12466737 | chr2 | 84230757 | + | 0.917 | 0.939 | 0.901 | 5963 | rs1899637 chr9 | 86765828 | + | 0.917 | 0.904 | 0.918 |
| 2925 | rs13386681 | chr2 | 85866540 | + | 0.933 | 0.922 | 0.92 | 5964 | rs17426617 chr9 | 87274653 | + | 0.95 | 0.911 | 0.92 |
| 2926 | rs6709371 | chr2 | 86721233 | + | 0.917 | 0.949 | 0.085 | 5965 | rs11141145 chr9 | 87710774 | + | 0.908 | 0.944 | 0.905 |
| 2927 | rs2970903 | chr2 | 88210706 | + | 0.051 | 0.082 | 0.907 | 5966 | rs10868351 chr9 | 87714371 | + | 0.943 | 0.94 | 0.907 |
| 2928 | rs12185577 | chr2 | 94821556 | + | 0.933 | 0.906 | 0.927 | 5967 | rs2183126 chr9 | 87882658 | + | 0.95 | 0.949 | 0.901 |
| 2929 | rs17842087 | chr2 | 94843502 | + | 0.908 | 0.932 | 0.901 | 5968 | rs11141259 chr9 | 87944057 | + | 0.917 | 0.922 | 0.941 |
| 2930 | rs7605434 | chr2 | 100925416 | + | 0.933 | 0.95 | 0.932 | 5969 | rs12378988 chr9 | 87945771 | + | 0.915 | 0.922 | 0.941 |
| 2931 | rs4851502 | chr2 | 101798800 | + | 0.942 | 0.904 | 0.923 | 5970 | rs11141283 chr9 | 87974166 | + | 0.908 | 0.917 | 0.941 |
| 2932 | rs3771179 | chr2 | 102320324 | + | 0.925 | 0.95 | 0.944 | 5971 | rs7869944 chr9 | 89422222 | + | 0.906 | 0.938 | 0.946 |
| 2933 | rs17031081 | chr2 | 105500825 | + | 0.904 | 0.948 | 0.941 | 5972 | rs17434563 chr9 | 90815756 | + | 0.95 | 0.928 | 0.946 |
| 2934 | rs4851792 | chr2 | 105519816 | + | 0.95 | 0.916 | 0.927 | 5973 | rs7864625 chr9 | 92673769 | + | 0.933 | 0.938 | 0.941 |
| 2935 | rs11675788 | chr2 | 105522774 | + | 0.95 | 0.917 | 0.941 | 5974 | rs7864740 chr9 | 92703382 | + | 0.95 | 0.908 | 0.945 |
| 2936 | rs17031192 | chr2 | 105523947 | + | 0.95 | 0.917 | 0.941 | 5975 | rs12342181 chr9 | 92964795 | + | 0.931 | 0.949 | 0.91 |
| 2937 | rs4851068 | chr2 | 105524879 | + | 0.942 | 0.917 | 0.923 | 5976 | rs356685 chr9 | 97009480 | + | 0.092 | 0.056 | 0.09 |
| 2938 | rs17031463 | chr2 | 105636935 | + | 0.925 | 0.922 | 0.923 | 5977 | rs356660 chr9 | 97045956 | + | 0.092 | 0.051 | 0.092 |
| 2939 | rs17031467 | chr2 | 105637516 | + | 0.924 | 0.927 | 0.923 | 5978 | rs356663 chr9 | 97078484 | + | 0.092 | 0.056 | 0.09 |

Fig. 9 Cont. 84

| | | | | | | | | | |
|---|---|---|---|---|---|---|---|---|---|
| 2940 | rs17031483 | chr2 | 105640075 | + | 0.917 | 0.916 | 0.929 | 5979 rs356671 chr9 | 97092528 + | 0.092 | 0.056 | 0.09 |
| 2941 | rs17031517 | chr2 | 105658099 | + | 0.925 | 0.921 | 0.923 | 5980 rs651009 chr9 | 97117713 + | 0.1 | 0.057 | 0.095 |
| 2942 | rs10496415 | chr2 | 107414552 | + | 0.933 | 0.939 | 0.923 | 5981 rs10978835 chr9 | 97496577 + | 0.917 | 0.939 | 0.914 |
| 2943 | rs17232035 | chr2 | 107444875 | + | 0.933 | 0.939 | 0.923 | 5982 rs10816522 chr9 | 97497645 + | 0.917 | 0.938 | 0.914 |
| 2944 | rs10496413 | chr2 | 107473982 | + | 0.933 | 0.903 | 0.919 | 5983 rs1739624C chr9 | 97778620 + | 0.925 | 0.938 | 0.905 |
| 2945 | rs908436 | chr2 | 107578753 | + | 0.942 | 0.939 | 0.901 | 5984 rs17396553 chr9 | 97790649 + | 0.925 | 0.939 | 0.905 |
| 2946 | rs17044957 | chr2 | 116253060 | + | 0.925 | 0.906 | 0.945 | 5985 rs10512243 chr9 | 97815280 + | 0.925 | 0.938 | 0.905 |
| 2947 | rs6721575 | chr2 | 118207356 | + | 0.902 | 0.906 | 0.95 | 5986 rs2479828 chr9 | 98090615 + | 0.05 | 0.073 | 0.086 |
| 2948 | rs10211133 | chr2 | 118213068 | + | 0.924 | 0.096 | 0.05 | 5987 rs16922319 chr9 | 99393885 + | 0.942 | 0.938 | 0.905 |
| 2949 | rs1547442 | chr2 | 118915377 | + | 0.058 | 0.92 | 0.946 | 5988 rs10986995 chr9 | 100407100 + | 0.922 | 0.939 | 0.927 |
| 2950 | rs6719887 | chr2 | 119261550 | + | 0.912 | 0.089 | 0.055 | 5989 rs10987005 chr9 | 100408986 + | 0.917 | 0.943 | 0.945 |
| 2951 | rs6735018 | chr2 | 119349085 | + | 0.058 | 0.901 | 0.909 | 5990 rs4606175 chr9 | 100463343 + | 0.905 | 0.939 | 0.919 |
| 2952 | rs12613245 | chr2 | 120910395 | + | 0.914 | 0.904 | 0.937 | 5991 rs12005789 chr9 | 102370962 + | 0.925 | 0.921 | 0.937 |
| 2953 | rs13016912 | chr2 | 120937543 | + | 0.93 | 0.067 | 0.095 | 5992 rs1774237C chr9 | 102382626 + | 0.933 | 0.922 | 0.92 |
| 2954 | rs1320869 | chr2 | 122850882 | + | 0.1 | 0.067 | 0.098 | 5993 rs12002878 chr9 | 102391316 + | 0.933 | 0.922 | 0.92 |
| 2955 | rs1453679 | chr2 | 122865769 | + | 0.05 | 0.911 | 0.946 | 5994 rs2052977 chr9 | 103033320 + | 0.942 | 0.911 | 0.945 |
| 2956 | rs17008898 | chr2 | 123380547 | + | 0.908 | 0.911 | 0.946 | 5995 rs10989452 chr9 | 103044971 + | 0.94 | 0.904 | 0.946 |
| 2957 | rs17008925 | chr2 | 123393260 | + | 0.908 | 0.911 | 0.946 | 5996 rs10990173 chr9 | 104352119 + | 0.902 | 0.904 | 0.917 |
| 2958 | rs1700894C | chr2 | 123410767 | + | 0.908 | 0.911 | 0.946 | 5997 rs12376672 chr9 | 104603316 + | 0.933 | 0.939 | 0.945 |
| 2959 | rs1518226 | chr2 | 123416704 | + | 0.925 | 0.911 | 0.946 | 5998 rs10990347 chr9 | 104632283 + | 0.942 | 0.939 | 0.937 |
| 2960 | rs1700896C | chr2 | 123421789 | + | 0.908 | 0.911 | 0.946 | 5999 rs10512306 chr9 | 104640700 + | 0.933 | 0.944 | 0.946 |
| 2961 | rs7564530 | chr2 | 123431227 | + | 0.908 | 0.911 | 0.946 | 6000 rs10990358 chr9 | 104643916 + | 0.942 | 0.939 | 0.944 |
| 2962 | rs17009047 | chr2 | 123450099 | + | 0.942 | 0.911 | 0.946 | 6001 rs10990355 chr9 | 104647864 + | 0.942 | 0.933 | 0.946 |
| 2963 | rs17009081 | chr2 | 123460871 | + | 0.95 | 0.911 | 0.946 | 6002 rs12380501 chr9 | 104650286 + | 0.941 | 0.944 | 0.94 |
| 2964 | rs1829454 | chr2 | 123729957 | + | 0.933 | 0.932 | 0.944 | 6003 rs4743599 chr9 | 104651778 + | 0.933 | 0.938 | 0.919 |
| 2965 | rs11893784 | chr2 | 124046748 | + | 0.923 | 0.938 | 0.922 | 6004 rs2220706 chr9 | 104673784 + | 0.95 | 0.944 | 0.95 |
| 2966 | rs17010412 | chr2 | 124186228 | + | 0.942 | 0.928 | 0.941 | 6005 rs408323 chr9 | 105125498 + | 0.925 | 0.944 | 0.917 |
| 2967 | rs7565438 | chr2 | 126239619 | + | 0.902 | 0.909 | 0.936 | 6006 rs17194561 chr9 | 108562670 + | 0.907 | 0.917 | 0.95 |
| 2968 | rs13418613 | chr2 | 126306989 | + | 0.917 | 0.939 | 0.918 | 6007 rs1097864C chr9 | 108591271 + | 0.058 | 0.05 | 0.098 |
| 2969 | rs11899372 | chr2 | 127490350 | + | 0.95 | 0.937 | 0.919 | 6008 rs7861530 chr9 | 108888735 + | 0.95 | 0.949 | 0.911 |
| 2970 | rs11903472 | chr2 | 127490368 | + | 0.95 | 0.928 | 0.902 | 6009 rs1007061 chr9 | 108922153 + | 0.933 | 0.928 | 0.905 |
| 2971 | rs22243934 | chr2 | 128122391 | + | 0.917 | 0.904 | 0.94 | 6010 rs947125 chr9 | 109207589 + | 0.942 | 0.928 | 0.941 |
| 2972 | rs11903623 | chr2 | 129174680 | + | 0.924 | 0.939 | 0.946 | 6011 rs12685872 chr9 | 109580956 + | 0.907 | 0.916 | 0.919 |
| 2973 | rs9808328 | chr2 | 129721268 | + | 0.938 | 0.948 | 0.917 | 6012 rs12339041 chr9 | 109610027 + | 0.95 | 0.909 | 0.937 |
| 2974 | rs4662666 | chr2 | 130306639 | + | 0.931 | 0.95 | 0.908 | 6013 rs1025572 chr9 | 109927055 + | 0.933 | 0.921 | 0.928 |

Fig. 9 Cont. 85

| | | | | | | | | | | | | |
|---|---|---|---|---|---|---|---|---|---|---|---|---|
| 2975 | rs13409247 | chr2 | 131473001 | + | 0.914 | 0.938 | 0.91 | 6014 | rs7581 | chr9 | 110819068 | + | 0.917 | 0.927 | 0.923 |
| 2976 | rs13431119 | chr2 | 133522978 | + | 0.941 | 0.903 | 0.914 | 6015 | rs1017482 | chr9 | 111081619 | + | 0.075 | 0.061 | 0.099 |
| 2977 | rs1430169 | chr2 | 133749957 | + | 0.949 | 0.91 | 0.923 | 6016 | rs10979808 | chr9 | 111094346 | + | 0.083 | 0.061 | 0.099 |
| 2978 | rs16823134 | chr2 | 133755345 | + | 0.915 | 0.95 | 0.946 | 6017 | rs10979838 | chr9 | 111152455 | + | 0.942 | 0.917 | 0.941 |
| 2979 | rs16830256 | chr2 | 134711461 | + | 0.942 | 0.939 | 0.919 | 6018 | rs4135185 | chr9 | 112055027 | + | 0.917 | 0.944 | 0.946 |
| 2980 | rs3791287 | chr2 | 134822337 | + | 0.933 | 0.949 | 0.905 | 6019 | rs4135163 | chr9 | 112057649 | + | 0.917 | 0.944 | 0.946 |
| 2981 | rs7557040 | chr2 | 135736030 | + | 0.922 | 0.917 | 0.94 | 6020 | rs10120395 | chr9 | 114321573 | + | 0.065 | 0.097 | 0.071 |
| 2982 | rs11888228 | chr2 | 135737477 | + | 0.934 | 0.912 | 0.92 | 6021 | rs10981613 | chr9 | 114836374 | + | 0.95 | 0.917 | 0.946 |
| 2983 | rs1368057 | chr2 | 137502559 | + | 0.95 | 0.912 | 0.946 | 6022 | rs1490743 | chr9 | 116075868 | + | 0.915 | 0.95 | 0.927 |
| 2984 | rs12614095 | chr2 | 137762081 | + | 0.95 | 0.926 | 0.902 | 6023 | rs12340324 | chr9 | 116881237 | + | 0.942 | 0.917 | 0.909 |
| 2985 | rs1367906 | chr2 | 139844033 | + | 0.902 | 0.943 | 0.936 | 6024 | rs10982585 | chr9 | 116966686 | + | 0.95 | 0.922 | 0.902 |
| 2986 | rs13399513 | chr2 | 139871915 | + | 0.907 | 0.938 | 0.935 | 6025 | rs10982590 | chr9 | 116967048 | + | 0.95 | 0.922 | 0.902 |
| 2987 | rs1341507C | chr2 | 139877206 | + | 0.904 | 0.938 | 0.927 | 6026 | rs1081771S | chr9 | 116974236 | + | 0.95 | 0.917 | 0.902 |
| 2988 | rs3953980 | chr2 | 140378401 | + | 0.949 | 0.917 | 0.927 | 6027 | rs10817720 | chr9 | 116976479 | + | 0.95 | 0.916 | 0.902 |
| 2989 | rs10496838 | chr2 | 140673695 | + | 0.933 | 0.946 | 0.929 | 6028 | rs16932349 | chr9 | 116996758 | + | 0.95 | 0.917 | 0.928 |
| 2990 | rs6709738 | chr2 | 141308722 | + | 0.917 | 0.933 | 0.937 | 6029 | rs10733614 | chr9 | 117188045 | + | 0.062 | 0.079 | 0.064 |
| 2991 | rs2380898 | chr2 | 141309922 | + | 0.917 | 0.933 | 0.938 | 6030 | rs10982792 | chr9 | 117351481 | + | 0.95 | 0.906 | 0.941 |
| 2992 | rs17577074 | chr2 | 141321513 | + | 0.936 | 0.906 | 0.933 | 6031 | rs10982793 | chr9 | 117351530 | + | 0.942 | 0.906 | 0.923 |
| 2993 | rs16844912 | chr2 | 141358187 | + | 0.95 | 0.911 | 0.913 | 6032 | rs7861033 | chr9 | 117658515 | + | 0.933 | 0.908 | 0.911 |
| 2994 | rs16844915 | chr2 | 141358329 | + | 0.95 | 0.915 | 0.909 | 6033 | rs7846933 | chr9 | 117729146 | + | 0.922 | 0.908 | 0.927 |
| 2995 | rs10496872 | chr2 | 141705178 | + | 0.908 | 0.949 | 0.911 | 6034 | rs2160816 | chr9 | 118325576 | + | 0.05 | 0.056 | 0.099 |
| 2996 | rs10496874 | chr2 | 141722430 | + | 0.933 | 0.95 | 0.919 | 6035 | rs1118059 | chr9 | 118329095 | + | 0.05 | 0.051 | 0.095 |
| 2997 | rs17543266 | chr2 | 141790341 | + | 0.933 | 0.95 | 0.919 | 6036 | rs7860140 | chr9 | 120263629 | + | 0.925 | 0.911 | 0.902 |
| 2998 | rs16846224 | chr2 | 141962820 | + | 0.914 | 0.938 | 0.945 | 6037 | rs10984040 | chr9 | 120283526 | + | 0.925 | 0.911 | 0.92 |
| 2999 | rs16846251 | chr2 | 141964817 | + | 0.917 | 0.933 | 0.946 | 6038 | rs10984041 | chr9 | 120287005 | + | 0.908 | 0.911 | 0.92 |
| 3000 | rs16846274 | chr2 | 141968319 | + | 0.933 | 0.933 | 0.941 | 6039 | rs10984051 | chr9 | 120295938 | + | 0.907 | 0.91 | 0.92 |
| 3001 | rs4271711 | chr2 | 141977209 | + | 0.945 | 0.943 | 0.943 | 6040 | rs17292795 | chr9 | 120950983 | + | 0.923 | 0.924 | 0.95 |
| 3002 | rs16855055 | chr2 | 141989895 | + | 0.942 | 0.938 | 0.946 | 6041 | rs10818294 | chr9 | 121103351 | + | 0.948 | 0.947 | 0.909 |
| 3003 | rs355565 | chr2 | 142123595 | + | 0.058 | 0.061 | 0.071 | 6042 | rs1971605 | chr9 | 125131608 | + | 0.058 | 0.062 | 0.098 |
| 3004 | rs355561 | chr2 | 142128248 | + | 0.1 | 0.062 | 0.071 | 6043 | rs17211963 | chr9 | 125258455 | + | 0.95 | 0.909 | 0.92 |
| 3005 | rs13408409 | chr2 | 142663983 | + | 0.917 | 0.95 | 0.914 | 6044 | rs38298S1 | chr9 | 125259527 | + | 0.95 | 0.91 | 0.928 |
| 3006 | rs1523705 | chr2 | 142680330 | + | 0.927 | 0.901 | 0.926 | 6045 | rs10986053 | chr9 | 125360824 | + | 0.917 | 0.95 | 0.946 |
| 3007 | rs6726882 | chr2 | 142959340 | + | 0.088 | 0.059 | 0.073 | 6046 | rs10986055 | chr9 | 125364335 | + | 0.924 | 0.944 | 0.945 |
| 3008 | rs17176773 | chr2 | 142991812 | + | 0.924 | 0.933 | 0.938 | 6047 | rs2416909 | chr9 | 125376970 | + | 0.917 | 0.949 | 0.946 |
| 3009 | rs13028667 | chr2 | 143659333 | + | 0.929 | 0.91 | 0.906 | 6048 | rs10818843 | chr9 | 125377517 | + | 0.917 | 0.95 | 0.94 |

Fig. 9 Cont. 86

| | | | | | | | | | |
|---|---|---|---|---|---|---|---|---|---|
| 3010 | rs12615318 | chr2 | 146070637 | + | 0.915 | 0.947 | 0.905 | 6049 rs16926684 chr9 | 125403612 + | 0.917 | 0.95 | 0.946 |
| 3011 | rs6707541 | chr2 | 146094950 | + | 0.942 | 0.944 | 0.905 | 6050 rs12351438 chr9 | 125427289 + | 0.917 | 0.95 | 0.938 |
| 3012 | rs23817S0 | chr2 | 146098706 | + | 0.942 | 0.949 | 0.905 | 6051 rs16926775 chr9 | 125521330 + | 0.95 | 0.939 | 0.95 |
| 3013 | rs17412908 | chr2 | 146510693 | + | 0.942 | 0.922 | 0.941 | 6052 rs16926787 chr9 | 125546110 + | 0.95 | 0.939 | 0.938 |
| 3014 | rs13430177 | chr2 | 148884131 | + | 0.925 | 0.949 | 0.946 | 6053 rs16926895 chr9 | 125640023 + | 0.908 | 0.928 | 0.912 |
| 3015 | rs2890923 | chr2 | 149014400 | + | 0.092 | 0.051 | 0.09 | 6054 rs7863739 chr9 | 125641077 + | 0.907 | 0.928 | 0.914 |
| 3016 | rs6430321 | chr2 | 149021028 | + | 0.092 | 0.05 | 0.093 | 6055 rs1106489 chr9 | 126005217 + | 0.908 | 0.949 | 0.932 |
| 3017 | rs6712173 | chr2 | 149026854 | + | 0.092 | 0.057 | 0.081 | 6056 rs10987199 chr9 | 128008808 + | 0.907 | 0.909 | 0.936 |
| 3018 | rs16828945 | chr2 | 149046583 | + | 0.949 | 0.95 | 0.927 | 6057 rs4836535 chr9 | 128086333 + | 0.95 | 0.91 | 0.949 |
| 3019 | rs16829008 | chr2 | 149052296 | + | 0.942 | 0.95 | 0.92 | 6058 rs3758330 chr9 | 129700053 + | 0.933 | 0.904 | 0.923 |
| 3020 | rs7592501 | chr2 | 149053581 | + | 0.942 | 0.95 | 0.923 | 6059 rs12352544 chr9 | 131960518 + | 0.942 | 0.945 | 0.904 |
| 3021 | rs16829022 | chr2 | 149055129 | + | 0.95 | 0.95 | 0.923 | 6060 rs12344915 chr9 | 131962050 + | 0.925 | 0.943 | 0.911 |
| 3022 | rs2341084 | chr2 | 151205712 | + | 0.054 | 0.094 | 0.087 | 6061 rs12376641 chr9 | 131969899 + | 0.933 | 0.944 | 0.901 |
| 3023 | rs16828946 | chr2 | 151476032 | + | 0.925 | 0.933 | 0.902 | 6062 rs4740227 chr9 | 133223390 + | 0.95 | 0.931 | 0.914 |
| 3024 | rs13001527 | chr2 | 153643739 | + | 0.933 | 0.927 | 0.905 | 6063 rs17536413 chr9 | 133307824 + | 0.93 | 0.943 | 0.936 |
| 3025 | rs1435030 | chr2 | 153666666 | + | 0.925 | 0.916 | 0.911 | 6064 rs4740240 chr9 | 133310175 + | 0.925 | 0.939 | 0.923 |
| 3026 | rs7601519 | chr2 | 153714738 | + | 0.932 | 0.91 | 0.918 | 6065 rs17536434 chr9 | 133311067 + | 0.932 | 0.944 | 0.928 |
| 3027 | rs10199044 | chr2 | 154175679 | + | 0.086 | 0.062 | 0.064 | 6066 rs10512414 chr9 | 133325228 + | 0.925 | 0.944 | 0.929 |
| 3028 | rs7368607 | chr2 | 154219562 | + | 0.078 | 0.052 | 0.093 | 6067 rs4740257 chr9 | 133382515 + | 0.915 | 0.918 | 0.923 |
| 3029 | rs6434796 | chr2 | 154225756 | + | 0.075 | 0.067 | 0.081 | 6068 rs749591 chr9 | 133384433 + | 0.917 | 0.921 | 0.929 |
| 3030 | rs9636320 | chr2 | 154458840 | + | 0.923 | 0.92 | 0.933 | 6069 rs870591 chr9 | 134052592 + | 0.943 | 0.949 | 0.902 |
| 3031 | rs16836094 | chr2 | 154693525 | + | 0.933 | 0.944 | 0.91 | 6070 rs7874131 chr9 | 136309541 + | 0.917 | 0.944 | 0.919 |
| 3032 | rs16836111 | chr2 | 154704867 | + | 0.931 | 0.937 | 0.906 | 6071 rs1179422C chr9 | 136335950 + | 0.911 | 0.904 | 0.926 |
| 3033 | rs16836115 | chr2 | 154708841 | + | 0.923 | 0.933 | 0.91 | 6072 rs11103553 chr9 | 136894826 + | 0.922 | 0.915 | 0.917 |
| 3034 | rs16836124 | chr2 | 154711093 | + | 0.941 | 0.944 | 0.902 | 6073 rs3860244 chr9 | 137620053 + | 0.917 | 0.944 | 0.92 |
| 3035 | rs13001607 | chr2 | 154922445 | + | 0.926 | 0.92 | 0.941 | 6074 rs9411311 chr9 | 139138713 + | 0.933 | 0.921 | 0.928 |
| 3036 | rs13035081 | chr2 | 154924670 | + | 0.912 | 0.946 | 0.937 | 6075 rs1223825C chr9 | 139166503 + | 0.075 | 0.067 | 0.089 |
| 3037 | rs1305010 | chr2 | 156237158 | + | 0.907 | 0.933 | 0.901 | 6076 rs11137172 chr9 | 139681451 + | 0.92 | 0.944 | 0.909 |
| 3038 | rs13388862 | chr2 | 156296588 | + | 0.943 | 0.902 | 0.918 | | | | |
| 3039 | rs4414634 | chr2 | 157274515 | + | 0.921 | 0.925 | 0.927 | | | | |

SYSTEM AND METHOD FOR ANALYZING DNA MIXTURES

This is a National Phase Application filed under 35 U.S.C. §371 as a national stage of PCT/IL2010/001019, filed on Dec. 2, 2010, an application claiming the benefit under 35 U.S.C. §119(e) of U.S. Provisional Application No. 61/266,292, filed on Dec. 3, 2009, and under 35 U.S.C. §119(e) of U.S. Provisional Application No. 61/286,271, filed on Dec. 14, 2009, the content of each of which is hereby incorporated by reference in their entirety.

FIELD OF THE INVENTION

This invention relates to analyzing DNA mixtures.

BACKGROUND OF THE INVENTION

The following prior art publications are considered as being relevant for an understanding of the invention.

[1.] N. P. Lovrich, M. J. Gaffney, T. C. Pratt, C. L. Johnson, C. H. Asplen, L. H. Hurst and T. M. Schellberg, National forensic DNA study report, National Institute of Justice (2003) http://www.ncjrs.gov/pdffiles1/nij/grants/203970.pdf.

[2.] J. M. Butler, Short tandem repeat typing technologies used in human identity testing. Biotechniques 43 (2007) ii-v.

[3.] C. Ladd, H. C. Lee, N. Yang and F. R. Bieber, Interpretation of complex forensic DNA mixtures. Croat. Med. J 42 (2001) 244-246.

[4.] G. Peter, C. Neumann, A. Kirkham, T. Clayton, J. Whitaker and J. Lambert, Interpretation of complex DNA profiles using empirical models and a method to measure their robustness. Forensic Sci. Int.: Genetics 2 (2008) 91-103.

[5.] A. J. Pakstis, W. C. Speed, J. R. Kidd and K. K. Kidd, Candidate SNPs for a universal individual identification panel. Hum. Genet. 121 (2007) 305-317.

[6.] K. K. Kidd, A. J. Pakstis, W. C. Speed, E. L. Grigorenko, S. L. Kajuna, N. J. Karoma, S. Kungulilo, J. J. Kim, R. B. Lu, A. Odunsi, F. Okonofua, J. Parnas, L. O. Schulz, O. V. Zhukova and J. R. Kidd, Developing a SNP panel for forensic identification of individuals. Forensic Sci. Int.: 164 (2006) 20-32.

[7.] B. Budowle and A. van Daal, Forensically relevant SNP classes. Biotechniques 44 (2008) 603-608, 610.

[8.] N. Horner, S. Szelinger, M. Redman, D. Duggan, W. Tembe, J. Muehling, J. V. Pearson, D. A. Stephan, S. F. Nelson and D. W. Craig, Resolving individuals contributing trace amounts of DNA to highly complex mixtures using high-density SNP genotyping microarrays. PLoS Genet. 4 (2008) e1000167.

[9.] J. S. Buckleton, C. M. Triggs and S. J. Walsh, Forensic DNA evidence interpretation, CRC Press, Boca Raton, 2005.

[10.] L. A. Foreman and I. W. Evett, Statistical analyses to support forensic interpretation for a new ten-locus str profiling system. Int. J. Legal Med. 114 (2001) 147-155.

[11.] The International HapMap Consortium, The international HapMap project. Nature 426 (2003) 789-796.

[12.] J. B. Fan, A. Oliphant, R. Shen, B. G. Kermani, F. Garcia, K. L. Gunderson, M. Hansen, F. Steemers, S. L. Butler, P. Deloukas, L. Galver, S. Hunt, C. McBride, M. Bibikova, T. Rubano, J. Chen, E. Wickham, D. Doucet, W. Chang, D. Campbell, B. Zhang, S. Kruglyak, D. Bentley, J. Haas, P. Rigault, L. Zhou, J. Stuelpnagel and M. S. Chee, Highly parallel SNP genotyping. Cold Spring Harb. Symp. Quant. Biol. 68 (2003) 69-78.

[13.] Y. Q. Hu and W. K. Fung, Evaluation of DNA mixtures involving two pairs of relatives. Int. J. Legal Med. 119 (2005) 251-259.

[14.] J. Ragoussis. Genotyping technologies for genetic research. Annu Rev Genomics Hum Genet. 2009; 10:117-33.

DNA profiling has become a major tool in the forensic world [1]. The current gold standard for forensic DNA profiling is the sizing of 9-15 short tandem repeat (STR) markers [2]. This method has been found to be very efficient for analyzing DNA profiles from specimens containing DNA from a single individual or a simple mixture of two individuals. However, the identification of an individual in complex mixtures (usually more than two individuals), has proven to be difficult [3, 4].

A number of studies have proposed to use bi-allelic single nucleotide polymorphisms (SNPs) for forensic identification [5-7]. These studies propose using SNPs with allele frequencies close to 0.5 in order to increase statistical power. For a given individual, and it is determined to what extent the individual's DNA, if present in the mixture can account for any difference in allelic frequencies in the mixture and the population at large. In a recent study, the use of high density SNP microarrays (including 500,000 SNPs or more) was shown to enable the identification of an individual in complex mixtures [8]. That study noted that with the large amount of information on allele frequencies of hundreds of thousands of SNPs, one can identify the presence of a single individual when the genotype of the individual is known for the same hundreds of thousands of SNPs, even if the DNA mixture contains DNA from thousands of individuals. The study was mainly presented in the context of the anonymity of individuals participating in large genome-wide association studies (GWAS). The use of their method for forensic purposes is suboptimal for various reasons. First, the method does not efficiently allow the exclusion of relatives, giving the defense an opportunity to claim that the suspect's relative rather than the suspect himself is represented in the mixture. Second, the method requires accurate allele frequency data for an appropriate reference population, which in many instances might not be available. Third, genotyping hundreds of thousands of SNPs provides genetic information which might be sensitive with regards to protecting individuals' privacy. Lastly, genotyping hundreds of thousands of SNPs is costly for the routine use in forensic laboratories.

SUMMARY OF THE INVENTION

In its first aspect, the present invention provides a method for determining whether DNA of an individual, referred to herein as "the suspect", is present in a sample containing DNA from two or more contributors. In accordance with this aspect of the invention, a panel of SNPs is used, and the presence or absence of the minor allele of each SNP on the panel is determined in the DNA mixture and in the suspect's DNA. As used herein the term "minor allele" refers to the allele of the SNP having the lowest frequency in a predetermined population among the two or more alleles of the SNP. If the number of rare alleles that are present in the suspect's DNA that are also present in the DNA mixture is above a predetermined threshold, then the suspect is implicated as a contributor to the mixture. Otherwise, the suspect is not implicated as being a contributor to the mixture. Since genotyping technologies are not error free, it is not necessary to detect all of the suspect's rare alleles from the panel in the mixture. Thus, as shown below, even if a small number of the suspect's rare alleles are absent from the mixture, it would still be possible to conclude with high degree of certainty that the suspect's DNA is present in the DNA mixture.

As used herein the tern "random man not excluded" (P(RMNE)) [9] refers to the probability that the DNA of a randomly selected individual which is known to be not present in a DNA mixture is erroneously determined to be present in the mixture (a "Type I error"). A P(RMNE)<$10^{-9}$ has been proposed to be an acceptable level of a type I error using a ten-locus STR profile [10].

The inventors have found, for example, that if the MAF of each allele on the panel is in the range of 0.05-0.1 in the predetermined population, then with a panel of 1000 SNPs, any randomly selected individual from the same population will typically carry 100-200 alleles on the panel. For such a randomly selected individual, the probability that all of these 100-200 alleles are present in the DNA mixture is usually below $10^{-9}$ i.e., under these conditions, the P(RMNE)<$10^{-9}$. The inventors have further found that under these conditions, P(RMNE)<$10^{-9}$ even when taking into account typical genotyping error rates, which are usually in the range of 0-1%

The invention can be carried out using any method of SNP genotyping. Methods of SNP genotyping are disclosed, for example, in [14], and include technologies provided by Affimetrix ("GeneChip") and Illumina ("Beadchips").

When it can be inferred that all of the contributors to the DNA mixture and the suspect are all from a common subpopulation (such as where the DNA sample was obtained at a remote village, tribe or isolated, reservation, where the suspect resides) a panel may be prepared using SNPs having MAFs in a predetermined range in that subpopulation. In other cases, for example in large cosmopolitan cities, the contributors to the mixture and the suspect may be of various ethnicities. In this case, a panel of SNPs could be used having MAFs in a predetermined range in each of two or more subpopulations.

A specific example of SNPs with an MAF of 0.05-0.1% in several racial groups (i.e., Caucasians, Africans and Asians) can be found for example in the table shown in FIG. 9, which can serve as a source from which the SNPs of the panel are chosen.

SNPs that are as separated from each other in the genome may be used in order to minimize linkage disequilibrium among them. For example, SNPs may be used that are at least 100 Kbp from each other.

Thus, in its first aspect, the invention provides a method for determining the presence or absence of an individual's DNA in a sample containing DNA, comprising:
 a. obtaining a sample containing DNA from two or more contributors;
 b. in a panel of a plurality of single nucleotide polymorphisms (SNPs), each SNP having a minor allele in a predetermined population, determining for each SNP whether the minor allele of the SNP is present in the sample;
 c. for each SNP in the panel, determining whether the minor allele of the SNP is present in the individual's DNA;
 d. If the number of minor alleles that are present in the individual's DNA that are also present in the DNA sample is above a predetermined threshold, concluding that the individual's DNA is present in the sample.

In the method of the invention, the number of SNPs in the panel can be selected to satisfy one or more requirements. For example, the number of SNPs in the panel can be selected so that an expected fraction of minor alleles that the DNA of a randomly selected individual from the predetermined population has in common with the panel out of all of the alleles on the panel is in a predetermined range, for example, in a range from 5% to 25%, or from 10% to 20% of the SNPs in the panel. The number of SNPs in the panel can be selected so that the probability that the DNA of a randomly selected individual from the population would not be excluded from the mixture, P(RMNE), is less than a predetermined probability, for example, less than $10^{-6}$, or $10^{-9}$. The number of SNPs in the panel can be in the range from 500 to 10,000, or in the range from 1000 to 2000.

The SNPs on the panel can be selected to satisfy one or more requirements. For example, the SNPs on the panel can be selected so that the minor allele of each SNP in the panel can have a minor allele frequency (MAF) in the predetermined population in a predetermined range, such as a MAF of each SNP is from 0.01 and 0.2 in the predetermined population. The SNPs on the panel can be selected so that an expected number of minor alleles that the DNA of a randomly selected individual from the predetermined population has in common with the panel out of all of the alleles on the panel is in a predetermined range. This range may be for example from 100 to 200. The SNPs on the panel can be selected so that the SNPs are separated from each other by a predetermined number of base pairs such as 100 Kbp.

The SNPs in the panel of SNPs may be selected from the SNPs given in the table shown in FIG. 9.

The step of determining whether an allele is present in a sample may comprise detecting hybridization between a DNA molecule in the sample and a DNA molecule complementary to the allele. The complementary DNA molecules may be attached to a surface to form an array of DNA molecules. Thus, in another of its aspects, the invention provides an array of DNA molecules for use in the method of the invention.

In another of its aspects, the method for estimating the number of individuals contributing to a DNA containing sample, comprising:
 a. for each SNP in a panel of SNPs, determining whether the minor allele is present in the sample;
 b. determining a number of individuals contributing DNA to the sample based on the fraction of minor alleles in the panel present in the sample from among all of the alleles in the panel;
 c. estimating the number of individuals contributing DNA to the sample based on the fraction of alleles in the panel present in the sample.

BRIEF DESCRIPTION OF THE DRAWINGS

In order to understand the invention and to see how it may be carried out in practice, embodiments will now be described, by way of non-limiting example only, with reference to the accompanying drawings, in which.

Figure 3:
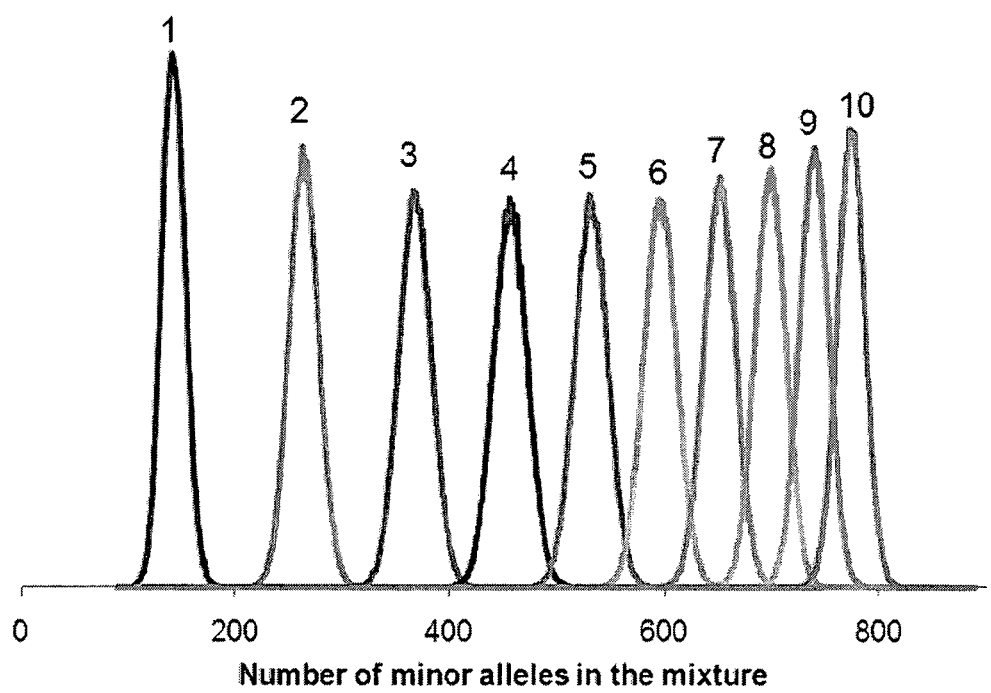
Figure 4:
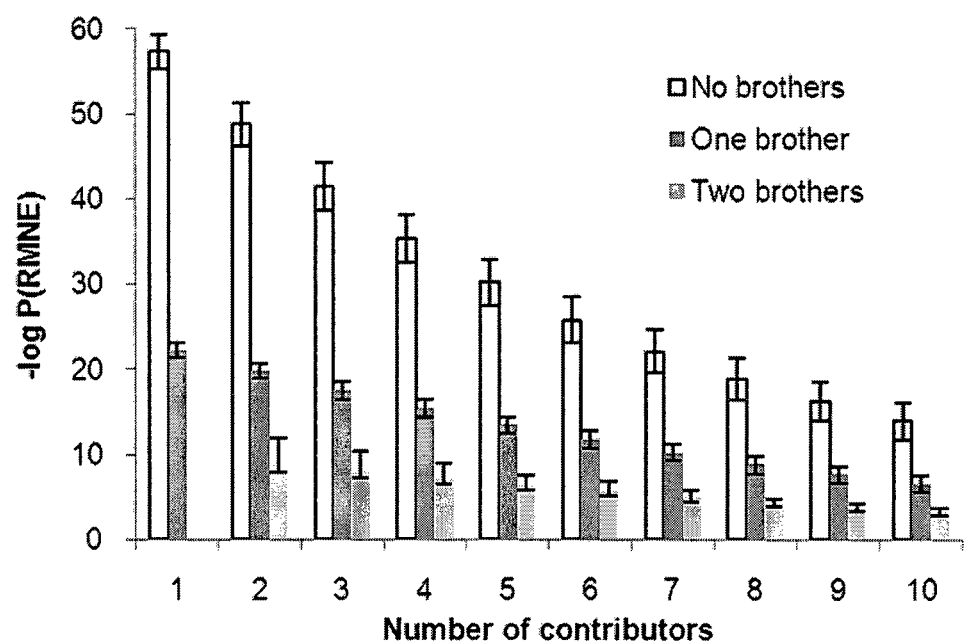
Figure 6:
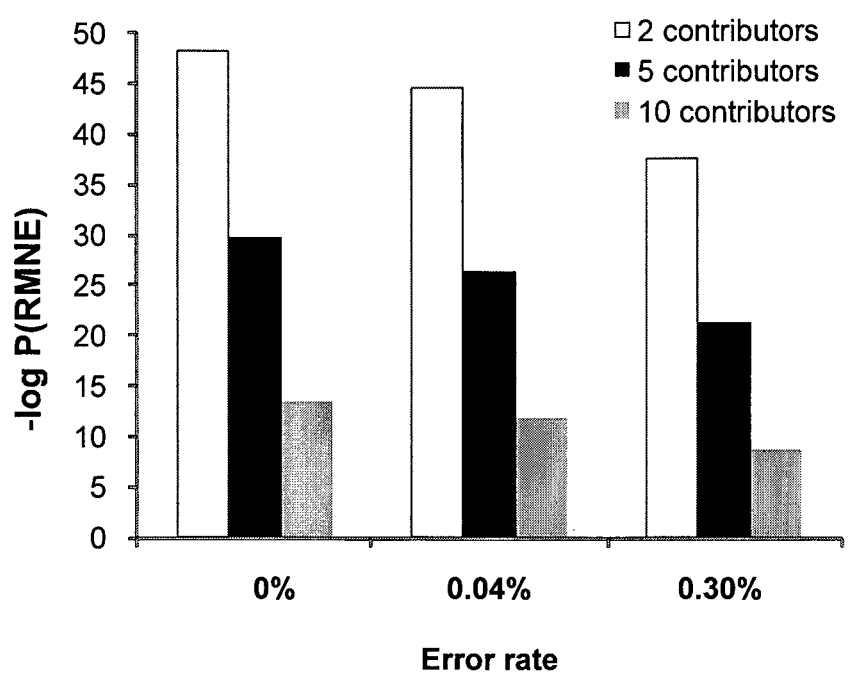
Figure 7:
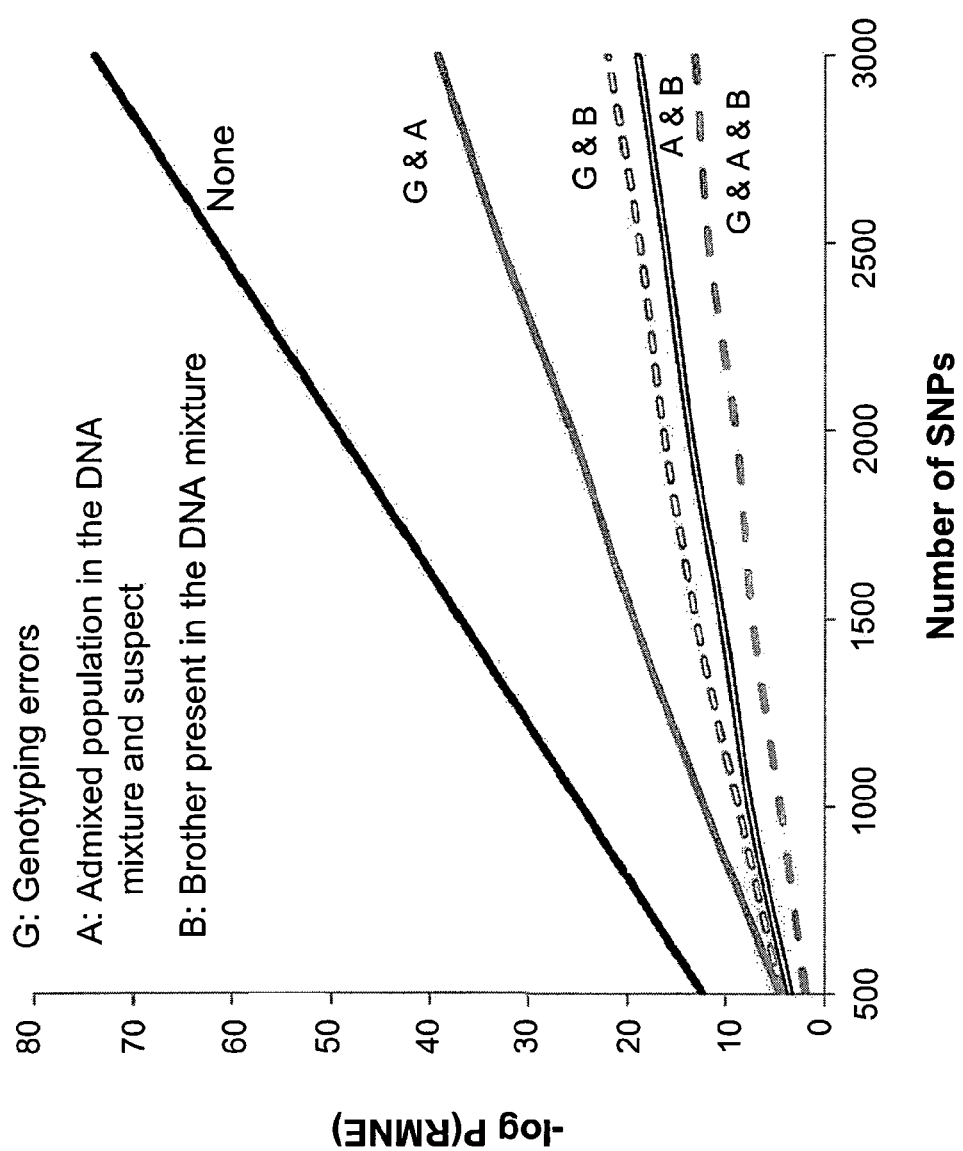
Figure 8:
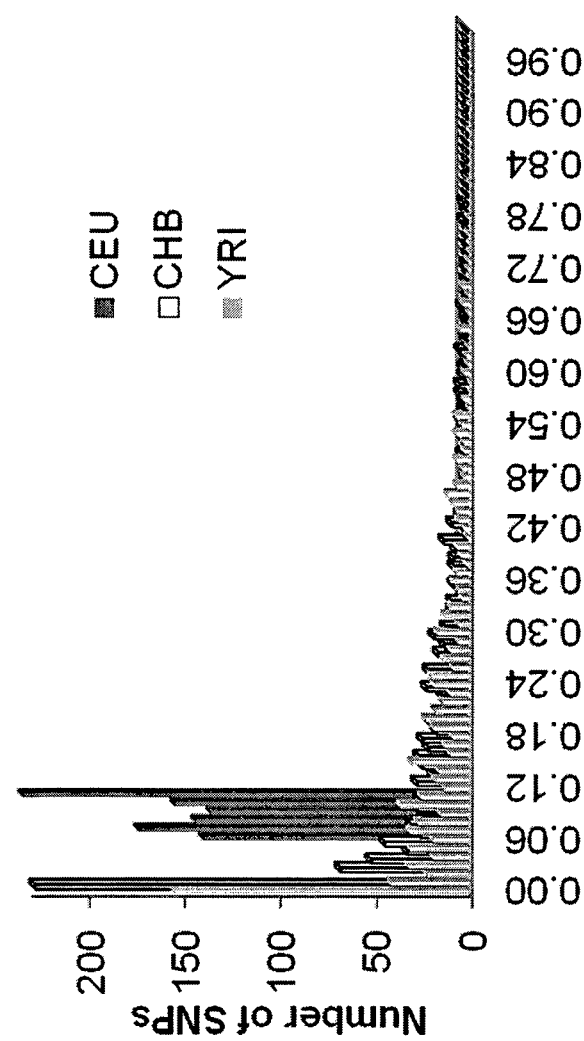

FIG. 3 shows empirical distribution of the number of minor alleles present in a mixture for mixtures comprising 1 to 10 contributors, obtained through 1,000,000 simulations (Y axis represents the probability density values);

FIG. 4 shows the median P(RMNE) as a function of the number of contributors to the mixture in which values without relatives in the mixture are presented in the red columns; with one brother in the mixture presented in the blue columns; and with two brothers in the mixture presented in the green columns, calculated from 20,000 simulations using a theoretical panel of 1000 SNPs each with 0.075 MAF and the error bars represent a 99% confidence interval;

FIG. 5 shows the median RMNE probabilities as a function of the ratio of CEU and non-CEU contributors in a mixture of eight contributors in which mixtures of CEU and CHB are presented in A, and mixtures of CEU and YRI are presented in B, with values for CEU suspects presented in the blue columns and for non-CEU suspects in the red columns by calculating P(RMNE) using CEU and non-CEU population allele frequencies respectively;

FIG. 6 shows expected P(RMNE) as a function of genotyping error rate assuming a power of 99% of detecting an individual present in the mixture, with values for mixtures with 2, 5 and 10 contributors presented in the blue, red and green columns, respectively;

FIG. 7 shows the median P(RMNE)a −log scale) as a function of the number of SNPs in the panel used. The upper blue line represents a simple scenario with no complications, whereas all other lines are combinations of 2 or 3 complications;

FIG. 8 shows the distribution of allele frequencies of a 1000 SNP panel in CEU, CHB, and YRI populations; and FIG. 9 shows a table of SNPs having an MAF of 0.05-0.1% in several racial groups.

DETAILED DESCRIPTION OF EMBODIMENTS

Calculating P(RMNE)

Assuming that all SNPs are accurately assessed for the individual (no genotyping errors) and that the presence or absence of each allele is accurately determined in the DNA mixture. Under these conditions, it can be concluded that the individual's DNA is present in the DNA mixtures if and only if all of the individual's alleles are present in the DNA mixture. Under this assumption, the probability of excluding an individual whose DNA is actually present in the DNA mixture is zero.

When looking at a specific SNPi with possible alleles A and B, the DNA of a randomly selected individual can be determined not to be present in the mixture in two cases:

(i) The individual's genotype is BB or AB, and no B alleles are present in the mixture. In this case, the probability of a randomly selected individual being excluded from a mixture comprising n contributors due to SNPi (PEi) equals:

$$PEi = (p(Ai)^2)^n \times (1-p(Ai)^2) \qquad (1)$$

Where p(Ai) is the frequency of the major allele A (the allele with the higher population frequency among the two SNP alleles) at the i-th SNP.

(ii) The individual's genotype is AA or AB, and no A alleles are present in the mixture. the PEi in this case is:

$$PEi = (p(Bi)^2)^n \times (1-p(Bi^2)) \qquad (2)$$

The overall probability of exclusion is the sum of (1) and (2). However, due to the significant difference in allele frequencies, exclusion due to (2) is typically about three orders of magnitude less likely than exclusion due to (1). The contribution of (2) to the exclusion probability can thus be neglected, and (1) will equal henceforth be used to calculate PEi).

Consequently, the probability of the DNA of a randomly selected individual not being excluded at site i, P(RMNEi) can be estimated as:

$$P(RMNEi) = 1 - PEi \qquad (3)$$

Probability of not being excluded across m sites will then be:

$$P(RMNE) = \prod_{i=1}^{m} (1 - PEi) \qquad (4)$$

(4) represents the P(RMNE) for a given panel of SNPs and a DNA mixture from m contributors. For a specific, simulated or actual mixture, with S sites capable of exclusion (sites exhibiting only the major allele A), the P(RMNE) is:

$$P(RMNE) = \prod_{i=1}^{S} P(Ai)^2 \qquad (5)$$

This probability is only indirectly affected by the actual number of contributors to the DNA mixture. The number of contributors to the DNA mixture affects the number of sites exhibiting the major allele only, which is the factor that directly affects the P(RMNE) in (5). Equation 5 can be used to calculate P(RMNE) even when the number of contributors is not known.

Optimal MAF

A MAF of 0.5 (the highest possible MAF) is not optimal as it is highly likely that in a mixture of DNA from several individuals both alleles will be present in the DNA mixture (for example, from two different individuals) thus reducing the ability of the method to exclude individuals. On the other hand, alleles with very low MAF will rarely be present in any suspect, thus again reducing the power of the method. The optimal MAF is the value of P(Ai) for which P(Ei) is maximal and can be obtained by differentiation of (1) by P(Ai), assuming P(Ai)=P(Aj)=MAF for all i,j. Setting the derivative to 0 and solving for P(Ai), results in:

$$MAF = 1 - \sqrt{\frac{n}{n+1}} \qquad \text{(Equation 6)}$$

where n is the number of contributors.

SNP Information and Selection

Allele frequencies for all SNPs were obtained from The International HapMap Project [11] for the following populations: Yoruba in Ibadan, Nigeria (YRI), Han Chinese in Beijing, China (CHB) and Utah residents with ancestry from northern and western Europe (CEU). A panel of 1000 SNPs was selected based on HapMap information for the CEU population. All SNPs in the panel had a MAF in the range of 0.05-0.1. SNPs were selected with maximal distances between them. The resulting panel contained 1000 SNP that are at least 1.7 Mbp apart one from the other.

Calculating P(RMNE) with Relatives Present in the DNA Mixture

As an extreme example of the situation where a relative's DNA is present in the mixture, the probability of an individual (absent from the mixture) not being excluded when one or two of his brothers are present in the DNA mixture was calculated. To exclude an individual under this scenario, the individual needs to be excluded both by the unrelated individuals and by his brother(s). Since the loci of the SNPs in the panel are close to one another, considerable linkage is expected between markers. The probability of exclusion is dependent on the number of sites for which the suspect has half or full identity by descent (IBD) with his relatives in the mixture. The general equation for calculating the probability of non exclusion of a random brother from a given mixture is:

$$P(RMNE) = \sum_{IBD1=0}^{S} \sum_{IBD0=0}^{S-IBD1} \left( P(IBD1) \times P(IBD0|IBD1) \times \prod_{i=1}^{IBD1} P(Ai) \times \prod_{i=1}^{IBD0} P(Ai)^2 \right) \quad (7)$$

where S is the number of potentially excluding SNPs in the mixture (containing only the major allele A), IBD0 is the number of sites among the number of potentially excluding SNPs in the mixture in which all the relatives of the suspect in the mixture have no IBD alleles in common with the suspect. IBD1 is the number of sites in which all the suspect's relatives in the mixture jointly have exactly one IBD allele in common with the suspect. The probabilities of a certain number of IBD0 sites and IBD1 sites are dependent since they come from the same limited pool of S sites. Hence the probability of fording a certain number of IBD1 sites and IBD0 sites is P(IBD1)×P(IBD0|IBD1). In IBD0 sites, the P(RMNE) is the same as in mixtures with no relative (i.e., as given by 5). In IBD1 sites, the suspect necessarily has at least one A allele since one of his alleles is common by descent with his relatives in the mixture, and all of his relatives were AA homozygotes. The probability that the second allele doesn't exclude the suspect is the probability of the major allele in the population P(Ai), and across all IBD1 sites:

$$\prod_{i=1}^{IBD1} P(Ai).$$

(7 sums a matrix of every possible number of IBD0 sites and IBD1 sites, with their probability of accruing multiplied by P(RMNE) in both IBD0 and IBD1 sites. The IBD0 and IBD1 distributions were obtained through simulations.

Simulations

Simulating individuals—Randomly selected individuals were simulated by assigning genotypes at each SNP by sampling alleles from a binomial distribution with allele frequencies as specified in the HapMap database, assuming a Hardy-Weinberg equilibrium. To simulate brothers, initially two random individuals (as before) were simulated to serve as parents. One random haploid genome was generated from each parent assuming a 1% proportion of recombination for 1 Mb of physical distance (two such haploid genomes constitute an individual). Independently repeating this process twice or three times generates two or three brothers.

Simulating distributions P(IBD1) and P(IBD0|IBD1) were calculated empirically using (7) and simulating the underlying distributions. For each specific mixture, the suspect and his relatives in the DNA mixture were simulated 1000 independent times. IBD1 and IBD0|IBD1 were approximately normally distributed with means and variances estimated from the 1000 simulations for each case. Then, the probability of each number of IBD1 and IBD0 sites was derived from a binomial approximation of the normal probability density function using the mean and standard deviation of the normal probability density function.

Results

The Effect of Number of SNPs, MAF and Number of Individuals in the Mixture

Figure 1A:
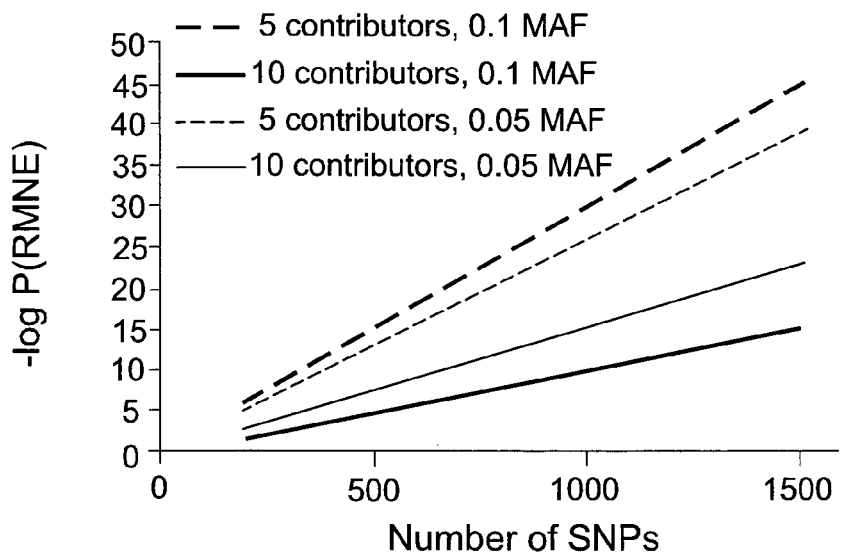
FIG. 1 shows the expected P(RMNE) (on a −log scale) as a function of the number of SNPs in the panel used (A); minor allele frequency, MAF, (B); and the number of contributors to the mixture, (C) Within each figure four lines are presented for different combinations of parameters.
Figure 1B:
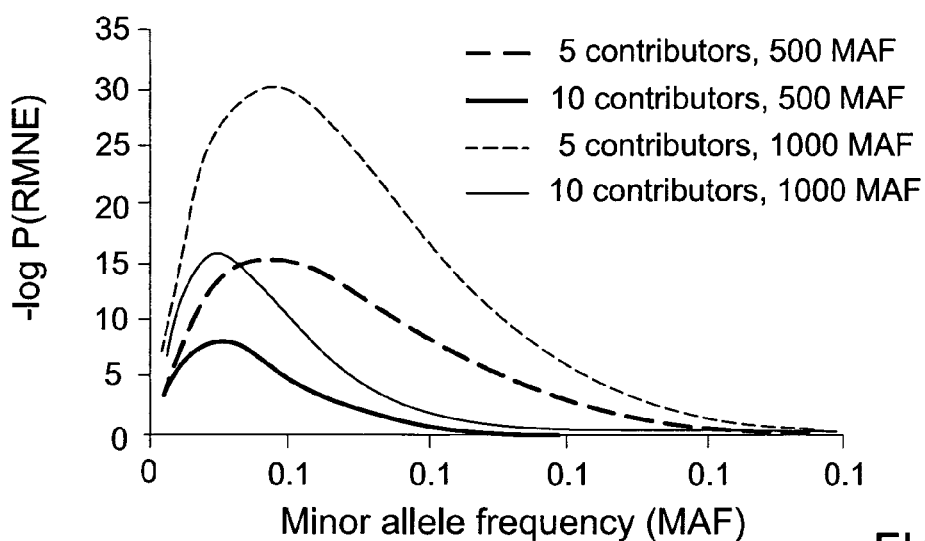
Figure 1C:
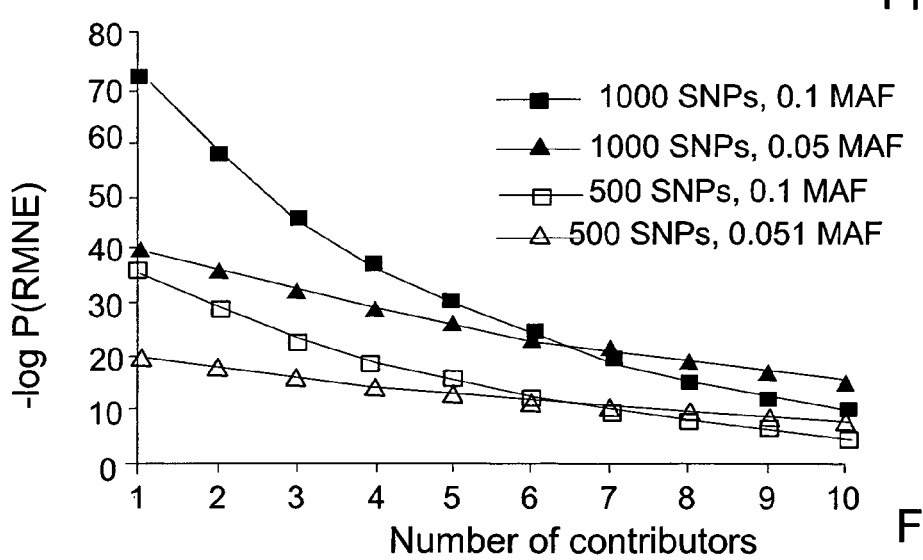

FIG. 1A presents P(RMNE) as a function of the number of SNPs used in the panel for different values of MAF (0.1 and 0.05, assuming all SNPs have the same MAF), and a different number of contributors to the DNA mixture (5 or 10).−log(P(RMNE)) is linear with the number of SNPs (P(RMNE) decreased with increasing number of SNPs), thus the number of SNPs have a dramatic effect in the efficiency of the samples used and even a modest increase in the number of SNPs will significantly decrease P(RMNE). For example, if under certain circumstances, P(RMNE)= $10^{-5}$, then doubling the number of SNPs used in the panel, while keeping all other factors unchanged, will decrease the P(RMNE) to $10^{-10}$. FIG. 1B presents P(RMNE) as a function of MAF of the SNPs (again assuming all SNPs have the same MAF) for different sizes of SNP panels (500 or 1000) and a different number of contributors to the DNA mixture (5 or 10). Consistent with (6), MAF has an optimum depending on the number of contributors to the DNA mixture. As can be seen in FIG. 1B, for 5 or 10 contributors the optimal MAF is 0.09 or 0.05 respectively. (For the case of 2 contributors to the DNA mixture, the optimal MAF is 0.18, not shown in FIG. 1B.) Mixtures with more than 10 individuals are not common and are relatively uninformative, whereas mixtures with less than 5 individuals can be highly informative even with suboptimal MAF for the SNPs used (see FIG. 1B). Therefore, for practical purposes a MAF range of 0.05-0.1 for all SNPs can be appropriate. FIG. 1C presents P(RMNE) as a function of the number of individuals in the mixture for different sizes of the SNP panel (500 or 1000) and different MAF (0.05 or 0.1). As the number of contributors to the DNA mixture increases, −log P(RMNE) decreases rapidly. Nevertheless, even with 10 contributors P(RMNE) remains significant under these conditions.

Figure 2:
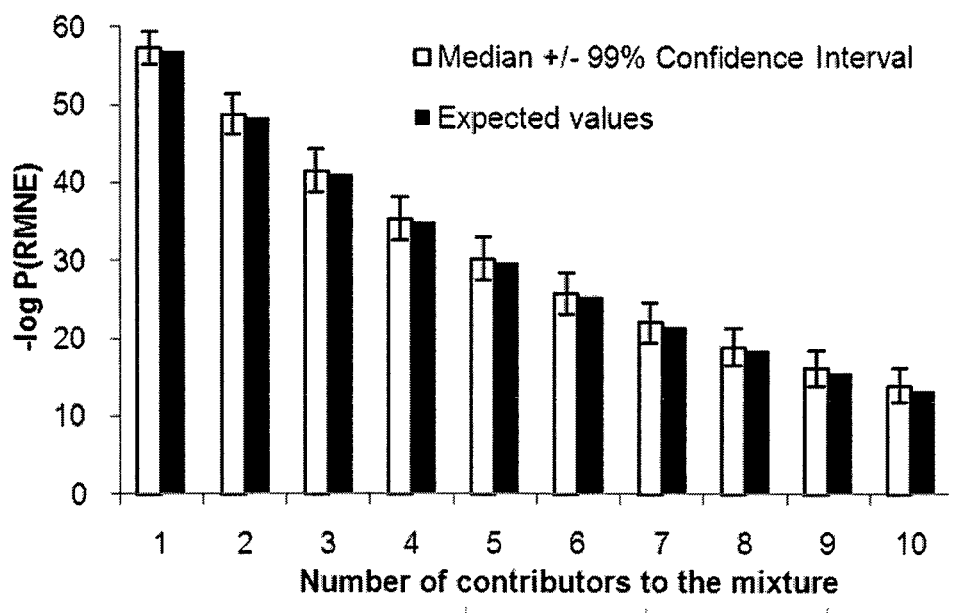
FIG. 2 shows P(RMNE) as a function of the number of contributors to the mixture, where the red columns represent the expected value with a theoretical panel of 1000 SNPs each with a MAF of 0.075, and the blue columns present the median results of 100,000 simulations with a panel of 1000 different SNPs (with MAFs between 0.05 and 0.1), and the error bars represent the 99% confidence interval as obtained from the simulations.

The results presented in FIG. 1 (A to C) are expected probabilities assuming that all SNPs have the same MAF. Typically, a DNA mixture will have a specific P(RMNE) calculated from (5), which deviates somewhat from the expected P(RMNE) as calculated from (4). Therefore, it is important to examine the variance around the expected P(RMNE). Simulations were carried out to estimate P(RMNE) variance. The simulations were run with a panel of 1000 SNPs, each with a different MAF all within the range of 0.05-0.1. The average MAF in this panel was 0.075. A total of 1,000,000 simulations were run (100,000 simulations for each number of contributors to the mixture from 1 to 10). Individuals in the mixture were simulated as described above and P(RMNE) for each iteration of the simulation was calculated using (5). FIG. 2 presents the results of the simulations for each number of contributors to the DNA mixture (blue columns). The bars correspond to a 99% confidence interval. These results indicate that although an actual result will deviate from the expected P(RMNE) value assuming all SNPs have a MAF of 0.075 (red columns), the deviation is minor and in most instances any actual result will fall close to the expected value. For mixtures of ten contributors, the median P(RMNE) was $1.09 \times 10^{-14}$ and out of 100,000 simulations the worst P(RMNE) obtained was $2.88 \times 10^{-11}$, well below the required threshold.

Estimating the Number of Contributors to a Mixture

As stated above, knowing the number of contributors is not required to calculate a specific P(RMNE) in an actual DNA mixture. Nevertheless, in many cases this information is forensically important on its own. The number of contributors will affect the number of rare alleles present so that the number of rare alleles present in a DNA mixture can provide information on the number of contributors to the mixture. The extent that this information can provide accurate information about the number of contributors can be evaluated using simulations. 100,000 simulations were performed for each mixture comprising between 1 to 10 contributors. FIG. 3 presents the distribution of the number of rare alleles present in the DNA mixture as obtained from the 100,000 simulations for each mixture (with 1 to 10 contributors). The number of rare alleles present in a mixture was normally distributed and the means of these distributions increased with the number of contributors. Thus, the number of rare alleles present in a DNA mixture can be used to estimate the number of contributors to the mixture. With 1-3 contributors, the number of rare alleles present will correctly determine the number of contributors in 99.9% of the cases; with 4-10 contributors the number of rare alleles will correctly determine the number of contributors in 91.17% of the cases, and will estimate the number of contributors within a ±1 range in virtually 100% of the cases.

The Effect of Close Relatives in the Mixture

Here we look into the effect of the presence of close relatives of the suspect in a DNA mixture. For this, P(RMNE) was calculated assuming that the suspect has one or two brothers present in the DNA mixture. A hypothetical panel of 1000 SNPs was used with a MAF 0.075 for each SNP. The P(RMNE) were calculated using (7). FIG. 4 presents the effect of the presence of brothers in the DNA mixture on the P(RMNE) of a randomly selected individual with one or two brothers present in the DNA mixture. The median and 99% confidence interval bars were obtained from 20,000 simulations for each mixture type. The median probability that a random brother would not be excluded from a mixture of up to 7 contributors including one brother is less than $10^{-9}$. For mixtures containing two brothers and up to four contributors to the mixture, the P(RMNE) is less than $10^{-6}$. It should be noted that a non-exclusion probability of $10^{-6}$ is quite significant when only potential brothers are considered.

The Effect of Population Specific Allele Frequencies

The analyses conducted in the previous sections assume that the reference allele frequencies for all SNPs are known. This assumption is reasonable when the individuals contributing to the DNA mixture and the suspect are all known to be from a population for which allele frequencies are known and the panel of SNPs was selected accordingly. In forensic work, individuals from distinct sub-populations, emigrants or tourists from different populations may be involved as suspects or contributors to a DNA mixture from a crime scene. Different populations may have different allele frequencies for the SNPs in the panel used, and thus will affect the P(RMNE). As an example, the allele frequency distribution of the panel of 1000 SNPs previously selected from the CEU population, all with a MAF in the range of 0.05-0.1, was examined. FIG. 8 presents the MAF distribution of these SNPs in YRI, CEU and CHB populations. The MAF distribution in YRI and CHB populations was found to differ significantly from CEU. About 19% were not polymorphic and about 22% had a MAF>0.25.

The presence of DNA in a mixture from individuals from different populations can cause two distinct problems. First, its presence in the mixture can increase the number of minor alleles in the mixture thus increasing the P(RMNE). However, this in general does not affect the accuracy of the P(RMNE). Second, if the suspects are arrested based on previous information that they belong to a certain population, then the P(RMNE) regarding those suspects could be calculated based on the allele frequencies in their population. This can improve the accuracy of the P(RMNE), possibly with reduced power. The case where reference allele frequencies for the suspect are unknown can be addressed by assuming "worst case" scenario allele frequencies.

Figure 5A:
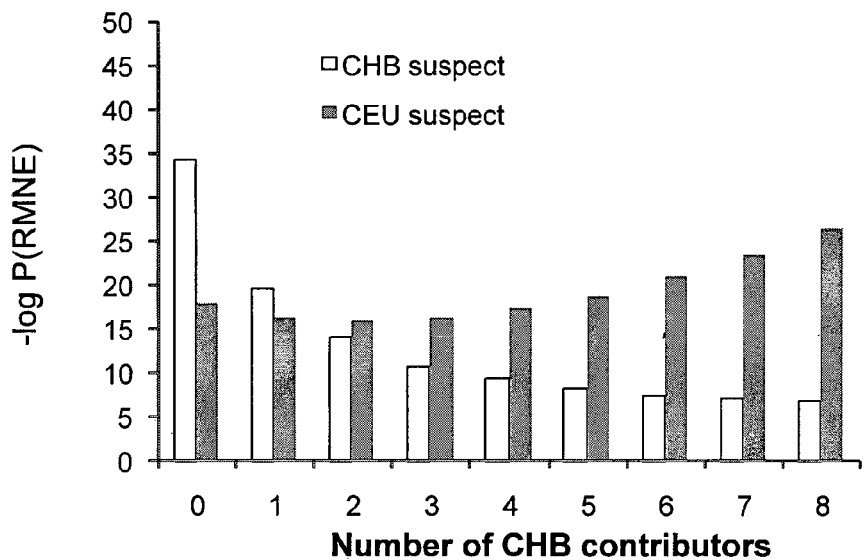
Figure 5B:
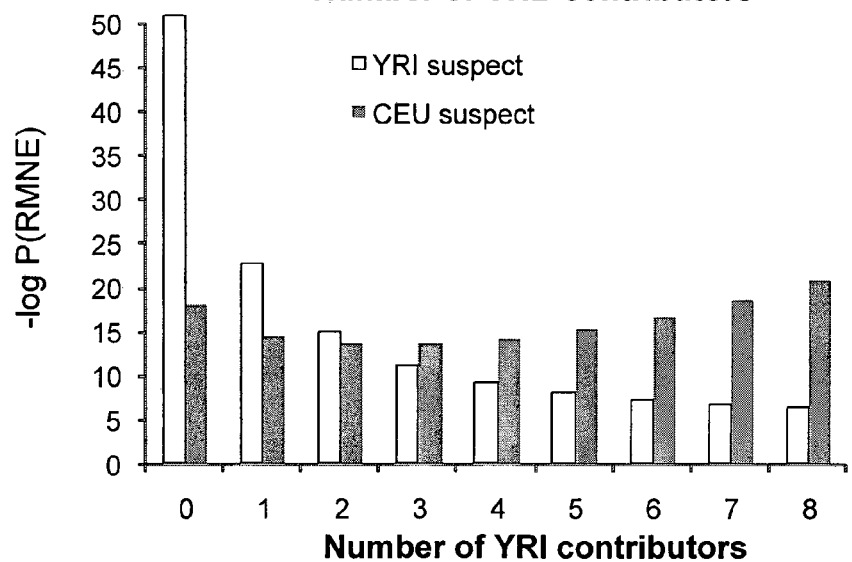

In order to study the effect of the presence of DNA from individuals from different populations in a mixture, 130 combinations of mixtures with varying numbers of CEU, CHB and YRI individuals were generated. For each combination 5000 independent simulations were run. The P(RMNE) for each simulation was calculated twice, once with CEU allele frequencies, for a random suspect, and a second time using CHB or YRI allele frequencies, for a suspect from each of those populations respectively. FIGS. 5A and 5B present, as an example, the P(RMNE) for mixtures containing 8 contributors with different ratios of contributors. As the number of contributors from a non-CEU population increases, the P(RMNE) of a CEU suspect decreases while the P(RMNE) for a non-CEU increases. This is caused by the fact that many of the SNPs in the non-CEU population have a MAF lower than that in the CEU population reducing the probability that a randomly selected individual from the CEU population is not excluded. A CEU suspect has a median P(RMNE)<$10^{-9}$ for any ratio of CEU to CHB or CEU to YRI in any mixture of up to 10 contributors. A CHB or YRI suspect has a median P(RMNE)<$10^{-9}$ in mixtures of 8 contributors if the number of CHB or YRI contributors to the mixture is below 4. Another exemplary result from the simulations (not shown) is that, for mixtures of up to 6 contributors, any number of CHB or YRI contributors to the mixture, with any suspect, the median P(RMNE) is <$10^{-9}$.

The Effect of Genotyping Errors

The analyses required to calculate a given P(RMNE) requires a genotype of the suspect with regard to the panel of SNPs and establishing which alleles are present in the DNA mixture with the same panel of SNPs. Genotyping procedures are not errorless and therefore it is important to consider the effect of genotyping errors. When genotyping an individual (the suspect) standard genotyping errors may occur at known rates for known genotyping platforms. In addition to genotyping errors, a given SNP may not produce a genotype, a factor quantified by the so called "call rate". For common genotyping platforms, call rates are high and have negligible effects on this process. For example, Illumina's BEADARRAY™ platform employing the Golden-Gate assay has a call rate of 99% and Affymetrix GeneChip® Human Mapping. 10K Array Xba 142 2.0 has a call rate of 92% [13]. The attributed genotyping errors for these technologies are 0.3% and 0.04%, respectively. Note that there is a correlation between call rate and error rate. If one only calls those results that look unambiguous then call rate decreases but so does error rate. Therefore it is safe to assume that the effective error rate for forensic analyses is at the lower end of reported rates, as one can decide to intentionally reduce calling rate and only call the results that seem unambiguous. The reduced calling rate can be compensated by simply increasing the number of SNPs in the panel used. When genotyping the DNA mixture, there are two conceptually different genotyping errors. The first consists of determining the presence of an allele that, in fact, is not present and the second consists of not detecting an allele that is present in the mixture. Both errors are affected by the standard genotyping error. However, the second error is also affected by the effective amount and quality of the DNA in the mixture that carries a given rare allele. If the suspect's DNA is present in the mixture at a relatively low quantity or quality, then the suspect's alleles may not be read and the suspect may erroneously be excluded from the mixture. This situation will result in establishing that the suspect is not in the mixture and thus it does not introduce erroneous convictions. Therefore, in this section we will analyze the effect of the standard genotyping error and will keep in mind that obviously one can miss the suspect's alleles if the quantity or quality of the DNA that he contributed to the mixture is too low.

The main problem genotyping errors pose, are wrong exclusions of suspects. This can happen when a rare allele of the suspect is not typed in the mixture, or when a rare allele not present in the mixture is erroneously typed as present in the suspect's DNA. In order to ensure that real contributors are not always (or too often) excluded, a certain (small) number of "excluding" SNPs should be allowed, while still declaring non-exclusion. An excluding SNP is one that has an allele detected in the suspect and not detected in the mixture. Increasing the number of allowed excluding SNPs results in an increased Type I error (i.e., increased P(RMNE)). Not allowing any excluding SNPs may result in a significantly reduced power for the identification of suspects in a DNA mixture. We assume that the number of wrongly excluding SNPs (denoted X) is binomially distributed with n=the number potentially excluding SNPs (the number of rare alleles in the suspect+the number of SNPs without rare alleles in the mixture) and p=the error rate. We define k as the number of excluding SNPs that should be allowed, and $\alpha$ as the desired power of detection. Then k is obtained by numerically solving the equation $P(X \leq k) > \alpha$.

FIG. 6 shows the P(RMNE) for mixtures of 2, 5 and 10 contributors with error rates typical of genotyping platforms, i.e., 0.04% or 0.3%. The appropriate number of allowed excluding SNPs (k) was obtained for $\alpha=0.99$. This resulted in 4-7 excluding SNPs allowed in the case of a 0.3% error rate and 1-2 "excluding" SNPs allowed in the case of a 0.04% error rate. As can be seen in FIG. 6, the effect of genotyping errors (at the error rates used) is quite minor. For all cases studied −log P(RMNE) does not decrease by more than 35% as a consequence of genotyping errors.

Combination of Effects

In each of the previous sections the effects of each of various factors on the results as investigated independently. In real life situations, a combination of factors can be present. Therefore, the effects of two or more complicating factors analyzed using a simulated DNA mixture with 6 contributors. The following three complicating factors: were used (i) a brother of the suspect is present in the DNA mixture; (ii) A DNA mixture comprising 3 CEU and 3 YRI, with the P(RMNE) calculated for a YRI suspect; and (iii) A genotyping error rate of 0.1% maintaining detection power of 99%. We then calculated the P(RMNE) for all three possible two-factor combinations, as well as for the case where all three factors are present. FIG. 7 presents the results as a function of the number of SNPs used in the panel. As the scenarios studied become more complex it is harder to reach a desired P(RMNE), say, below $10^{-9}$. A panel of 1000 SNPs may fail to ensure such a low P(RMNE) in complex scenarios. However, with a panel of 2000 SNPs, the P(RMNE) falls below the desired limit in all of the scenarios here considered.

The invention claimed is:

1. A method for determination of the presence or absence of an individual's DNA in a sample comprising a DNA mixture having the DNA of two or more contributors, the method comprising:
   a) starting with
      i) the sample comprising a DNA mixture having the DNA of two or more contributors (DNA mixture sample),
      ii) a DNA sample from the individual (individual's DNA sample), and
      iii) a solid support having associated therewith an array of 500-10,000 DNA molecules for detecting the presence or absence of single nucleotide polymorphisms (SNPs), wherein (A) every DNA molecule associated with the solid support is a part of the array, (B) each of the DNA molecules in the array corresponds to a different SNP, each SNP having a minor allele in a predetermined population, which minor allele has a minor allele frequency (MAF) from 0.01 to 0.2 in the predetermined population, and (C) each of the DNA molecules in the array corresponds to one of the SNPs by being complementary to the minor allele,
   determining, for each SNP to which a DNA molecule in the array corresponds (SNP in the array), whether the minor allele of the SNP is present in the DNA mixture sample, by detecting the hybridization between the DNA molecules in the array and the DNA of the DNA mixture sample;
   b) for each SNP in the array, determining whether the minor allele of the SNP is present in the individual's DNA sample, by detecting the hybridization between the DNA molecules in the array and the DNA of said individual's DNA sample; and
   c) concluding that the individual's DNA is present in the DNA mixture sample based solely on whether the number of minor alleles that are present in the individual's DNA sample that are also present in the DNA mixture sample is above a predetermined threshold.

2. The method according to claim 1, wherein the number of SNPs in the array is selected so that an expected fraction of minor alleles that the DNA of a randomly selected individual from the predetermined population has in common with the array out of all of the alleles in the array is from 5% to 25% of the SNPs in the array.

3. The method according to claim 1, wherein the number of SNPs in the array is selected so that the probability that the DNA of a randomly selected individual from the population would not be excluded from the sample, probability of Random Man not excluded [P(RMNE)], is less than $10^{-6}$.

4. The method according to claim 1, wherein an expected number of minor alleles that the DNA of a randomly selected individual from the predetermined population has in common with the array out of all of the SNPs in the array is from 100 to 200.

5. The method according to claim 1, wherein the SNPs in the array are separated from each other in the genome by at least 100 Kbp.

6. The method according to claim 1, wherein the step of determining whether an allele is present in the DNA mixture sample or in the individual's DNA sample comprises detecting hybridization between a DNA molecule in the array complementary to the allele and a DNA molecule in the DNA mixture sample or in the individual's DNA sample.

7. The method according to claim 6, wherein the DNA molecules are attached to the solid support to form the array of DNA molecules.

8. A solid support having attached thereto an array of 500 to 10,000 DNA molecules for detecting the presence or absence of single nucleotide polymorphisms (SNPs),
   wherein every DNA molecule attached to the solid support is a part of said array,
   wherein each of the DNA molecules in said array corresponds to a different SNP, each SNP having a minor allele in a predetermined population, which minor allele has a minor allele frequency (MAF) from 0.01 to 0.2 in the predetermined population, and
   wherein each of the DNA molecules in said array corresponds to one of said SNPs by being complementary to the minor allele of the SNP.

* * * * *